(12) United States Patent
Elzi et al.

(10) Patent No.: US 12,305,171 B2
(45) Date of Patent: May 20, 2025

(54) COMPOSITIONS AND METHODS FOR TREATING CANCER

(71) Applicant: bioAffinity Technologies, Inc., San Antonio, TX (US)

(72) Inventors: David J. Elzi, San Antonio, TX (US); William E. Bauta, San Antonio, TX (US); Vivienne I. Rebel, San Antonio, TX (US)

(73) Assignee: bioAffinity Technologies, Inc., San Antonio, TX (US)

( * ) Notice: Subject to any disclaimer, the term of this patent is extended or adjusted under 35 U.S.C. 154(b) by 935 days.

(21) Appl. No.: 17/359,905

(22) Filed: Jun. 28, 2021

(65) Prior Publication Data

US 2023/0035774 A1 Feb. 2, 2023

Related U.S. Application Data

(63) Continuation-in-part of application No. PCT/US2019/068423, filed on Dec. 23, 2019.

(60) Provisional application No. 63/044,771, filed on Jun. 26, 2020, provisional application No. 62/785,592, filed on Dec. 27, 2018.

(51) Int. Cl.
  *C12N 15/113* (2010.01)
  *C12Q 1/68* (2018.01)

(52) U.S. Cl.
  CPC ...... *C12N 15/1138* (2013.01); *C12N 2310/14* (2013.01); *C12N 2310/315* (2013.01); *C12N 2320/30* (2013.01)

(58) Field of Classification Search
  None
  See application file for complete search history.

(56) References Cited

U.S. PATENT DOCUMENTS

| | | | |
|---|---|---|---|
| 6,239,270 B1 | 5/2001 | Akerstrom et al. |
| 9,044,461 B2 | 6/2015 | Quadros et al. |
| 10,113,201 B2 | 10/2018 | Davuluri |
| 2003/0004311 A1 | 1/2003 | Baker et al. |
| 2006/0234260 A1 | 10/2006 | Griffais et al. |
| 2008/0050393 A1 | 2/2008 | Tang et al. |
| 2011/0195523 A1 | 8/2011 | Ogasawara et al. |
| 2014/0068793 A1 | 3/2014 | Quadros et al. |

FOREIGN PATENT DOCUMENTS

| | | |
|---|---|---|
| WO | 0153455 A2 | 7/2001 |
| WO | 2007117657 A2 | 10/2007 |
| WO | 2007/140506 | 12/2007 |
| WO | 2007140506 A1 | 12/2007 |
| WO | 2008/116171 | 3/2008 |
| WO | 2008116171 A1 | 9/2008 |
| WO | 2017/011907 | 1/2017 |
| WO | 2017011907 A1 | 1/2017 |
| WO | 2017/223273 | 12/2017 |
| WO | 2017223273 A1 | 12/2017 |
| WO | 2020139866 A2 | 7/2020 |

OTHER PUBLICATIONS

"Predicted: Seriola lalandi dorsalis pleckstrin homology and RhoGEF domain containing G3 (plekhg3), mRNA", NCBI Reference Sequence; XM_023408803.1, https://www.ncbi.nlm.nih.gov/nucleotide/XM_023408803.1?report=genbank&log$=nuclalign&blast_rank=9&RID=HYEUPBOB014, 2017, 1-3.

Andersen, Rikke K., et al., "Melanoma tumors frequently acquire LRP2/megalin expression, which modulates melanoma cell proliferation and survival rates", Pigment Cell & Melanoma Research, vol. 28, Issue 3, 2015, 267-280.

Lai, Shao-Chiang, et al., "Down-regulation of Transcobalamin Receptor TCbIR/CD320 by siRNA Inhibits Cobalamin uptake and Proliferation of Cells in Culture", Exp Cell Res., No. 317, No. 11, 2011, 1603-1607.

Leary, Meghan, et al., "Sensitization of Drug Resistant Cancer Cells: A Matter of Combination Therapy", Cancers, vol. 10, No. 483, 2018, 1-18.

Monteagudo, Silvia, et al., "Inhibition of p42 MAPK using a nonviral vector-delivered siRNA potentiates the anti-tumor effect of metformin in prostate cancer cells", Nanomedicine, vol. 7, No. 4, 2012, 493-506.

*Primary Examiner* — Sean McGarry
(74) *Attorney, Agent, or Firm* — Peacock Law P.C.; Janeen Vilven

(57) ABSTRACT

A double stranded RNA interference (RNAi) agent comprising at least one of (i) a first double-stranded ribonucleic acid (dsRNA) for inhibiting the expression of a CD320 gene wherein the first dsRNA comprises a sense strand and an antisense strand forming a duplex, (ii) a second dsRNA for inhibiting the expression of a LRP2 gene wherein the second dsRNA comprises a sense strand and an antisense strand forming a duplex, or (iii) a cocktail of (i) and (ii) and wherein the sense strand of the first dsRNA is at least substantially complementary to the antisense strand of the first dsRNA and the sense strand of the second dsRNA is at least substantially complementary to the antisense strand of the second dsRNA and the use of the RNAi agent as a pharmaceutical composition for the treatment of cancer in subjects in need of treatment.

15 Claims, 20 Drawing Sheets

Specification includes a Sequence Listing.

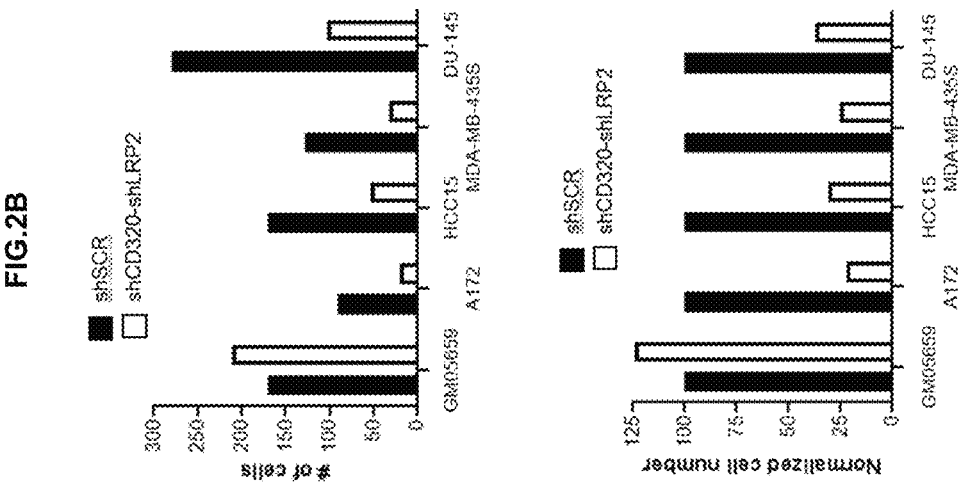
FIG. 2B
FIG. 2C
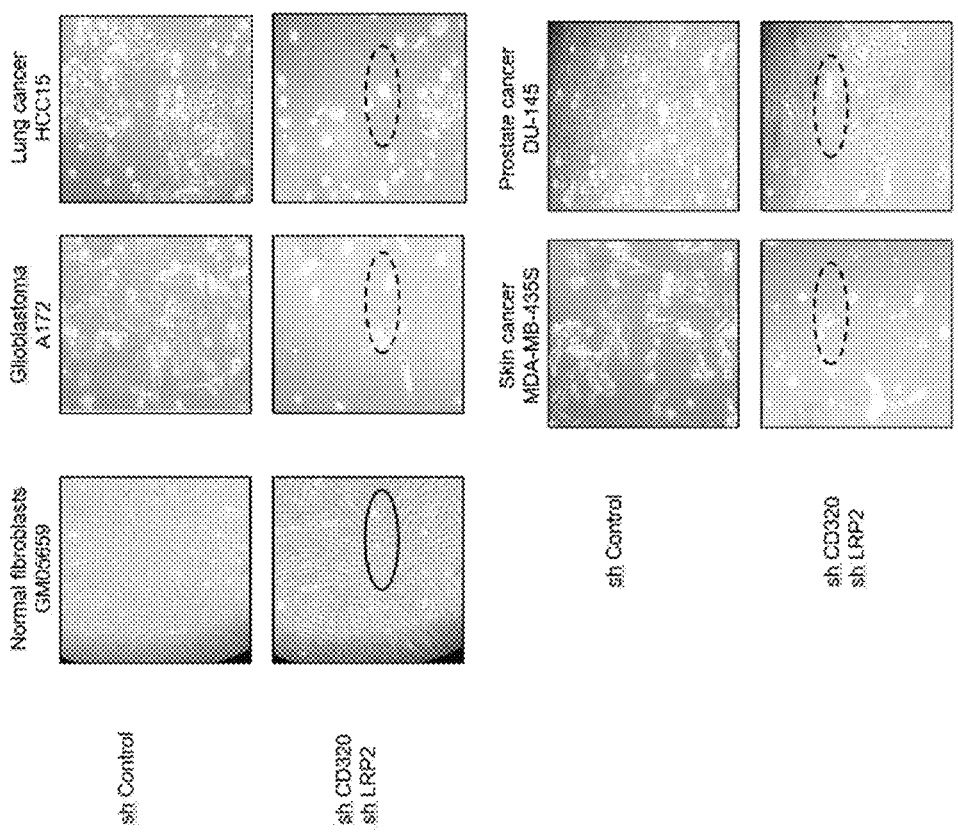
FIG. 2A

CD320 protein levels LRP2 protein levels

HEK 293 (embryonic kidney)

MDA-MB-435S (melanoma)

MDA-MB-231 (Breast)

CD320 protein levels LRP2 protein levels

LnCAP
(Prostate)

MCF-7
(breast)

U251
(glioblastoma)

CD320 protein levels

A172 (glioblastoma)

DU-145 (prostate)

GM05659 (normal fibroblast)

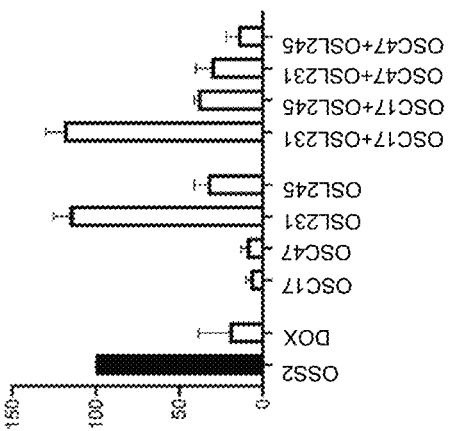
FIG. 9A GM05659 (Normal)
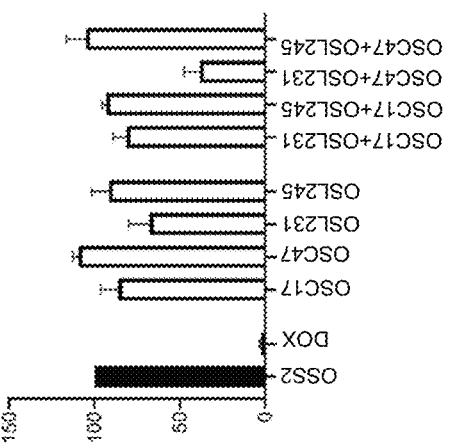
FIG. 9B HCC15 (Lung)
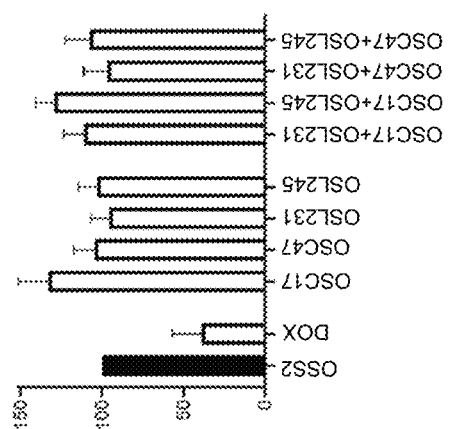
FIG. 9C H157 (Lung)
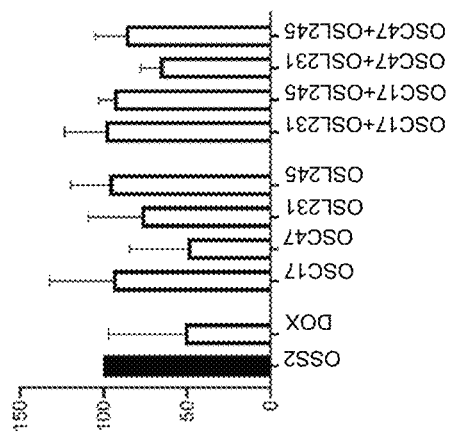
FIG. 9D A172 (Brain)
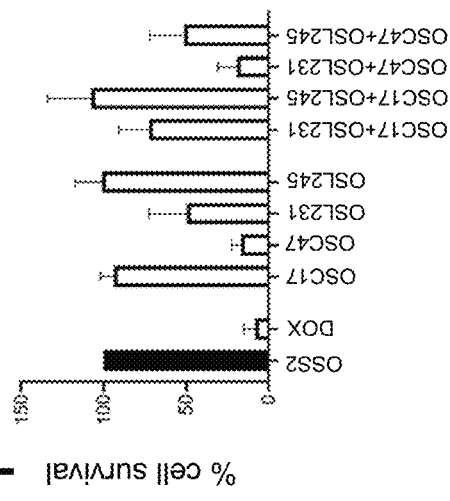
FIG. 9E U251 (Brain)
% cell survival

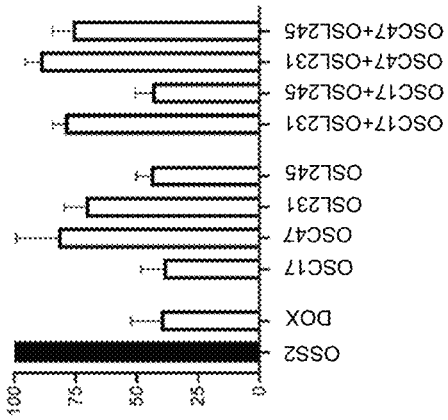
FIG. 10A MCF7 (Breast)
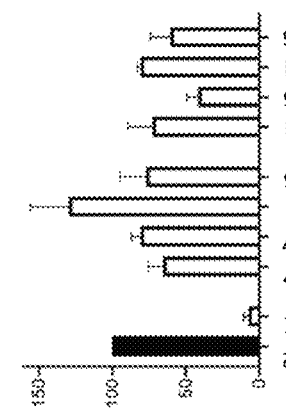
FIG. 10B MDA-231 (Breast)
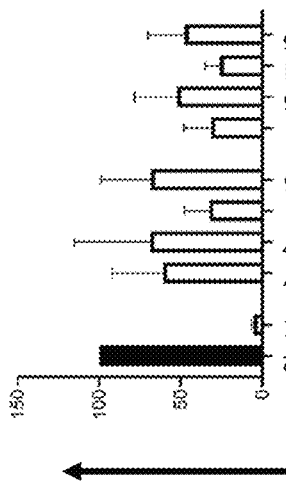
FIG. 10C DU145 (Prostate)
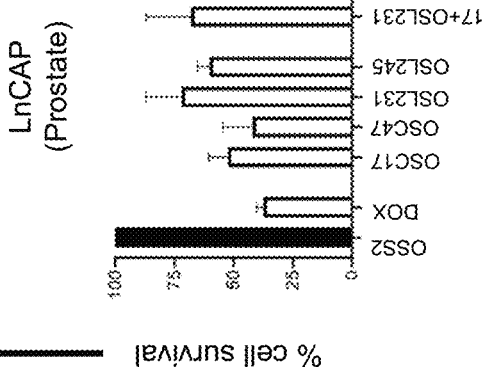
FIG. 10D LnCAP (Prostate)
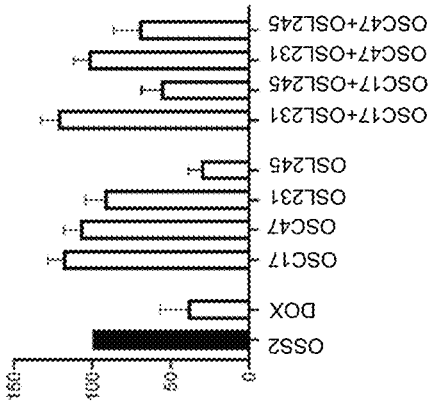
FIG. 10E MDA-435S (Skin)
% cell survival

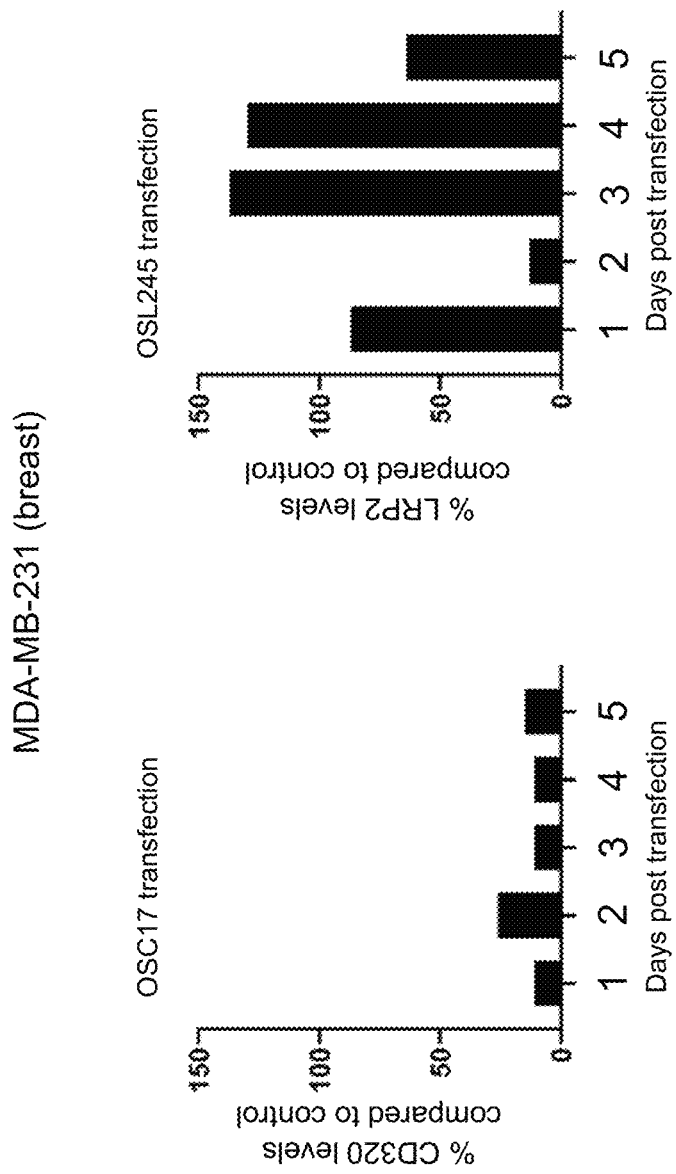

FIG.16A MDA-MB-231 (breast)
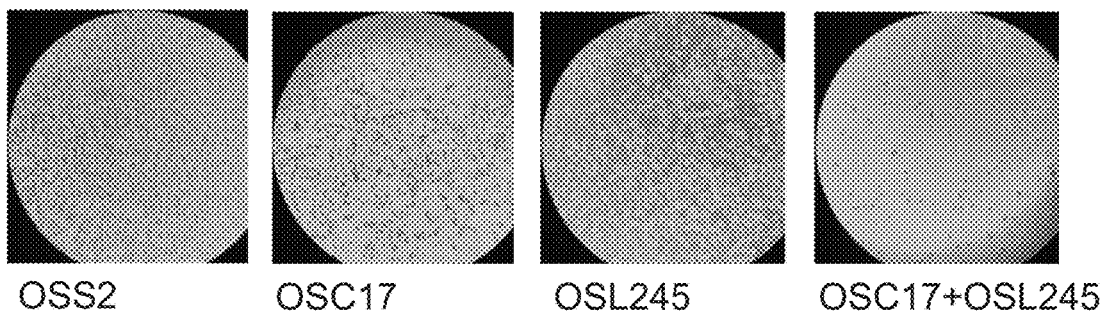
OSS2  OSC17  OSL245  OSC17+OSL245
FIG.16B DU145 (prostate)
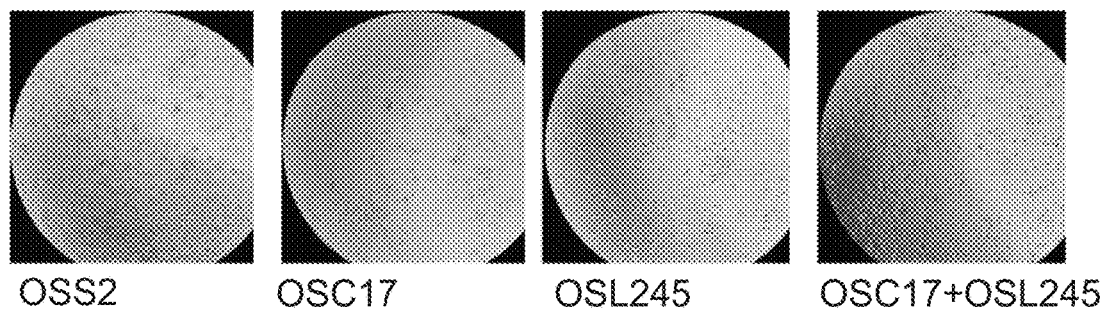
OSS2  OSC17  OSL245  OSC17+OSL245
FIG.16C LnCAP (prostate)
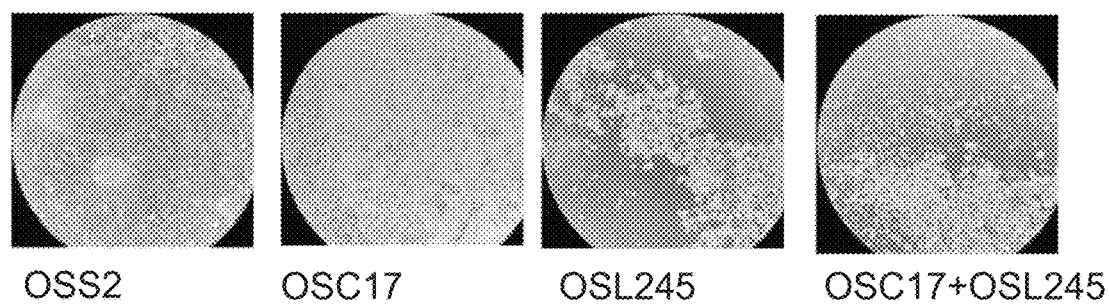
OSS2  OSC17  OSL245  OSC17+OSL245
FIG.16D MDA-MB-435S (skin)
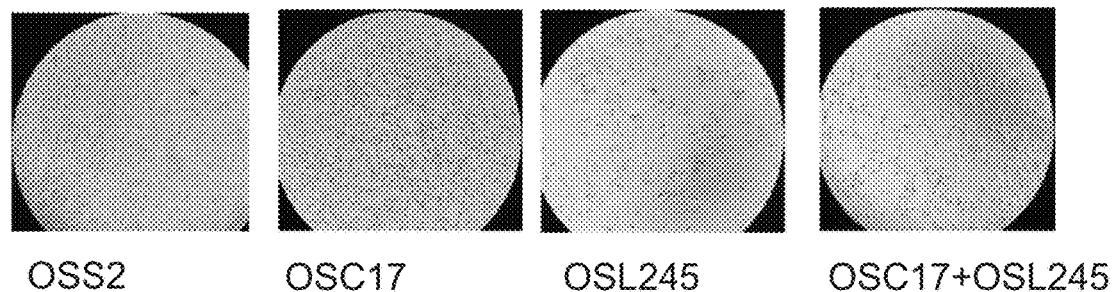
OSS2  OSC17  OSL245  OSC17+OSL245

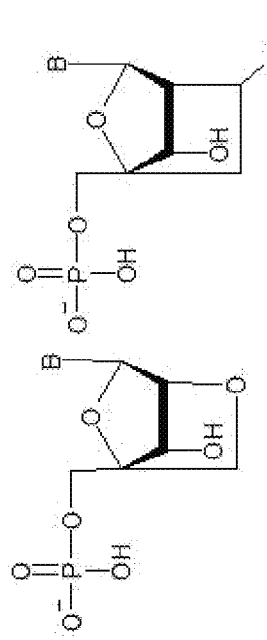
FIG. 19B
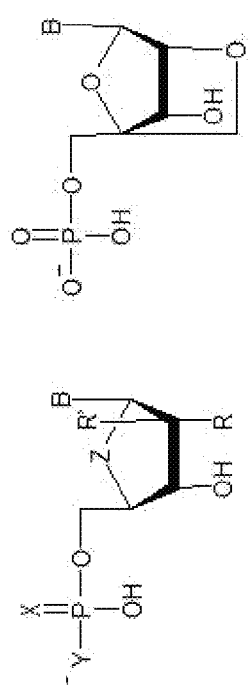
FIG. 19A
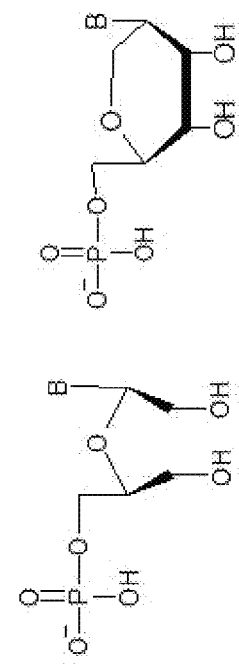
FIG. 19C
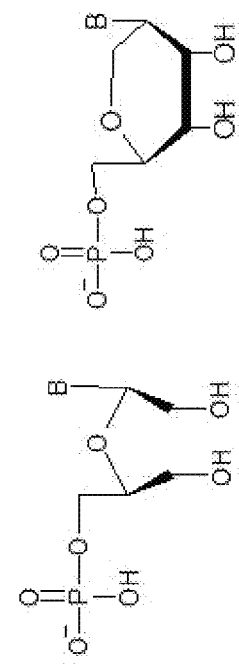
FIG. 19D
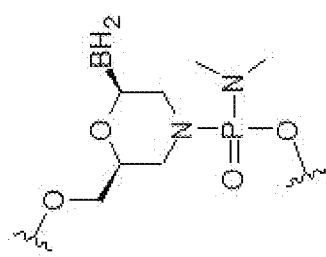
FIG. 19E
FIG. 19F
FIG. 19G

COMPOSITIONS AND METHODS FOR TREATING CANCER

CROSS-REFERENCE TO RELATED APPLICATIONS

This application is a Continuation-In-Part application of International Patent Application No. PCT/US2019/068423, filed on Dec. 23, 2019, titled "Compositions and Methods for Treating Cancer", which claim priority to and the benefit of U.S. Provisional Patent Application No. 62/785,592, titled "Compositions and Methods for Treating Cancer", filed on Dec. 27, 2018. This application also claims priority to and the benefit of the filing of U.S. Provisional Patent Application No. 63/044,771, filed on Jun. 26, 2020, titled "Compositions and Methods for Treating Cancer". The specification and claims thereof are incorporated herein by reference.

SEQUENCE LISTING

The instant application contains a Sequence Listing which has been submitted electronically in ASCII format and is hereby incorporated by reference in its entirety. Said ASCII copy, created on Jun. 24, 2021, is named 32064-1035_CIP_SL.txt and is 446,136 bytes in size.

BACKGROUND

A variety of cancer therapies and treatments exist such as surgical resection of solid tumors, radiation, and chemotherapy. While surgical resection and radiation are used on localized tumors, chemotherapy is often delivered systemically and impacts both cancer and non-cancer cells, leading to severe and even life-threatening side effects. Older cancer drugs, including alkylators, nucleotide antimetabolites, and tubulin poisons, cause significant side effects because they are similarly toxic to normal cells as to cancer cells, especially those normal cells undergoing routine cell division in the intestine, scalp, and skin. For this reason, much of the effort in contemporary cancer drug discovery is devoted to finding targeted therapeutics which differentiate between cancer cells and normal cells (Neidle et al., (2014) Cancer Drug Design and Discovery). This has led to drugs which inhibit the function of oncolytic proteins that are mutated, overexpressed, or abnormally hyperactive in cancer but not in normal cells. Examples of such drugs include kinase inhibitors, histone deacetylase inhibitors, proteasome inhibitors, mTOR inhibitors, BCL2 inhibitors, and isocitrate dehydrogenase inhibitors. Significant effort has also been devoted to targeting cell surface antigens which are differentially expressed in cancer cells compared to normal cells. Monoclonal antibodies and antibody-drug conjugates targeting cancer cell surface antigens have thus been developed as cancer therapeutics (Beck et al., (2017) Nat Rev Drug Disc 16, 315-337). Another point of differentiation between cancer cells and normal cells is metabolism. It was discovered many years ago that many cancer cells utilize glucose fermentation to generate ATP as opposed to the process of oxidative phosphorylation used by normal cells. A drug targeting isocitrate dehydrogenase, involved in abnormal glucose metabolism in cancer cells, was recently approved by the FDA (Dhillon (2018) Drugs 78, 1509-1516). Abnormalities in one-carbon metabolism, which encompasses the folate and methionine cycles and affects nucleotide synthesis and DNA methylation as a way of controlling gene expression, are strongly associated with some cancers (Fanidi et al., (2019) Int J Cancer 145, 1499-1503; Yang (2018) Front Oncol 8, 493). In this connection, it has been known for a long time that certain synthetic analogs of folic acid (antifolates) can inhibit the growth of cancer cells. It is also known that some cancer cells are dependent for survival on the amino acid methionine. If methionine is restricted, the cancer cells die, while this has little effect on normal cells. In recent years, evidence has begun to emerge that some cancer cells might have an abnormal dependency on vitamin B12. The nature of this dependency is not understood but might, in part, involve the use of vitamin B12 as a catalytic cofactor by the enzyme methionine synthase in one-carbon metabolism.

Vitamin B12 (cobalamin) is an essential micronutrient in the human diet. It is a cofactor for the metabolic enzymes methionine synthase and methylmalonyl-CoA mutase (Fedosov et al., (2012) Water Soluble Vitamins (book) 56, 347-367). After oral ingestion and transport through the intestine, cobalamin is almost completely protein bound in plasma to the chaperone proteins transcobalamin 1 (TCN1, haptocorrin, R-binder) (TCO1_HUMAN) and transcobalamin 2 (TCN2) (TCO2_HUMAN). The TCN2-cobalamin complex (TCN2-Cbl) is taken up by most cells using the process of receptor-mediated endocytosis and has a plasma half-life of 1-15 h. TCN2 has a high affinity and specificity for cobalamin in its various dietary and nutritional supplement forms, such as methyl cobalamin, adenosyl cobalamin and cyanocobalamin (Fedosov et al., (2007) Biochem 46, 6446-6458). TCN1 is a glycoprotein that exists in two different forms in plasma (Marzolo and Farfan (2011) Biol Res 44, 81-105). The most abundant form is sialylated and has a plasma half-life of about 10 days (Bor (2004) Clin Chem 50, 1043-1049). A less abundant form is desialylated and has a plasma half-life of a few minutes. Unlike TCN2-Cbl, which can be taken up by almost all cell types, the transcobalamin 1-cobalamin complex (TCN1-Cbl) is quickly taken up by certain liver cells, only in its desialylated form, by receptor-mediated endocytosis.

CD320 and LRP2 are two receptors involved in the uptake of cobalamin as TCN2-Cbl. CD320, a member of the low-density lipoprotein receptor (LDLR) family, is constitutively expressed in most cells and is the receptor primarily responsible for the uptake of cobalamin (Quadros (2013) Biochimie 95, 1008-1018). CD320 is overexpressed in some types of cancer (Sycel et al., (2013) Anticancer Res 33, 4203-4212; Amagasaki (1990) Blood 76, 1380-1386). There is also evidence that CD320 facilitates the transport of TCN2-Cbl through the blood-brain barrier into the brain (Lai et al.; (2013) FASEB 27, 2468-2475). LRP2 is another receptor in the LDLR family. It is expressed most highly in the kidney but also in other tissues. In addition to cobalamin, LRP2 also transports sundry proteins and small molecules, including albumin, insulin and vitamin D (Mazolo et al., (2011) Biol Res 44, 89-105). In the liver, the asialoglycoprotein receptor (ASGR) uptakes TCN1-Cbl by receptor-mediated endocytosis so long as TCN1 is in its desialylated form. Normal liver cells and liver cancer cells express very high levels of ASGR (50,000 receptors per cell), making this receptor attractive as a portal for delivering drugs to the liver (Luo et al., (2017) Biomedicine and Pharmacotherapy 88, 87-94; Stockert (1995) Physiological Rev 75, 595-609; Soda et al., Blood (1985) 65, 795-802).

After receptor mediated endocytosis, cobalamin is sequestered in the endosome, where the endosomal membrane prevents passive egress to the cytosol. A specialized protein (cblF) facilitates the transport of cobalamin through the endosomal membrane to the cytosol (Banerjee et al., (2009) Curr Opin Chem Bio 13, 484-491).

BRIEF SUMMARY OF THE INVENTION

One embodiment of the present invention provides for a double stranded RNA interference (RNAi) agent comprising at least one of (i) a first double-stranded ribonucleic acid (dsRNA) for inhibiting the expression of a CD320 gene wherein the first dsRNA comprises a sense strand and an antisense strand forming a duplex, (ii) a second dsRNA for inhibiting the expression of a LRP2 gene wherein the second dsRNA comprises a sense strand and an antisense strand forming a duplex, or (iii) a cocktail of (i) and (ii) and wherein the sense strand of the first dsRNA is at least substantially complementary to the antisense strand of the first dsRNA and the sense strand of the second dsRNA is at least substantially complementary to the antisense strand of the second dsRNA. For example, the antisense strand of (i) the first dsRNA includes a region of complementarity to a CD320 RNA transcript and for example the sense strand of (i) the first dsRNA is selected from Table 5. The antisense strand of (ii) the second dsRNA includes a region of complementarity to an LRP2 RNA transcript and the sense strand of (ii) the second dsRNA are selected from Table 6. In one example, (i) the first dsRNA or (ii) the second dsRNA comprises a duplex region which is 16-30 nucleotide pairs in length. In another example, (i) the first dsRNA or (ii) the second dsRNA comprises a duplex region which is 21-23 nucleotide pairs in length. In one embodiment, the double stranded RNAi agent includes at least one strand of: (i) the first dsRNA or (ii) the second dsRNA which comprises a 3' overhang of at least 2 nucleotides. Further still, in one embodiment, the antisense strand of (i) the first dsRNA, comprises the nucleotide sequence selected from (5'→3'):

(SEQ ID NO: 17)
CAGUUGCGCAGUUUCUUGUCAGUUCdTdT;

(SEQ ID NO 18)
CAGUUGCGCAGUUUCUUGUCAGUUCdT*dT;

(SEQ ID NO 19)
mCmAmGmUmUmGmCmGmCmAmGmUmUmUmCmUmU mGmUmCmAmGmUmUmCdT*dT;

(SEQ ID NO 21)
mCmAmGmUmUmGmCmGmCmAmGmUmUmUmCmUmU mGmUmCmAmGmUmUmC;

(SEQ ID NO 23)
CmAmGmUmUmGmCmGmCmAmGmUmUmUmCmUmUm

GmUmCmAmGmUmUmCdT*dT;

(SEQ ID NO 24)
mC2fAmG2fUmU2fGmC2fGmC2fAmG2fUmU2f

UmC2fUmU2fGmU2fGmC2fAmG2fUmU2fUmCdT*dT;

(SEQ ID NO 25)
mC2fAmG2fUmU2fGmC2fGmC2fAmG2fUmU2f

UmC2fUmU2fGmU2fGmC2fAmG2fUmU2fUmC;

(SEQ ID NO 28)
2fCmA2fGmU2fUmG2fCmG2fCmA2fGmU2fUm

U2fCmU2fUmG2fUmC2fAmG2fUmU2fCdT*dT;

(SEQ ID NO 29)
2fCmA2fGmU2fUmG2fCmG2fCmA2fGmU2fUm

U2fCmU2fUmG2fUmC2fAmG2fUmU2fC;

(SEQ ID NO 30)
mC2fA2fG2fU2fU2fG2fC2fG2fC2fA2fG2fU

2fU2fU2fC2fU2fU2fG2fU2fC2fA2fG2fU2 fU2fCdT*dT;

(SEQ ID NO 32)
mC2fAmG2fUmU2fGmC2fGmC2fAmG2fUmU2f

UmC2fUmU2fGmU2fCmA2fGmU2fUmCdT*dT;

(SEQ ID NO 33)
mC2fAmG2fUmU2fGmC2fGmC2fAmG2fUmU2f

UmC2fUmU2fGmU2fCmA2fGmU;

(SEQ ID NO 34)
mC2fAmG2fUmU2fGmC2fGmC2fAmG2fUmU2f

UmC2fU2fU2fG2fU2fC2fA2fG2fU);

wherein, mA, mC, mG, and mU are 2'-O-methyl adenosine, cytidine, guanosine, or uridine, respectively; 2fA, 2fC, 2fG, and 2fU are 2'-fluoro adenosine, cytidine, guanosine, or uridine, respectively; and * is a phosphorothioate linkage; and the sense strand is at least substantially complementary to the antisense strand.

Further still, in another embodiment, the double stranded RNAi agent includes the antisense strand of (i) the first dsRNA, that comprises the nucleotide sequence selected from (5'→3')

(SEQ ID NO 64)
AAGAGCUCAGGUCUCUGAGGGdTdT;

(SEQ ID NO 65)
AAGAGCUCAGGUCUCUGAGGGdT*dT;

(SEQ ID NO 66)
mAmAmGmAmGmCmUmCmAmGmGmUmCmUmCmUmGmAmGm

GmGdT*dT;

(SEQ ID NO 68)
mAmAmGmAmGmCmUmCmAmGmGmUmCmUmCmUmGmAmGm

GmG;

(SEQ ID NO 71)
mA2fAmG2fAmG2fCmU2fCmA2fGmG2fUmC2fUmC2f

UmG2fAmG2fGmGdT*dT;

(SEQ ID NO 72)
mA2fAmG2fAmG2fCmU2fCmA2fGmG2fUmC2fUmC2f

UmG2fAmG2fGmG;

(SEQ ID NO 75)
2fAmA2fGmA2fGmC2fUmC2fAmG2fGmU2fCmU2fCm

U2fGmA2fGmG2fGdT*dT;

(SEQ ID NO 76)
2fAmA2fGmA2fGmC2fUmC2fAmG2fGmU2fCmU2fCm

U2fGmA2fGmG2fG;

(SEQ ID NO 77)
mA2fA2fGmA2fGmC2fUmC2fAmG2fGmU2fCmU2fCm

U2fGmA2fGmG2fG;

(SEQ ID NO 78)
mA2fA2fGmA2fGmC2fUmC2fAmG2fGmU2fCmU2fCm

U2fGmA2fGmG2fGdT*dT;

(SEQ ID NO 79)
2fAmA2fGmA2fGmC2fUmC2fAmG2fGmU2fCmU2fCm

U2fGmA2fGmG2fGdT*dT;

(SEQ ID NO 81)
2fAmA2fGmA2fGmC2fUmC2fAmG2fGmU2fCmU2fC2 fU2fG2fA2fG2fG2fG;

wherein, mA, mC, mG, and mU are 2'-O-methyl adenosine, cytidine, guanosine, or uridine, respectively; 2fA, 2fC, 2fG, and 2fU are 2'-fluoro adenosine, cytidine, guanosine, or uridine, respectively; and * is a phosphorothioate linkage; and the sense strand is at least substantially complementary to the antisense strand.

In another embodiment the double stranded RNAi agent of (ii) the second dsRNA comprises the nucleotide sequence selected from (5'→3')

(SEQ ID NO: 417)
UUUGAUAGCACCAAACCUAGAGCCCdTdT;

(SEQ ID NO: 418)
UUUGAUAGCACCAAACCUAGAGCCCdT*dT;

(SEQ ID NO: 419)
mUm[mUmGmAmUmAmGmCmAmCmCmAmAmAmCmCmUmAmGmAmGmCmCm

CdT*dT;

(SEQ ID NO: 421)
mUmUmGmAmUmAmGmCmAmCmCmAmAmAmCmCmUmAmGmAmGmCmCm

C;

(SEQ ID NO: 424)
mU2fUmU2fGmA2fUmA2fGmC2fAmC2fCmA2fAmA2fCmC2fUmA2f

GmA2fGmC2fCmCdT*dT];

(SEQ ID NO: 425)
mU2fUmU2fGmA2fUmA2fGmC2fAmC2fCmA2fAmA2fCmC2fUmA2f

GmA2fGmC2fCmC;

(SEQ ID NO: 429)
mU2fAmU2fCmC2fAmA2fCmC2fUmC2fGmA2fUmA2fGmC2fAmA2f

CmA2fCmC2fGmC;

(SEQ ID NO: 430)
mU2fU2fU2fG2fA2fU2fA2fG2fC2fA2fC2fC2fA2fA2fA2fC2f

C2fU2fA2fG2fA2fG2fC2fC2fCdT*dT;

(SEQ ID NO: 432)
mU2fUmU2fGmA2fUmA2fGmC2fAmC2fCmA2fAmA2fCmC2fUmA2f

GmA2fGmC2fCmCdT*dT;

(SEQ ID NO: 433)
mU2fUmU2fGmA2fUmA2fGmC2fAmC2fCmA2fAmA2fCmC2fUmA2f

GmA2fGmC;
and (SEQ ID NO: 434)
mU2fUmU2fGmA2fUmA2fGmC2fAmC2fCmA2fAmA2fC2fC2fU2fA 2fG2fA2fG2fC wherein, mA, mC, mG, and mU are 2'-O-methyl adenosine, cytidine, guanosine, or uridine, respectively; 2fA, 2fC, 2fG, and 2fU are 2'-fluoro adenosine, cytidine, guanosine, or uridine, respectively; and * is a phosphorothioate linkage; and the sense strand is at least substantially complementary to the antisense strand.

In a further embodiment, the double stranded RNAi agent antisense strand of (ii) the second dsRNA comprises the nucleotide sequence selected from (5'→3')

(SEQ ID NO: 448)
UUUGCAAUGACUCUCCUAUCAGUCCdTdT (SEQ ID NO: 449)
UUUGCAAUGACUCUCCUAUCAGUCCdT*dT;

(SEQ ID NO: 450)
mUmUmUmGmCmAmAmUmGmAmCmUmCmUmCmCmUmAmUmCmAmGmUmCm

CdT*dT;

(SEQ ID NO: 452)
mUmUmUmGmCmAmAmUmGmAmCmUmCmUmCmCmUmAmUmCmAmGmUmCm

C;

(SEQ ID NO: 455)
mU2fUmU2fGmC2fAmA2fUmG2fAmC2fUmC2fUmC2fCmU2fAmU2f

CmA2fGmU2fCmCdT*dT;

(SEQ ID NO: 456)
mU2fUmU2fGmC2fAmA2fUmG2fAmC2fUmC2fUmC2fCmU2fAmU2f

CmA2fGmU2fCmC;

(SEQ ID NO: 458)
mU2fUmU2fGmC2fAmA2fUmG2fAmC2fUmC2fUmC2fCmU2fAmU2f

CmA2fCmU2fCmC;

(SEQ ID NO: 459)
2fUmU2fUmG2fCmA2fAmU2fGmA2fCmU2fCmU2fCmC2fUmA2fUm

C2fAmG2fUmC2fCdT*dT;

(SEQ ID NO: 460)
mU2fAmU2fCmC2fUmA2fAmG2fUmC2fAmC2fAmC2fGmU2fUmU2f

GmA2fCmU2fGmC;

(SEQ ID NO: 461)
mU2fU2fU2fG2fC2fA2fA2fU2fG2fA2fC2fU2fC2fU2fC2fC2f

U2fA2fU2fC2fA2fG2fU2fC2fCdT*dT;

(SEQ ID NO: 463)
mU2fUmU2fGmC2fAmA2fUmG2fAmC2fUmC2fUmC2fCmU2fAmU2f

CmA2fGmU2fCmCdT*dT;

```
                                                     (SEQ ID NO: 464)
mU2fUmU2fGmC2fAmA2fUmG2fAmC2fUmC2fUmC2fCmU2fAmU2f

CmA2fGmU;

(SEQ ID NO: 465)
mU2fUmU2fGmC2fAmA2fUmG2fAmC2fUmC2fUmC2fC2fU2fA2fU

2fC2fA2fG2fU
``` wherein, mA, mC, mG, and mU are 2'-O-methyl adenosine, cytidine, guanosine, or uridine, respectively; 2fA, 2fC, 2fG, and 2fU are 2'-fluoro adenosine, cytidine, guanosine, or uridine, respectively; and * is a phosphorothioate linkage; and
the sense strand is at least substantially complementary to the antisense strand.

For example, when the RNAi agent comprises (iii) the combination of (i) the first dsRNA and (ii) the second dsRNA, the antisense strand of (i) the first dsRNA is selected from

```
                                                     (SEQ ID NO: 17)
CAGUUGCGCAGUUUCUUGUCAGUUCdTdT;

(SEQ ID NO 18)
CAGUUGCGCAGUUUCUUGUCAGUUCdT*dT;

(SEQ ID NO 64)
AAGAGCUCAGGUCUCUGAGGGdTdT;
and (SEQ ID NO 65)
AAGAGCUCAGGUCUCUGAGGGdT*dT;
and the antisense strand of (ii) the second dsRNA is
selected from
                                                     (SEQ ID NO: 417)
UUUGAUAGCACCAAACCUAGAGCCCdTdT;

(SEQ ID NO: 418)
UUUGAUAGCACCAAACCUAGAGCCCdT*dT;

(SEQ ID NO: 448)
UUUGCAAUGACUCUCCUAUCAGUCCdTdT;
and (SEQ ID NO: 449)
UUUGCAAUGACUCUCCUAUCAGUCCdT*dT;
``` wherein * is a phosphorothioate linkage; and
the sense strand is at least substantially complementary to the antisense strand.

In one embodiment, (i) the first dsRNA has the duplex structure of (SEQ ID NOs: 17 and 110) or (SEQ ID NOs: 18 and 111). In another (ii) the second dsRNA has the duplex structure of (SEQ ID NOs: 417 and 808) or (SEQ ID NOs: 448 and 822).

Another embodiment provides for an isolated cell comprising a double stranded RNAi gent of (i), (ii) or (iii).

For example, the sense strand of (i) the first dsRNA is no more than 30 nucleotides in length, and the antisense strand of (i) the first dsRNA is no more than 30 nucleotides in length. For example, the sense strand of (ii) the second dsRNA is no more than 30 nucleotides in length, and the antisense strand is no more than 30 nucleotides in length.

Yet another embodiment provides a pharmaceutical composition for inhibiting expression of a CD320 gene, the pharmaceutical composition comprising a double stranded RNAi agent (i) or (iii). Further the pharmaceutical composition may include an excipient.

Yet another embodiment provides a pharmaceutical composition for inhibiting expression of an LRP2 gene, the composition comprising a double stranded RNAi agent (ii) or (iii). Further the pharmaceutical composition may include an excipient.

Another embodiment of the present invention provides a method for inhibiting proliferation of a cancer cell (CC) comprising contacting of the CC with an inhibitor of CD320 add/or LRP2 in an amount effective to inhibit proliferation of the CC. For example, the CC may express CD320 and/or LRP2 or both.

Another embodiment of the present invention provides a method for treating a therapeutically-resistant cancer in a subject who has previously received a therapy, comprising administering to the subject an inhibitor of CD320 add/or LRP2 in an amount effective to inhibit or kill cancer cells (CCs) present in the therapeutically-resistant cancer.

Another embodiment of the present invention provides a method for treating cancer in a subject who has recurring or relapsed cancer comprising administering to a subject an inhibitor of CD320 add/or LRP2 in an amount effective to inhibit or kill CCs in the cancer.

The CC is from a cancer selected from melanoma, glioblastoma, lung carcinoma, breast carcinoma, triple negative breast carcinoma, hepatocellular carcinoma, renal carcinoma, pancreatic carcinoma, ovarian carcinoma and prostate carcinoma.

The CD320 inhibitor is selected from an antibody that binds CD320, a small molecule inhibitor of CD320, and a RNAi agent that hybridizes to a nucleic acid sequence encoding CD320.

Further, the method of inhibiting proliferation of a CC, treating a therapeutically resistive cancer in a subject or has a recurring or relapsed cancer comprises administering a cancer therapeutic in combination with an RNAi agent that hybridizes to an mRNA encoding for CD320 or an RNAi agent that hybridizes to an mRNA encoding for LRP2. For example, the cancer therapeutic is selected from the antifolate class, epigenetic modulatory class, or a small molecule or protein inhibitor of CD320 function or LRP2 function, such as an antibody for CD320 or an antibody for LRP2. Further still, the method further comprises administering metformin. For example, the RNAi agent comprises an antisense strand of Table 5 or of Table 6.

The inhibitor is selected from the group consisting of an antibody that binds LRP2, a small molecule inhibitor of LRP2, and an RNAi agent that hybridizes to a nucleic acid sequence encoding LRP2. For example, the method further comprises administering a cancer therapeutic selected from the antifolate class, epigenetic modulatory class, or the small molecule or protein inhibitor of LRP2 function, such as an antibody, in combination with an RNAi agent that hybridizes to an mRNA encoding for LRP2.

The method further comprises administering a cancer therapeutic in combination with an RNAi agent that hybridizes to an mRNA encoding for LRP2.

One embodiment of the present invention provides for a method for inhibiting proliferation of a cancer cell (CC) comprising contacting of a CC with a composition comprising an inhibitor of CD320 and an inhibitor of LRP2 in an amount effective to inhibit proliferation of the CC. For example, the composition is a cocktail comprising i) the CD320 inhibitor selected from an antibody that binds CD320, a small molecule inhibitor of CD320, and a RNAi agent that hybridizes to a nucleic acid encoding CD320 and any combination thereof, and the LRP2 inhibitor selected from an antibody that binds LRP2, a small molecule inhibitor of LRP2, and a RNAi agent that hybridizes to a nucleic acid sequence encoding LRP2 and any combination thereof. Further, the method further comprises administering a cancer therapeutic selected from the antifolate class and epigenetic modulatory class. For example, the RNAi agent that hybridizes to the mRNA encoding for CD320 comprises a first double-stranded ribonucleic acid (dsRNA) for inhibiting expression of CD320, wherein the first dsRNA comprises a sense strand and an antisense strand, the antisense strand comprising a region of complementarity to a CD320 RNA transcript and the RNAi agent that hybridizes to the mRNA encoding for LRP2 comprises a second dsRNA for inhibiting expression of LRP2, wherein the second dsRNA comprises a sense strand and an antisense strand, the antisense strand comprising a region of complementarity to an LRP2 RNA transcript. In a further example, the antisense strand that is complementary to CD320 RNA transcript is selected from Table 5 and the antisense strand that is complementary to the RNA transcript for LRP2 is selected from Table 6. The method further comprises administering a cancer therapeutic selected from the antifolate class and epigenetic modulatory class. The method further comprises administering a cancer therapeutic selected from the immunomodulatory class. Further still, the method further comprises administering metformin.

One aspect of one embodiment of the present invention provides a method for the inhibition of CD320 and LRP2 protein expression, such that the levels of these proteins are reduced in treated cells compared to their endogenous levels in untreated cells; this inhibition may also be referred to as the knockdown of CD320 and LRP2 expression. The method entails the use of a cocktail of small interfering RNA molecules, otherwise known as siRNAs, which guide the mRNA sequences encoding for either CD320 or LRP2 into an enzymatic complex which leads to targeted destruction of these mRNAs.

Another aspect of the present invention provides a method for the individual or concurrent inhibition of LRP2 and CD320 protein expression, which inhibits the growth of many cancer cells as compared to non-cancer (normal) cells. In some instances, CD320 or LRP2 protein knockdown alone is sufficient to severely inhibit cancer cell proliferation compared to normal cells.

Another aspect of the present invention provides for inhibition of cancer cell proliferation by inhibiting LRP2 receptor expression.

Mechanistic investigations into the selectivity of porphyrin uptake by cancer cells led to several nonobvious compounds and methods of using the compound(s). It was discovered that the knockdown of the expression of either CD320 gene or LRP2 gene or the simultaneous knockdown of the expression of CD320 gene and LRP2 gene caused cell death or inhibition of cell growth in a panel of lung cancer cell lines, compared to normal fibroblasts. The experimental outline is illustrated in FIG. 1. In these experiments, cells were plated on day 0. The next day (day 1), virus particles encoding short hairpin RNAs (shRNAs) directed to the CD320 gene and the LRP2 gene or an irrelevant shRNA control were added to the cell culture together with protamine sulfate, a reagent that facilitates cell entry of the virus particles.

Further investigations revealed that knockdown of the expression of either the CD320 gene or LRP2 gene or the simultaneous knockdown of the expression of CD320 and LRP2 genes using small interfering RNAs (siRNAs) caused cell death or inhibition of cell growth in a panel of cancer cell lines that included lung cancer, prostate cancer, breast cancer, glioblastoma and melanoma, compared to normal fibroblasts (FIG. 9-10). It was also found that that knockdown of one gene, either CD320 or LRP2, led to increased expression of the other in some cancer cell lines.

One aspect of the present invention provides for the knockdown of the CD320 receptor, the LRP2 receptor or the simultaneous knockdown of both in vivo and in vitro cancer cells that express CD320 mRNA and/or LRP2 mRNA.

Another aspect of the present invention is a method to inhibit cell growth or cause cell death of cancer cells treated with a compound as described herein, while leaving normal cells unaffected or inhibiting cell growth to a lesser degree or producing less cell death as compared to a cancer cell treated with the same amount of the compound.

Another aspect of a first compound and method of use is a selective therapy which inhibits proliferation of cancer cells and/or kills cancer cells with an inhibition of LRP2 Receptor while leaving normal cells unharmed.

Another aspect of a second compound and method of use is a selective therapy which inhibits proliferation of cancer cells and/or kills cancer cells with an inhibition of CD320 Receptor while leaving normal cells unharmed.

Another aspect of the present invention provides for treating a cancer by administering a therapy to selectively inhibit proliferation of a cancer cell(s) and/or kill a cancer cell(s) with one or more of the following, a first compound that is an inhibitor of CD320 receptor, a second compound that is an inhibitor of LRP2 receptor or a combination thereof.

DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings:

FIGS. 2 A-C illustrates sensitivity of cancer cell lines to knockdown of CD320 and LRP2. Normal cells (GM05659 fibroblasts) or cancer cells were infected with lentiviruses expressing shRNAs to control sequences or to shCD320 and shLRP2 as described in FIG. 1. The cells were grown as described in FIG. 1. On the ninth day after transfection with the lentiviruses, pictures of the cells were taken. The solid oval indicates healthy growth of normal fibroblast infected with shRNAs to CD320 and LRP2. The broken line ovals indicate unhealthy dying cancer cells infected with shRNAs targeting CD320 and LRP2 (FIG. 2A). The fields of cells in FIG. 2A were counted and quantified and illustrated in FIG. 2B. The data in FIG. 2B were normalized to the number of control cells and illustrated in FIG. 2C. FIG. 2C. shows that the cultures of cells infected with lentivirus encoding the shRNAs against CD320 and LRP2 (white bars) contain far fewer cells than the cultures of cells exposed to the shRNA control (black bar).

FIG. 5A-C represent the fold change of protein levels compared to siScramble (OSS2).

FIGS. 9 A-E illustrate graphs of the percent cell survival of siCD320 and siLRP2 on cell proliferation—Cell lines representative of several types of cancers (lung, brain) or normal fibroblasts were transfected with individual or combinations of siRNAs targeting CD320 (OSC17, OSC47) or LRP2 (05L231, OSL245), individually at 20 nM or in combination (10 nM each), or a negative control siRNA (OSS2) (20 nM) as indicated. Cells were repeatedly transfected as outlined in Table 9 for efficient toxicity, then assayed for viability by the CTG assay. Doxorubicin-treated cells served as a positive control for cell toxicity in our assays (Table 8).

FIGS. 10 A-E illustrate graphs of the effects of siCD320 and siLRP2 on cell proliferation—Cell lines representative of several types of cancers (breast, prostate, skin) were transfected with individual or combinations of siRNAs targeting CD320 (OSC17, OSC47) or LRP2 (05L231, OSL245) as indicated. Cells were repeatedly transfected as outlined in Table 9 for efficient toxicity, then assayed for viability by the CTG assay. Doxorubicin-treated cells served as a positive control for cell toxicity in our assays (Table 8).

FIGS. 12A-B illustrate graphs of the duration of the knockdown effect for siCD320 and siLRP2 on MDA-MD-231 cells. A representative breast cancer cell line (MDA-MD-231) was transfected on Day 0 with 20 nM of an siRNA targeting CD320 (OSC17) or an siRNA targeting LRP2 (05L245) or a negative control siRNA (OSS2) and the percentage of protein knockdown was analyzed daily over a period of five days by western blot. Protein levels were normalized to the negative control (OSS2).

FIGS. 16 A-D illustrate plated cells showing the effects of siCD320 and siLRP2 on four cell lines. Cell lines representative of four types of cancers (breast, two prostate, skin) were transfected with siRNAs targeting CD320 (OSC17) or LRP2 (05L245) individually at 20 nM or in combination (10 nM each) or a negative control siRNA (OSS2) (20 nM) as indicated. Cells were repeatedly transfected for efficient toxicity as in Table 9 and then analyzed by microscopy as indicated.

FIGS. 19A-G illustrates the structures for unnatural nucleotides which may be incorporated within the sequence of an RNAi. "B" represents a natural (G, C, A, U) RNA nucleobase, a DNA nucleobase, or an unnatural nucleobase. FIG. 19A shows certain chemical modifications to the ribose 2'-position and phosphate moieties. FIGS. 19B-D shows skeletal modifications to the ribose moiety that comprise bridging groups. FIG. 19E shows a deletion of the C2'-C3' bond. FIGS. 19F-G shows other skeletal modifications to the ribose moiety wherein a six-membered ring replaces the five-membered ring.

DETAILED DESCRIPTION OF THE INVENTION

Figure 1:
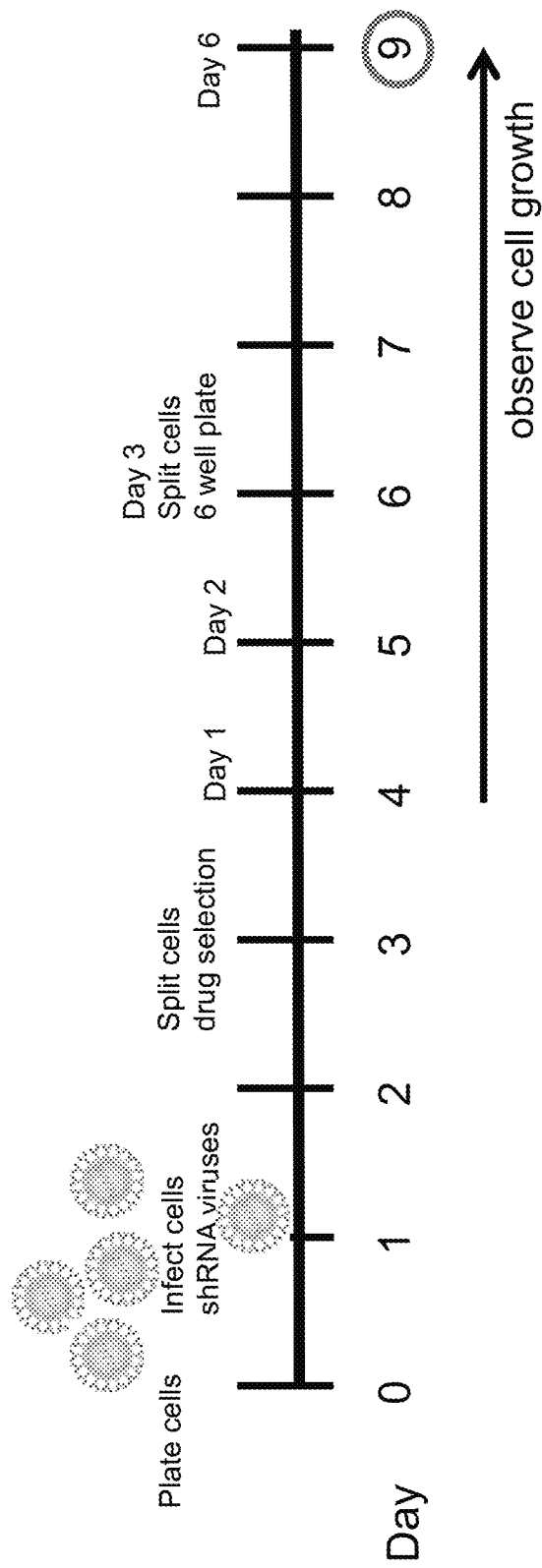
FIG. 1 illustrates an experimental design for knocking down CD320 and LRP2 in a cell. Cells were plated on day 0. The next day (day 1), virus particles encoding short hairpin RNAs (shRNAs) directed at the CD320 and LRP2 mRNA or a non-targeting shRNA control were added to the cell culture together with protamine sulfate, a reagent that facilitates cell entry of the virus particles. Table 1 shows the sequences that were used. Each shRNA coding sequence was also combined with a unique drug resistance gene, which would allow for selecting those cells that had taken up the shRNA; cells that had not taken up the shRNA would not survive. On day 2, drug selection was started. On day 3, the cells were harvested and plated in a new dish. Only the cells with a drug resistance gene, i.e., those cells that had taken up shRNA virus particles would survive this re-plating procedure. From day 4 on, each culture was closely observed for cell growth. Cells infected with the non-targeting negative control shRNA continued growing—data not shown. The results for the cell lines that expressed the CD320+LRP2 shRNAs are shown in Table 1.
Figure 3A:
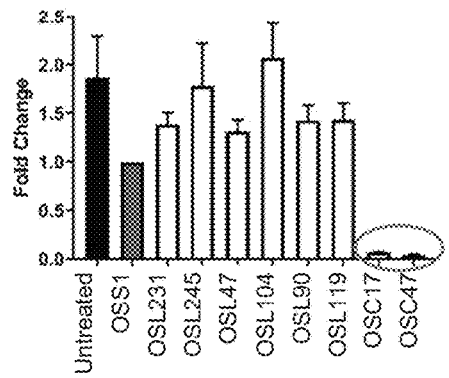
FIGS. 3 A-F illustrate graphs of protein levels resulting from transfection of HEK293, MDA-MB-435S and MDA-MB-231 cells with siRNA to LRP2 and CD320. HEK293, MDA-MB-435S and MDA-MB-231 cells were transfected with 20 nM of indicated siRNAs and incubated for 48 hours. siRNAs targeting CD320 are designated OSC17 and OSC47. siRNAs targeting LRP2 are designated OSL245, OSL47, OSL104, OSL90 and OSL119. Whole cell lysates were prepared and immunoblotted for CD320 and LRP2 protein levels. The protein levels were normalized to a housekeeping control gene unaffected by the siRNA transfection. The graphs FIGS. 3 A-F represent the fold change of protein levels compared to siScramble (OSS1 or OSS2). (Average +/− SEM is shown, n=3).
Figure 3D:
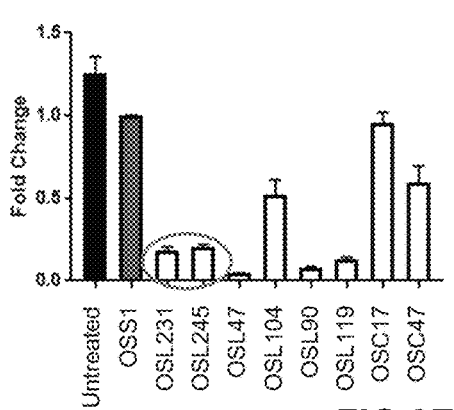
Figure 3B:
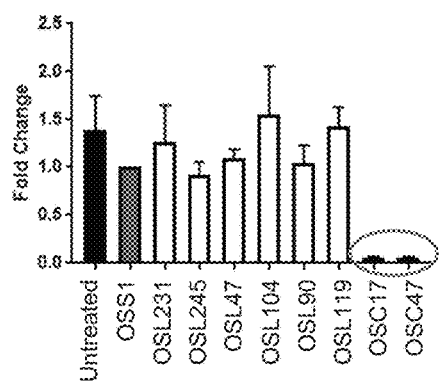
Figure 3E:
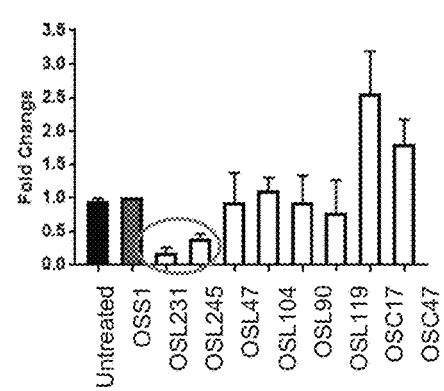
Figure 3C:
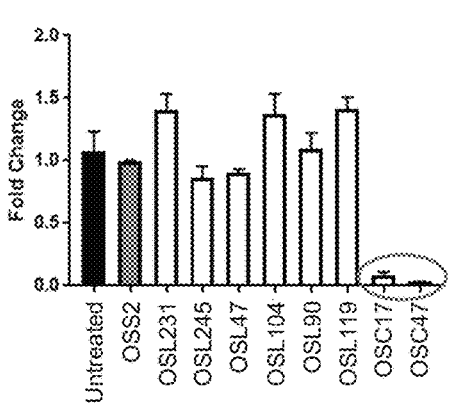
Figure 3F:
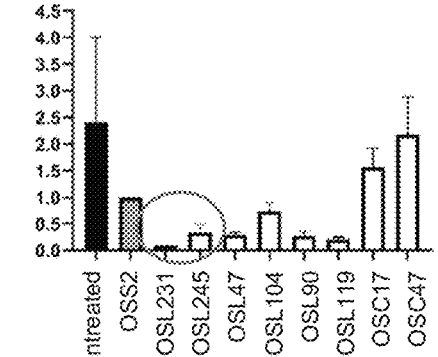
Figure 4A:
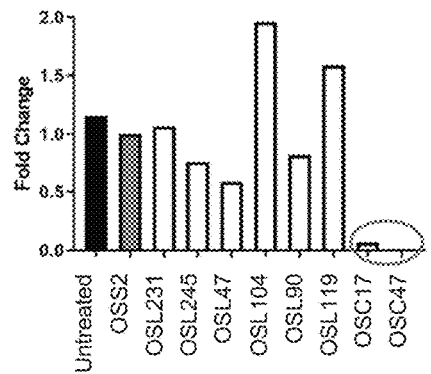
FIGS. 4 A-F illustrate a graph of cells after transfection of LnCAP, MCF-7 and U251 cells with siRNA to LRP2 and CD320. LnCAP, MCF-7 and U251 cells were transfected with 20 nM of indicated siRNAs and incubated for 48 hours. siRNAs targeting CD320 are designated OSC17 and OSC47. siRNAs targeting LRP2 are designated OSL245, OSL47, OSL104, OSL90 and OSL119). Whole cell lysates were prepared and immunoblotted for CD320 and LRP2 protein levels. The protein levels were normalized to a housekeeping control gene unaffected by the siRNA transfection. The graphs FIGS. 4 A-F represent the fold change of protein levels compared to siScramble (OSS2).
Figure 4D:
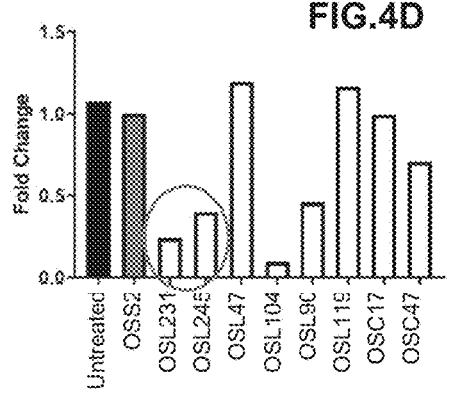
Figure 4B:
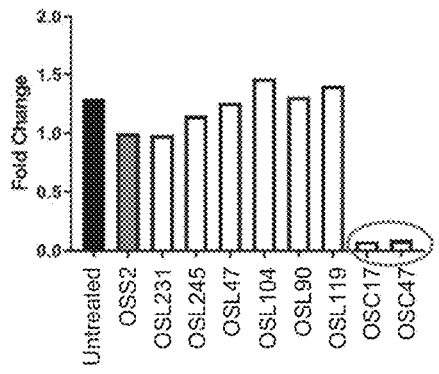
Figure 4E:
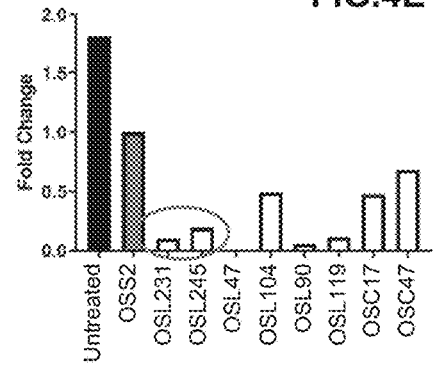
Figure 4C:
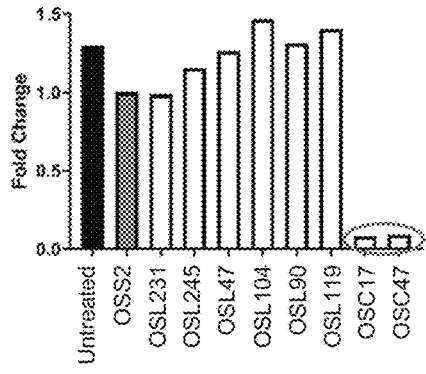
Figure 4F:
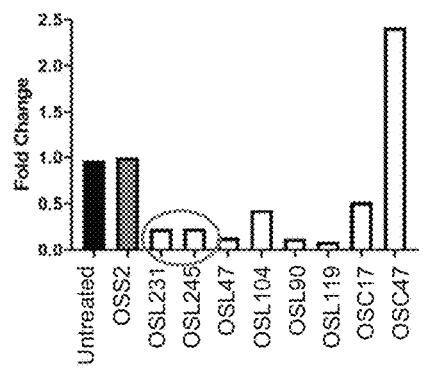

One or more embodiment of the present invention provides methods and RNAi compounds for modulating the expression of a CD320 gene and/or an LRP2 gene in a cell. In certain embodiments, expression of a CD320 gene and/or a LRP2 gene is reduced or inhibited using an CD320 and/or LRP2 specific RNAi. Such inhibition can be useful in treating disorders such as cancer and/or creating cell lines that are useful for screening drugs that treat cancer The present invention also relates to a method for knocking down (partially or completely) the targeted genes.

One embodiment of the method of producing knockdown cells and organisms comprises introducing into a cell or organism in which a gene (referred to as a targeted gene) to be knocked down, an siRNA of about 16 to about 30 nucleotides (nt) that targets the gene and maintaining the resulting cell or organism under conditions under which RNAi occurs, resulting in degradation of the mRNA of the targeted gene, thereby producing knockdown cells or organisms. Knockdown cells and organisms produced by the present method are also the subject of embodiment of the present invention.

An embodiment of the present invention also relates to a method of examining or assessing the function of a gene in a cell or organism. In one embodiment, RNA of about 16 to about 30 nt which targets mRNA of the gene for degradation is introduced into a cell or organism in which RNAi occurs. The cell or organism is referred to as a test cell or organism. The cell or organism is referred to as a test cell organism. The test cell or organism is maintained under conditions under which degradation of mRNA of the gene occurs. The phenotype of the test cell or organism is then observed and compared to that of an appropriate control cell or organism, such as a corresponding cell or organism that is treated in the same manner except that the gene is not targeted. A 16 to 30 nt RNA that does not target the mRNA for degradation can be introduced into the control cell or organism in place of the siRNA introduced into the test cell or organism, although it is not necessary to do so. A difference between the phenotypes of the test and control cells or organisms provides information about the function of the degraded mRNA.

The RNA of about 16 to about 30 nucleotides is isolated or synthesized and then introduced into a cell or organism in which RNAi occurs (test cell or test organism). The test cell or test organism is maintained under conditions under which degradation of the mRNA occurs. The phenotype of the test cell or organism is then observed and compared to that of an appropriate control, such as a corresponding cell or organism that is treated in the same manner as the test cell or organism except that the targeted gene is not targeted. A difference between the phenotypes of the test and control cells or organisms provides information about the function of the targeted gene. The information provided may be sufficient to identify (define) the function of the gene or may be used in conjunction with information obtained from other assays or analyses to do so.

An embodiment of the present invention also encompasses a method of treating a disease or condition associated with the presence of a protein in an individual, comprising administering to the individual RNA of from about 16 to about 30 nucleotides which targets the mRNA of the protein (the mRNA that encodes the protein) for degradation. As a result, the protein is not produced or is not produced to the extent it would be in the absence of the treatment.

Figure 14:
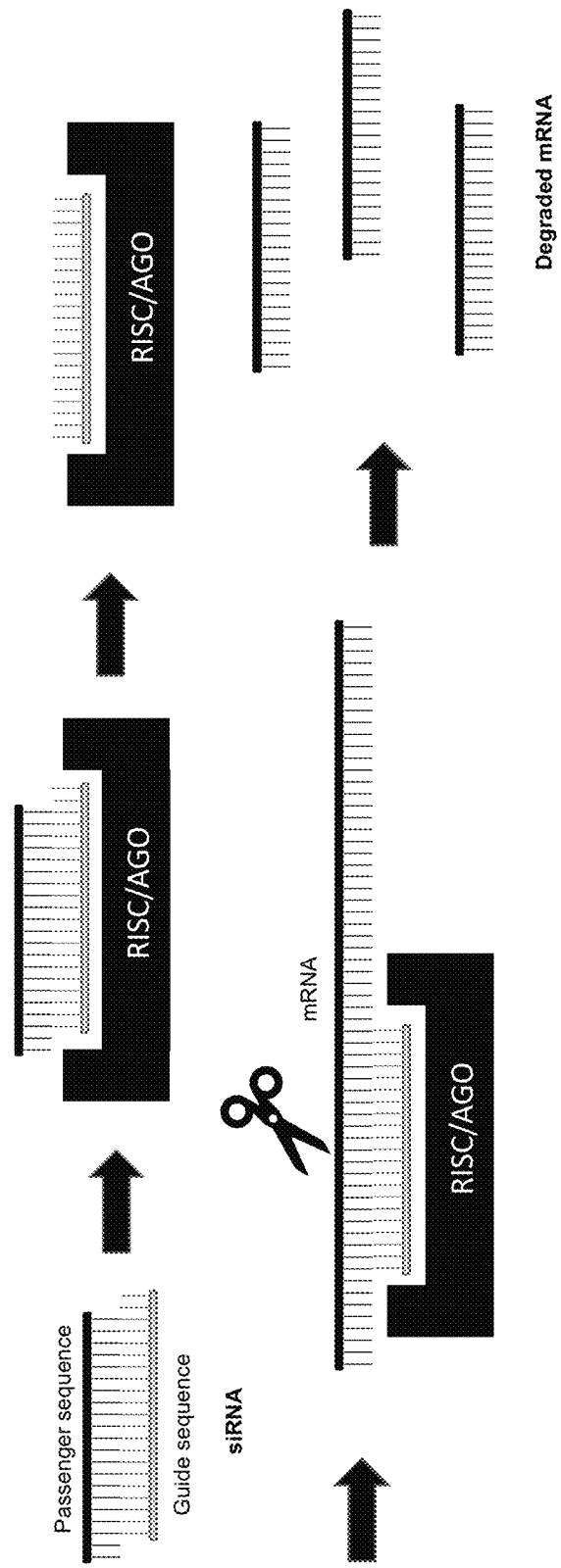
FIG. 14 is a schematic that illustrates that siRNAs are short RNA duplexes of generally 16 to 30 nucleotides; the guide sequence of the siRNA is complementary to a mRNA expressed in the cell. Exogenous siRNA duplexes are introduced into the cell via a method of transfection. The siRNA duplexes are separated via the RISC/AGO (RNA-induced silencing complex) complex, whereby the guide strand of the siRNA hybridizes with its complementary mRNA molecule. The mRNA is degraded by the RISC/AGO complex, which has RNAse activity, resulting in mRNA degradation, and the protein encoded by the mRNA is not produced. This causes the "knockdown" effect or reduced protein levels of the gene targeted by the siRNA compared to control treated cells.

FIG. 14 shows that siRNAs are short RNA duplexes of generally 16 to 30 nucleotides; the sequence of the siRNA is complementary to a mRNA expressed in the cell. Exogenous siRNA duplexes are introduced into the cell via a method of transfection. The siRNA duplexes are unwound via the RNA-induced silencing complex (RISC), whereby the guide strand of the siRNA hybridizes with its complementary mRNA molecule. The mRNA is degraded by the RISC/AGO complex, which has RNAse cleave activity. The end result is that the mRNA targeted by the siRNA is degraded, and the protein encoded by the mRNA is not produced. This causes the "knockdown" effect or reduced protein levels of the gene targeted by the siRNA compared to control treated cells.

In one embodiment, at least one strand of the RNA molecule has a 3' overhang from about 1 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length or, for example, the overhang can be up to 14 nucleotides if the guide strand were a 27-mer. In one embodiment the RNA molecule is double stranded, one strand has a 3' overhang and the other strand can be blunt-ended or have an overhang. In the embodiment in which the RNA molecule is double stranded and both strands comprise an overhang, the length of the overhangs may be the same or different for each strand. In a particular embodiment, the RNA of the present invention comprises 21-27 nucleotide strands which are Watson-Crick paired and which have overhangs of from about 1 to about 3, particularly about 2, nucleotides on both 3' ends of the RNA. In order to further enhance the stability of the RNA of the present invention, the 3' overhangs can be stabilized against degradation. In one embodiment, the RNA is stabilized by including purine nucleotides, such as adenosine or guanosine nucleotides. Alternatively, substitution of pyrimidine nucleotides by unnatural nucleotides, e.g., substitution of uridine 2 nucleotide 3' overhangs by 2'-deoxythymidine, is tolerated and does not affect the efficiency of RNAi. The absence of a 2' hydroxyl significantly enhances the nuclease resistance of the overhang in tissue culture medium. The 3'-overhangs can be further stabilized by introduction of phosphorothioate groups in place of the phosphodiesters.

The 16-30 nt RNA molecules of the present invention can be obtained using a number of techniques known to those of skill in the art. For example, the RNA can be chemically synthesized or recombinantly produced using methods known in the art.

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

Figure 17:
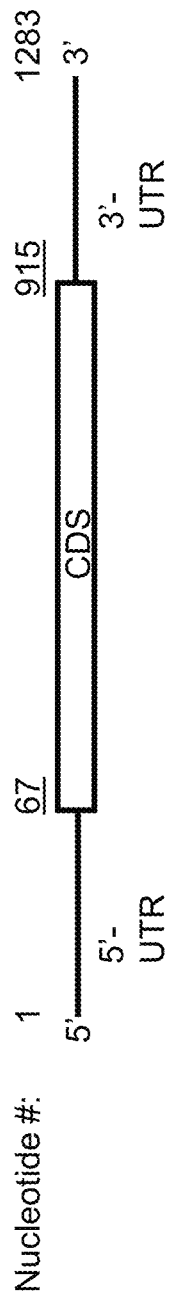
FIG. 17 illustrates a graphical depiction of CD320 mRNA. UTR references the untranslated region, and the CDS references the protein coding sequence.

As used herein, "CD320" refers to the gene or protein. CD320 is also known as 8D6 antigen, CD320 antigen, 8D6A, transcobalamin receptor, FDC-SM-8D6, FDC-Signaling Molecule 8D6, 8D6, TCBLR, TCblR, TCN2R. The term CD320 includes human CD320, the amino acid and nucleotide sequence of which may be found in, for example, GenBank Accession No. NM_016579.4 and NM_001165895.2; mouse CD320, the amino acid and nucleotide sequence of which may be found in, for example, GenBank Accession No. NM_019421.3; rat CD320, the amino acid and nucleotide sequence of which may be found in, for example, GenBank Accession No. NM_001014201.1. Additional examples of CD320 mRNA sequences are readily available using, e.g., GenBank. Additional information is found at FIG. 17.

The CD320 DNA sequence from *Homo sapiens* is as follows: >NM_016579.4 *Homo sapiens* CD320 molecule (CD320), transcript variant 1, DNA (SEQ ID NO. 935)
GTGCGCGTGCGCAGGGATAAGAGAGCGGTCTGGACAGCGCGTGGCCGGC

GCCGCTGTGGGGACAGCATGAGCGGCGGTTGGATGGCGCAGGTTGGAGC

GTGGCGAACAGGGGCTCTGGGCCTGGCGCTGCTGCTGCTGCTCGGCCTC

-continued

GGACTAGGCCTGGAGGCCGCCGCGAGCCCGCTTTCCACCCCGACCTCTG

CCCAGGCCGCAGGCCCCAGCTCAGGCTCGTGCCCACCCACCAAGTTCCA

GTGCCGCACCAGTGGCTTATGCGTGCCCCTCACCTGGCGCTGCGACAGG

GACTTGGACTGCAGCGATGGCAGCGATGAGGAGGAGTGCAGGATTGAGC

CATGTACCCAGAAAGGGCAATGCCCACCGCCCCTGGCCTCCCCTGCCC

CTGCACCGGCGTCAGTGACTGCTCTGGGGGAACTGACAAGAAACTGCGC

AACTGCAGCCGCCTGGCCTGCCTAGCAGGCGAGCTCCGTTGCACGCTGA

GCGATGACTGCATTCCACTCACGTGGCGCTGCGACGGCCACCCAGACTG

TCCCGACTCCAGCGACGAGCTCGGCTGTGGAACCAATGAGATCCTCCCG

GAAGGGGATGCCACAACCATGGGGCCCCCTGTGACCCTGGAGAGTGTCA

CCTCTCTCAGGAATGCCACAACCATGGGGCCCCCTGTGACCCTGGAGAG

TGTCCCCTCTGTCGGGAATGCCACATCCTCCTCTGCCGGAGACCAGTCT

GGAAGCCCAACTGCCTATGGGGTTATTGCAGCTGCTGCGGTGCTCAGTG

CAAGCCTGGTCACCGCCACCCTCCTCCTTTTGTCCTGGCTCCGAGCCCA

GGAGCGCCTCCGCCCACTGGGGTTACTGGTGGCCATGAAGGAGTCCCTG

CTGCTGTCAGAACAGAAGACCTCGCTGCCCTGAGGACAAGCACTTGCCA

CCACCGTCACTCAGCCCTGGGCGTAGCCGGACAGGAGGAGAGCAGTGAT

GCGGATGGGTACCCGGGCACACCAGCCCTCAGAGACCTGAGCTCTTCTG

GCCACGTGGAACCTCGAACCCGAGCTCCTGCAGAAGTGGCCCTGGAGAT

TGAGGGTCCCTGGACACTCCCTATGGAGATCCGGGGAGCTAGGATGGGG

AACCTGCCACAGCCAGAACTGAGGGGCTGGCCCCAGGCAGCTCCCAGGG

GGTAGAACGGCCCTGTGCTTAAGACACTCCTGCTGCCCCGTCTGAGGGT

GGCGATTAAAGTTGCTTCACATCCTCAAAAAAAAAAAAAAAAAAAAAAA

AAAAAAAAA.

A protein sequence from CD320 derived from the mRNA sequence above is as follows: >sp|Q9NPF0|CD320_HUMAN CD320 antigen OS=*Homo sapiens* OX=9606 GN=CD320 PE=1 SV=1

(SEQ ID NO. 936)
MSGGWMAQVGAWRTGALGLALLLLGLGLGLEAAASPLSTPTSAQAAGP

SSGSCPPTKFQCRTSGLCVPLTWRCDRDLDCSDGSDEEECRIEPCTQKG

QCPPPPGLPCPCTGVSDCSGGTDKKLRNCSRLACLAGELRCTLSDDCIP

LTWRCDGHPDCPDSSDELGCGTNEILPEGDATTMGPPVTLESVTSLRNA

TTMGPPVTLESVPSVGNATSSSAGDQSGSPTAYGVIAAAAVLSASLVTA

TLLLLSWLRAQERLRPLGLLVAMKESLLLSEQKTSLP

The CD320 DNA sequence from *Homo sapiens* is as follows: >NM_001165895.2 *Homo sapiens* CD320 molecule (CD320), transcript variant 2, DNA (SEQ ID NO. 937)
GCGTGCGCGTGCGCAGGGATAAGAGAGCGGTCTGGACAGCGCGTGGCCG

GCGCCGCTGTGGGGACAGCATGAGCGGCGGTTGGATGGCGCAGGTTGGA

GCGTGGCGAACAGGGGCTCTGGGCCTGGCGCTGCTGCTGCTGCTCGGCC

-continued

```
TCGGACTAGGCCTGGAGGCCGCCGCGAGCCCGCTTTCCACCCCGACCTC

TGCCCAGGCCGCAGGGATTGAGCCATGTACCCAGAAAGGGCAATGCCCA

CCGCCCCCTGGCCTCCCCTGCCCCTGCACCGGCGTCAGTGACTGCTCTG

GGGGAACTGACAAGAAACTGCGCAACTGCAGCCGCCTGGCCTGCCTAGC

AGGCGAGCTCCGTTGCACGCTGAGCGATGACTGCATTCCACTCACGTGG

CGCTGCGACGGCCACCCAGACTGTCCCGACTCCAGCGACGAGCTCGGCT

GTGGAACCAATGAGATCCTCCCGGAAGGGGATGCCACAACCATGGGGCC

CCCTGTGACCCTGGAGAGTGTCACCTCTCTCAGGAATGCCACAACCATG

GGGCCCCCTGTGACCCTGGAGAGTGTCCCCTCTGTCGGGAATGCCACAT

CCTCCTCTGCCGGAGACCAGTCTGGAAGCCCAACTGCCTATGGGGTTAT

TGCAGCTGCTGCGGTGCTCAGTGCAAGCCTGGTCACCGCCACCCTCCTC

CTTTTGTCCTGGCTCCGAGCCCAGGAGCGCCTCCGCCCACTGGGGTTAC

TGGTGGCCATGAAGGAGTCCCTGCTGCTGTCAGAACAGAAGACCTCGCT

GCCCTGAGGACAAGCACTTGCCACCACCGTCACTCAGCCCTGGGCGTAG

CCGGACAGGAGGAGAGCAGTGATGCGGATGGGTACCCGGGCACACCAGC

CCTCAGAGACCTGAGCTCTTCTGGCCACGTGGAACCTCGAACCCGAGCT

CCTGCAGAAGTGGCCCTGGAGATTGAGGGTCCCTGGACACTCCCTATGG

AGATCCGGGGAGCTAGGATGGGGAACCTGCCACAGCCAGAACTGAGGGG

CTGGCCCCAGGCAGCTCCCAGGGGGTAGAACGGCCCTGTGCTTAAGACA

CTCCTGCTGCCCCGTCTGAGGGTGGCAATTAAAGTTGCTTCACATCCTC
```

A protein sequence from CD320 derived from the DNA sequence above is as follows: >sp|Q9NPF0-2|CD320_HUMAN Isoform 2 of CD320 antigen OS=*Homo sapiens* OX=9606 GN=CD320

(SEQ ID NO. 938)
```
MSGGWMAQVGAWRTGALGLALLLLLGLGLGLEAAASPLSTPTSAQAAGI

EPCTQKGQCPPPPGLPCPCTGVSDCSGGTDKKLRNCSRLACLAGELRCT

LSDDCIPLTWRCDGHPDCPDSSDELGCGTNEILPEGDATTMGPPVTLES

VTSLRNATTMGPPVTLESVPSVGNATSSSAGDQSGSPTAYGVIAAAAVL

SASLVTATLLLLSWLRAQERLRPLGLLVAMKESLLLSEQKTSLP
```

Figure 18:
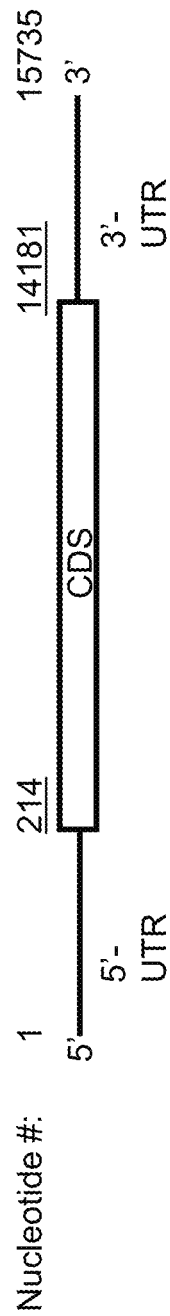
FIG. 18 illustrates a graphical depiction of LRP2 mRNA UTR references the untranslated region, and the CDS references the protein coding sequence.
Figure 20:
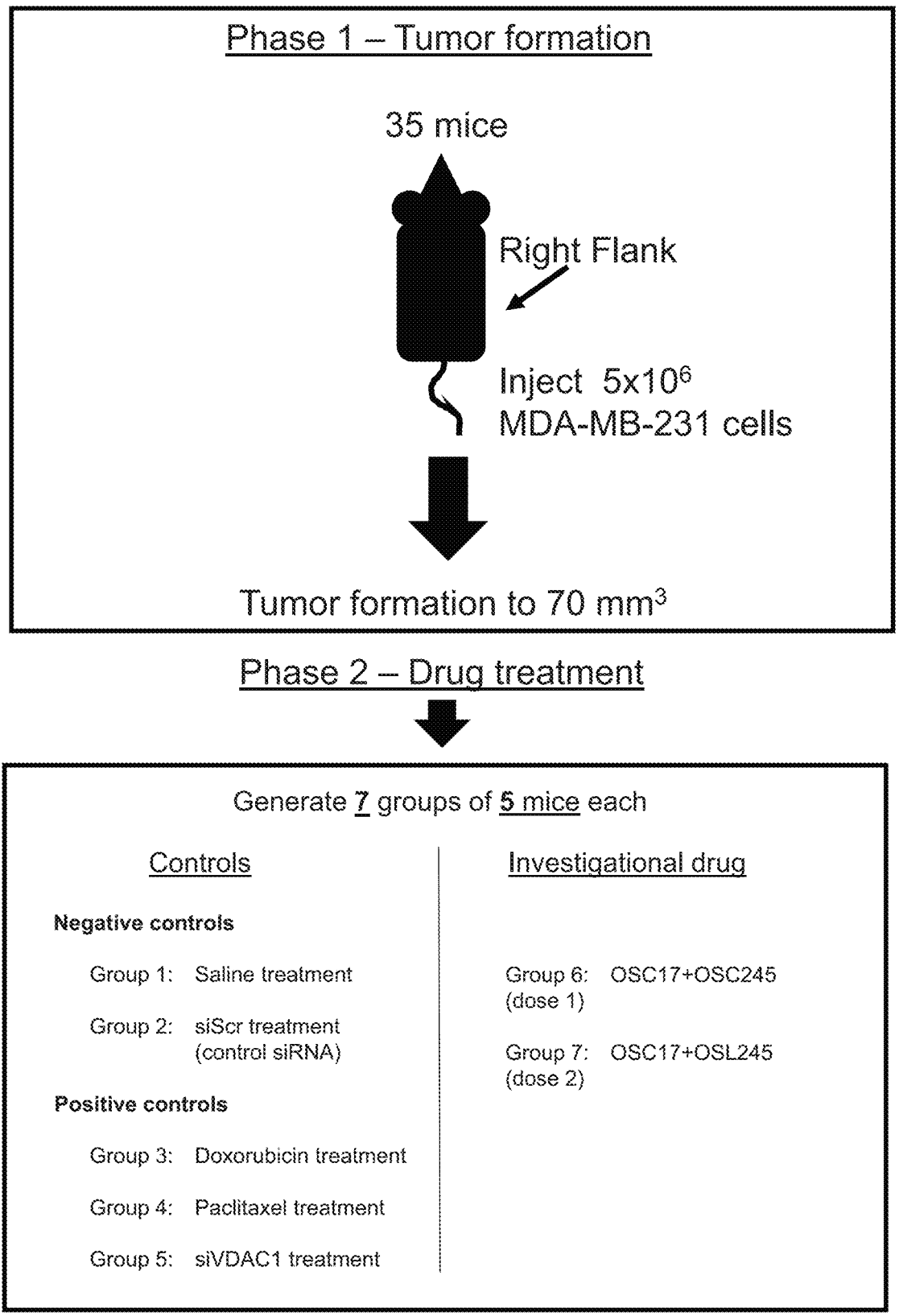
FIG. 20 illustrates a schematic for the in vivo murine xenograft model for breast cancer. MDA-MB-231 cells were implanted into the flank of NSG mice and grown to a volume of 70 mm$^3$ after which siRNAs targeting CD320 (OSC17) and LRP2 (05L245) were injected intratumorally once every fourth day.

Further, as used herein, "LRP2" refers to the gene or protein. LRP2 is also known as megalin, LRP-2, Glycoprotein 330, DBS, GP330, Gp330, Calcium Sensor Protein, Heymann Nephritis Antigen Homolog, Low-Density Lipoprotein Receptor-Related Protein 2, EC 1.1.2.3, EC 3.4.21.9, LDL receptor related protein 2. The term LRP2 includes human LRP2, the amino acid and nucleotide sequence of which may be found in, for example, GenBank Accession No. NM_004525.3; mouse LRP2, the amino acid and nucleotide sequence of which may be found in, for example, GenBank Accession No. NM_001081088.2; rat LRP2, the amino acid and nucleotide sequence of which may be found in, for example, GenBank Accession No. NM_030827.1. Additional examples of LRP2 mRNA sequences are readily available using, e.g., GenBank. Additional information is found at FIG. 18.

One example of LRP2 is: >NM_004525.3 *Homo sapiens* LDL receptor related protein 2 (LRP2), DNA:

(SEQ ID NO. 939)
```
GGTCTAAAGGGCTTTATGCACTGTCTGGAGGGTGGGGACTGGCGCGGGTAGAAAACGGGATGCCTCGGGC

GTGGGGGCAGGCTTTTGGCCACTAGGAGCTGGCGGAGGTGCAGACCTAAAGGAGCGTTCGCTAGCAGAGG

CGCTGCCGGTGCGGTGTGCTACGCGCGCCCACCTCCCGGGGAAGGAACGGCGAGGCCGGGGACCGTCGCG

GAGATGGATCGCGGGCCGGCAGCAGTGGCGTGCACGCTGCTCCTGGCTCTCGTCGCCTGCCTAGCGCCGG

CCAGTGGCCAAGAATGTGACAGTGCGCATTTTCGCTGTGGAAGTGGGCATTGCATCCCTGCAGACTGGAG

GTGTGATGGGACCAAAGACTGTTCAGATGACGCGGATGAAATTGGCTGCGCTGTTGTGACCTGCCAGCAG

GGCTATTTCAAGTGCCAGAGTGAGGGACAATGCATCCCCAACTCCTGGGTGTGTGACCAAGATCAAGACT

GTGATGATGGCTCAGATGAACGTCAAGATTGCTCACAAAGTACATGCTCAAGTCATCAGATAACATGCTC

CAATGGTCAGTGTATCCCAAGTGAATACAGGTGCGACCACGTCAGAGACTGCCCCGATGGAGCTGATGAG

AATGACTGCCAGTACCCAACATGTGAGCAGCTTACTTGTGACAATGGGGCCTGCTATAACACCAGTCAGA

AGTGTGATTGGAAAGTTGATTGCAGGGACTCCTCAGATGAAATCAACTGCACTGAGATATGCTTGCACAA

TGAGTTTTCATGTGGCAATGGAGAGTGTATCCCTCGTGCTTATGTCTGTGACCATGACAATGATTGCCAA

GACGGCAGTGACGAACATGCTTGCAACTATCCGACCTGCGGTGGTTACCAGTTCACTTGCCCCAGTGGCC

GATGCATTTATCAAAACTGGGTTTGTGATGGAGAAGATGACTGTAAAGATAATGGAGATGAAGATGGATG

TGAAAGCGGTCCTCATGATGTTCATAAATGTTCCCCAAGAGAATGGTCTTGCCCAGAGTCGGGACGATGC

ATCTCCATTTATAAAGTTTGTGATGGATTTTAGATTGCCCAGGAAGAGAAGATGAAAACAACACTAGTA

CCGGAAAATACTGTAGTATGACTCTGTGCTCTGCCTTGAACTGCCAGTACCAGTGCCATGAGACGCCGTA

TGGAGGAGCGTGTTTTTGTCCCCCAGGTTATATCATCAACCACAATGACAGCCGTACCTGTGTTGAGTTT
```

-continued

```
GATGATTGCCAGATATGGGGAATTTGTGACCAGAAGTGTGAAAGCCGACCTGGCCGTCACCTGTGCCACT
GTGAAGAAGGGTATATCTTGGAGCGTGGACAGTATTGCAAAGCTAATGATTCCTTTGGCGAGGCCTCCAT
TATCTTCTCCAATGGTCGGGATTTGTTAATTGGTGATATTCATGGAAGGAGCTTCCGGATCCTAGTGGAG
TCTCAGAATCGTGGAGTGGCCGTGGGTGTGGCTTTCCACTATCACCTGCAAAGAGTTTTTTGGACAGACA
CCGTGCAAAATAAGGTTTTTTCAGTTGACATTAATGGTTTAAATATCCAAGAGGTTCTCAATGTTTCTGT
TGAAACCCCAGAGAACCTGGCTGTGGACTGGGTTAATAATAAAATCTATCTAGTGGAAACCAAGGTCAAC
CGCATAGATATGGTAAATTTGGATGGAAGCTATCGGGTTACCCTTATAACTGAAAACTTGGGGCATCCTA
GAGGAATTGCCGTGGACCCAACTGTTGGTTATTTATTTTTCTCAGATTGGGAGAGCCTTTCTGGGGAACC
TAAGCTGGAAAGGGCATTCATGGATGGCAGCAACCGTAAAGACTTGGTGAAAACAAAGCTGGGATGGCCT
GCTGGGGTAACTCTGGATATGATATCGAAGCGTGTTTACTGGGTTGACTCTCGGTTTGATTACATTGAAA
CTGTAACTTATGATGGAATTCAAAGGAAGACTGTAGTTCATGGAGGCTCCCTCATTCCTCATCCCTTTGG
AGTAAGCTTATTTGAAGGTCAGGTGTTCTTTACAGATTGGACAAAGATGGCCGTGCTGAAGGCAAACAAG
TTCACAGAGACCAACCCACAAGTGTACTACCAGGCTTCCCTGAGGCCCTATGGAGTGACTGTTTACCATT
CCCTCAGACAGCCCTATGCTACCAATCCGTGTAAAGATAACAATGGGGGCTGTGAGCAGGTCTGTGTCCT
CAGCCACAGAACAGATAATGATGGTTTGGGTTTCCGTTGCAAGTGCACATTCGGCTTCCAACTGGATACA
GATGAGCGCCACTGCATTGCTGTTCAGAATTTCCTCATTTTTTCATCCCAAGTTGCTATTCGTGGGATCC
CGTTCACCTTGTCTACCCAGGAAGATGTCATGGTTCCAGTTTCGGGGAATCCTTCTTTCTTTGTCGGGAT
TGATTTTGACGCCCAGGACAGCACTATCTTTTTTTCAGATATGTCAAAACACATGATTTTTAAGCAAAAG
ATTGATGGCACAGGAAGAGAAATTCTCGCAGCTAACAGGGTGGAAAATGTTGAAAGTTTGGCTTTTGATT
GGATTTCAAAGAATCTCTATTGGACAGACTCTCATTACAAGAGTATCAGTGTCATGAGGCTAGCTGATAA
AACGAGACGCACAGTAGTTCAGTATTTAAATAACCCACGGTCGGTGGTAGTTCATCCTTTTGCCGGGTAT
CTATTCTTCACTGATTGGTTCCGTCCTGCTAAAATTATGAGAGCATGGAGTGACGGATCTCACCTCTTGC
CTGTAATAAACACTACTCTTGGATGGCCCAATGGCTTGGCCATCGATTGGGCTGCTTCACGATTGTACTG
GGTAGATGCCTATTTTGATAAAATTGAGCACAGCACCTTTGATGGTTTAGACAGAAGAAGACTGGGCCAT
ATAGAGCAGATGACACATCCGTTTGGACTTGCCATCTTTGGAGAGCATTTATTTTTTACTGACTGGAGAC
TGGGTGCCATTATTCGAGTCAGGAAAGCAGATGGTGGAGAAATGACAGTTATCCGAAGTGGCATTGCTTA
CATACTGCATTTGAAATCGTATGATGTCAACATCCAGACTGGTTCTAACGCCTGTAATCAACCCACGCAT
CCTAACGGTGACTGCAGCCACTTCTGCTTCCCGGTGCCAAATTTCCAGCGAGTGTGTGGGTGCCCTTATG
GAATGAGGCTGGCTTCCAATCACTTGACATGCGAGGGGACCCAACCAATGAACCACCCACAGAGCAGTG
TGGCTTATTTTCCTTCCCCTGTAAAAATGGCAGATGTGTGCCCAATTACTATCTCTGTGATGGAGTCGAT
GATTGTCATGATAACAGTGATGAGCAACTATGTGGCACACTTAATAATACCTGTTCATCTTCGGCGTTCA
CCTGTGGCCATGGGGAGTGCATTCCTGCACACTGGCGCTGTGACAAACGCAACGACTGTGTGGATGGCAG
TGATGAGCACAACTGCCCCACCCACGCACCTGCTTCCTGCCTTGACACCCAATACACCTGTGATAATCAC
CAGTGTATCTCAAAGAACTGGGTCTGTGACACAGACAATGATTGTGGGGATGGATCTGATGAAAAGAACT
GCAATTCGACAGAGACATGCCAACCTAGTCAGTTTAATTGCCCCAATCATCGATGTATTGACCTATCGTT
TGTCTGTGATGGTGACAAGGATTGTGTTGATGGATCTGATGAGGTTGGTTGTGTATTAAACTGTACTGCT
TCTCAATTCAAGTGTGCCAGTGGGGATAAATGTATTGGCGTCACAAATCGTTGTGATGGTGTTTTTGATT
GCAGTGACAACTCGGATGAAGCAGGCTGTCCAACCAGGCCTCCTGGTATGTGCCACTCAGATGAATTTCA
GTGCCAAGAAGATGGTATCTGCATCCCGAACTTCTGGGAATGTGATGGGCATCCAGACTGCCTCTATGGA
TCTGATGAGCACAATGCCTGTGTCCCCAAGACTTGCCCTTCATCATATTTCCACTGTGACAACGGAAACT
GCATCCACAGGGCATGGCTCTGTGATCGGGACAATGACTGCGGGGATATGAGTGATGAGAAGGACTGCCC
```

-continued

```
TACTCAGCCCTTTCGCTGTCCTAGTTGGCAATGGCAGTGTCTTGGCCATAACATCTGTGTGAATCTGAGT

GTAGTGTGTGATGGCATCTTTGACTGCCCCAATGGGACAGATGAGTCCCCACTTTGCAATGGGAACAGCT

GCTCAGATTTCAATGGTGGTTGTACTCACGAGTGTGTTCAAGAGCCCTTTGGGGCTAAATGCCTATGTCC

ATTGGGATTCTTACTTGCCAATGATTCTAAGACCTGTGAAGACATAGATGAATGTGATATTCTAGGCTCT

TGTAGCCAGCACTGTTACAATATGAGAGGTTCTTTCCGGTGCTCGTGTGATACAGGCTACATGTTAGAAA

GTGATGGGAGGACTTGCAAAGTTACAGCATCTGAGAGTCTGCTGTTACTTGTGGCAAGTCAGAACAAAAT

TATTGCCGACAGTGTCACCTCCCAGGTCCACAATATCTATTCATTGGTCGAGAATGGTTCTTACATTGTA

GCTGTTGATTTTGATTCAATTAGTGGTCGTATCTTTTGGTCTGATGCAACTCAGGGTAAAACCTGGAGTG

CGTTTCAAAATGGAACGGACAGAAGAGTGGTATTTGACAGTAGCATCATCTTGACTGAAACTATTGCAAT

AGATTGGGTAGGTCGTAATCTTTACTGGACAGACTATGCTCTGGAAACAATTGAAGTCTCCAAAATTGAT

GGGAGCCACAGGACTGTGCTGATTAGTAAAAACCTAACAAATCCAAGAGGACTAGCATTAGATCCCAGAA

TGAATGAGCATCTACTGTTCTGGTCTGACTGGGGCCACCACCCTCGCATCGAGCGAGCCAGCATGGACGG

CAGCATGCGCACTGTCATTGTCCAGGACAAGATCTTCTGGCCCTGCGGCTTAACTATTGACTACCCCAAC

AGACTGCTCTACTTCATGGACTCCTATCTTGATTACATGGACTTTTGTGATTATAATGGACACCATCGGA

GACAGGTGATAGCCAGTGATTTGATTATACGGCACCCCTATGCCCTAACTCTCTTTGAAGACTCTGTGTA

CTGGACTGACCGTGCTACTCGTCGGGTTATGCGAGCCAACAAGTGGCATGGAGGGAACCAGTCAGTTGTA

ATGTATAATATTCAATGGCCCCTTGGGATTGTTGCGGTTCATCCTTCGAAACAACCAAATTCCGTGAATC

CATGTGCCTTTTCCCGCTGCAGCCATCTCTGCCTGCTTTCCTCACAGGGGCCTCATTTTTACTCCTGTGT

TTGTCCTTCAGGATGGAGTCTGTCTCCTGATCTCCTGAATTGCTTGAGAGATGATCAACCTTTCTTAATA

ACTGTAAGGCAACATATAATTTTTGGAATCTCCCTTAATCCTGAGGTGAAGAGCAATGATGCTATGGTCC

CCATAGCAGGGATACAGAATGGTTTAGATGTTGAATTTGATGATGCTGAGCAATACATCTATTGGGTTGA

AAATCCAGGTGAAATTCACAGAGTGAAGACAGATGGCACCAACAGGACAGTATTTGCTTCTATATCTATG

GTGGGGCCTTCTATGAACCTGGCCTTAGATTGGATTTCAAGAAACCTTTATTCTACCAATCCTAGAACTC

AGTCAATCGAGGTTTTGACACTCCACGGAGATATCAGATACAGAAAAACATTGATTGCCAATGATGGGAC

AGCTCTTGGAGTTGGCTTTCCAATTGGCATAACTGTTGATCCTGCTCGTGGGAAGCTGTACTGGTCAGAC

CAAGGAACTGACAGTGGGGTTCCTGCCAAGATCGCCAGTGCTAACATGGATGGCACATCTGTGAAAACTC

TCTTTACTGGGAACCTCGAACACCTGGAGTGTGTCACTCTTGACATCGAAGAGCAGAAACTCTACTGGGC

AGTCACTGGAAGAGGAGTGATTGAAAGAGGAAACGTGGATGGAACAGATCGAATGATCCTGGTACACCAG

CTTTCCCACCCCTGGGGAATTGCAGTCCATGATTCTTTCCTTTATTATACTGATGAACAGTATGAGGTCA

TTGAAAGAGTTGATAAGGCCACTGGGGCCAACAAAATAGTCTTGAGAGATAATGTTCCAAATCTGAGGGG

TCTTCAAGTTTATCACAGACGCAATGCCGCCGAATCCTCAAATGGCTGTAGCAACAACATGAATGCCTGT

CAGCAGATTTGCCTGCCTGTACCAGGAGGATTGTTTTCCTGCGCCTGTGCCACTGGATTTAAACTCAATC

CTGATAATCGGTCCTGCTCTCCATATAACTCTTTCATTGTTGTTTCAATGCTGTCTGCAATCAGAGGCTT

TAGCTTGGAATTGTCAGATCATTCAGAAACCATGGTGCCGGTGGCAGGCCAAGGACGAAACGCACTGCAT

GTGGATGTGGATGTGTCCTCTGGCTTTATTTATTGGTGTGATTTTAGCAGCTCAGTGGCATCTGATAATG

CGATCCGTAGAATTAAACCAGATGGATCTTCTCTGATGAACATTGTGACACATGGAATAGGAGAAAATGG

AGTCCGGGGTATTGCAGTGGATTGGGTAGCAGGAAATCTTTATTTCACCAATGCCTTTGTTTCTGAAACA

CTGATAGAAGTTCTGCGGATCAATACTACTTACCGCCGTGTTCTTCTTAAAGTCACAGTGGACATGCCTA

GGCATATTGTTGTAGATCCCAAGAACAGATACCTCTTCTGGGCTGACTATGGGCAGAGACCAAAGATTGA

GCGTTCTTTCCTTGACTGTACCAATCGAACAGTGCTTGTGTCAGAGGGCATTGTCACACCACGGGGCTTG
```

-continued

```
GCAGTGGACCGAAGTGATGGCTACGTTTATTGGGTTGATGATTCTTTAGATATAATTGCAAGGATTCGTA

TCAATGGAGAGAACTCTGAAGTGATTCGTTATGGCAGTCGTTACCCAACTCCTTATGGCATCACTGTTTT

TGAAAATTCTATCATATGGGTAGATAGGAATTTGAAAAGATCTTCCAAGCCAGCAAGGAACCAGAGAAC

ACAGAGCCACCCACAGTGATAAGAGACAATATCAACTGGCTAAGAGATGTGACCATCTTTGACAAGCAAG

TCCAGCCCCGGTCACCAGCAGAGGTCAACAACAACCCTTGCTTGGAAAACAATGGTGGGTGCTCTCATCT

CTGCTTTGCTCTGCCTGGATTGCACACCCCAAAATGTGACTGTGCCTTTGGGACCCTGCAAAGTGATGGC

AAGAATTGTGCCATTTCAACAGAAAATTTCCTCATCTTTGCCTTGTCTAATTCCTTGAGAAGCTTACACT

TGGACCCTGAAAACCATAGCCCACCTTTCCAAACAATAAATGTGGAAAGAACTGTCATGTCTCTAGACTA

TGACAGTGTAAGTGATAGAATCTACTTCACACAAAATTTAGCCTCTGGAGTTGGACAGATTTCCTATGCC

ACCCTGTCTTCAGGGATCCATACTCCAACTGTCATTGCTTCAGGTATAGGGACTGCTGATGGCATTGCCT

TTGACTGGATTACTAGAAGAATTTATTACAGTGACTACCTCAACCAGATGATTAATTCCATGGCTGAAGA

TGGGTCTAACCGCACTGTGATAGCCCGCGTTCCAAAACCAAGAGCAATTGTGTTAGATCCCTGCCAAGGG

TACCTGTACTGGGCTGACTGGGATACACATGCCAAAATCGAGAGAGCCACATTGGGAGGAAACTTCCGCG

TACCCATTGTGAACAGCAGTCTGGTCATGCCCAGTGGGCTGACTCTGGACTATGAAGAGGACCTTCTCTA

CTGGGTGGATGCTAGTCTGCAGAGGATTGAACGCAGCACTCTGACGGGCGTGGATCGTGAAGTCATTGTC

AATGCAGCCGTTCATGCTTTTGGCTTGACTCTCTATGGCCAGTATATTTACTGGACTGACTTGTACACAC

AAAGAATTTACCGAGCTAACAAATATGACGGGTCAGGTCAGATTGCAATGACCACAAATTTGCTCTCCCA

GCCCAGGGGAATCAACACTGTTGTGAAGAACCAGAAACAACAGTGTAACAATCCTTGTGAACAGTTTAAT

GGGGGCTGCAGCCATATCTGTGCACCAGGTCCAAATGGTGCCGAGTGCCAGTGTCCACATGAGGGCAACT

GGTATTTGGCCAACAACAGGAAGCACTGCATTGTGGACAATGGTGAACGATGTGGTGCATCTTCCTTCAC

CTGCTCCAATGGGCGCTGCATCTCGGAAGAGTGGAAGTGTGATAATGACAACGACTGTGGGGATGGCAGT

GATGAGATGGAAAGTGTCTGTGCACTTCACACCTGCTCACCGACAGCCTTCACCTGTGCCAATGGGCGAT

GTGTCCAATACTCTTACCGCTGTGATTACTACAATGACTGTGGTGATGGCAGTGATGAGGCAGGGTGCCT

GTTCAGGGACTGCAATGCCACCACGGAGTTTATGTGCAATAACAGAAGGTGCATACCTCGTGAGTTTATC

TGCAATGGTGTAGACAACTGCCATGATAATAACACTTCAGATGAGAAAAATTGCCCTGATCGCACTTGCC

AGTCTGGATACACAAAATGTCATAATTCAAATATTTGTATTCCTCGCGTTTATTTGTGTGACGGAGACAA

TGACTGTGGAGATAACAGTGATGAAAACCCTACTTATTGCACCACTCACACGTGCAGCAGCAGTGAGTTC

CAATGCGCATCTGGGCGCTGTATTCCTCAACATTGGTATTGTGATCAAGAAACAGATTGTTTTGATGCCT

CTGATGAACCTGCCTCTTGTGGTCACTCTGAGCGAACATGCCTAGCTGATGAGTTCAAGTGTGATGGTGG

GAGGTGCATCCCAAGCGAATGGATCTGTGACGGTGATAATGACTGTGGGGATATGAGTGACGAGGATAAA

AGGCACCAGTGTCAGAATCAAAACTGCTCGGATTCCGAGTTTCTCTGTGTAAATGACAGACCTCCGGACA

GGAGGTGCATTCCCCAGTCTTGGGTCTGTGATGGCGATGTGGATTGTACTGACGGCTACGATGAGAATCA

GAATTGCACCAGGAGAACTTGCTCTGAAAATGAATTCACCTGTGGTTACGGACTGTGTATCCCAAAGATA

TTCAGGTGTGACCGGCACAATGACTGTGGTGACTATAGCGACGAGAGGGGCTGCTTATACCAGACTTGCC

AACAGAATCAGTTTACCTGTCAGAACGGGCGCTGCATTAGTAAAACCTTCGTCTGTGATGAGGATAATGA

CTGTGGAGACGGATCTGATGAGCTGATGCACCTGTGCCACACCCCAGAACCCACGTGTCCACCTCACGAG

TTCAAGTGTGACAATGGGCGCTGCATCGAGATGATGAAACTCTGCAACCACCTAGATGACTGTTTGGACA

ACAGCGATGAGAAAGGCTGTGGCATTAATGAATGCCATGACCCTTCAATCAGTGGCTGCGATCACAACTG

CACAGACACCTTAACCAGTTTCTATTGTTCCTGTCGTCCTGGTTACAAGCTCATGTCTGACAAGCGGACT

TGTGTTGATATTGATGAATGCACAGAGATGCCTTTTGTCTGTAGCCAGAAGTGTGAGAATGTAATAGGCT

CCTACATCTGTAAGTGTGCCCCAGGCTACCTCCGAGAACCAGATGGAAAGACCTGCCGGCAAAACAGTAA
```

-continued

```
CATCGAACCCTATCTCATTTTTAGCAACCGTTACTATTTGAGAAATTTAACTATAGATGGCTATTTTTAC
TCCCTCATCTTGGAAGGACTGGACAATGTTGTGGCATTAGATTTTGACCGAGTAGAGAAGAGATTGTATT
GGATTGATACACAGAGGCAAGTCATTGAGAGAATGTTTCTGAATAAGACAAACAAGGAGACAATCATAAA
CCACAGACTACCAGCTGCAGAAAGTCTGGCTGTAGACTGGGTTTCCAGAAAGCTCTACTGGTTGGATGCC
CGCCTGGATGGCCTCTTTGTCTCTGACCTCAATGGTGGACACCGCCGCATGCTGGCCCAGCACTGTGTGG
ATGCCAACAACACCTTCTGCTTTGATAATCCCAGAGGACTTGCCCTTCACCCTCAATATGGGTACCTCTA
CTGGGCAGACTGGGGTCACCGCGCATACATTGGGAGAGTAGGCATGGATGGAACCAACAAGTCTGTGATA
ATCTCCACCAAGTTAGAGTGGCCTAATGGCATCACCATTGATTACACCAATGATCTACTCTACTGGGCAG
ATGCCCACCTGGGTTACATAGAGTACTCTGATTTGGAGGGCCACCATCGACACACGGTGTATGATGGGGC
ACTGCCTCACCCTTTCGCTATTACCATTTTTGAAGACACTATTTATTGGACAGATTGGAATACAAGGACA
GTGGAAAAGGGAAACAAATATGATGGATCAAATAGACAGACACTGGTGAACACAACACACAGACCATTTG
ACATCCATGTGTACCATCCATATAGGCAGCCCATTGTGAGCAATCCCTGTGGTACCAACAATGGTGGCTG
TTCTCATCTCTGCCTCATCAAGCCAGGAGGAAAAGGGTTCACTTGCGAGTGTCCAGATGACTTCCGCACC
CTTCAGCTGAGTGGCAGCACCTACTGCATGCCCATGTGCTCCAGCACCCAGTTCCTGTGCGCTAACAATG
AAAAGTGCATTCCTATCTGGTGGAAATGTGATGGACAGAAAGACTGCTCAGATGGCTCTGATGAACTGGC
CCTTTGCCCGCAGCGCTTCTGCCGACTGGGACAGTTCCAGTGCAGTGACGGCAACTGCACCAGCCCGCAG
ACTTTATGCAATGCTCACCAAAATTGCCCTGATGGGTCTGATGAAGACCGTCTTCTTTGTGAGAATCACC
ACTGTGACTCCAATGAATGGCAGTGCGCCAACAAACGTTGCATCCCAGAATCCTGGCAGTGTGACACATT
TAACGACTGTGAGGATAACTCAGATGAAGACAGTTCCCACTGTGCCAGCAGGACCTGCCGGCCGGGCCAG
TTTCGGTGTGCTAATGGCCGCTGCATCCCGCAGGCCTGGAAGTGTGATGTGGATAATGATTGTGGAGACC
ACTCGGATGAGCCCATTGAAGAATGCATGAGCTCTGCCCATCTCTGTGACAACTTCACAGAATTCAGCTG
CAAAACAAATTACCGCTGCATCCCAAAGTGGGCCGTGTGCAATGGTGTAGATGACTGCAGGGACAACAGT
GATGAGCAAGGCTGTGAGGAGAGGACATGCCATCCTGTGGGGATTTCCGCTGTAAAAATCACCACTGCA
TCCCTCTTCGTTGGCAGTGTGATGGGCAAAATGACTGTGGAGATAACTCAGATGAGGAAAACTGTGCTCC
CCGGGAGTGCACAGAGAGCGAGTTTCGATGTGTCAATCAGCAGTGCATTCCCTCGCGATGGATCTGTGAC
CATTACAACGACTGTGGGGACAACTCAGATGAACGGGACTGTGAGATGAGGACCTGCCATCCTGAATATT
TTCAGTGTACAAGTGGACATTGTGTACACAGTGAACTGAAATGCGATGGATCCGCTGACTGTTTGGATGC
GTCTGATGAAGCTGATTGTCCCACACGCTTTCCTGATGGTGCATACTGCCAGGCTACTATGTTCGAATGC
AAAAACCATGTTTGTATCCCGCCATATTGGAAATGTGATGGCGATGATGACTGTGGCGATGGTTCAGATG
AAGAACTTCACCTGTGCTTGGATGTTCCCTGTAATTCACCAAACCGTTTCCGGTGTGACAACAATCGCTG
CATTTATAGTCATGAGGTGTGCAATGGTGTGGATGACTGTGGAGATGGAACTGATGAGACAGAGGAGCAC
TGTAGAAAACCGACCCCTAAACCTTGTACAGAATATGAATATAAGTGTGGCAATGGGCATTGCATTCCAC
ATGACAATGTGTGTGATGATGCCGATGACTGTGGTGACTGGTCCGATGAACTGGGTTGCAATAAAGGAAA
AGAAAGAACATGTGCTGAAAATATATGCGAGCAAAATTGTACCCAATTAAATGAAGGAGGATTTATCTGC
TCCTGTACAGCTGGGTTCGAAACCAATGTTTTTGACAGAACCTCCTGTCTAGATATCAATGAATGTGAAC
AATTTGGGACTTGTCCCCAGCACTGCAGAAATACCAAAGGAAGTTATGAGTGTGTCTGTGCTGATGGCTT
CACGTCTATGAGTGACCGCCCTGGAAAACGATGTGCAGCTGAGGGTAGCTCTCCTTTGTTGCTACTGCCT
GACAATGTCCGAATTCGAAAATATAATCTCTCATCTGAGAGGTTCTCAGAGTATCTTCAAGATGAGGAAT
ATATCCAAGCTGTTGATTATGATTGGGATCCCAAGGACATAGGCCTCAGTGTTGTGTATTACACTGTGCG
AGGGGAGGGCTCTAGGTTTGGTGCTATCAAACGTGCCTACATCCCCAACTTTGAATCCGGCCGCAATAAT
```

-continued

```
CTTGTGCAGGAAGTTGACCTGAAACTGAAATACGTAATGCAGCCAGATGGAATAGCAGTGGACTGGGTTG
GAAGGCATATTTACTGGTCAGATGTCAAGAATAAACGCATTGAGGTGGCTAAACTTGATGGAAGGTACAG
AAAGTGGCTGATTTCCACTGACCTGGACCAACCAGCTGCTATTGCTGTGAATCCCAAACTAGGGCTTATG
TTCTGGACTGACTGGGGAAAGGAACCTAAAATCGAGTCTGCCTGGATGAATGGAGAGGACCGCAACATCC
TGGTTTTCGAGGACCTTGGTTGGCCAACTGGCCTTTCTATCGATTATTTGAACAATGACCGAATCTACTG
GAGTGACTTCAAGGAGGACGTTATTGAAACCATAAAATATGATGGGACTGATAGGAGAGTCATTGCAAAG
GAAGCAATGAACCCTTACAGCCTGGACATCTTTGAAGACCAGTTATACTGGATATCTAAGGAAAAGGGAG
AAGTATGGAAACAAAATAAATTTGGGCAAGGAAAGAAAGAGAAAACGCTGGTAGTGAACCCTTGGCTCAC
TCAAGTTCGAATCTTTCATCAACTCAGATACAATAAGTCAGTGCCCAACCTTTGCAAACAGATCTGCAGC
CACCTCTGCCTTCTGAGACCTGGAGGATACAGCTGTGCCTGTCCCCAAGGCTCCAGCTTTATAGAGGGGA
GCACCACTGAGTGTGATGCAGCCATCGAACTGCCTATCAACCTGCCCCCCCCATGCAGGTGCATGCACGG
AGGAAATTGCTATTTTGATGAGACTGACCTCCCCAAATGCAAGTGTCCTAGCGGCTACACCGGAAAATAT
TGTGAAATGGCGTTTTCAAAAGGCATCTCTCCAGGAACAACCGCAGTAGCTGTGCTGTTGACAATCCTCT
TGATCGTCGTAATTGGAGCTCTGGCAATTGCAGGATTCTTCCACTATAGAAGGACCGGCTCCCTTTTGCC
TGCTCTGCCCAAGCTGCCAAGCTTAAGCAGTCTCGTCAAGCCCTCTGAAAATGGGAATGGGGTGACCTTC
AGATCAGGGGCAGATCTTAACATGGATATTGGAGTGTCTGGTTTTGGACCTGAGACTGCTATTGACAGGT
CAATGGCAATGAGTGAAGACTTTGTCATGGAAATGGGGAAGCAGCCCATAATATTTGAAAACCCAATGTA
CTCAGCCAGAGACAGTGCTGTCAAAGTGGTTCAGCCAATCCAGGTGACTGTATCTGAAAATGTGGATAAT
AAGAATTATGGAAGTCCCATAAACCCTTCTGAGATAGTTCCAGAGACAAACCCAACTTCACCAGCTGCTG
ATGGAACTCAGGTGACAAAATGGAATCTCTTCAAACGAAAATCTAAACAAACTACCAACTTTGAAAATCC
AATCTATGCACAGATGGAGAACGAGCAAAAGGAAAGTGTTGCTGCGACACCACCTCCATCACCTTCGCTC
CCTGCTAAGCCTAAGCCTCCTTCGAGAAGAGACCCAACTCCAACCTATTCTGCAACAGAAGACACTTTTA
AAGACACCGCAAATCTTGTTAAAGAAGACTCTGAAGTATAGCTATACCAGCTATTTAGGGAATAATTAGA
AACACACTTTTGCACATATATTTTTTACAAACAGATGAAAAAAGTTAACATTCAGTACTTTATGAAAAAA
ATATATTTTTCCCTGTTTGCCTATAGTTGGAGGTATCCTGTGTGTCTTTTTTTACTTATGCCGTCTCATA
TTTTTACAAATAATTATCACAATGTACTATATGTATATCTTTGCACTGAAGTTGTCTGAAGGTAATACTA
TAAATATATTGTATATTTGTAAATTTTGGAAAGATTATCCTGTTACTGAATTTGCTAATAAAGATGTCTG
CTGATTTGGTTGGTGATCATTATAGTAAATGATCCAACAAGAAAAGGAATTGACTGGGGACCTTTAGCCG
TGTCTAAAGAAGAGGCACCACTCATATTTCCTATAAAATTATCTAGGAAAGGAATCCAGGCCCCGCTCTT
GGGTCCATTTTTACACATTAGCACTTAATTAATGTTCAATATTACATGTCAATTTGATTAATGGCTATGT
TGATAGGGGCCACTATGTGTTGTATAGACATCTGGACTTGACTGTAGACTCCTCAGATAATACAGAAGGT
AGGAAAAGCAATTCAGTTTGGCCCTTCTGTGTGTTGGCATTGTCTAACCAGAACTCTCTGTTTCATGTGT
GTTCTCTCACTAGCTGCCAAGACAACATTTTTATTTGTGATGTCTATGAGGAAATCCCATATCATTAAGT
GCCAGTGTCCTGCATTGAGTTTGTGGTTAATTAAATGAGCTCTTCTGCTGATGGACCCTGGAGCAATTTC
TCCCCTCACCTGACATTCAAGGTGGTCACCTGCCCTAGTAGTTGGAGCTCAGTAGCTGAATTTCTGAAAC
CAAATCTGTGTCTTCATAAAATAAGGTGCAAAAAAAAAAAATACCAGTTAAGTAAAGCCTCAACTGGGTT
TTTGTTTCTATGAAAATATCATTATAATCACTATTTATTTCCTAAGTTGAACCTGAATAGAAAGGGAAAC
CATTCTTATTAAGCTTTTTATTAGGCCCTGTGGCTAAATGTGTACATTTATATTAGAATGTACTGTACAG
TCCAGATCTTTTCTTTAATTCTTATTGGTTTTTTTTTTTTTTTTTTTAGAGATGGAGTCTTGCTATA
TTGCCAAGGCTGATCTTGAAGTCCTGGGCTCAAGTGATCCTCCCACCTCAGCCTCCTGAGTGGTTGGGGT
TACGGGCGTGAGCCACTGTGCCTGGCTTCCAGCTCTCCTCTTAAATAGTGGGTATAGTCTGCACAACAGG
```

-continued

```
AACCATGGCAGGAATATACACTTTCCCATAGCAAATAGCATACCTGACTCTCTGTGCTAATATTGCACAT
TTGTTAAACAATGAATGAATGGATGGATGGATGGATGGATGAATGAATGAAACATATACTACTGATTATT
TTATTCCAGAGTTCTCAAAATATTTGTTGCTGATATTTTGAGTGCTGACTGTAATTACTTTGATTAGATA
AACAACTGGAAATAATGCTGCTGAAAAAGTTCTAATAAATGTGTATTTTATCAGA.
```

One example of a protein sequence from the above LRP2 DNA is: >sp|P98164|LRP2_HUMAN Low-density lipoprotein receptor-related protein 2 OS=Homo sapiens OX=9606 GN=LRP2 PE=1 SV=3

(SEQ ID NO. 940)
MDRGPAAVACTLLLALVACLAPASGQECDSAHFRCGSGHCIPADWRCDG

TKDCSDDADEIGCAVVTCQQGYFKCQSEGQCIPNSWVCDQDQDCDDGSD

ERQDCSQSTCSSHQITCSNGQCIPSEYRCDHVRDCPDGADENDCQYPTC

EQLTCDNGACYNTSQKCDWKVDCRDSSDEINCTEICLHNEFSCGNGECI

PRAYVCDHDNDCQDGSDEHACNYPTCGGYQFTCPSGRCIYQNWVCDGED

DCKDNGDEDGCESGPHDVHKCSPREWSCPESGRCISIYKVCDGILDCPG

REDENNTSTGKYCSMTLCSALNCQYQCHETPYGGACFCPPGYIINHNDS

RTCVEFDDCQIWGICDQKCESRPGRHLCHCEEGYILERGQYCKANDSFG

EASIIFSNGRDLLIGDIHGRSFRILVESQNRGVAVGVAFHYHLQRVFWT

DTVQNKVFSVDINGLNIQEVLNVSVETPENLAVDWVNNKIYLVETKVNR

IDMVNLDGSYRVTLITENLGHPRGIAVDPTVGYLFFSDWESLSGEPKLE

RAFMDGSNRKDLVKTKLGWPAGVTLDMISKRVYWVDSRFDYIETVTYDG

IQRKTVVHGGSLIPHPFGVSLFEGQVFFTDWTKMAVLKANKFTETNPQV

YYQASLRPYGVTVYHSLRQPYATNPCKDNNGGCEQVCVLSHRTDNDGLG

FRCKCTFGFQLDTDERHCIAVQNFLIFSSQVAIRGIPFTLSTQEDVMVP

VSGNPSFFVGIDFDAQDSTIFFSDMSKHMIFKQKIDGTGREILAANRVE

NVESLAFDWISKNLYWTDSHYKSISVMRLADKTRRTVVQYLNNPRSVVV

HPFAGYLFFTDWFRPAKIMRAWSDGSHLLPVINTTLGWPNGLAIDWAAS

RLYWVDAYFDKIEHSTFDGLDRRRLGHIEQMTHPFGLAIFGEHLFFTDW

RLGAIIRVRKADGGEMTVIRSGIAYILHLKSYDVNIQTGSNACNQPTHP

NGDCSHFCFPVPNFQRVCGCPYGMRLASNHLTCEGDPTNEPPTEQCGLF

SFPCKNGRCVPNYYLCDGVDDCHDNSDEQLCGTLNNTCSSSAFTCGHGE

CIPAHWRCDKRNDCVDGSDEHNCPTHAPASCLDTQYTCDNHQCISKNWV

CDTDNDCGDGSDEKNCNSTETCQPSQFNCPNHRCIDLSFVCDGDKDCVD

GSDEVGCVLNCTASQFKCASGDKCIGVTNRCDGVFDCSDNSDEAGCPTR

PPGMCHSDEFQCQEDGICIPNFWECDGHPDCLYGSDEHNACVPKTCPSS

YFHCDNGNCIHRAWLCDRDNDCGDMSDEKDCPTQPFRCPSWQWQCLGHN

ICVNLSVVCDGIFDCPNGTDESPLCNGNSCSDFNGGCTHECVQEPFGAK

CLCPLGFLLANDSKTCEDIDECDILGSCSQHCYNMRGSFRCSCDTGYML

ESDGRTCKVTASESLLLLVASQNKIIADSVTSQVHNIYSLVENGSYIVA

VDFDSISGRIFWSDATQGKTWSAFQNGTDRRVVFDSSIILTETIAIDWV

GRNLYWTDYALETIEVSKIDGSHRTVLISKNLTNPRGLALDPRMNEHLL

FWSDWGHHPRIERASMDGSMRTVIVQDKIFWPCGLTIDYPNRLLYFMDS

YLDYMDFCDYNGHHRRQVIASDLIIRHPYALTLFEDSVYWTDRATRRVM

RANKWHGGNQSVVMYNIQWPLGIVAVHPSKQPNSVNPCAFSRCSHLCLL

SSQGPHFYSCVCPSGWSLSPDLLNCLRDDQPFLITVRQHIIFGISLNPE

VKSNDAMVPIAGIQNGLDVEFDDAEQYIYWVENPGEIHRVKTDGTNRTV

FASISMVGPSMNLALDWISRNLYSTNPRTQSIEVLTLHGDIRYRKTLIA

NDGTALGVGFPIGITVDPARGKLYWSDQGTDSGVPAKIASANMDGTSVK

TLFTGNLEHLECVTLDIEEQKLYWAVTGRGVIERGNVDGTDRMILVHQL

SHPWGIAVHDSFLYYTDEQYEVIERVDKATGANKIVLRDNVPNLRGLQV

YHRRNAAESSNGCSNNMNACQQICLPVPGGLFSCACATGFKLNPDNRSC

SPYNSFIVVSMLSAIRGFSLELSDHSETMVPVAGQGRNALHVDVDVSSG

FIYWCDFSSSVASDNAIRRIKPDGSSLMNIVTHGIGENGVRGIAVDWVA

GNLYFTNAFVSETLIEVLRINTTYRRVLLKVTVDMPRHIVVDPKNRYLF

WADYGQRPKIERSFLDCTNRTVLVSEGIVTPRGLAVDRSDGYVYWVDDS

LDIIARIRINGENSEVIRYGSRYPTPYGITVFENSIIWVDRNLKKIFQA

SKEPENTEPPTVIRDNINWLRDVTIFDKQVQPRSPAEVNNNPCLENNGG

CSHLCFALPGLHTPKCDCAFGTLQSDGKNCAISTENFLIFALSNSLRSL

HLDPENHSPPFQTINVERTVMSLDYDSVSDRIYFTQNLASGVGQISYAT

LSSGIHTPTVIASGIGTADGIAFDWITRRIYYSDYLNQMINSMAEDGSN

RTVIARVPKPRAIVLDPCQGYLYWADWDTHAKIERATLGGNFRVPIVNS

SLVMPSGLTLDYEEDLLYWVDASLQRIERSTLTGVDREVIVNAAVHAFG

LTLYGQYIYWTDLYTQRIYRANKYDGSGQIAMTTNLLSQPRGINTVVKN

QKQQCNNPCEQFNGGCSHICAPGPNGAECQCPHEGNWYLANNRKHCIVD

NGERCGASSFTCSNGRCISEEWKCDNDNDCGDGSDEMESVCALHTCSPT

AFTCANGRCVQYSYRCDYYNDCGDGSDEAGCLFRDCNATTEFMCNNRRC

IPREFICNGVDNCHDNNTSDEKNCPDRTCQSGYTKCHNSNICIPRVYLC

DGDNDCGDNSDENPTYCTTHTCSSSEFQCASGRCIPQHWYCDQETDCFD

ASDEPASCGHSERTCLADEFKCDGGRCIPSEWICDGDNDCGDMSDEDKR

HQCQNQNCSDSEFLCVNDRPPDRRCIPQSWVCDGDVDCTDGYDENQNCT

RRTCSENEFTCGYGLCIPKIFRCDRHNDCGDYSDERGCLYQTCQQNQFT

CQNGRCISKTFVCDEDNDCGDGSDELMHLCHTPEPTCPPHEFKCDNGRC

IEMMKLCNHLDDCLDNSDEKGCGINECHDPSISGCDHNCTDTLTSFYCS

CRPGYKLMSDKRTCVDIDECTEMPFVCSQKCENVIGSYICKCAPGYLRE

PDGKTCRQNSNIEPYLIFSNRYYLRNLTIDGYFYSLILEGLDNVVALDF

-continued

```
DRVEKRLYWIDTQRQVIERMFLNKTNKETIINHRLPAAESLAVDWVSRK
LYWLDARLDGLFVSDLNGGHRRMLAQHCVDANNTFCFDNPRGLALHPQY
GYLYWADWGHRAYIGRVGMDGTNKSVIISTKLEWPNGITIDYTNDLLYW
ADAHLGYIEYSDLEGHHRHTVYDGALPHPFAITIFEDTIYWTDWNTRTV
EKGNKYDGSNRQTLVNTTHRPFDIHVYHPYRQPIVSNPCGTNNGGCSHL
CLIKPGGKGFTCECPDDFRTLQLSGSTYCMPMCSSTQFLCANNEKCIPI
WWKCDGQKDCSDGSDELALCPQRFCRLGQFQCSDGNCTSPQTLCNAHQN
CPDGSDEDRLLCENHHCDSNEWQCANKRCIPESWQCDTFNDCEDNSDED
SSHCASRTCRPGQFRCANGRCIPQAWKCDVDNDCGDHSDEPIEECMSSA
HLCDNFTEFSCKTNYRCIPKWAVCNGVDDCRDNSDEQGCEERTCHPVGD
FRCKNHHCIPLRWQCDGQNDCGDNSDEENCAPRECTESEFRCVNQQCIP
SRWICDHYNDCGDNSDERDCEMRTCHPEYFQCTSGHCVHSELKCDGSAD
CLDASDEADCPTRFPDGAYCQATMFECKNHVCIPPYWKCDGDDDCGDGS
DEELHLCLDVPCNSPNRFRCDNNRCIYSHEVCNGVDDCGDGTDETEEHC
RKPTPKPCTEYEYKCGNGHCIPHDNVCDDADDCGDWSDELGCNKGKERT
CAENICEQNCTQLNEGGFICSCTAGFETNVFDRTSCLDINECEQFGTCP
QHCRNTKGSYECVCADGFTSMSDRPGKRCAAEGSSPLLLLPDNVRIRKY
NLSSERFSEYLQDEEYIQAVDYDWDPKDIGLSVVYYTVRGEGSRFGAIK
RAYIPNFESGRNNLVQEVDLKLKYVMQPDGIAVDWVGRHIYWSDVKNKR
IEVAKLDGRYRKWLISTDLDQPAAIAVNPKLGLMFWTDWGKEPKIESAW
MNGEDRNILVFEDLGWPTGLSIDYLNNDRIYWSDFKEDVIETIKYDGTD
RRVIAKEAMNPYSLDIFEDQLYWISKEKGEVWKQNKFGQGKKEKTLVVN
PWLTQVRIFHQLRYNKSVPNLCKQICSHLCLLRPGGYSCACPQGSSFIE
GSTTECDAAIELPINLPPPCRCMHGGNCYFDETDLPKCKCPSGYTGKYC
EMAFSKGISPGTTAVAVLLTILLIVVIGALAIAGFFHYRRTGSLLPALP
KLPSLSSLVKPSENGNGVTFRSGADLNMDIGVSGFGPETAIDRSMAMSE
DFVMEMGKQPIIFENPMYSARDSAVKVVQPIQVTVSENVDNKNYGSPIN
PSEIVPETNPTSPAADGTQVTKWNLFKRKSKQTTNFENPIYAQMENEQK
ESVAATPPPSPSLPAKPKPPSRRDPTPTYSATEDTFKDTANLVKEDSE
V.
```

As used herein, "target sequence" refers to a contiguous portion of the nucleotide sequence of an mRNA molecule formed during the transcription of a gene of interest for example a CD320 gene or an LRP2 gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine, 2'-deoxythymidine or thymidine. However, it will be understood that the term "ribonucleotide" or "nucleotide" or "deoxyribonucle-otide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

The term "siRNA" refers to a compound, cocktail, composition or agent that contains RNA as that term is defined herein, and which mediates the targeted cleavage of an RNA transcript via the RISC/AGO (RNA-induced silencing complex) complex, whereby the guide strand of the siRNA hybridizes with its complementary mRNA molecule. The mRNA is degraded by the RISC/AGO complex, which has RNAse cleave activity, resulting in mRNA degradation and the protein encoded by the mRNA is not produced or is produced at a reduced level as compared to untreated cell. This causes the "knockdown" effect or reduced protein levels of the gene targeted by the siRNA compared to control treated cells. The siRNA modulates, e.g., inhibits, the expression of CD320 in a cell or LRP2 in a cell, e.g., a cell within a subject, such as a mammalian subject.

In one embodiment, an RNAi agent of the invention includes a single stranded RNA that interacts with a target RNA sequence, e.g., a CD320 or LRP2 target mRNA sequence, to direct the cleavage of the target RNA. Without wishing to be bound by theory, it is believed that long double stranded RNA introduced into cells is broken down into siRNA by a Type III endonuclease known as Dicer (Sharp et al. (2001) Genes Dev. 15:485). Dicer, a ribonuclease-III-like enzyme, processes the dsRNA into 19-23 base pair (bp) short interfering RNAs with characteristic two base 3' overhangs (Bernstein, et al., (2001) Nature 409:363). Initially, the siRNAs may consist of two RNA strands, an antisense (or guide) strand and a sense (or passenger) strand, which form a duplex that varies in length from 10-80 bp in length with or without a 3' nucleotide overhang. A dsRNA can include one or more single-stranded overhang(s) of one or more nucleotides. In one embodiment, at least one end of the dsRNA has a single-stranded nucleotide overhang of 1 to 4, generally 1 or 2 nucleotides. In another embodiment, the antisense strand of the dsRNA has 1-10 nucleotide overhangs each at the 3' end and the 5' end over the sense strand. In further embodiments, the sense strand of the dsRNA has 1-10 nucleotide overhangs each at the 3' end and the 5' end over the antisense strand.

The siRNA are then incorporated into an RNA-induced silencing complex (RISC) where one or more helicases unwind the siRNA duplex, enabling the complementary antisense (guide) strand to guide target recognition (Nykanen, et al., (2001) Cell 107:309). Upon binding to the appropriate target mRNA, one or more endonucleases within the RISC cleave the target to induce silencing (Elbashir, et al., (2001) Genes Dev. 15:188). Thus, in one aspect the invention relates to a single stranded RNA (siRNA) generated within a cell and which promotes the formation of a RISC complex to effect silencing of the target gene, i.e., a CD320 or LRP2 gene. Accordingly, the term "siRNA" is also used herein to refer to an RNAi as described above.

In another embodiment, the RNAi agent may be a single-stranded siRNA that is introduced into a cell or organism to inhibit a target mRNA. Single-stranded RNAi agents bind to the RISC endonuclease Argonaute 2, which then cleaves the target mRNA. The single-stranded siRNAs are generally 15-80 nucleotides and may be chemically modified to improve metabolic stability and activity; wherein one or multiple pyrimidine nucleotides could be modified as 2'-deoxy-2'-fluoronucleotides, one or more purine nucleotides could be modified as 2'-deoxypurine nucleotides and, moreover, wherein terminal cap modifications could be present at the 3' or 5' ends; particularly by the introduction of one or more 2'-deoxythymidine nucleotides, or by the introduction of one or more phosphorothioate groups linking any nucleotides in the sequence but especially at the 3' and 5' end. In addition, a 3'-terminal phosphate or vinylphosphonate group could be introduced. Examples of such modifications would include but not be limited to modifications to the ribose moieties of the nucleotides such as: 2'-deoxy, 2'-deoxyfluoro, 2'-methoxy (2'-O-methyl) (Hutvanger et al., (2004) PLOS Biol 2, 0465-0475; Janas et al., (2019) Nuc Acid Res 47, 3306-3320; Jackson et al., (2006) RNA 12, 1197-1205), and 2'-methoxyethyl, wherein it is understood that the stereochemistry of the 2'-substituent could be in the ribo- or arabino-orientation. Another modification could be 2'-trifluoromethoxy. Other modifications to the ribose moieties could include bridging modifications such that the 2'-carbon of the sugar moiety is covalently linked to the 4'-carbon of the sugar moiety by a methylene or methoxymethylene group to afford bridged nucleotides described in the art as LNA and (S)-cET, respectively (Corey et al., (2018) Nuc Acid Res 46; 1584-1600). In addition, the sugar moiety could be modified by removal of the bond between carbons C2' and C3' to afford "open" chain nucleotides analogous to those described in WO 2011/139843 A2. The ribose moiety of the RNA nucleotides could also be replaced by a morpholino group to afford PMO nucleotides. Modifications to the phosphate diester moieties of the nucleotides are also possible and could include but not be limited to replacement of the phosphodiester group by phosphorothioate and thiophosphoramidate (Eckstein et al., (2014) Nuc Acid Therapeutics 24, 374-387). The ends of the strand could be modified with 2'-deoxynucleotides such as dT and, further, the dT nucleotides could be modified by phosphorothioate groups in place of diphosphate esters. The design and testing of single-stranded siRNAs are described in U.S. Pat. No. 8,101,348 and in Lima et al., (2012) Cell 150: 883-894, the entire contents of each of which are hereby incorporated herein by reference. Any of the antisense nucleotide sequences described herein may be used as a single-stranded siRNA as described herein or as chemically modified by the methods described in Lima et al., (2012) Cell 150; 883-894.

In another embodiment, an "RNAi" for use in the compositions, uses, and methods of the invention is a double-stranded RNA and is referred to herein as a "double stranded RNAi agent," "double-stranded RNA (dsRNA) molecule," "dsRNA agent," or "dsRNA". The term "dsRNA" refers to a complex of ribonucleic acid molecules, having a duplex structure comprising two anti-parallel and substantially complementary nucleic acid strands, referred to as having "sense" (passenger) and "antisense" (guide) orientations with respect to a target RNA, i.e., a CD320 gene or LRP2 gene. In some embodiments of the invention, a double-stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide and/or a modified nucleotide. In addition, as used in this specification, an "RNAi agent" may include ribonucleotides with chemical modifications (Corey et al., (2018) Nuc Acid Res 46; 1584-1600); an RNAi agent may include substantial modifications at multiple nucleotides or at a single nucleotide. Such modifications may include all types of modifications disclosed herein or known in the art. Any such modifications, as used in a siRNA type molecule, are encompassed by "RNAi agent" for the purposes of this specification and claims. Examples of such modifications would include but not be limited to modifications to the ribose moieties of the nucleotides such as: 2'-deoxy, 2'-deoxyfluoro, 2'-methoxy (2'-O-methyl) (Hutvanger et al., (2004) PLOS Biol 2, 0465-0475; Janas et al., (2019) Nuc Acid Res 47, 3306-3320; Jackson et al., (2006) RNA 12, 1197-1205), and 2'-methoxyethyl, wherein it is understood that the stereochemistry of the 2'-substituent could be in the ribo- or arabino-orientation. Another modification could be 2'-trifluoromethoxy. Other modifications to the ribose moieties could include bridging modifications such that the 2'-carbon of the sugar moiety is covalently linked to the 4'-carbon of the sugar moiety by a methylene or methoxymethylene group to afford bridged nucleotides described in the art as LNA and (S)-cET, respectively (Corey et al., (2018) Nuc Acid Res 46; 1584-1600). In addition, the sugar moiety could be modified by removal of the bond between carbons C2' and C3' to afford "open" chain nucleotides analogous to those described in WO 2011/139843 A2. The ribose moiety of the RNA nucleotides could also be replaced by a morpholino group to afford PMO nucleotides. Modifications to the phosphate diester moieties of the nucleotides are also possible and could include but not be limited to replacement of the phosphodiester group by phosphorothioate and thiophosphoramidate (Eckstein et al., (2014) Nuc Acid Therapeutics 24, 374-387). The ends of the sense and antisense strands could be modified with 2'-deoxynucleotides such as dT and, further, the dT nucleotides could be modified by phosphorothioate groups in place of diphosphate esters (FIG. 19).

Chemical modifications to the ribonucleotides could be made at any individual or combination of nucleotides in the antisense and sense strands. In some cases, all the nucleotides in either the antisense or sense strand, or in both the antisense and sense strands are chemically modified (Allerson et al., (2005) J Med Chem 48, 901-904). In other cases, only some of the nucleotides in the antisense or sense strand, or in both the antisense and sense strands are chemically modified (Chiu et al., (2003) RNA 9, 1034-1048). In yet other cases, the modifications could follow a pattern of alternating 2'-methoxy and 2'-fluoro modifications to either or both strands of the siRNA and sometimes the complementary nucleotides of the antisense and sense strands could contain chemical modifications which are not identical, for example, where one member of a complementary nucleotide pair has a 2'-methoxy modification and the other member has a 2'-fluoro modification (Choung et al. (2006) Biochem Biophys Res Commun 342, 919-927; Hassler et al., (2018) Nucleic Acid Res 46, 2185-2196).

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi agent may comprise one or more nucleotide overhangs.

In one embodiment, an RNAi agent of the invention is a dsRNA of 20-30 nucleotides that interacts with a target RNA sequence, e.g., a CD320 target mRNA sequence or a LRP2 target mRNA sequence, to direct the cleavage of the target RNA.

The term "antisense strand" refers to the strand of a double stranded RNAi agent which includes a region that is substantially complementary to a target sequence (e.g., a human CD320 mRNA or a LRP2 mRNA). As used herein, the term "region complementary to part of an mRNA encoding CD320 or LRP2" refers to a region on the antisense strand that is substantially complementary to part of a mRNA sequence that codes for either CD320 or LRP2. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus. For example, substantially complementary can in certain embodiments mean that in a hybridized pair of nucleobase sequences, at least 85% but not all of the bases in a contiguous sequence of a first polynucleotide will hybridize with the same number of bases in a contiguous sequence of a second polynucleotide.

The term "sense strand," as used herein, refers to the strand of a dsRNA that includes a region that is substantially complementary to a region of the antisense strand.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. For example, a complementary sequence is sufficient to allow the relevant function of the nucleic acid to proceed, e.g., RNAi. The skilled person will be able to determine the set of conditions most appropriate for a test of complementarity of two sequences in accordance with the ultimate application of the hybridized nucleotides.

Sequences can be "fully complementary" with respect to each when there is base-pairing of the nucleotides of the first nucleotide sequence with the nucleotides of the second nucleotide sequence over the entire length of the first and second nucleotide sequences. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding CD320 or an mRNA encoding LRP2) including a 5' UTR, an open reading frame (ORF), or a 3' UTR. For example, a polynucleotide is complementary to at least a part of a CD320 mRNA or LRP2 mRNA if the sequence is substantially complementary to a non-interrupted portion of an mRNA encoding CD320 or LRP2.

The term "inhibiting," as used herein, is used interchangeably with "reducing," "silencing," "downregulating," "suppressing" and other similar terms, and includes any level of inhibition.

The phrase "inhibiting expression of a CD320," "inhibiting expression of a LRP2" as used herein, includes inhibition of expression of any CD320 or LRP2 gene (such as the identified gene from, e.g., a mouse, a rat, a monkey, or a human) as well as variants, (e.g., naturally occurring variants), or mutants of the identified gene. Thus, the CD320 or LRP2 gene may be a wild-type CD320 or LRP2 gene, a mutant CD320 or LRP2 gene, or a transgenic CD320 or LRP2 gene in the context of a genetically manipulated cell, group of cells, or organism.

"Inhibiting expression of a CD320 gene" or "Inhibiting expression of a LRP2 gene" includes any level of inhibition of a CD320 gene or a LRP2 gene, e.g., at least partial suppression of the expression of a CD320 or LRP2 gene, such as an inhibition of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In a preferred embodiment the inhibition is assessed by expressing the level of CD320 or LRP2 protein in treated cells as a percentage of the level of mRNA in control cells, using the following formula:

Normalized protein level for treated cells/Normalized protein level for control cells. The control cells are the negative control siRNA. Normalized means the protein level is normalized to the level of a housekeeping protein.

The expression of a CD320 or LRP2 gene may be assessed based on the level of any variable associated with CD320 or LRP2 gene expression, e.g., CD320 or LRP2 mRNA level, CD320 or LRP2 protein level. Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

Contacting a cell with a RNAi agent, either ds or ss as used herein, includes contacting a cell by any possible means whether in vivo or in vitro. Contacting a cell with a RNAi agent includes contacting a cell in vitro with the RNAi agent or contacting a cell in vivo with the RNAi agent. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

A "patient" or "subject," as used herein, is intended to include either a human or non-human animal, preferably a mammal, e.g., a monkey. Most preferably, the subject or patient is a human.

A "CD320-associated disease," as used herein, is intended to include any disease associated with a perturbation of the CD320 gene, or protein, polymorphisms, single nucleotide polymorphisms (SNPs) as well as epigenetic modifications of the CD320 gene. Such a disease may be caused, for example, by excess production of the CD320 protein, by CD320 gene mutations, by abnormal cleavage of the CD320 protein, by abnormal folding of the CD320 protein, by abnormal interactions between CD320 itself or with other proteins or other endogenous or exogenous substances. For example, cancer may be a CD320-associated disease. The degree of inhibition of protein expression may be measured by western blotting.

A "LRP2-associated disease," as used herein, is intended to include any disease associated with a perturbation of the LRP2 gene, protein, polymorphisms, SNPs as well as epigenetic modifications of the CD320 gene. Such a disease may be caused, for example, by excess production of the LRP2 protein, by LRP2 gene mutations, by abnormal cleavage of the LRP2 protein, by abnormal folding of the LRP2 protein, by abnormal interactions between LRP2 molecules and other proteins or other endogenous or exogenous substances. For example, cancer may be a LRP2-associated disease. The degree of inhibition of protein expression may be measured by western blotting.

"Therapeutically effective amount," as used herein, is intended to include the amount of an RNAi agent that, when administered to a cell or a patient for treating a CD320 associated disease or a LRP2 associated disease, is sufficient to effect treatment of the disease (e.g., by diminishing, ameliorating or maintaining the existing disease or one or more symptoms of disease or by preferentially causing the death of a disease cell as compared to a non-disease cell). The "therapeutically effective amount" may vary depending on the RNAi agent, how the agent is administered, the disease and its severity and the history, age, weight, family history, genetic makeup, stage of pathological processes mediated by CD320 or LRP2 expression, the types of preceding or concomitant treatments, if any, and other individual characteristics of the patient to be treated.

"Prophylactically effective amount," as used herein, is intended to include the amount of an RNAi agent that, when administered to a subject who does not yet experience or display symptoms of a CD320 associated disease or a LRP2 associated disease, but who may be predisposed to the disease, is sufficient to prevent or ameliorate the disease or one or more symptoms of the disease. Ameliorating the disease includes slowing the course of the disease or reducing the severity of later-developing disease. The "prophylactically effective amount" may vary depending on the RNAi agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylactically effective amount" also includes an amount of an RNAi agent that produces some desired local or systemic effect at a reasonable benefit/risk ratio applicable to any treatment. RNAi agents employed in the methods of the present invention may be administered in a sufficient amount to produce a reasonable benefit/risk ratio applicable to such treatment.

Pharmaceutical Compositions

The methods described herein include administration of a LRP2 inhibiting composition and/or a CD320 inhibiting composition, e.g., a first siRNA targeting a CD320 gene and/or a second siRNA targeting a LRP2 gene. In some embodiments, the LRP2 inhibiting composition and/or the CD320 inhibiting composition is a pharmaceutical composition.

The methods described herein also include administration of one or multiple LRP2 inhibiting compositions and/or one or multiple CD320 inhibiting compositions, e.g., one or more siRNAs targeting a CD320 gene and/or one or more siRNAs targeting an LRP2 gene. It is understood that such compositions could be chemically modified in a variety of ways and that such modifications need not be identical in compositional mixtures. In some embodiments, the LRP2 inhibiting composition and/or the CD320 inhibiting composition is a pharmaceutical composition.

The pharmaceutical compositions of the present invention may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g., intraparenchymal, intrathecal or intraventricular, administration.

The compositions can be delivered in a manner to target a particular tissue, such as the lung cells or breast cells or brain cells or bladder cells or uterine cells or cervix cells or prostate cells. Pharmaceutical compositions can be delivered by injection directly into the brain. The injection can be by stereotactic injection into a particular region of the brain (e.g., the substantia nigra, cortex, hippocampus, striatum, or globus pallidus), or the dsRNA can be delivered into multiple regions of the central nervous system (e.g., into multiple regions of the brain, and/or into the spinal cord). The dsRNA can also be delivered into diffuse regions of the brain (e.g., diffuse delivery to the cortex of the brain). In general siRNAs are administered 1) by intratumoral injection, 2) by systemic injection, 3) by slow release from an implanted polymer. Other tissue specificity could be achieved by antibody or small molecule conjugation, or by a tissue-specific delivery device (e.g., a catheter can be used to deliver to the bladder).

In one embodiment, an RNAi targeting either LRP2 or the CD320 can be delivered by way of a cannula or other delivery device having one end implanted in a tissue. The cannula can be connected to a reservoir of the RNAi composition. The flow or delivery can be mediated by a pump, e.g., an osmotic pump or minipump. In one embodiment, a pump and reservoir are implanted in an area distant from the tissue, e.g., in the abdomen, and delivery is affected by a conduit leading from the pump or reservoir to the site of release.

Accordingly, in some embodiments, the pharmaceutical compositions described herein comprise one or more pharmaceutically acceptable excipients. The pharmaceutical compositions described herein are formulated for administration to a subject.

As used herein, a pharmaceutical composition or medicament includes a pharmacologically effective amount of at least one of the described RNAi agents and one or more pharmaceutically acceptable excipients. Pharmaceutically acceptable excipients (excipients) are substances other than the Active Pharmaceutical Ingredient (API, therapeutic product, e.g., CD320 RNAi agent or LRP2 RNAi agent) that are intentionally included in the drug delivery system. Excipients do not exert or are not intended to exert a therapeutic effect at the intended dosage. Excipients can act to a) aid in processing of the drug delivery system during manufacture, b) protect, support, or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor.RTM. ELTM (BASF, Parsippany, N.J.) or phosphate buffered saline (PBS). The composition, understood to include formulations and drug delivery systems, should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Dosage and Timing

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the LRP2 inhibiting composition and or the CD320-inhibiting compositions encompassed by the invention can be made using conventional methodologies or on the basis of in vivo testing using an appropriate animal model, as described elsewhere herein.

In general, a suitable dose of a pharmaceutical composition of the LRP2 inhibiting composition and/or the CD320-inhibiting composition will be in the range of 0.01 to 300.0 milligrams per kilogram body weight of the recipient per day, generally in the range of 1 to 50 mg per kilogram body weight per day.

For example, the LRP2 inhibiting composition and/or the CD320-inhibiting composition can be an siRNA composition of one or more siRNAs, and can be administered at, 0.01 mg/kg, 0.05 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.628 mg/kg, 2 mg/kg, 3 mg/kg, 5.0 mg/kg, 10 mg/kg, 20 mg/kg, 30 mg/kg, 40 mg/kg, 50 mg/kg, 100 mg/kg, 200 mg/kg, 400 mg/kg per single dose. In another embodiment, the dosage is between 0.15 mg/kg and 0.3 mg/kg. For example, the LRP2 and/or the CD320-inhibiting composition can be administered at a dose of 0.15 mg/kg, 0.2 mg/kg, 0.25 mg/kg, or 0.3 mg/kg. In an embodiment, the LRP2 and/or the CD320-inhibiting composition is administered at a dose of 0.3 mg/kg.

The pharmaceutical composition may be administered once daily, or once or twice every 5, 10, 15, 20, 21, 22, 23, 24, 25, 26, 27, 28, 29, or 30 days. The dosage unit can be compounded for delivery over several days, e.g., using a conventional sustained release formulation which provides sustained release of the LRP2 inhibiting composition and/or the CD320-inhibiting composition over a several day period. Sustained release formulations are well known in the art and are particularly useful for delivery of agents at a particular site, such as could be used with the agents of the present invention.

In an embodiment, the LRP2-inhibiting composition and/or the CD320-inhibiting composition is dependent upon the tumor cell line, and the dosage is 0.3 mg/kg, and wherein the dose is administered once every 21 days. In another embodiment, the effective amount is 0.3 mg/kg and the effective amount is administered once every 21 days via a 70 minute infusion of 1 mL/min for 15 minutes followed by 3 mL/min for 55 minutes. In another embodiment, the effective amount is 0.3 mg/kg and the effective amount is administered at two doses every 21-28 days via a 60 minute infusion of 3.3 mL/min, or via a 70 minute infusion of 1.1 mL/min for 15 minutes followed by 3.3 mL/min for 55 minutes A dosage of a LRP2-inhibiting composition and/or the CD320-inhibiting composition can be adjusted for treatment A LRP2-inhibiting composition and/or the CD320-inhibiting composition can be administered in combination with other known agents effective in treatment of pathological processes mediated by target gene expression.

In another embodiment, the pharmaceutical composition is formulated for administration according to a dosage regimen described herein, e.g., not more than once every four weeks, not more than once every three weeks, not more than once every two weeks, or not more than once every week. In another embodiment, the administration of the pharmaceutical composition can be maintained for a month or longer, e.g., one, two, three, or six months, or one year or longer.

In embodiments of the pharmaceutical compositions described herein, the RNAi (e.g., dsRNA) is administered with a buffer solution. In embodiments, the buffer solution comprises acetate, citrate, prolamine, carbonate, or phosphate or any combination thereof. In embodiments, the buffer solution is phosphate buffered saline (PBS).

In embodiments of the pharmaceutical compositions described herein, the composition is administered intravenously.

In embodiments of the pharmaceutical compositions described herein, the composition is administered subcutaneously.

In certain embodiments, a pharmaceutical composition, e.g., a composition described herein, includes a lipid formulation. In embodiments, the composition is administered intravenously.

In some embodiments, a pharmaceutical composition, e.g., a composition described herein, includes a cationic polyamine formulation or nanoparticle (e.g., JetPEI). In some embodiments, the composition is administered intravenously.

In another embodiment, the pharmaceutical composition is formulated for administration according to a dosage regimen described herein, e.g., not more than once every four weeks, not more than once every three weeks, not more than once every two weeks, or not more than once every week. In another embodiment, the administration of the pharmaceutical composition can be maintained for a month or longer, e.g., one, two, three, or six months, or one year or longer.

In another embodiment, a composition containing an RNAi agent featured in the invention, e.g., a dsRNA targeting LRP2 or CD320, is administered with a non-RNAi therapeutic agent, such as an agent known to treat a cancer such as lung cancer. In another embodiment, a composition containing an RNAi agent featured in the invention, e.g., a dsRNA targeting LRP2 and/or CD320, is administered along with a non-RNAi therapeutic regimen, such as radiation, chemotherapy, immunotherapy, photodynamic therapy or a combination thereof.

In an aspect provided herein is a method of inhibiting LRP2 and/or CD320 expression in a cell, the method comprising: (a) introducing into the cell an RNAi agent (e.g., a dsRNA) described herein and (b) maintaining the cell of step (a) for a time sufficient to obtain degradation of the mRNA transcript of an LRP2 gene and/or CD320 gene, thereby inhibiting expression of the LRP2 gene and/or CD320 gene in the cell.

In an aspect provided herein is a method for reducing or inhibiting the expression of LRP2 gene and/or CD320 genes in a cell. The method includes: (a) introducing into the cell one or more complimentary double-stranded ribonucleic acid (dsRNA) molecules, in which one sequence is designated the sense strand and the other sequence the anti-sense strand, and wherein the anti-sense strand has significant complementarity to a portion of mRNA encoding for LRP2 or CD320. The complimentary region is 15-30 nucleotides in length, and generally 19-24 nucleotides in length, and the dsRNA, upon entering a cell expressing LRP2 and/or CD320, inhibits the expression of the LRP2 protein and/or CD320 protein by at least 10%, e.g., at least 20%, at least 30%, at least 40% or more; (b) single or repeated treatment of the cell with dsRNAs, as described in part (a), so as to maintain the inhibition of LRP2 and/or CD320 protein expression over a desired period of time by at least 10%, e.g., at least 20%, at least 30%, at least 40% or more.

In embodiments of the foregoing methods of inhibiting LRP2 and/or CD320 expression in a cell, the cell is treated ex vivo, in vitro, or in vivo. In embodiments, the cell is a melanoma, glioblastoma, lung carcinoma, triple negative breast carcinoma, renal carcinoma, pancreatic carcinoma, hepatocellular carcinoma, ovarian carcinoma and prostate carcinoma.

In some embodiments, the cell is present in a subject in need of treatment, prevention and/or management of a CD320-associated disease or a LRP2-associated disease.

In embodiments, the expression of LRP2 and/or CD320 is inhibited by at least 30%.

In embodiments, the RNAi (e.g., dsRNA) has an $IC_{50}$ in the range of 0.01-50 nM.

In embodiments, the RNAi (e.g., dsRNA) has an $IC_{50}$ in the range of 0.01-1 nM.

In certain embodiments, the cell is a mammalian cell (e.g., a human, non-human primate, or rodent cell).

In one embodiment, the cell is treated ex vivo, in vitro, or in vivo (e.g., the cell is present in a subject (e.g., a patient in need of treatment, prevention and/or management of a disorder related to LRP2 and/or CD320 expression).

In one embodiment, the subject is a mammal (e.g., a human) at risk, or diagnosed with a proliferation disorder.

In embodiments, the RNAi (e.g., dsRNA) is formulated as an lipid nanoparticle (LNP) polyplex (polyamine) formulation.

In embodiments, RNAi (e.g., dsRNA) is administered at a dose of 0.05001-500.01 mg/kg.

In embodiments, the RNAi (e.g., dsRNA) is administered at a concentration of 0.01 mg/kg-50.1 mg/kg bodyweight of the subject.

In embodiments, the RNAi (e.g., dsRNA) is formulated as an LNP formulation and is administered at a dose of 0.050.1-50.5 mg/kg.

In embodiments, the RNAi (e.g., dsRNA) has an $IC_{50}$ in the range of 0.01-10 nM.

In embodiments, the RNAi (e.g., dsRNA) or composition comprising the RNAi is administered according to a dosing regimen. In embodiments, the RNAi (e.g., dsRNA) or composition comprising the RNAi is administered as a single dose or at multiple doses, e.g., according to a dosing regimen.

The term "sample," as used herein, includes a collection of fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from a tumor. In preferred embodiments, a "sample derived from a subject" refers to blood or plasma drawn from the subject. In further embodiments, a "sample derived from a subject" refers to tissue biopsy derived from the subject.

In one embodiment, an RNAi (e.g., a dsRNA) featured herein includes a first sequence of a dsRNA that is selected from the group consisting of the sense sequences of Table 1 and a second sequence that is selected from the group consisting of the corresponding antisense sequences of Table 1. It is understood that the suffix A (e.g., OSC17A) represents the antisense strand whereas the suffix S (e.g., OSC17S) represents the sense strand. In those instances when we refer to an siRNA with no suffix (e.g., OSC17), we mean that to indicate the dsRNA comprised of the antisense and sense strands corresponding to that number (e.g., OSC17A paired with OSC17S).

In some embodiments the RNAi is from about 15 to about 25 nucleotides in length, and in other embodiments the RNAi is from about 25 to about 30 nucleotides in length. An RNAi targeting CD320, upon contact with a cell expressing CD320, inhibits the expression of a CD320 gene by at least 10%, at least 20%, at least 25%, at least 30%, at least 35% or at least 40% or more, such as when assayed by a method as described herein. In one embodiment, the RNAi targeting CD320 is formulated in a stable nucleic acid lipid particle (SNALP).

In some embodiments the RNAi is from about 15 to about 25 nucleotides in length, and in other embodiments the RNAi is from about 25 to about 30 nucleotides in length. An RNAi targeting LRP2, upon contact with a cell expressing LRP2, inhibits the expression of a LRP2 gene by at least 10%, at least 20%, at least 25%, at least 30%, at least 35% or at least 40% or more, such as when assayed by a method as described herein. In one embodiment, the RNAi targeting LRP2 is formulated in a stable nucleic acid lipid particle (SNALP).

In some embodiments the RNAi is from about 15 to about 25 nucleotides in length, and in other embodiments the RNAi is from about 25 to about 30 nucleotides in length. An RNAi targeting CD320, upon contact with a cell expressing CD320, inhibits the expression of a CD320 gene by at least 10%, at least 20%, at least 25%, at least 30%, at least 35% or at least 40% or more, such as when assayed by a method as described herein. In one embodiment, the RNAi targeting CD320 is formulated as a complex, which may exist as a nanoparticle, with a cationic polyamine.

In some embodiments the RNAi is from about 15 to about 25 nucleotides in length, and in other embodiments the RNAi is from about 25 to about 30 nucleotides in length. An RNAi targeting LRP2, upon contact with a cell expressing LRP2, inhibits the expression of a LRP2 gene by at least 10%, at least 20%, at least 25%, at least 30%, at least 35% or at least 40% or more, such as when assayed by a method as described herein. In one embodiment, the RNAi targeting LRP2 is formulated as a complex, which may exist as a nanoparticle, with a cationic polyamine.

Referring now to Table 1—DNA sequences are illustrated, which are subsequently transcribed into shRNA, which hence targets the CD320 or LRP2 mRNA for destruction in the cell. shRNA sequences used in lentiviral vectors illustrates the sequences that were used to target the CD320 sequence coding for the CD320 protein and the LRP2 sequence coding for the LRP2 protein. The Each vector that carried a shRNA coding sequence also contained a unique drug resistance gene which would allow for selecting those cells that had taken up the shRNA as those cells that had not taken up the shRNA having the unique drug resistance gene would not survive. On day 2, drug selection was started. On day 3, the cells were harvested and plated in a new dish. Only the cells with a drug resistance gene, i.e., those cells that had taken up shRNA virus particles would survive this re-plating procedure. From day 4 on, each culture was closely observed for cell growth. The cells that were infected with the irrelevant control shRNA kept on growing as expected (since the shRNA was essentially a non-functional shRNA)—data not shown. The results for the cell lines that took up the CD320+LRP2 shRNAs are shown in Table 1.

TABLE 1

| Name | Target | Sense Sequence | Anti-Sense Sequence | Location in DNA |
|---|---|---|---|---|
| shScramble | non-targeting control | CCTAAGGTTAAGTCGCCCTCG(SEQ ID NO. 941) | CGAGGGCGACTTAACCTTAGG(SEQ ID NO. 942) | N/A |
| shCD320-#27 | CD320 (NM_016579.3) | CCCTCAGAGACCTGAGCTCTT(SEQ ID NO. 943) | AAGAGCTCAGGTCTCTGAGGG(SEQ ID NO. 944) | 1006-1026 |
| shLRP2-#89 | LRP2 (NM_004525.2) | CCTGTAATAAACACTACTCTT(SEQ ID NO. 945) | AAGAGTAGTGTTTATTACAGG(SEQ ID NO. 946) | 2800-2820 |

The preliminary studies show that cancer cells are selectively killed by CD320 and LRP2 knockdown, while normal cells remain unaffected (Table 2).

Table 2 shows the effect of simultaneous knockdown of CD320 and LRP2 on cell viability.

TABLE 2

|  |  | Outcome of CD320/LRP2 knockdown | |
|---|---|---|---|
|  |  | Cell arrest/death | Alive |
| Cancer (Lung) | HCC15 | ✓ | |
|  | H157 | ✓ | |
|  | H358 | ✓ | |
|  | H1999 | ✓ | |
| Non-cancer | Normal fibroblast | | ✓ |
|  | LDLR mutant fibroblast | | ✓ |

Additional cancer cell lines were also treated with the compounds described herein to determine whether cancer cell lines were more susceptible to growth inhibition and toxicity as compared to non-cancer cells of the same origin. Cell lines from skin, prostate, and brain cancers were screened similarly to the experimental outline in FIG. 1. Table 3 summarizes the effects of simultaneous knockdown of CD320 and LRP2 in cancer and normal cells.

TABLE 3

| Cell | shSCR | shCD320 | shLRP2 | shCD320 + shLRP2 | Comments |
|---|---|---|---|---|---|
| Normal cells | | | | | |
| GM05659 | +++ | +++ | +++ | +++ | no effect of knockdown |
| GM00701 | +++ | ++ | +++ | +++ | cells grow very slow; hard to determine if any affect of knockdown |
| SAEC | pending | | | | |
| Lung cells | | | | | |
| HCC15 | +++ | + | + | + | cells strongly affected by knockdown |
| H157 | +++ | + | ++ | + | senescent phenotype |
| H358 | +++ | ++ | ++ | ++ | morphology changes; cells rounded |
| H1993 | +++ | ++ | ++ | + | cells rounded; morphology change |
| Melanoma Cells | | | | | |
| MDA-MB-4353 | +++ | ++ | + | + | morphology change; cells strongly affected by double knockdown |
| Prostate cells | | | | | |
| LncAP | +++ | ++ | ++ | + | cells rounded; morphology change |
| PC3 | +++ | +++ | ++ | +++ | cells minimally to not affected by knockdown |
| DU-145 | +++ | ++ | + | ++ | cells modestly affected by knockdown |
| Glioblastoma | | | | | |
| A172 | +++ | + | + | 0 | cells strongly affected by knockdown |
| U251MG | +++ | + | ++ | 0 | cells strongly affected by knockdown |
| U343 | +++ | +++ | ++ | +++ | cells modestly affected by LRP knockdown |
| T98G | +++ | +++ | ++ | ++ | cells slightly affected by knockdown |

+++ cells unaffected compared to shSCR (control)
++ cells modestly affected compared to shSCR (control)
+ cells significantly affected compared to shSCR (control)
0 vast majority of cells killed compared to shSCR (control)

The screening results showed that lung, prostate, skin, and brain cancer cell lines were growth-inhibited or killed by the simultaneous knockdown ("double knockdown") of CD320 and LRP2, while non-cancerous cells were unaffected.

Referring now to FIG. 2, representative pictures of the cells were taken to record their phenotypes after the double knockdown of CD320 and LRP2 and to illustrate the sensitivity of cancer cell lines to knockdown of the expression of CD320 and LRP2 proteins.

Normal cells (GM05659 fibroblasts) or cancer cells were infected with lentiviruses expressing shRNAs to control sequences or to shCD320 and shLRP2 as described in FIG. 1. The cells were grown as described in FIG. 1. On the ninth day after transfection with the lentiviruses, pictures of the cells were taken. The solid line ovals indicate healthy growth of normal fibroblast infected with shRNAs to CD320 and LRP2. The broken line ovals indicate unhealthy dying cells of cancer cell lines infected with shRNAs to CD320 and LRP2.

These results support use of the compounds as therapeutics based upon decreasing expression of CD320 and LRP2 protein preferentially resulting in detrimental effects in cancer cells as compared to non-cancer cells. The original experiments were conducted using shRNAs delivered by lentiviral vectors. Short inhibitory RNAs (siRNAs), having a sequence complimentary to a portion of the CD320 protein and/or the LRP2 protein were designed. The siRNAs can be chemically modified to increase their stability and potency and reduce their immunogenicity, and multiple platforms exist for their delivery in clinical applications.

siRNA sequences that efficiently knock down the protein levels of LRP2 and/or CD320 were designed and identified. Table 4 is a list of siRNA sequences complementary to mRNA for CD320 or LRP2 that were tested for their ability to knock down CD320 or LRP2 protein, respectively (see FIG. 3, FIG. 4, FIG. 5, FIG. 12, and FIG. 15).

TABLE 4

| ID | Passenger Sequence | Target | Size | Nucleotide start site | Location |
|---|---|---|---|---|---|
| OSS1 | CCUAAGGUU AAGUCGCCC UCG (SEQ ID NO. 947) | none | 21 | N/A | N/A |
| OSS2 | UGGUUUACA UGUUGUGUG A (SEQ ID NO. 948) | none | 19 | N/A | N/A |
| OSL231 | GGGCUCUAG GUUUGGUGC UAUCAAA (SEQ ID NO. 949) | LRP2 NM_004525.2 | 25 | 12537 | CDS |
| OSL245 | GGACUGAUA GGAGAGUCA UUGCAAA (SEQ ID NO. 950) | LRP2 NM_004525.2 | 25 | 12995 | CDS |
| OSL47 | CCUGUAAUA AACACUACU CUU (SEQ ID NO. 951) | LRP2 NM_004525.2 | 21 | 2800 | CDS |

TABLE 4-continued

| ID | Passenger Sequence | Target | Size | Nucleotide start site | Location |
|---|---|---|---|---|---|
| OSL104 | CCUUCUAUG AACCUGGCC UUA (SEQ ID NO. 952) | LRP2 NM_004525.2 | 21 | 5677 | CDS |
| OSL90 | GUGAUUUGA UUAUACGGC A (SEQ ID NO. 953) | LRP2 NM_004525.2 | 19 | 5126 | CDS |
| OSL119 | CCUCAAAUG GCUGUAGCA A (SEQ ID NO. 954) | LRP2 NM_004525.2 | 19 | 6266 | CDS |
| OSC17 | GAACUGACA AGAAACUGC GCAACUG (SEQ ID NO. 955) | CD320 NM_016579.3 | 25 | 422 | CDS |
| OSC47 | CCCUCAGAG ACCUGAGCU CUU (SEQ ID NO. 956) | CD320 NM_016579.3 | 21 | 1006 | 3'-UTR |

The list of all potential siRNA sequences is quite large. We have identified 340 potential siRNA sequences to LRP2 and 59 potential siRNA sequences to CD320. (See Table 5 and Table 6 for the complete list and Table 5A and Table 6A identify the target position and sequence that is complementary for each antisense sequence identified). In addition, chemical modifications can be made to these siRNA sequences to improve their stability and reduce their off-target effects. siRNA molecules are vulnerable to metabolic degradation, for example by RNase or DNase enzymes. Chemical modification of siRNA molecules by incorporation of one or more unnatural, that is, manmade, nucleotides within the sequence can render siRNAs resistant to such metabolic degradation and increase their biological half-life in the cell or in plasma. Moreover, the inclusion of manmade nucleotides at strategic locations within the siRNA sequence can decrease the immunogenicity of the siRNA and improve the selectivity for the guide strand over the passenger strand. Modified siRNA molecules may incorporate manmade nucleotides of a single type or may include multiple manmade nucleotides of different types. Manmade nucleotides may include, but are not limited to, those which contain chemical modifications to the ribose moiety or to the phosphate moieties (FIG. 19 and Table 7). Examples of manmade nucleotides include, but are not limited to, the structures shown in the Table 7. Moreover, modification of multiple structural elements may be combined. In addition, modification may be made to the nucleobase B, which, in addition to the natural RNA nucleobases (G, C, A, U), may include unnatural bases, such as those containing a sulfur atom (e.g., thiouracil).

TABLE 7

Nucleotide modifications corresponding to FIG. 19A

| Designation[a] | Y | X | Z | R | R' | B (nucleobase) |
|---|---|---|---|---|---|---|
| [2fN] | O | O | O | F | H | G, C, A, U, other |
| 2'-FANA | O | O | O | H | F | G, C, A, U, other |
| [mN] | O | O | O | OMe | H | G, C, A, U, other |
| 2'-MOE | O | O | O | $CH_2CH_2OMe$ | H | G, C, A, U, other |
| 2'-EA | O | O | O | $CH_2CH_2NH_2$ | H | G, C, A, U, other |
| 2'-DMEA | O | O | O | $CH_2CH_2NMe_2$ | H | G, C, A, U, other |
| 2'-DMAP | O | O | O | $CH_2CH_2CH_2NMe_2$ | H | G, C, A, U, other |
| * as in N1*N2 | O | S | O | OH | H | G, C, A, U, other |
| ** as in N1**N2 | S | S | O | OH | H | G, C, A, U, other |
| 2'-deoxy | O | O | O | H | H | G, C, A, U, other |
| 4'-S | O | O | S | H | H | G, C, A, U, other |
| F-SRNA | O | O | S | F | H | G, C, A, U, other |
| Me-SRNA | O | O | S | OMe | H | G, C, A, U, other |
| 4'-S-FANA | O | O | S | H | F | G, C, A, U, other |

[a] N designates an arbitrary ribonucleotide or deoxyribonucleotide or analogs thereof.

In some embodiments, chemical modification is made to the phosphodiester group which covalently connects two nucleotides, such that, for example, one or two oxygen atoms in that group are substituted with sulfur atoms, as indicated by a single or double asterisk between two nucleotides to represent the replacement of one or two oxygen atoms with sulfur in the phosphodiester (Table 7 and FIG. 19A). In some embodiments, the siRNA sequences may include other manmade nucleotides wherein further structural modifications have been made to the ribose moiety, such as the addition of bridging atoms that covalently link carbons 2' and 5' of the ribose moiety (FIG. 19B-C) or positions 1' and 2' of the ribose moiety (FIG. 19D), or alternatively, changes to the size of the sugar ring in a given nucleotide, for example, deletion of the bond between carbons 2' and 3' of the ribose moiety (FIG. 19E), or increasing the size of the sugar ring from five to six atoms (FIG. 19F-G).

TABLE 5

CD320

| OS ID | Antisense Strand (5' TO 3') | OSID | Sense Strand (5' TO 3') |
|---|---|---|---|
| OSC1A | UCUUAUCCCUGCGCACGCGCA[dT][dT] (SEQ ID NO 1) | OSC1S | UGCGCGUGCGCAGGGAUAAGA[dT][dT] (SEQ ID NO: 94) |
| OSC2A | UCUCUUAUCCCUGCGCACGCG[dT][dT] (SEQ ID NO 2) | OSC2S | CGCGUGCGCAGGGAUAAGAGA[dT][dT] (SEQ ID NO: 95) |
| OSC3A | AUGCUGUCCCCACAGCGGCGC[dT][dT] (SEQ ID NO 3) | OSC3S | GCGCCGCUGUGGGGACAGCAU[dT][dT] (SEQ ID NO: 96) |
| OSC4A | AUCCAACCGCCGCUCAUGCUG[dT][dT] (SEQ ID NO 4) | OSC4S | CAGCAUGAGCGGCGGUUGGAU[dT][dT] (SEQ ID NO: 97) |
| OSC5A | UGGAAAGCGGGCUCGCGGCGG[dT][dT] (SEQ ID NO 5) | OSC5S | CCGCCGCGAGCCCGCUUUCCA[dT][dT] (SEQ ID NO: 98) |
| OSC6A | AACUUGGUGGGUGGGCACGAG[dT][dT] (SEQ ID NO 6) | OSC6S | CUCGUGCCCACCCACCAAGUU[dT][dT] (SEQ ID NO: 99) |
| OSC7A | UGGAACUUGGUGGGUGGGCAC[dT][dT] (SEQ ID NO 7) | OSC7S | GUGCCCACCCACCAAGUUCCA[dT][dT] (SEQ ID NO: 100) |
| OSC8A | ACUGGAACUUGGUGGGUGGGC[dT][dT] (SEQ ID NO 8) | OSC8S | GCCCACCCACCAAGUUCCAGU[dT][dT] (SEQ ID NO: 101) |
| OSC9A | UAAGCCACUGGUGCGGCACUG[dT][dT] (SEQ ID NO 9) | OSC9S | CAGUGCCGCACCAGUGGCUUA[dT][dT] (SEQ ID NO: 102) |
| OSC10A | ACGCAUAAGCCACUGGUGCGG[dT][dT] (SEQ ID NO 10) | OSC10S | CCGCACCAGUGGCUUAUGCGU[dT][dT] (SEQ ID NO: 103) |
| OSC11A | UCCAAGUCCCUGUCGCAGCGC[dT][dT] (SEQ ID NO 11) | OSC11S | GCGCUGCGACAGGGACUUGGA[dT][dT] (SEQ ID NO: 104) |
| OSC12A | UCCUCAUCGCUGCCAUCGCUG[dT][dT] (SEQ ID NO 12) | OSC12S | CAGCGAUGGCAGCGAUGAGGA[dT][dT] (SEQ ID NO: 105) |
| OSC13A | UCACUGACGCCGGUGCAGGGG[dT][dT] (SEQ ID NO 13) | OSC13S | CCCCUGCACCGGCGUCAGUGA[dT][dT] (SEQ ID NO: 106) |

TABLE 5-continued

| CD320 | | | |
|---|---|---|---|
| OS ID | Antisense Strand (5' TO 3') | OSID | Sense Strand (5' TO 3') |
| OSC14A | UUGUCAGUUCCCCCAGAGCAG[dT][dT](SEQ ID NO 14) | OSC14S | CUGCUCUGGGGGAACUGACAA[dT][dT] (SEQ ID NO: 107) |
| OSC15A | UUCUUGUCAGUUCCCCCAGAG[dT][dT](SEQ ID NO 15) | OSC15S | CUCUGGGGGAACUGACAAGAA[dT][dT] (SEQ ID NO: 108) |
| OSC16A | AGUUUCUUGUCAGUUCCCCCA[dT][dT](SEQ ID NO 16) | OSC16S | UGGGGGAACUGACAAGAAACU[dT][dT] (SEQ ID NO: 109) |
| OSC17A-1 | CAGUUGCGCAGUUUCUUGUCAGUUC[dT][dT] (SEQ ID NO 17) | OSC17S-1 | GAACUGACAAGAAACUGCGCAACUG[dT][dT](SEQ ID NO: 110) |
| OSC17A-2 | CAGUUGCGCAGUUUCUUGUCAGUUC[dT]*[dT] (SEQ ID NO 18) | OSC17S-2 | GAACUGACAAGAAACUGCGCAACUG[dT]*[dT](SEQ ID NO: 111) |
| OSC17A-3 | [mC][mA][mG][mU][mU][mG][mC][mG][mC][mA][mG][mU][mU][mU][mC][mU][mU][mG][mU][mC][mA][mG][mU][mU][mC][dT]*[dT]] (SEQ ID NO 19) | OSC17S-3 | [mG][mA][mA][mC][mU][mG][mA][mC][mA][mA][mG][mA][mA][mA][mC][mU][mG][mC][mG][mC][mA][mA][mC][mU][mG][dT]*[dT](SEQ ID NO: 112) |
| OSC17A-4 | [mC][mA][mG][mU][mU][mG][mC][mG][mC][mA][mG][mU][mU][mU][mC][mU][mU][mG][mU][mC][mA][mG][mU][mU][mC][dT]*[dT]] (SEQ ID NO 20) | OSC17S-4 | [mG][mA][mA][mC][mU][mG][mA][mC][mA][mA][mG][mA][mA][mA][mC][mU][mG][mC][mG][mC][mA][mA][mC][mU][mG] (SEQ ID NO: 113) |
| OSC17A-5 | [mC][mA][mG][mU][mU][mG][mC][mG][mC][mA][mG][mU][mU][mU][mC][mU][mU][mG][mU][mC][mA][mG][mU][mU][mC]](SEQ ID NO 21) | OSC17S-5 | [mG][mA][mA][mC][mU][mG][mA][mC][mA][mA][mG][mA][mA][mA][mC][mU][mG][mC][mG][mC][mA][mA][mC][mU][mG][dT]*[dT](SEQ ID NO: 114) |
| OSC17A-6 | [mC][mA][mG][mU][mU][mG][mC][mG][mC][mA][mG][mU][mU][mU][mC][mU][mU][mG][mU][mC][mA][mG][mU][mU][mC]](SEQ ID NO 22) | OSC17S-6 | [mG][mA][mA][mC][mU][mG][mA][mC][mA][mA][mG][mA][mA][mA][mC][mU][mG][mC][mG][mC][mA][mA][mC][mU][mG] (SEQ ID NO: 115) |
| OSC17A-7 | [mC][mA][mG][mU][mU][mG][mC][mG][mC][mA][mG][mU][mU][mU][mC][mU][mU][mG][mU][mC][mA][mG][mU][mU][mC][dT]*[dT]] (SEQ ID NO 23) | OSC17S-7 | GAACUGACAAGAAACUGCGCAACUG[dT]*[dT] (SEQ ID NO: 116) |
| OSC17A-8 | [mC][2fA][mG][2fU][mU][2fG][mC][2fG][mC][2fA][mG][2fU][mU][2fU][mC][2fU][mU][2fG][mU][2fC][mA][2fG][mU][2fU][mC][dT]*[dT](SEQ ID NO 24) | OSC17S-8 | [2fG][mA][2fA][mC][2fU][mG][2fA][mC][2fA][mA][2fG][mA][2fA][mA][2fC][mU][2fG][mC][2fG][mC][2fA][mA][2fC][mU][2fG][dT]*[dT](SEQ ID NO: 117) |
| OSC17A-9 | [mC][2fA][mG][2fU][mU][2fG][mC][2fG][mC][2fA][mG][2fU][mU][2fU][mC][2fU][mU][2fG][mU][2fC][mA][2fG][mU][2fU][mC](SEQ ID NO 25) | OSC17S-9 | [2fG][mA][2fA][mC][2fU][mG][2fA][mC][2fA][mA][2fG][mA][2fA][mA][2fC][mU][2fG][mC][2fG][mC][2fA][mA][2fC][mU][2fG][dT]*[dT](SEQ ID NO: 118) |
| OSC17A-10 | [mC][2fA][mG][2fU][mU][2fG][mC][2fG][mC][2fA][mG][2fU][mU][2fU][mC][2fU][mU][2fG][mU][2fC][mA][2fG][mU][2fU][mC][dT]*[dT] (SEQ ID NO 26) | OSC17S-10 | [2fG][mA][2fA][mC][2fU][mG][2fA][mC][2fA][mA][2fG][mA][2fA][mA][2fC][mU][2fG][mC][2fG][mC][2fA][mA][2fC][mU][2fG](SEQ ID NO: 119) |
| OSC17A-11 | [mC][2fA][mG][2fU][mU][2fG][mC][2fG][mC][2fA][nnG][2fU][mU][2fU][mC][2fU][mU][2fG][mU][2fC][mA][2fG][mU][2fU][mC](SEQ ID NO 27) | OSC17S-11 | [2fG][mA][2fA][mC][2fU][mG][2fA][mC][2fA][mA][2fG][mA][2fA][mA][2fC][mU][2fG][mC][2fG][mC][2fA][mA][2fC][mU][2fG](SEQ ID NO: 120) |
| OSC17A-12 | [2fC][mA][2fG][mU][2fU][mG][2fC][mG][2fC][mA][2fG][mU][2fU][mU][2fC][mU][2fU][mG][2fU][mC][2fA][mG][2fU][mU][2fC][dT]*[dT] (SEQ ID NO 28) | OSC17S-12 | [mG][2fA][mA][2fC][mU][2fG][mA][2fC][mA][2fA][mG][2fA][mA][2fA][mC][2fU][mG][2fC][mG][2fC][mA][2fA][mC][2fU][mG][dT]*[dT](SEQ ID NO: 121) |
| OSC17A-13 | [2fC][mA][2fG][mU][2fU][mG][2fC][mG][2fC][mA][2fG][mU][2fU][mU][2fC][mU][2fU][mG][2fU][mC][2fA][mG][2fU][mU][2fC](SEQ ID NO 29) | OSC17S-13 | [mG][2fA][mA][2fC][mU][2fG][mA][2fC][mA][2fA][mG][2fA][mA][2fA][mC][2fU][mG][2fC][mG][2fC][mA][2fA][mC][2fU][mG](SEQ ID NO: 122) |
| OSC17A-14 | [mC][2fA][2fG][2fU][2fU][2fG][2fC][2fG][2fC][2fA][2fG][2fU][2fU][2fU][2fC][2fU][2fU][2fG][2fU][2fC][2fA][2fG][2fU][2fU][2fC][dT]*[dT](SEQ ID NO 30) | OSC17S-14 | [2fU][mG][2fA][mC][2fA][mA][2fG][mA][2fA][mA][2fC][mU][2fG][mC][2fG][mC][2fA][mA][2fC][mU][2fG][dT]*[dT](SEQ ID NO: 123) |

TABLE 5-continued

CD320

| OS ID | Antisense Strand (5' TO 3') | OSID | Sense Strand (5' TO 3') |
|---|---|---|---|
| OSC17A-15 | [mC][2fA][2fG][2fU][2fU][2fG][2fC][2fG][2fC][2fA][2fG][2fU][2fU][2fC][2fU][2fU][2fG][2fU][2fC][2fA][2fG][2fU][2fU][2fC][dT]*[dT](SEQ ID NO 31) | OSC17S-15 | [2fG][mA][2fA][mA][2fC][mU][2fG][mC][2fG][mC][2fA][mA][2fC][mU][2fG][dT]*[dT](SEQ ID NO: 124) |
| OSC17A-16 | [mC][2fA][mG][2fU][mU][2fG][mC][2fG][mC][2fA][G][2fU][mU][2fU][mC][2fU][mU][2fG][mU][2fC][mA][2fG][mU][2fU][mC][dT]*[dT](SEQ ID NO 32) | OSC17S-16 | [2fG][mA][2fA][mA][2fC][mU][2fG][mC][2fG][mC][2fA][mA][2fC][mU][2fG][dT]*[dT](SEQ ID NO: 125) |
| OSC17A-17 | [mC][2fA][mG][2fU][mU][2fG][mC][2fG][mC][2fA][mG][2fU][mU][2fU][mC][2fU][mU][2fG][mU][2fC][mA][2fG][mU](SEQ ID NO 33) | OSC17S-17 | [2fG][mA][2fA][mA][2fC][mU][2fG][mC][2fG][mC][2fA][mA][2fC][mU][2fG](SEQ ID NO: 126) |
| OSC17A-18 | [mC][2fA][mG][2fU][mU][2fG][mC][2fG][mC][2fA][mG][2fU][mU][2fU][mC][2fU][2fU][2fG][2fU][2fC][2fA][2fG][2fU](SEQ ID NO 34) | OSC17S-18 | [2fG][mA][2fA][mA][2fC][mU][2fG][mC][2fG][mC][2fA][mA][2fC][mU][2fG](SEQ ID NO: 127) |
| OSC18A | AUGCAGUCAUCGCUCAGCGUG[dT][dT](SEQ ID NO 35) | OSC18S | CACGCUGAGCGAUGACUGCAU[dT][dT](SEQ ID NO: 128) |
| OSC19A | AAUGCAGUCAUCGCUCAGCGU[dT][dT](SEQ ID NO 36) | OSC19S | ACGCUGAGCGAUGACUGCAUU[dT][dT](SEQ ID NO: 129) |
| OSC20A | UGGAAUGCAGUCAUCGCUCAG[dT][dT](SEQ ID NO 37) | OSC20S | CUGAGCGAUGACUGCAUUCCA[dT][dT](SEQ ID NO: 130) |
| OSC21A | AGUGGAAUGCAGUCAUCGCUC[dT][dT](SEQ ID NO 38) | OSC21S | GAGCGAUGACUGCAUUCCACU[dT][dT](SEQ ID NO: 131) |
| OSC22A | ACAGUCUGGGUGGCCGUCGCA[dT][dT](SEQ ID NO 39) | OSC22S | UGCGACGGCCACCCAGACUGU[dT][dT](SEQ ID NO: 132) |
| OSC23A | AUUGGUUCCACAGCCGAGCUC[dT][dT](SEQ ID NO 40) | OSC23S | GAGCUCGGCUGUGGAACCAAU[dT][dT](SEQ ID NO: 133) |
| OSC24A | UCUCAUUGGUUCCACAGCCGA[dT][dT](SEQ ID NO 41) | OSC24S | UCGGCUGUGGAACCAAUGAGA[dT][dT](SEQ ID NO: 134) |
| OSC25A | AUCUCAUUGGUUCCACAGCCG[dT][dT](SEQ ID NO 42) | OSC25S | CGGCUGUGGAACCAAUGAGAU[dT][dT](SEQ ID NO: 135) |
| OSC26A | AGGAUCUCAUUGGUUCCACAG[dT][dT](SEQ ID NO 43) | OSC26S | CUGUGGAACCAAUGAGAUCCU[dT][dT](SEQ ID NO: 136) |
| OSC27A | UGAGAGAGGUGACACUCUCCA[dT][dT](SEQ ID NO 44) | OSC27S | UGGAGAGUGUCACCUCUCUCA[dT][dT](SEQ ID NO: 137) |
| OSC28A | UGGUUGUGGCAUUCCUGAGAG[dT][dT](SEQ ID NO 45) | OSC28S | CUCUCAGGAAUGCCACAACCA[dT][dT](SEQ ID NO: 138) |
| OSC29A | UGGCAUUCCCGACAGAGGGGA[dT][dT](SEQ ID NO 46) | OSC29S | UCCCCUCUGUCGGGAAUGCCA[dT][dT](SEQ ID NO: 139) |
| OSC30A | AGGAUGUGGCAUUCCCGACAG[dT][dT](SEQ ID NO 47) | OSC30S | CUGUCGGGAAUGCCACAUCCU[dT][dT](SEQ ID NO: 140) |
| OSC31A | UUCCAGACUGGUCUCCGGCAG[dT][dT](SEQ ID NO 48) | OSC31S | CUGCCGGAGACCAGUCUGGAA[dT][dT](SEQ ID NO: 141) |
| OSC32A | AUAACCCCAUAGGCAGUUGGG[dT][dT](SEQ ID NO 49) | OSC32S | CCCAACUGCCUAUGGGGUUAU[dT][dT](SEQ ID NO: 142) |
| OSC33A | UUGCACUGAGCACCGCAGCAG[dT][dT](SEQ ID NO 50) | OSC33S | CUGCUGCGGUGCUCAGUGCAA[dT][dT](SEQ ID NO: 143) |
| OSC34A | AAAAGGAGGAGGGUGGCGGUG[dT][dT](SEQ ID NO 51) | OSC34S | CACCGCCACCCUCCUCCUUUU[dT][dT](SEQ ID NO: 144) |
| OSC35A | ACAAAAGGAGGAGGGUGGCGG[dT][dT](SEQ ID NO 52) | OSC35S | CCGCCACCCUCCUCCUUUUGU[dT][dT](SEQ ID NO: 145) |
| OSC36A | ACCAGUAACCCCAGUGGGCGG[dT][dT](SEQ ID NO 53) | OSC36S | CCGCCCACUGGGGUUACUGGU[dT][dT](SEQ ID NO: 146) |

TABLE 5-continued

CD320

| OS ID | Antisense Strand (5' TO 3') | OSID | Sense Strand (5' TO 3') |
|---|---|---|---|
| OSC37A | UUCAUGGCCACCAGUAACCCC[dT][dT] (SEQ ID NO 54) | OSC37S | GGGGUUACUGGUGGCCAUGAA[dT][dT] (SEQ ID NO: 147) |
| OSC38A | ACUCCUUCAUGGCCACCAGUA[dT][dT] (SEQ ID NO 55) | OSC38S | UACUGGUGGCCAUGAAGGAGU[dT][dT] (SEQ ID NO: 148) |
| OSC39A | UUCUGACAGCAGCAGGGACUC[dT][dT] (SEQ ID NO 56) | OSC39S | GAGUCCCUGCUGCUGUCAGAA[dT][dT] (SEQ ID NO: 149) |
| OSC40A | UCUGUUCUGACAGCAGCAGGG[dT][dT] (SEQ ID NO 57) | OSC40S | GGCUGCUGCUGUCAGAACAGA[dT][dT] (SEQ ID NO: 150) |
| OSC41A | UCUUCUGUUCUGACAGCAGCA[dT][dT] (SEQ ID NO 58) | OSC41S | UGCUGCUGUCAGAACAGAAGA[dT][dT] (SEQ ID NO: 151) |
| OSC42A | AGGUCUUCUGUUCUGACAGCA[dT][dT] (SEQ ID NO 59) | OSC42S | UGCUGUCAGAACAGAAGACCU[dT][dT] (SEQ ID NO: 152) |
| OSC43A | UUGUCCUCAGGGCAGCGAGGU[dT][dT] (SEQ ID NO 60) | OSC43S | ACCUCGCUGCCCUGAGGACAA[dT][dT] (SEQ ID NO: 153) |
| OSC44A | AAGUGCUUGUCCUCAGGGCAG[dT][dT] (SEQ ID NO 61) | OSC44S | CUGCCCUGAGGACAAGCACUU[dT][dT] (SEQ ID NO: 154) |
| OSC45A | UACCCAUCCGCAUCACUGCUC[dT][dT] (SEQ ID NO 62) | OSC45S | GAGCAGUGAUGCGGAUGGGUA[dT][dT] (SEQ ID NO: 155) |
| OSC46A | UCUCUGAGGGCUGGUGUGCCC[dT][dT] (SEQ ID NO 63) | OSC46S | GGGCACACCAGCCCUCAGAGA[dT][dT] (SEQ ID NO: 156) |
| OSC47A-1 | AAGAGCUCAGGUCUCUGAGGG[dT][dT] (SEQ ID NO 64) | OSC47S-1 | CCCUCAGAGACCUGAGCUCUU[dT][dT] (SEQ ID NO: 157) |
| OSC47A-2 | AAGAGCUCAGGUCUCUGAGGG[dT]*[dT] (SEQ ID NO 65) | OSC47S-2 | CCCUCAGAGACCUGAGCUCUU[dT]*[dT] (SEQ ID NO: 158) |
| OSC47A-3 | [mA][mA][mA][mG][mC][mU][mC][mA][mG][mG][mU][mC][mU][mC][mU][mG][mA][mG][mG][mG][dT]*[dT] (SEQ ID NO 66) | OSC47S-3 | [mC][mC][mC][mU][mC][mA][mG][mA][mG][mA][mC][mC][mU][mG][mA][mG][mC][mU][mC][mU][mU][dT]*[dT] (SEQ ID NO: 159) |
| OSC47A-4 | [mA][mA][mG][mA][mG][mC][mU][mC][mA][mG][mG][mU][mC][mU][mC][mU][mG][mA][mG][mG][mG][dT]*[dT] (SEQ ID NO 67) | OSC47S-4 | [mC][mC][mC][mU][mC][mA][mG][mA][mG][mA][mC][mC][mU][mG][mA][mG][mC][mU][mC][mU][mU] (SEQ ID NO: 160) |
| OSC47A-5 | [mA][mA][mG][mA][mG][mC][mU][mC][mA][mG][mG][mU][mC][mU][mC][mU][mG][mA][mG][mG][mG] (SEQ ID NO 68) | OSC47S-5 | [mC][mC][mC][mU][mC][mA][mG][mA][mG][mA][mC][mC][mU][mG][mA][mG][mC][mU][mC][mU][mU][dT]*[dT] (SEQ ID NO: 161) |
| OSC47A-6 | [mA][mA][mG][mA][mG][mC][mU][mC][mA][mG][mG][mU][mC][mU][mC][mU][mG][mA][mG][mG][mG] (SEQ ID NO 69) | OSC47S-6 | [mC][mC][mC][mU][mC][mA][mG][mA][mG][mA][mC][mC][mU][mG][mA][mG][mC][mU][mC][mU][mU] (SEQ ID NO: 162) |
| OSC47A-7 | [mA][mA][mG][mA][mG][mC][mU][mC][mA][mG][mG][mU][mC][mU][mC][mU][mG][mA][mG][mG][mG][dT]*[dT] (SEQ ID NO 70) | OSC47S-7 | CCCUCAGAGACCUGAGCUCUU[dT]*[dT] (SEQ ID NO: 163) |
| OSC47A-8 | [mA][2fA][mG][2fA][mG][2fC][mU][2fC][mA][2fG][mG][2fU][mC][2fU][mC][2fU][mG][2fA][mG][2fG][mG][dT]*[dT] (SEQ ID NO 71) | OSC47S-8 | [2fC][mC][2fC][mU][2fC][mA][2fG][mA][2fG][mA][2fC][mC][2fU][mG][2fA][mG][2fC][mU][2fC][mU][2fU][dT]*[dT] (SEQ ID NO: 164) |
| OSC47A-9 | [mA][2fA][mG][2fA][mG][2fC][mU][2fC][mA][2fG][mG][2fU][mC][2fU][mC][2fU][mG][2fA][mG][2fG][mG] (SEQ ID NO 72) | OSC47S-9 | [2fC][mC][2fC][mU][2fC][mA][2fG][mA][2fG][mA][2fC][mC][2fU][mG][2fA][mG][2fC][mU][2fC][mU][2fU][dT]*[dT] (SEQ ID NO: 165) |
| OSC47A-10 | [mA][2fA][mG][2fA][mG][2fC][mU][2fC][mA][2fG][mG][2fU][mC][2fU][mC][2fU][mG][2fA][mG][2fG][mG][dT]*[dT] (SEQ ID NO 73) | OSC47S-10 | [2fC][mC][2fC][mU][2fC][mA][2fG][mA][2fG][mA][2fC][mC][2fU][mG][2fA][mG][2fC][mU][2fC][mU][2fU] (SEQ ID NO: 166) |
| SC47A-11 | [mA][2fA][mG][2fA][mG][2fC][mU][2fC][mA][2fG][mG][2fU][mC][2fU][mC][2fU][mG][2fA][mG][2fG][mG] (SEQ ID NO 74) | OSC47S-11 | [2fC][mC][2fC][mU][2fC][mA][2fG][mA][2fG][mA][2fC][mC][2fU][mG][2fA][mG][2fC][mU][2fC][mU][2fU] (SEQ ID NO: 167) |

TABLE 5-continued

CD320

| OS ID | Antisense Strand (5' TO 3') | OSID | Sense Strand (5' TO 3') |
|---|---|---|---|
| OSC47A-12 | [2fA][mA][2fG][mA][2fG][mC][2fU][mC][2fA][mG][2fG][mU][2fC][mU][2fC][mU][2fG][mA][2fG][mG][2fG][dT]*[dT](SEQ ID NO 75) | OSC47S-12 | [mC][2fC][mC][2fU][mC][2fA][mG][2fA][mG][2fA][mC][2fC][mU][2fG][mA][2fG][mC][2fU][mC][2fU][mU][dT][dT]*(SEQ ID NO: 168) |
| OSC47A-13 | [2fA][mA][2fG][mA][2fG][mC][2fU][mC][2fA][mG][2fG][mU][2fC][mU][2fC][mU][2fG][mA][2fG][mG][2fG](SEQ ID NO 76) | OSC47S-13 | [2fC][mC][2fC][mU][2fC][mA][2fG][mA][2fG][mA][2fC][mC][2fU][mG][2fA][mG][2fC][mU][2fC][mU][2fU]-LIG-LINKER(SEQ ID NO: 169) |
| OSC47A-14 | [mA][2fA][2fG][mA][2fG][mC][2fU][mC][2fA][mG][2fG][mU][2fC][mU][2fC][mU][2fG][mA][2fG][mG][2fG](SEQ ID NO 77) | OSC47S-14 | [2fC][mC][2fC][mU][2fC][mA][2fG][mA][2fG][mA][2fC][mC][2fU][mG][2fA][mG][2fC][mU][2fC][mU][2fU][dT]*[dT](SEQ ID NO: 170) |
| OSC47A-15 | [mA][2fA][2fG][mA][2fG][mC][2fU][mC][2fA][mG][2fG][mU][2fC][mU][2fC][mU][2fG][mA][2fG][mG][2fG][dT]*[dT](SEQ ID NO 78) | OSC47S-15 | [2fG][mA][2fG][mA][2fC][mC][2fU][mG][2fA][mG][2fC][mU][2fC][mU][2fU][dT]*[dT](SEQ ID NO: 171) |
| OSC47A-16 | [2fA][mA][2fG][mA][2fG][mC][2fU][mC][2fA][mG][2fG][mU][2fC][mU][2fC][mU][2fG][mA][2fG][mG][2fG][dT]*[dT](SEQ ID NO 79) | OSC47S-16 | [2fG][mA][2fG][mA][2fC][mC][2fU][mG][2fA][mG][2fC][mU][2fC][mU][2fU][dT]*[dT](SEQ ID NO: 172) |
| OSC47A-17 | [2fA][mA][2fG][mA][2fG][mC][2fU][mC][2fA][mG][2fG][mU][2fC][mU][2fC][mU][2fG][mA][2fG][mG][2fG][dT]*[dT](SEQ ID NO 80) | OSC47S-17 | [2fG][mA][2fG][mA][2fC][mC][2fU][mG][2fA][mG][2fC][mU][2fC][mU][2fU](SEQ ID NO: 173) |
| OSC47A-18 | [2fA][mA][2fG][mA][2fG][mC][2fU][mC][2fA][mG][2fG][mU][2fC][mU][2fC][mU][2fG][2fA][2fG][2fG][2fG](SEQ ID NO 81) | OSC47S-18 | [2fG][mA][2fG][mA][2fC][mC][2fU][mG][2fA][mG][2fC][mU][2fC][mU][2fU](SEQ ID NO: 174) |
| OSC48A | AAGAGCUCAGGUCUCUGAGGG[dT][dT](SEQ ID NO 82) | OSC48S | CCCUCAGAGACCUGAGCUCUU[dT][dT] (SEQ ID NO: 175) |
| OSC49A | AGAAGAGCUCAGGUCUCUGAG[dT][dT](SEQ ID NO 83) | OSC49S | CUCAGAGACCUGAGCUCUUCU[dT][dT] (SEQ ID NO: 176) |
| OSC50A | AUAGGGAGUGUCCAGGGACCC[dT][dT](SEQ ID NO 84) | OSC50S | GGGUCCCUGGACACUCCCUAU[dT][dT] (SEQ ID NO: 177) |
| OSC51A | UCCAUAGGGAGUGUCCAGGGA[dT][dT](SEQ ID NO 85) | OSC51S | UCCCUGGACACUCCCUAUGGA[dT][dT] (SEQ ID NO: 178) |
| OSC52A | AUCUCCAUAGGGAGUGUCCAG[dT][dT](SEQ ID NO 86) | OSC52S | CUGGACACUCCCUAUGGAGAU[dT][dT] (SEQ ID NO: 179) |
| OSC53A | UCAGUUCUGGCUGUGGCAGGU[dT][dT](SEQ ID NO 87) | OSC53S | ACCUGCCACAGCCAGAACUGA[dT][dT] (SEQ ID NO: 180) |
| OSC54A | UUCUACCCCUGGGAGCUGCC[dT][dT](SEQ ID NO 88) | OSC54S | GGCAGCUCCCAGGGGUAGAA[dT][dT] (SEQ ID NO: 181) |
| OSC55A | AAGCACAGGGCCGUUCUACCC[dT][dT](SEQ ID NO 89) | OSC55S | GGGUAGAACGGCCCUGUGCUU[dT][dT] (SEQ ID NO: 182) |
| OSC56A | UGUCUUAAGCACAGGGCCGUU[dT][dT](SEQ ID NO 90) | OSC56S | AACGGCCCUGUGCUUAAGACA[dT][dT] (SEQ ID NO: 183) |
| OSC57A | AGUGUCUUAAGCACAGGGCCG[dT][dT](SEQ ID NO 91) | OSC57S | CGGCCCUGUGCUUAAGACACU[dT][dT] (SEQ ID NO: 184) |
| OSC58A | UUUUUUGAGGAUGUGAAGCAA[dT][dT] (SEQ ID NO 92) | OSC58S | UUGCUUCACAUCCUCAAAAAA[dT][dT] (SEQ ID NO: 185) |
| OSC59A | UUUUUUUGAGGAUGUGAAGCA[dT][dT] (SEQ ID NO 93) | OSC59S | UGCUUCACAUCCUCAAAAAAA[dT][dT] (SEQ ID NO: 186) |

TABLE 6

LRP2

| OS ID | Antisense Strand (5' TO 3') | OS ID | Sense Strand (5' TO 3') |
|---|---|---|---|
| OSL1A | UACUUUGUGAGCAAUCUUGAC[dT][dT](SEQ ID NO: 187) | OSL1S | GUCAAGAUUGCUCACAAAGUA[dT][dT] (SEQ ID NO: 561) |
| OSL2A | AUUCACUUGGGAUACACUGAC[dT][dT](SEQ ID NO: 188) | OSL2S | GUCAGUGUAUCCCAAGUGAAU[dT][dT] (SEQ ID NO: 562) |
| OSL3A | ACAUGAAAACUCAUUGUGCAA[dT][dT](SEQ ID NO: 189) | OSL3S | UUGCACAAUGAGUUUUCAUGU[dT][dT] (SEQ ID NO: 563) |
| OSL4A | UCUUUACAGUCAUCUUCUCCA[dT][dT](SEQ ID NO: 190) | OSL4S | UGGAGAAGAUGACUGUAAAGAUA[dT][dT] (SEQ ID NO: 564) |
| OSL5A | UAUCUUUACAGUCAUCUUCUC[dT][dT](SEQ ID NO: 191) | OSL5S | GAGAAGAUGACUGUAAAGAUA[dT][dT] (SEQ ID NO: 565) |
| OSL6A | AACAUUUAUGAACAUCAUGAG[dT][dT](SEQ ID NO: 192) | OSL6S | CUCAUGAUGUUCAUAAAUGUU[dT][dT] (SEQ ID NO: 566) |
| OSL7A | UCACAAACUUUAUAAAUGGAG[dT][dT](SEQ ID NO: 193) | OSL7S | CUCCAUUUAUAAAGUUUGUGA[dT][dT] (SEQ ID NO: 567) |
| OSL8A | AUCACAAACUUUAUAAAUGGA[dT][dT](SEQ ID NO: 194) | OSL8S | UCCAUUUAUAAAGUUUGUGAU[dT][dT] (SEQ ID NO: 568) |
| OSL9A | AUACUACAGUAUUUUCCGGUA[dT][dT](SEQ ID NO: 195) | OSL9S | UACCGGAAAAUACUGUAGUAU[dT][dT] (SEQ ID NO: 569) |
| OSL10A | UCAUACUACAGUAUUUUCCGG[dT][dT](SEQ ID NO: 196) | OSL10S | CCGGAAAAUACUGUAGUAUGA[dT][dT] (SEQ ID NO: 570) |
| OSL11A | ACAAAUUCCCCAUAUCUGGCA[dT][dT](SEQ ID NO: 197) | OSL11S | UGCCAGAUAUGGGGAAUUUGU[dT][dT] (SEQ ID NO: 571) |
| OSL12A | AAGAUAUACCCUUCUUCACAG[dT][dT](SEQ ID NO: 198) | OSL12S | CUGUGAAGAAGGGUAUAUCUU[dT][dT] (SEQ ID NO: 572) |
| OSL13A | UUAGCUUUGCAAUACUGUCCA[dT][dT](SEQ ID NO: 199) | OSL13S | UGGACAGUAUUGCAAAGCUAA[dT][dT] (SEQ ID NO: 573) |
| OSL14A | AUCAUUAGCUUUGCAAUACUG[dT][dT](SEQ ID NO: 200) | OSL14S | CAGUAUUGCAAAGCUAAUGAU[dT][dT] (SEQ ID NO: 574) |
| OSL15A | AAAGGAAUCAUUAGCUUUGCA[dT][dT](SEQ ID NO: 201) | OSL15S | UGCAAAGCUAAUGAUUCCUUU[dT][dT] (SEQ ID NO: 575) |
| OSL16A | AUGAAUAUCACCAAUUAACAA[dT][dT](SEQ ID NO: 202) | OSL16S | UUGUUAAUUGGUGAUAUUCAU[dT][dT] (SEQ ID NO: 576) |
| OSL17A | AAAAACCUUAUUUGCACGG[dT][dT](SEQ ID NO: 203) | OSL17S | CCGUGCAAAUAAGGUUUUUU[dT][dT] (SEQ ID NO: 577) |
| OSL18A | UGAAAAACCUUAUUUGCAC[dT][dT](SEQ ID NO: 204) | OSL18S | GUGCAAAUAAGGUUUUUUCA[dT][dT] (SEQ ID NO: 578) |
| OSL19A | AAUGUCAACUGAAAAACCUU[dT][dT](SEQ ID NO: 205) | OSL19S | AAGGUUUUUUCAGUUGACAUU[dT][dT] (SEQ ID NO: 579) |
| OSL20A | UAAUGUCAACUGAAAAAACCU[dT][dT](SEQ ID NO: 206) | OSL20S | AGGUUUUUUCAGUUGACAUUA[dT][dT] (SEQ ID NO: 580) |
| OSL21A | UUAAACCAUUAAUGUCAACUG[dT][dT](SEQ ID NO: 207) | OSL21S | CAGUUGACAUUAAUGGUUUAA[dT][dT] (SEQ ID NO: 581) |
| OSL22A | UAUUUAAACCAUUAAUGUCAA[dT][dT](SEQ ID NO: 208) | OSL22S | UUGACAUUAAUGGUUUAAAUA[dT][dT] (SEQ ID NO: 582) |
| OSL23A | UAGAUUUUAUUAUUAACCCAG[dT][dT](SEQ ID NO: 209) | OSL23S | CUGGGUUAAUAAUAAAAUCUA[dT][dT] (SEQ ID NO: 583) |
| OSL24A | AUAGAUUUUAUUAUUAACCCA[dT][dT](SEQ ID NO: 210) | OSL24S | UGGGUUAAUAAUAAAAUCUAU[dT][dT] (SEQ ID NO: 584) |
| OSL25A | AAAUUUACCAUAUCUAUGCGG[dT][dT](SEQ ID NO: 211) | OSL25S | CCGCAUAGAUAUGGUAAAUUU[dT][dT] (SEQ ID NO: 585) |

TABLE 6-continued

LRP2

| OS ID | Antisense Strand (5' TO 3') | OS ID | Sense Strand (5' TO 3') |
|---|---|---|---|
| OSL26A | AAGUUUUCAGUUAUAAGGGUA[dT][dT](SEQ ID NO: 212) | OSL26S | UACCCUUAUAACUGAAAACUU[dT][dT] (SEQ ID NO: 586) |
| OSL27A | AAUAAAUAACCAACAGUUGGG[dT][dT](SEQ ID NO: 213) | OSL27S | CCCAACUGUUGGUUAUUUAUU[dT][dT] (SEQ ID NO: 587) |
| OSL28A | AGAAAAAUAAAUAACCAACAG[dT][dT](SEQ ID NO: 214) | OSL28S | CUGUUGGUUAUUUAUUUUUCU[dT][dT] (SEQ ID NO: 588) |
| OSL29A | AUAUCAUAUCCAGAGUUACCC[dT][dT](SEQ ID NO: 215) | OSL29S | GGGUAACUCUGGAUAUGAUAU[dT][dT] (SEQ ID NO: 589) |
| OSL30A | AGUUUCAAUGUAAUCAAACCG[dT][dT](SEQ ID NO: 216) | OSL30S | CGGUUUGAUUACAUUGAAACU[dT][dT] (SEQ ID NO: 590) |
| OSL31A | UUACAGUUUCAAUGUAAUCAA[dT][dT](SEQ ID NO: 217) | OSL31S | UUGAUUACAUUGAAACUGUAA[dT][dT] (SEQ ID NO: 591) |
| OSL32A | AUAAGUUACAGUUUCAAUGUA[dT][dT](SEQ ID NO: 218) | OSL32S | UACAUUGAAACUGUAACUUAU[dT][dT] (SEQ ID NO: 592) |
| OSL33A | UCUUUACACGGAUUGGUAGCA[dT][dT](SEQ ID NO: 219) | OSL33S | UGCUACCAAUCCGUGUAAAGA[dT][dT] (SEQ ID NO: 593) |
| OSL34A | AAAAUCAAUCCCGACAAAGAA[dT][dT](SEQ ID NO: 220) | OSL34S | UUCUUUGUCGGGAUUGAUUUU[dT][dT] (SEQ ID NO: 594) |
| OSL35A | UCUGAAAAAAGAUAGUGCUG[dT][dT](SEQ ID NO: 221) | OSL35S | CAGCACUAUCUUUUUUCAGA[dT][dT] (SEQ ID NO: 595) |
| OSL36A | AUCUGAAAAAAGAUAGUGCU[dT][dT](SEQ ID NO: 222) | OSL36S | AGCACUAUCUUUUUUCAGAU[dT][dT] (SEQ ID NO: 596) |
| OSL37A | AAAAUCAUGUGUUUUGACAU[dT][dT](SEQ ID NO: 223) | OSL37S | AUGUCAAAACACAUGAUUUUU[dT][dT] (SEQ ID NO: 597) |
| OSL38A | UUUGCUUAAAAAUCAUGUGUU[dT][dT](SEQ ID NO: 224) | OSL38S | AACACAUGAUUUUUAAGCAAA[dT][dT] (SEQ ID NO: 598) |
| OSL39A | AACUUUCAACAUUUUCCACCC[dT][dT](SEQ ID NO: 225) | OSL39S | GGGUGGAAAAUGUUGAAAGUU[dT][dT] (SEQ ID NO: 599) |
| OSL40A | UUGAAAUCCAAUCAAAAGCCA[dT][dT](SEQ ID NO: 226) | OSL40S | UGGCUUUUGAUUGGAUUUCAA[dT][dT] (SEQ ID NO: 600) |
| OSL41A | UUUGAAAUCCAAUCAAAAGCC[dT][dT](SEQ ID NO: 227) | OSL41S | GGCUUUUGAUUGGAUUUCAA[dT][dT] (SEQ ID NO: 601) |
| OSL42A | UAGAGAUUCUUUGAAAUCCAA[dT][dT](SEQ ID NO: 228) | OSL42S | UUGGAUUUCAAAGAAUCUCUA[dT][dT] (SEQ ID NO: 602) |
| OSL43A | AUAGAGAUUCUUUGAAAUCCA[dT][dT](SEQ ID NO: 229) | OSL43S | UGGAUUUCAAAGAAUCUCUAU[dT][dT] (SEQ ID NO: 603) |
| OSL44A | UUUAAAUACUGAACUACUGUG[dT][dT](SEQ ID NO: 230) | OSL44S | CACAGUAGUUCAGUAUUUAAA[dT][dT] (SEQ ID NO: 604) |
| OSL45A | UAUUUAAAUACUGAACUACUG[dT][dT](SEQ ID NO: 231) | OSL45S | CAGUAGUUCAGUAUUUAAAUA[dT][dT] (SEQ ID NO: 605) |
| OSL46A | AUAGAUACCCGGCAAAAGGAU[dT][dT](SEQ ID NO: 232) | OSL46S | AUCCUUUUGCCGGGUAUCUAU[dT][dT] (SEQ ID NO: 606) |
| OSL47A | AAGAGUAGUGUUUAUUACAGG[dT][dT](SEQ ID NO: 233) | OSL47S | CCCCUGUAAUAAACACUACUC[dT][dT] (SEQ ID NO: 607) |
| OSL48A | AUCAAAAUAGGCAUCUACCCA[dT][dT](SEQ ID NO: 234) | OSL48S | UGGGUAGAUGCCUAUUUUGAU[dT][dT] (SEQ ID NO: 608) |
| OSL49A | UCAAUUUUAUCAAAAUAGGCA[dT][dT](SEQ ID NO: 235) | OSL49S | UGCCUAUUUUGAUAAAAUUGA[dT][dT] (SEQ ID NO: 609) |
| OSL50A | UAAAUGCUCUCCAAAGAUGGC[dT][dT](SEQ ID NO: 236) | OSL50S | GCCAUCUUUGGAGAGCAUUUA[dT][dT] (SEQ ID NO: 610) |

TABLE 6-continued

LRP2

| OS ID | Antisense Strand (5' TO 3') | OS ID | Sense Strand (5' TO 3') |
|---|---|---|---|
| OSL51A | UCAAAUGCAGUAUGUAAGCAA[dT][dT](SEQ ID NO: 237) | OSL51S | UUGCUUACAUACUGCAUUUGA[dT][dT] (SEQ ID NO: 611) |
| OSL52A | UUCAAAUGCAGUAUGUAAGCA[dT][dT](SEQ ID NO: 238) | OSL52S | UGCUUACAUACUGCAUUUGAA[dT][dT] (SEQ ID NO: 612) |
| OSL53A | UGAUUACAGGCGUUAGAACCA[dT][dT](SEQ ID NO: 239) | OSL53S | UGGUUCUAACGCCUGUAAUCA[dT][dT] (SEQ ID NO: 613) |
| OSL54A | UGUUAUCAUGACAAUCAUCGA[dT][dT](SEQ ID NO: 240) | OSL54S | UCGAUGAUUGUCAUGAUAACA[dT][dT] (SEQ ID NO: 614) |
| OSL55A | UUAUCACAGGUGUAUUGGGUG[dT][dT](SEQ ID NO: 241) | OSL55S | CACCCAAUACACCUGUGAUAA[dT][dT] (SEQ ID NO: 615) |
| OSL56A | AUUAUCACAGGUGUAUUGGGU[dT][dT](SEQ ID NO: 242) | OSL56S | ACCCAAUACACCUGUGAUAAU[dT][dT] (SEQ ID NO: 616) |
| OSL57A | AGUUCUUUGAGAUACACUGGU[dT][dT](SEQ ID NO: 243) | OSL57S | ACCAGUGUAUCUCAAAGAACU[dT][dT] (SEQ ID NO: 617) |
| OSL58A | UCGAAUUGCAGUUCUUUUCAU[dT][dT](SEQ ID NO: 244) | OSL58S | AUGAAAAGAACUGCAAUUCGA[dT][dT] (SEQ ID NO: 618) |
| OSL59A | UCAAUACAUCGAUGAUUGGGG[dT][dT](SEQ ID NO: 245) | OSL59S | CCCCAAUCAUCGAUGUAUUGA[dT][dT] (SEQ ID NO: 619) |
| OSL60A | AACGAUAGGUCAAUACAUCGA[dT][dT](SEQ ID NO: 246) | OSL60S | UCGAUGUAUUGACCUAUCGUU[dT][dT] (SEQ ID NO: 620) |
| OSL61A | ACAAACGAUAGGUCAAUACAU[dT][dT](SEQ ID NO: 247) | OSL61S | AUGUAUUGACCUAUCGUUUGU[dT][dT] (SEQ ID NO: 621) |
| OSL62A | UCAAAAACACCAUCACAACGA[dT][dT](SEQ ID NO: 248) | OSL62S | UCGUUGUGAUGGUGUUUUUGA[dT][dT] (SEQ ID NO: 622) |
| OSL63A | UCACAUUCCCAGAAGUUCGGG[dT][dT](SEQ ID NO: 249) | OSL63S | CCCGAACUUCUGGGAAUGUGA[dT][dT] (SEQ ID NO: 623) |
| OSL64A | AUCACAUUCCCAGAAGUUCGG[dT][dT](SEQ ID NO: 250) | OSL64S | CCGAACUUCUGGGAAUGUGAU[dT][dT] (SEQ ID NO: 624) |
| OSL65A | UGAUGAAGGGCAAGUCUUGGG[dT][dT](SEQ ID NO: 251) | OSL65S | CCCAAGACUUGCCCUUCAUCA[dT][dT] (SEQ ID NO: 625) |
| OSL66A | AGAAUCAUUGGCAAGUAAGAA[dT][dT](SEQ ID NO: 252) | OSL66S | UUCUUACUUGCCAAUGAUUCU[dT][dT] (SEQ ID NO: 626) |
| OSL67A | UAUCACAUUCAUCUAUGUCUU[dT][dT](SEQ ID NO: 253) | OSL67S | AAGACAUAGAUGAAUGUGAUA[dT][dT] (SEQ ID NO: 627) |
| OSL68A | AAUAUCACAUUCAUCUAUGUC[dT][dT](SEQ ID NO: 254) | OSL68S | GACAUAGAUGAAUGUGAUAUU[dT][dT] (SEQ ID NO: 628) |
| OSL69A | AACAUGUAGCCUGUAUCACAC[dT][dT](SEQ ID NO: 255) | OSL69S | GUGUGAUACAGGCUACAUGUU[dT][dT] (SEQ ID NO: 629) |
| OSL70A | UCACUUUCUAACAUGUAGCCU[dT][dT](SEQ ID NO: 256) | OSL70S | AGGCUACAUGUUAGAAAGUGA[dT][dT] (SEQ ID NO: 630) |
| OSL71A | AUCACUUUCUAACAUGUAGCC[dT][dT](SEQ ID NO: 257) | OSL71S | GGCUACAUGUUAGAAAGUGAU[dT][dT] (SEQ ID NO: 631) |
| OSL72A | AAUGUAAGAACCAUUCUCGAC[dT][dT](SEQ ID NO: 258) | OSL72S | GUCGAGAAUGGUUCUUACAUU[dT][dT] (SEQ ID NO: 632) |
| OSL73A | UACAAUGUAAGAACCAUUCUC[dT][dT](SEQ ID NO: 259) | OSL73S | GAGAAUGGUUCUUACAUUGUA[dT][dT] (SEQ ID NO: 633) |
| OSL74A | AAAAUCAACAGCUACAAUGUA[dT][dT](SEQ ID NO: 260) | OSL74S | UACAUUGUAGCUGUUGAUUUU[dT][dT] (SEQ ID NO: 634) |
| OSL75A | AUUGAAUCAAAAUCAACAGCU[dT][dT](SEQ ID NO: 261) | OSL75S | AGCUGUUGAUUUUGAUUCAAU[dT][dT] (SEQ ID NO: 635) |

TABLE 6-continued

LRP2

| OS ID | Antisense Strand (5' TO 3') | OS ID | Sense Strand (5' TO 3') |
|---|---|---|---|
| OSL76A | UAAUUGAAUCAAAAUCAACAG[dT][dT](SEQ ID NO: 262) | OSL76S | CUGUUGAUUUUGAUUCAAUUA[dT][dT] (SEQ ID NO: 636) |
| OSL77A | AAGAUACGACCACUAAUUGAA[dT][dT](SEQ ID NO: 263) | OSL77S | UUCAAUUAGUGGUCGUAUCUU[dT][dT] (SEQ ID NO: 637) |
| OSL78A | AGUUUCAGUCAAGAUGAUGCU[dT][dT](SEQ ID NO: 264) | OSL78S | AGCAUCAUCUUGACUGAAACU[dT][dT] (SEQ ID NO: 638) |
| OSL79A | AAUAGUUUCAGUCAAGAUGAU[dT][dT](SEQ ID NO: 265) | OSL79S | AUCAUCUUGACUGAAACUAUU[dT][dT] (SEQ ID NO: 639) |
| OSL80A | UAUUGCAAUAGUUUCAGUCAA[dT][dT](SEQ ID NO: 266) | OSL80S | UUGACUGAAACUAUUGCAAUA[dT][dT] (SEQ ID NO: 640) |
| OSL81A | UCUAUUGCAAUAGUUUCAGUC[dT][dT](SEQ ID NO: 267) | OSL81S | GACUGAAACUAUUGCAAUAGA[dT][dT] (SEQ ID NO: 641) |
| OSL82A | AAUCUAUUGCAAUAGUUUCAG[dT][dT](SEQ ID NO: 268) | OSL82S | CUGAAACUAUUGCAAUAGAUU[dT][dT] (SEQ ID NO: 642) |
| OSL83A | AUUUUGGAGACUUCAAUUGUU[dT][dT](SEQ ID NO: 269) | OSL83S | AACAAUUGAAGUCUCCAAAAU[dT][dT] (SEQ ID NO: 643) |
| OSL84A | UUAGGUUUUUACUAAUCAGCA[dT][dT](SEQ ID NO: 270) | OSL84S | UGCUGAUUAGUAAAAACCUAA[dT][dT] (SEQ ID NO: 644) |
| OSL85A | UCAUUCUGGGAUCUAAUGCUA[dT][dT](SEQ ID NO: 271) | OSL85S | UAGCAUUAGAUCCCAGAAUGA[dT][dT] (SEQ ID NO: 645) |
| OSL86A | UUCAUUCUGGGAUCUAAUGCU[dT][dT](SEQ ID NO: 272) | OSL86S | AGCAUUAGAUCCCAGAAUGAA[dT][dT] (SEQ ID NO: 646) |
| OSL87A | AGUAGAUGCUCAUUCAUUCUG[dT][dT](SEQ ID NO: 273) | OSL87S | CAGAAUGAAUGAGCAUCUACU[dT][dT] (SEQ ID NO: 647) |
| OSL88A | AUUAUAAUCACAAAAGUCCAU[dT][dT](SEQ ID NO: 274) | OSL88S | AUGGACUUUUGUGAUUAUAAU[dT][dT] (SEQ ID NO: 648) |
| OSL89A | UCCAUUAUAAUCACAAAAGUC[dT][dT](SEQ ID NO: 275) | OSL89S | GACUUUUGUGAUUAUAAUGGA[dT][dT] (SEQ ID NO: 649) |
| OSL90A | UGCCGUAUAAUCAAAUCAC[dT][dT](SEQ ID NO: 276) | OSL90S | GUGUGAUUUGAUUAUACGGCA[dT][dT] (SEQ ID NO: 650) |
| OSL91A | AUAUUAUACAUUACAACUGAC[dT][dT](SEQ ID NO: 277) | OSL91S | GUCAGUUGUAAUGUAUAAUAU[dT][dT] (SEQ ID NO: 651) |
| OSL92A | AUUGAAUAUUAUACAUUACAA[dT][dT](SEQ ID NO: 278) | OSL92S | UUGUAAUGUAUAAUAUUCAAU[dT][dT] (SEQ ID NO: 652) |
| OSL93A | AAUUUGGUUGUUUCGAAGGAU[dT][dT](SEQ ID NO: 279) | OSL93S | AUCCUUCGAAACAACCAAAUU[dT][dT] (SEQ ID NO: 653) |
| OSL94A | ACGGAAUUUGGUUGUUUCGAA[dT][dT](SEQ ID NO: 280) | OSL94S | UUCGAAACAACCAAAUUCCGU[dT][dT] (SEQ ID NO: 654) |
| OSL95A | UUACAGUUAUUAAGAAAGGUU[dT][dT](SEQ ID NO: 281) | OSL95S | AACCUUUCUUAAUAACUGUAA[dT][dT] (SEQ ID NO: 655) |
| OSL96A | UCCAAAAAUUAUAUGUUGCCU[dT][dT](SEQ ID NO: 282) | OSL96S | AGGCAACAUAUAAUUUUUGGA[dT][dT] (SEQ ID NO: 656) |
| OSL97A | UUCCAAAAAUUAUAUGUUGCC[dT][dT](SEQ ID NO: 283) | OSL97S | GGCAACAUAUAAUUUUUGGAA[dT][dT] (SEQ ID NO: 657) |
| OSL98A | UCUAAACCAUUCUGUAUCCCU[dT][dT](SEQ ID NO: 284) | OSL98S | AGGGAUACAGAAUGGUUUAGA[dT][dT] (SEQ ID NO: 658) |
| OSL99A | AUCUAAACCAUUCUGUAUCCC[dT][dT](SEQ ID NO: 285) | OSL99S | GGGAUACAGAAUGGUUUAGAU[dT][dT] (SEQ ID NO: 659) |
| OSL100A | UUCAACAUCUAAACCAUUCUG[dT][dT](SEQ ID NO: 286) | OSL100S | CAGAAUGGUUUAGAUGUUGAA[dT][dT] (SEQ ID NO: 660) |

TABLE 6-continued

LRP2

| OS ID | Antisense Strand (5' TO 3') | OS ID | Sense Strand (5' TO 3') |
|---|---|---|---|
| OSL101A | AUUUUCAACCCAAUAGAUGUA[dT][dT](SEQ ID NO: 287) | OSL101S | UACAUCUAUUGGGUUGAAAAU[dT][dT] (SEQ ID NO: 661) |
| OSL102A | UAUAGAAGCAAAUACUGUCCU[dT][dT](SEQ ID NO: 288) | OSL102S | AGGACAGUAUUUGCUUCUAUA[dT][dT] (SEQ ID NO: 662) |
| OSL103A | UAGAUAUAGAAGCAAAUACUG[dT][dT](SEQ ID NO: 289) | OSL103S | CAGUAUUUGCUUCUAUAUCUA[dT][dT] (SEQ ID NO: 663) |
| OSL104A | UAAGGCCAGGUUCAUAGAAGG[dT][dT](SEQ ID NO: 290) | OSL104S | CCUUCUAUGAACCUGGCCU[dT][dT](SEQ ID NO: 664) |
| OSL105A | UCUUGAAAUCCAAUCUAAGGC[dT][dT](SEQ ID NO: 291) | OSL105S | GCCUUAGAUUGGAUUUCAAGA[dT][dT] (SEQ ID NO: 665) |
| OSL106A | AUAAAGGUUUCUUGAAAUCCA[dT][dT](SEQ ID NO: 292) | OSL106S | UGGAUUUCAAGAAACCUUUAU[dT][dT] (SEQ ID NO: 666) |
| OSL107A | UCAAAACCUCGAUUGACUGAG[dT][dT](SEQ ID NO: 293) | OSL107S | CUCAGUCAAUCGAGGUUUUGA[dT][dT] (SEQ ID NO: 667) |
| OSL108A | UUCUGUAUCUGAUAUCUCCGU[dT][dT](SEQ ID NO: 294) | OSL108S | ACGGAGAUAUCAGAUACAGAA[dT][dT] (SEQ ID NO: 668) |
| OSL109A | UUUCUGUAUCUGAUAUCUCCG[dT][dT](SEQ ID NO: 295) | OSL109S | CGGAGAUAUCAGAUACAGAAA[dT][dT] (SEQ ID NO: 669) |
| OSL110A | UUUUUCUGUAUCUGAUAUCUC[dT][dT](SEQ ID NO: 296) | OSL110S | GAGAUAUCAGAUACAGAAAAA[dT][dT] (SEQ ID NO: 670) |
| OSL111A | AUCAAUGUUUUCUGUAUCUG[dT][dT](SEQ ID NO: 297) | OSL111S | CAGAUACAGAAAAACAUUGAU[dT][dT] (SEQ ID NO: 671) |
| OSL112A | AUAAAGGAAAGAAUCAUGGAC[dT][dT](SEQ ID NO: 298) | OSL112S | GUCCAUGAUUCUUUCCUUUAU[dT][dT] (SEQ ID NO: 672) |
| OSL113A | AAUAAAGGAAAGAAUCAUGGA[dT][dT](SEQ ID NO: 299) | OSL113S | UCCAUGAUUCUUUCCUUUAUU[dT][dT] (SEQ ID NO: 673) |
| OSL114A | UCAGUAUAAUAAAGGAAAGAA[dT][dT](SEQ ID NO: 300) | OSL114S | UUCUUUCCUUUAUUAUACUGA[dT][dT] (SEQ ID NO: 674) |
| OSL115A | UUUCAAUGACCUCAUACUGUU[dT][dT](SEQ ID NO: 301) | OSL115S | AACAGUAUGAGGUCAUUGAAA[dT][dT] (SEQ ID NO: 675) |
| OSL116A | AUUUGGAACAUUAUCUCUCAA[dT][dT](SEQ ID NO: 302) | OSL116S | UUGAGAGAUAAUGUUCCAAAU[dT][dT] (SEQ ID NO: 676) |
| OSL117A | AGAUUUGGAACAUUAUCUCUC[dT][dT](SEQ ID NO: 303) | OSL117S | GAGAGAUAAUGUUCCAAAUCU[dT][dT] (SEQ ID NO: 677) |
| OSL118A | UCAGAUUUGGAACAUUAUCUC[dT][dT](SEQ ID NO: 304) | OSL118S | GAGAUAAUGUUCCAAAUCUGA[dT][dT] (SEQ ID NO: 678) |
| OSL119A | UUGCUACAGCCAUUUGAGG[dT][dT](SEQ ID NO: 305) | OSL119S | CCUCAAAUGGCUGUAGCAA[dT][dT](SEQ ID NO: 679) |
| OSL120A | AUGAAAGAGUUAUAUGGAGAG[dT][dT](SEQ ID NO: 306) | OSL120S | CUCUCCAUAUAACUCUUUCAU[dT][dT] (SEQ ID NO: 680) |
| OSL121A | ACAAUGAAAGAGUUAUAUGGA[dT][dT](SEQ ID NO: 307) | OSL121S | UCCAUAUAACUCUUUCAUUGU[dT][dT] (SEQ ID NO: 681) |
| OSL122A | UGAAACAACAAUGAAAGAGUU[dT][dT](SEQ ID NO: 308) | OSL122S | AACUCUUUCAUUGUUGUUUCA[dT][dT] (SEQ ID NO: 682) |
| OSL123A | AUUGAAACAACAAUGAAAGAG[dT][dT](SEQ ID NO: 309) | OSL123S | CUCUUUCAUUGUUGUUUCAAU[dT][dT] (SEQ ID NO: 683) |
| OSL124A | AGCUAAAGCCUCUGAUUGCAG[dT][dT](SEQ ID NO: 310) | OSL124S | CUGCAAUCAGAGGCUUUAGCU[dT][dT] (SEQ ID NO: 684) |
| OSL125A | AAGCUAAAGCCUCUGAUUGCA[dT][dT](SEQ ID NO: 311) | OSL125S | UGCAAUCAGAGGCUUUAGCUU[dT][dT] (SEQ ID NO: 685) |

TABLE 6-continued

LRP2

| OS ID | Antisense Strand (5' TO 3') | OS ID | Sense Strand (5' TO 3') |
|---|---|---|---|
| OSL126A | ACAAUUCCAAGCUAAAGCCUC[dT][dT](SEQ ID NO: 312) | OSL126S | GAGGCUUUAGCUUGGAAUUGU[dT][dT] (SEQ ID NO: 686) |
| OSL127A | UGACAAUUCCAAGCUAAAGCC[dT][dT](SEQ ID NO: 313) | OSL127S | GGCUUUAGCUUGGAAUUGUCA[dT][dT] (SEQ ID NO: 687) |
| OSL128A | UGAAUGAUCUGACAAUUCCAA[dT][dT](SEQ ID NO: 314) | OSL128S | UUGGAAUUGUCAGAUCAUUCA[dT][dT] (SEQ ID NO: 688) |
| OSL129A | AUGUUCAUCAGAGAAGAUCCA[dT][dT](SEQ ID NO: 315) | OSL129S | UGGAUCUUCUCUGAUGAACAU[dT][dT] (SEQ ID NO: 689) |
| OSL130A | UAUUCCAUGUGUCACAAUGUU[dT][dT](SEQ ID NO: 316) | OSL130S | AACAUUGUGACACAUGGAAUA[dT][dT] (SEQ ID NO: 690) |
| OSL131A | ACUUCUAUCAGUGUUUCAGAA[dT][dT](SEQ ID NO: 317) | OSL131S | UUCUGAAACACUGAUAGAAGU[dT][dT] (SEQ ID NO: 691) |
| OSL132A | UAUUGAUCCGCAGAACUUCUA[dT][dT](SEQ ID NO: 318) | OSL132S | UAGAAGUUCUGCGGAUCAAUA[dT][dT] (SEQ ID NO: 692) |
| OSL133A | UGUUCUGGGAUCUACAACAA[dT][dT](SEQ ID NO: 319) | OSL133S | UUGUUGUAGAUCCCAAGAACA[dT][dT] (SEQ ID NO: 693) |
| OSL134A | AAAGAACGCUCAAUCUUUGGU[dT][dT](SEQ ID NO: 320) | OSL134S | ACCAAAGAUUGAGCGUUCUUU[dT][dT] (SEQ ID NO: 694) |
| OSL135A | UAAACGUAGCCAUCACUUCGG[dT][dT](SEQ ID NO: 321) | OSL135S | CCGAAGUGAUGGCUACGUUUA[dT][dT] (SEQ ID NO: 695) |
| OSL136A | AUCUAAAGAAUCAUCAACCCA[dT][dT](SEQ ID NO: 322) | OSL136S | UGGGUUGAUGAUUCUUUAGAU[dT][dT] (SEQ ID NO: 696) |
| OSL137A | UUAUAUCUAAAGAAUCAUCAA[dT][dT](SEQ ID NO: 323) | OSL137S | UUGAUGAUUCUUUAGAUAUAA[dT][dT] (SEQ ID NO: 697) |
| OSL138A | AUAGAAUUUUCAAAAACAGUG[dT][dT](SEQ ID NO: 324) | OSL138S | CACUGUUUUUGAAAAUUCUAU[dT][dT] (SEQ ID NO: 698) |
| OSL139A | UGAUAGAAUUUUCAAAAACAG[dT][dT](SEQ ID NO: 325) | OSL139S | CUGUUUUUGAAAAUUCUAUCA[dT][dT] (SEQ ID NO: 699) |
| OSL140A | UUUCAAAUUCCUAUCUACCCA[dT][dT](SEQ ID NO: 326) | OSL140S | UGGGUAGAUAGGAAUUUGAAA[dT][dT] (SEQ ID NO: 700) |
| OSL141A | UUUUCAAAUUCCUAUCUACCC[dT][dT](SEQ ID NO: 327) | OSL141S | GGGUAGAUAGGAAUUUGAAAA[dT][dT] (SEQ ID NO: 701) |
| OSL142A | AUAUUGUCUCUUAUCACUGUG[dT][dT](SEQ ID NO: 328) | OSL142S | CACAGUGAUAAGAGACAAUAU[dT][dT] (SEQ ID NO: 702) |
| OSL143A | UGAUAUUGUCUCUUAUCACUG[dT][dT](SEQ ID NO: 329) | OSL143S | CAGUGAUAAGAGACAAUAUCA[dT][dT] (SEQ ID NO: 703) |
| OSL144A | UGAAAUGGCACAAUUCUUGCC[dT][dT](SEQ ID NO: 330) | OSL144S | GGCAAGAAUUGUGCCAUUUCA[dT][dT] (SEQ ID NO: 704) |
| OSL145A | UGUUGAAAUGGCACAAUUCUU[dT][dT](SEQ ID NO: 331) | OSL145S | AAGAAUUGUGCCAUUUCAACA[dT][dT] (SEQ ID NO: 705) |
| OSL146A | AAUUUUCUGUUGAAAUGGCAC[dT][dT](SEQ ID NO: 332) | OSL146S | GUGCCAUUUCAACAGAAAAUU[dT][dT] (SEQ ID NO: 706) |
| OSL147A | AAAUUUUCUGUUGAAAUGGCA[dT][dT](SEQ ID NO: 333) | OSL147S | UGCCAUUUCAACAGAAAAUUU[dT][dT] (SEQ ID NO: 707) |
| OSL148A | AUUAGACAAGGCAAAGAUGAG[dT][dT](SEQ ID NO: 334) | OSL148S | CUCAUCUUUGCCUUGUCUAAU[dT][dT] (SEQ ID NO: 708) |
| OSL149A | ACAUUUAUUGUUUGGAAAGGU[dT][dT](SEQ ID NO: 335) | OSL149S | ACCUUUCCAAACAAUAAAUGU[dT][dT] (SEQ ID NO: 709) |
| OSL150A | AUCACUUACACUGUCAUAGUC[dT][dT](SEQ ID NO: 336) | OSL150S | GACUAUGACAGUGUAAGUGAU[dT][dT] (SEQ ID NO: 710) |

TABLE 6-continued

LRP2

| OS ID | Antisense Strand (5' TO 3') | OS ID | Sense Strand (5' TO 3') |
|---|---|---|---|
| OSL151A | UAGAUUCUAUCACUUACACUG[dT][dT](SEQ ID NO: 337) | OSL151S | CAGUGUAAGUGAUAGAAUCUA[dT][dT] (SEQ ID NO: 711) |
| OSL152A | AGUAGAUUCUAUCACUUACAC[dT][dT](SEQ ID NO: 338) | OSL152S | GUGUAAGUGAUAGAAUCUACU[dT][dT] (SEQ ID NO: 712) |
| OSL153A | UUUUGUGUGAAGUAGAUUCUA[dT][dT](SEQ ID NO: 339) | OSL153S | UAGAAUCUACUUCACACAAAA[dT][dT] (SEQ ID NO: 713) |
| OSL154A | UAAAUUUUGUGUGAAGUAGAU[dT][dT](SEQ ID NO: 340) | OSL154S | AUCUACUUCACACAAAAUUUA[dT][dT] (SEQ ID NO: 714) |
| OSL155A | UCUAGUAAUCCAGUCAAAGGC[dT][dT](SEQ ID NO: 341) | OSL155S | GCCUUUGACUGGAUUACUAGA[dT][dT] (SEQ ID NO: 715) |
| OSL156A | AAUUCUUCUAGUAAUCCAGUC[dT][dT](SEQ ID NO: 342) | OSL156S | GACUGGAUUACUAGAAGAAUU[dT][dT] (SEQ ID NO: 716) |
| OSL157A | UAAAUUCUUCUAGUAAUCCAG[dT][dT](SEQ ID NO: 343) | OSL157S | CUGGAUUACUAGAAGAAUUUA[dT][dT] (SEQ ID NO: 717) |
| OSL158A | AUAAAUUCUUCUAGUAAUCCA[dT][dT](SEQ ID NO: 344) | OSL158S | UGGAUUACUAGAAGAAUUUAU[dT][dT] (SEQ ID NO: 718) |
| OSL159A | AUAUACUGGCCAUAGAGAGUC[dT][dT](SEQ ID NO: 345) | OSL159S | GACUCUCUAUGGCCAGUAUAU[dT][dT] (SEQ ID NO: 719) |
| OSL160A | UUCUUUGUGUGUACAAGUCAG[dT][dT](SEQ ID NO: 346) | OSL160S | CUGACUUGUACACACAAAGAA[dT][dT] (SEQ ID NO: 720) |
| OSL161A | AAUUCUUUGUGUGUACAAGUC[dT][dT](SEQ ID NO: 347) | OSL161S | GACUUGUACACACAAAGAAUU[dT][dT] (SEQ ID NO: 721) |
| OSL162A | UCGGUAAAUUCUUUGUGUGUA[dT][dT](SEQ ID NO: 348) | OSL162S | UACACACAAAGAAUUUACCGA[dT][dT] (SEQ ID NO: 722) |
| OSL163A | UGUUACACUGUUGUUUCUGGU[dT][dT](SEQ ID NO: 349) | OSL163S | ACCAGAAACAACAGUGUAACA[dT][dT] (SEQ ID NO: 723) |
| OSL164A | AUUGUUACACUGUUGUUUCUG[dT][dT](SEQ ID NO: 350) | OSL164S | CAGAAACAACAGUGUAACAAU[dT][dT] (SEQ ID NO: 724) |
| OSL16A5 | AAACUGUUCACAAGGAUUGUU[dT][dT](SEQ ID NO: 351) | OSL165S | AACAAUCCUUGUGAACAGUUU[dT][dT] (SEQ ID NO: 725) |
| OSL166A | ACAUCGUUCACCAUUGUCCAC[dT][dT](SEQ ID NO: 352) | OSL166S | GUGGACAAUGGUGAACGAUGU[dT][dT] (SEQ ID NO: 726) |
| OSL167A | UGUUAUUGCACAUAAACUCCG[dT][dT](SEQ ID NO: 353) | OSL167S | CGGAGUUUAUGUGCAAUAACA[dT][dT] (SEQ ID NO: 727) |
| OSL168A | UCUGUUAUUGCACAUAAACUC[dT][dT](SEQ ID NO: 354) | OSL168S | GAGUUUAUGUGCAAUAACAGA[dT][dT] (SEQ ID NO: 728) |
| OSL169A | UUAUGACAUUUUGUGUAUCCA[dT][dT](SEQ ID NO: 355) | OSL169S | UGGAUACACAAAAUGUCAUAA[dT][dT] (SEQ ID NO: 729) |
| OSL170A | UGAAUUAUGACAUUUUGUGUA[dT][dT](SEQ ID NO: 356) | OSL170S | UACACAAAAUGUCAUAAUUCA[dT][dT] (SEQ ID NO: 730) |
| OSL171A | UUUGAAUUAUGACAUUUUGUG[dT][dT](SEQ ID NO: 357) | OSL171S | CACAAAAUGUCAUAAUUCAAA[dT][dT] (SEQ ID NO: 731) |
| OSL172A | UACAAAUAUUUGAAUUAUGAC[dT][dT](SEQ ID NO: 358) | OSL172S | GUCAUAAUUCAAAUAUUUGUA[dT][dT] (SEQ ID NO: 732) |
| OSL173A | AAAUAAACGCGAGGAAUACAA[dT][dT](SEQ ID NO: 359) | OSL173S | UUGUAUUCCUCGCGUUUAUUU[dT][dT] (SEQ ID NO: 733) |
| OSL174A | AAUAAGUAGGGUUUUCAUCAC[dT][dT](SEQ ID NO: 360) | OSL174S | GUGAUGAAAACCCUACUAUU[dT][dT] (SEQ ID NO: 734) |
| OSL175A | UCACAAUACCAAUGUUGAGGA[dT][dT](SEQ ID NO: 361) | OSL175S | UCCUCAACAUUGGUAUUGUGA[dT][dT] (SEQ ID NO: 735) |

TABLE 6-continued

LRP2

| OS ID | Antisense Strand (5' TO 3') | OS ID | Sense Strand (5' TO 3') |
|---|---|---|---|
| OSL176A | UGUUUCUUGAUCACAAUACCA[dT][dT](SEQ ID NO: 362) | OSL176S | UGGUAUUGUGAUCAAGAAACA[dT][dT] (SEQ ID NO: 736) |
| OSL177A | AACAAUCUGUUUCUUGAUCAC[dT][dT](SEQ ID NO: 363) | OSL177S | GUGAUCAAGAAACAGAUUGUU[dT][dT] (SEQ ID NO: 737) |
| OSL178A | UUUACACAGAGAAACUCGGAA[dT][dT](SEQ ID NO: 364) | OSL178S | UUCCGAGUUUCUCUGUGUAAA[dT][dT] (SEQ ID NO: 738) |
| OSL179A | AUUUACACAGAGAAACUCGGA[dT][dT](SEQ ID NO: 365) | OSL179S | UCCGAGUUUCUCUGUGUAAAU[dT][dT] (SEQ ID NO: 739) |
| OSL180A | UUCUGAUUCUCAUCGUAGCCG[dT][dT](SEQ ID NO: 366) | OSL180S | CGGCUACGAUGAGAAUCAGAA[dT][dT] (SEQ ID NO: 740) |
| OSL181A | AUUUUCAGAGCAAGUUCUCCU[dT][dT](SEQ ID NO: 367) | OSL181S | AGGAGAACUUGCUCUGAAAAU[dT][dT] (SEQ ID NO: 741) |
| OSL182A | AUAUCUUUGGGAUACACAGUC[dT][dT](SEQ ID NO: 368) | OSL182S | GACUGUGUAUCCCAAAGAUAU[dT][dT] (SEQ ID NO: 742) |
| OSL183A | AGGUAAACUGAUUCUGUUGGC[dT][dT](SEQ ID NO: 369) | OSL183S | GCCAACAGAAUCAGUUUACCU[dT][dT] (SEQ ID NO: 743) |
| OSL184A | AUAGAAACUGGUUAAGGUGUC[dT][dT](SEQ ID NO: 370) | OSL184S | GACACCUUAACCAGUUUCUAU[dT][dT] (SEQ ID NO: 744) |
| OSL185A | ACAAUAGAAACUGGUUAAGGU[dT][dT](SEQ ID NO: 371) | OSL185S | ACCUUAACCAGUUUCUAUUGU[dT][dT] (SEQ ID NO: 745) |
| OSL186A | UCAUCAAUAUCAACACAAGUC[dT][dT](SEQ ID NO: 372) | OSL186S | GACUUGUGUUGAUAUUGAUGA[dT][dT] (SEQ ID NO: 746) |
| OSL187A | AGAUGUAGGAGCCUAUUACAU[dT][dT](SEQ ID NO: 373) | OSL187S | AUGUAAUAGGCUCCUACAUCU[dT][dT] (SEQ ID NO: 747) |
| OSL188A | UCGAUGUUACUGUUUUGCCGG[dT][dT](SEQ ID NO: 374) | OSL188S | CCGGCAAAACAGUAACAUCGA[dT][dT] (SEQ ID NO: 748) |
| OSL189A | UUGCUAAAAUGAGAUAGGGU[dT][dT](SEQ ID NO: 375) | OSL189S | ACCCUAUCUCAUUUUAGCAA[dT][dT] (SEQ ID NO: 749) |
| OSL190A | AUUUCUCAAAUAGUAACGGUU[dT][dT](SEQ ID NO: 376) | OSL190S | AACCGUUACUAUUUGAGAAAU[dT][dT] (SEQ ID NO: 750) |
| OSL191A | AAUUUCUCAAAUAGUAACGGU[dT][dT](SEQ ID NO: 377) | OSL191S | ACCGUUACUAUUUGAGAAAUU[dT][dT] (SEQ ID NO: 751) |
| OSL192A | AAAUUUCUCAAAUAGUAACGG[dT][dT](SEQ ID NO: 378) | OSL192S | CCGUUACUAUUUGAGAAAUUU[dT][dT] (SEQ ID NO: 752) |
| OSL193A | AGUUAAAUUUCUCAAAUAGUA[dT][dT](SEQ ID NO: 379) | OSL193S | UACUAUUUGAGAAAUUUAACU[dT][dT] (SEQ ID NO: 753) |
| OSL194A | AUCUAUAGUUAAAUUUCUCAA[dT][dT](SEQ ID NO: 380) | OSL194S | UUGAGAAAUUUAACUAUAGAU[dT][dT] (SEQ ID NO: 754) |
| OSL195A | UAAAAAUAGCCAUCUAUAGUU[dT][dT](SEQ ID NO: 381) | OSL195S | AACUAUAGAUGGCUAUUUUA[dT][dT] (SEQ ID NO: 755) |
| OSL196A | AUCUAAUGCCACAACAUUGUC[dT][dT](SEQ ID NO: 382) | OSL196S | GACAAUGUUGUGGCAUUAGAU[dT][dT] (SEQ ID NO: 756) |
| OSL197A | AAUCCAAUACAAUCUCUUCUC[dT][dT](SEQ ID NO: 383) | OSL197S | GAGAAGAGAUUGUAUUGGAUU[dT][dT] (SEQ ID NO: 757) |
| OSL198A | ACAUUCUCUCAAUGACUUGCC[dT][dT](SEQ ID NO: 384) | OSL198S | GGCAAGUCAUUGAGAGAAUGU[dT][dT] (SEQ ID NO: 758) |
| OSL199A | AUGAUUGUCUCCUUGUUUGUC[dT][dT](SEQ ID NO: 385) | OSL199S | GACAAACAAGGAGACAAUCAU[dT][dT] (SEQ ID NO: 759) |
| OSL200A | AUUAUCACAGACUUGUUGGUU[dT][dT](SEQ ID NO: 386) | OSL200S | AACCAACAAGUCUGUGAUAAU[dT][dT] (SEQ ID NO: 760) |

TABLE 6-continued

LRP2

| OS ID | Antisense Strand (5' TO 3') | OS ID | Sense Strand (5' TO 3') |
|---|---|---|---|
| OSL201A | UUCAAAAAUGGUAAUAGCGAA[dT][dT](SEQ ID NO: 387) | OSL201S | UUCGCUAUUACCAUUUUUGAA[dT][dT] (SEQ ID NO: 761) |
| OSL202A | UCUUCAAAAAUGGUAAUAGCG[dT][dT](SEQ ID NO: 388) | OSL202S | CGCUAUUACCAUUUUUGAAGA[dT][dT] (SEQ ID NO: 762) |
| OSL203A | AUUUGUUUCCCUUUUCCACUG[dT][dT](SEQ ID NO: 389) | OSL203S | CAGUGGAAAAGGGAAACAAAU[dT][dT] (SEQ ID NO: 763) |
| OSL204A | AUUUGAUCCAUCAUAUUUGUU[dT][dT](SEQ ID NO: 390) | OSL204S | AACAAAUAUGAUGGAUCAAAU[dT][dT] (SEQ ID NO: 764) |
| OSL205A | UAUAUGGAUGGUACACAUGGA[dT][dT](SEQ ID NO: 391) | OSL205S | UCCAUGUGUACCAUCCAUAUA[dT][dT] (SEQ ID NO: 765) |
| OSL206A | AAAGAAGACGGUCUUCAUCAG[dT][dT](SEQ ID NO: 392) | OSL206S | CUGAUGAAGACCGUCUUCUUU[dT][dT] (SEQ ID NO: 766) |
| OSL207A | UGAAUUCUGUGAAGUUGUCAC[dT][dT](SEQ ID NO: 393) | OSL207S | GUGACAACUUCACAGAAUUCA[dT][dT] (SEQ ID NO: 767) |
| OSL208A | ACAAUGUCCACUUGUACACUG[dT][dT](SEQ ID NO: 394) | OSL208S | CGGUGUACAAGUGGACAUUGU[dT][dT] (SEQ ID NO: 768) |
| OSL209A | ACACAAUGUCCACUUGUACAC[dT][dT](SEQ ID NO: 395) | OSL209S | GUGUACAAGUGGACAUUGUGU[dT][dT] (SEQ ID NO: 769) |
| OSL210A | UUUUUGCAUUCGAACAUAGUA[dT][dT](SEQ ID NO: 396) | OSL210S | UACUAUGUUCGAAUGCAAAAA[dT][dT] (SEQ ID NO: 770) |
| OSL211A | AUGGUUUUUGCAUUCGAACAU[dT][dT](SEQ ID NO: 397) | OSL211S | AUGUUCGAAUGCAAAAACCAU[dT][dT] (SEQ ID NO: 771) |
| OSL212A | AUACAAACAUGGUUUUUGCAU[dT][dT](SEQ ID NO: 398) | OSL212S | AUGCAAAAACCAUGUUUGUAU[dT][dT] (SEQ ID NO: 772) |
| OSL213A | AUCACAUUUCCAAUAUGGCGG[dT][dT](SEQ ID NO: 399) | OSL213S | CCGCCAUAUUGGAAAUGUGAU[dT][dT] (SEQ ID NO: 773) |
| OSL214A | UGAAGUUCUUCAUCUGAACCA[dT][dT](SEQ ID NO: 400) | OSL214S | UGGUUCAGAUGAAGAACUUCA[dT][dT] (SEQ ID NO: 774) |
| OSL215A | AUAAAUGCAGCGAUUGUUGUC[dT][dT](SEQ ID NO: 401) | OSL215S | GACAACAAUCGCUGCAUUUAU[dT][dT] (SEQ ID NO: 775) |
| OSL216A | AUUCUGUACAAGGUUUAGGGG[dT][dT](SEQ ID NO: 402) | OSL216S | CCCCUAAACCUUGUACAGAAU[dT][dT] (SEQ ID NO: 776) |
| OSL217A | UAUUCUGUACAAGGUUUAGGG[dT][dT](SEQ ID NO: 403) | OSL217S | CCCUAAACCUUGUACAGAAUA[dT][dT] (SEQ ID NO: 777) |
| OSL218A | AUUCAUAUUCUGUACAAGGUU[dT][dT](SEQ ID NO: 404) | OSL218S | AACCUUGUACAGAAUAUGAAU[dT][dT] (SEQ ID NO: 778) |
| OSL219A | UAUUCAUAUUCUGUACAAGGU[dT][dT](SEQ ID NO: 405) | OSL219S | ACCUUGUACAGAAUAUGAAUA[dT][dT] (SEQ ID NO: 779) |
| OSL220A | UUAUAUUCAUAUUCUGUACAA[dT][dT](SEQ ID NO: 406) | OSL220S | UUGUACAGAAUAUGAAUAUAA[dT][dT] (SEQ ID NO: 780) |
| OSL221A | UAUUGCAACCCAGUUCAUCGG[dT][dT](SEQ ID NO: 407) | OSL221S | CCGAUGAACUGGGUUGCAAUA[dT][dT] (SEQ ID NO: 781) |
| OSL222A | AUAUUUUCAGCACAUGUUCUU[dT][dT](SEQ ID NO: 408) | OSL222S | AAGAACAUGUGCUGAAAAUAU[dT][dT] (SEQ ID NO: 782) |
| OSL223A | UUAAUUGGGUACAAUUUUGCU[dT][dT](SEQ ID NO: 409) | OSL223S | AGCAAAAUUGUACCCAAUUAA[dT][dT] (SEQ ID NO: 783) |
| OSL224A | AAAAACAUUGGUUUCGAACCC[dT][dT](SEQ ID NO: 410) | OSL224S | GGGUUCGAAACCAAUGUUUUU[dT][dT] (SEQ ID NO: 784) |
| OSL225A | UGUCAAAAACAUUGGUUUCGA[dT][dT](SEQ ID NO: 411) | OSL225S | UCGAAACCAAUGUUUUUGACA[dT][dT] (SEQ ID NO: 785) |

TABLE 6-continued

LRP2

| OS ID | Antisense Strand (5' TO 3') | OS ID | Sense Strand (5' TO 3') |
|---|---|---|---|
| OSL226A | UUCGAAUUCGGACAUUGUCAG[dT][dT](SEQ ID NO: 412) | OSL226S | CUGACAAUGUCCGAAUUCGAA[dT][dT] (SEQ ID NO: 786) |
| OSL227A | AUUAUAUUUCGAAUUCGGAC[dT][dT](SEQ ID NO: 413) | OSL227S | GUCCGAAUUCGAAAAUAUAAU[dT][dT] (SEQ ID NO: 787) |
| OSL228A | AGAUUAUAUUUCGAAUUCGG[dT][dT](SEQ ID NO: 414) | OSL228S | CCGAAUUCGAAAAUAUAAUCU[dT][dT] (SEQ ID NO: 788) |
| OSL229A | UCAUCUUGAAGAUACUCUGAG[dT][dT](SEQ ID NO: 415) | OSL229S | CUCAGAGUAUCUUCAAGAUGA[dT][dT] (SEQ ID NO: 789) |
| OSL230A | UAUAUUCCUCAUCUUGAAGAU[dT][dT](SEQ ID NO: 416) | OSL230S | AUCUUCAAGAUGAGGAAUAUA[dT][dT] (SEQ ID NO: 790) |
| OSL231A-1 | UUUGAUAGCACCAAACCUAGAGCCC[dT][dT] (SEQ ID NO: 417) | OSL231S-1 | GGGCUCUAGGUUUGGUGCUAUCAAA[dT][dT](SEQ ID NO: 791) |
| OSL231A-2 | UUUGAUAGCACCAAACCUAGAGCCC[dT]*[dT] (SEQ ID NO: 418) | OSL231S-2 | GGGCUCUAGGUUUGGUGCUAUCAAA[dT]*[dT](SEQ ID NO: 792) |
| OSL231A-3 | [mU][mU][mU][mG][mA][mU][mA][mG][mC][mA][mC][mC][mA][mA][mA][mC][mC][mU][mA][mG][mA][mG][mC][mC][mC][dT]*[dT] (SEQ ID NO: 419) | OSL231S-3 | [mG][mG][mG][mC][mU][mC][mU][mA][mG][mG][mU][mU][mU][mG][mG][mU][mG][mC][mU][mA][mU][mC][mA][mA][mA][dT]*[dT](SEQ ID NO: 793) |
| OSL231A-4 | [mU][mU][mU][mG][mA][mU][mA][mG][mC][mA][mC][mC][mA][mA][mA][mC][mC][mU][mA][mG][mA][mG][mC][mC][mC][dT]*[dT] (SEQ ID NO: 420) | OSL231S-4 | [mG][mG][mG][mC][mU][mC][mU][mA][mG][mG][mU][mU][mU][mG][mG][mU][mG][mC][mU][mA][mU][mC][mA][mA][mA] (SEQ ID NO: 794) |
| OSL231A-5 | [mU][mU][mU][mG][mA][mU][mA][mG][mC][mA][mC][mC][mA][mA][mA][mC][mC][mU][mA][mG][mA][mG][mC][mC][mC](SEQ ID NO: 421) | OSL231S-5 | [mG][mG][mG][mC][mU][mC][mU][mA][mG][mG][mU][mU][mU][mG][mG][mU][mG][mC][mU][mA][mU][mC][mA][mA][mA][dT]*[dT](SEQ ID NO: 795) |
| OSL231A-6 | [mU][mU][mU][mG][mA][mU][mA][mG][mC][mA][mC][mC][mA][mA][mA][mC][mC][mU][mA][mG][mA][mG][mC][mC][mC](SEQ ID NO: 422) | OSL231S-6 | [mG][mG][mG][mC][mU][mC][mU][mA][mG][mG][mU][mU][mU][mG][mG][mU][mG][mC][mU][mA][mU][mC][mA][mA][mA] (SEQ ID NO: 796) |
| OSL231A-7 | [mU][mU][mU][mG][mA][mU][mA][mG][mC][mA][mC][mC][mA][mA][mA][mC][mC][mU][mA][mG][mA][mG][mC][mC][mC][dT]*[dT] (SEQ ID NO: 423) | OSL231S-7 | GGGCUCUAGGUUUGGUGCUAUCAAA[dT]*[dT](SEQ ID NO: 797) |
| OSL231A-8 | [mU][2fU][mU][2fG][mA][2fU][mA][2fG][mC][2fA][mC][2fC][mA][2fA][mA][2fC][mC][2fU][mA][2fG][mA][2fG][mC][2fC][mC][dT]*[dT] (SEQ ID NO: 424) | OSL231S-8 | [2fG][mG][2fG][mC][2fU][mC][2fU][mA][2fG][mG][2fU][mU][2fU][mG][2fG][mU][2fG][mC][2fU][mA][2fU][mC][2fA][mA][2fA][dT]*[dT] (SEQ ID NO: 798) |
| OSL231A-9 | [mU][2fU][mU][2fG][mA][2fU][mA][2fG][mC][2fA][mC][2fC][mA][2fA][mA][2fC][mC][2fU][mA][2fG][mA][2fG][mC][2fC][mC] (SEQ ID NO: 425) | OSL231S-9 | [2fG][mG][2fG][mC][2fU][mC][2fU][mA][2fG][mG][2fU][mU][2fU][mG][2fG][mU][2fG][mC][2fU][mA][2fU][mC][2fA][mA][2fA][dT]*[dT] (SEQ ID NO: 799) |
| OSL231A-10 | [mU][2fU][mU][2fG][mA][2fU][mA][2fG][mC][2fA][mC][2fC][mA][2fA][mA][2fC][mC][2fU][mA][2fG][mA][2fG][mC][2fC][mC][dT]*[dT] (SEQ ID NO: 426) | OSL231S-10 | [2fG][mG][2fG][mC][2fU][mC][2fU][mA][2fG][mG][2fU][mU][2fU][mG][2fG][mU][2fG][mC][2fU][mA][2fU][mC][2fA][mA][2fA][mA](SEQ ID NO: 800) |
| OSL231A-11 | [2fU][mU][2fU][mG][2fA][mU][2fA][mG][2fC][mA][2fC][mC][2fA][mA][2fA][mC][2fC][mU][2fA][mG][2fA][mG][2fC][mC][2fC](SEQ ID NO: 427) | OSL231S-11 | [2fG][mG][2fG][mC][2fU][mC][2fU][mA][2fG][mG][2fU][mU][2fU][mG][2fG][mU][2fG][mC][2fU][mA][2fU][mC][2fA][mA][2fA](SEQ ID NO: 801) |
| OSL231A-12 | [2fU][mU][2fU][mG][2fA][mU][2fA][mG][2fC][mA][2fC][mC][2fA][mA][2fA][mC][2fC][mU][2fA][mG][2fA][mG][2fC][mC][dT]*[dT] (SEQ ID NO: 428) | OSL231S-12 | [mG][2fG][mG][2fC][mU][2fC][mU][2fA][mG][2fG][mU][2fU][mU][2fG][mG][2fu][mG][2fC][mU][2fA][mU][2fC][mA][2fA][mA][dT]*[dT](SEQ ID NO: 802) |
| OSL231A-13 | [mU][2fU][mU][2fC][mA][2fA][mA][2fC][mC][2fU][mC][2fG][mA][2fU][mA][2fG][mC][2fA][mA][2fC][mA][2fC][mC][2fG][mC](SEQ ID NO: 429) | OSL231S-13 | [2fG][mG][2fG][mC][2fU][mC][2fU][mA][2fG][mG][2fU][mU][2fU][mG][2fG][mU][2fG][mC][2fU][mA][2fU][mC][2fA][mA][2fA]-LINKER-LIG(SEQ ID NO: 803) |

TABLE 6-continued

LRP2

| OS ID | Antisense Strand (5' TO 3') | OS ID | Sense Strand (5' TO 3') |
|---|---|---|---|
| OSL231A-14 | [mU][2fU][2fU][2fG][2fA][2fU][2fA][2fG][2fC][2fA][2fC][2fC][2fA][2fA][2fA][2fC][2fC][2fU][2fA][2fG][2fA][2fG][2fC][2fC][2fC][dT]*[dT] (SEQ ID NO: 430) | OSL231S-14 | [2fU][mC][2fU][mA][2fG][mU][2fU][mG][2fG][mU][2fG][mC][2fU][mA][2fU][mC][2fA][mA][2fA][dT]*[dT] (SEQ ID NO: 804) |
| OSL231A-15 | [mU][2fU][2fU][2fG][2fA][2fU][2fA][2fG][2fC][2fA][2fC][2fC][2fA][2fA][2fA][2fC][2fC][2fU][2fA][2fG][2fA][2fG][2fC][2fC][2fC][dT]*[dT] (SEQ ID NO: 431) | OSL231S-15 | [2fU][mU][2fU][mG][2fG][mU][2fG][mC][2fU][mA][2fU][mC][2fA][mA][2fA][dT]*[dT](SEQ ID NO: 805) |
| OSL231A-16 | [mU][2fU][mU][2fG][mA][2fU][mA][2fG][mC][2fA][mC][2fC][mA][2fA][mA][2fC][mC][2fU][mA][2fG][mA][2fG][mC][2fC][mC][dT]*[dT] (SEQ ID NO: 432) | OSL231S-16 | [2fU][mU][2fU][mG][2fG][mU][2fG][mC][2fU][mA][2fU][mC][2fA][mA][2fA][dT]*[dT](SEQ ID NO: 806) |
| OSL231A-17 | [mU][2fU][mU][2fG][mA][2fU][mA][2fG][C][2fA][mC][2fC][mA][2fA][mA][2fC][mC][2fU][mA][2fG][mA][2fG][mC](SEQ ID NO: 433) | OSL231S-17 | [2fU][mU][2fU][mG][2fG][mU][2fG][mC][2fU][mA][2fU][mC][2fA][mA][2fA] (SEQ ID NO: 807) |
| OSL231A-18 | [mU][2fU][mU][2fG][mA][2fU][mA][2fG][mC][2fA][mC][2fC][mA][2fA][mA][2fC][2fC][2fU][2fA][2fG][2fA][2fG][2fC](SEQ ID NO: 434) | OSL231S-18 | [2fU][mU][2fU][mG][2fG][mU][2fG][mC][2fU][mA][2fU][mC][2fA][mA][2fA] (SEQ ID NO: 808) |
| OSL232A | UCAAAGUUGGGGAUGUAGGCA[dT][dT](SEQ ID NO: 435) | OSL232S | UGCCUACAUCCCCAACUUUGA[dT][dT] (SEQ ID NO: 809) |
| OSL233A | UCAGUUUCAGGUCAACUUCCU[dT][dT](SEQ ID NO: 436) | OSL233S | AGGAAGUUGACCUGAAACUGA[dT][dT] (SEQ ID NO: 810) |
| OSL234A | UACGUAUUUCAGUUUCAGGUC[dT][dT](SEQ ID NO: 437) | OSL234S | GACCUGAAACUGAAAUACGUA[dT][dT] (SEQ ID NO: 811) |
| OSL235A | UUACGUAUUUCAGUUUCAGGU[dT][dT](SEQ ID NO: 438) | OSL235S | ACCUGAAACUGAAAUACGUAA[dT][dT] (SEQ ID NO: 812) |
| OSL236A | AGUUUAGCCACCUCAAUGCGU[dT][dT](SEQ ID NO: 439) | OSL236S | ACGCAUUGAGGUGGCUAAACU[dT][dT] (SEQ ID NO: 813) |
| OSL237A | AACAUAAGCCCUAGUUUGGGA[dT][dT](SEQ ID NO: 440) | OSL237S | UCCCAAACUAGGGCUUAUGUU[dT][dT] (SEQ ID NO: 814) |
| OSL238A | UCGAUUUUAGGUUCCUUUCCC[dT][dT](SEQ ID NO: 441) | OSL238S | GGGAAAGGAACCUAAAAUCGA[dT][dT] (SEQ ID NO: 815) |
| OSL239A | UCGAAACCAGGAUGUUGCGG[dT][dT](SEQ ID NO: 442) | OSL239S | CCGCAACAUCCUGGUUUUCGA[dT][dT] (SEQ ID NO: 816) |
| OSL240A | UCAAAUAAUCGAUAGAAAGGC[dT][dT](SEQ ID NO: 443) | OSL240S | GCCUUUCUAUCGAUUAUUUGA[dT][dT] (SEQ ID NO: 817) |
| OSL241A | UUGUUCAAAUAAUCGAUAGAA[dT][dT](SEQ ID NO: 444) | OSL241S | UUCUAUCGAUUAUUUGAACAA[dT][dT] (SEQ ID NO: 818) |
| OSL242A | UUAUGGUUUCAAUAACGUCCU[dT][dT](SEQ ID NO: 445) | OSL242S | AGGACGUUAUUGAAACCAUAA[dT][dT] (SEQ ID NO: 819) |
| OSL243A | UUUUAUGGUUUCAAUAACGUC[dT][dT](SEQ ID NO: 446) | OSL243S | GACGUUAUUGAAACCAUAAAA[dT][dT] (SEQID NO: 820) |
| OSL244A | AUUUUAUGGUUUCAAUAACGU[dT][dT](SEQ ID NO: 447) | OSL244S | ACGUUAUUGAAACCAUAAAAU[dT][dT] (SEQ ID NO: 821) |
| OSL245A-1 | UUUGCAAUGACUCUCCUAUCAGCC[dT][dT] (SEQ ID NO: 448) | OSL245S-1 | GGACUGAUAGGAGAGUCAUUGCAAA[dT][dT](SEQ ID NO: 822) |
| OSL245A-2 | UUUGCAAUGACUCUCCUAUCAGCC[dT]*[dT] (SEQ ID NO: 449) | OSL245S-2 | GGACUGAUAGGAGAGUCAUUGCAA]A[dT]*[dT](SEQ ID NO: 823) |
| OSL245A-3 | [mU][mU][mU][mG][mC][mA][mA][mU][mG][mA][mC][mU][mC][mU][mC][mC][mU][mA][mU][mC][mA][mG][mU][mC][mC][dT]*[dT] (SEQ ID NO: 450) | OSL245S-3 | [mG][mG][mA][mC][mU][mG][mA][mU][mA][mG][mG][mA][mG][mA][mG][mU][mC][mA][mU][mU][mG][mC][mA][mA][mA][dT]*[dT](SEQ ID NO: 824) |

TABLE 6-continued

LRP2

| OS ID | Antisense Strand (5' TO 3') | OS ID | Sense Strand (5' TO 3') |
|---|---|---|---|
| OSL245A-4 | [mU][mU][mU][mG][mC][mA][mA][mU][mG][mA][mC][mU][mC][mU][mC][mC][mU][mA][mU][mC][mA][mG][mU][mC][mC][dT]*[dT] (SEQ ID NO: 451) | OSL245S-4 | [mG][mG][mA][mC][mU][mG][mA][mU][mA][mG][mG][mA][mG][mA][mG][mU][mC][mA][mU][mU][mG][mC][mA][mA][mA] (SEQ ID NO: 825) |
| OSL245A-5 | [mU][mU][mU][mG][mC][mA][mA][mU][mG][mA][mC][mU][mC][mU][mC][mC][mU][mA][mU][mC][mA][mG][mU][mC][mC] (SEQ ID NO: 452) | OSL245S-5 | [mG][mG][mA][mC][mU][mG][mA][mU][mA][mG][mG][mA][mG][mA][mG][mU][mC][mA][mU][mU][mG][mC][mA][mA][mA][dT]*[dT] (SEQ ID NO: 826) |
| OSL245A-6 | [mU][mU][mU][mG][mC][mA][mA][mU][mG][mA][mC][mU][mC][mU][mC][mC][mU][mA][mU][mC][mA][mU][mC][mC] (SEQ ID NO: 453) | OSL245S-6 | [mG][mG][mA][mC][mU][mG][mA][mU][mA][mG][mG][mA][mG][mA][mG][mU][mC][mA][mU][mU][mG][mC][mA][mA][mA] (SEQ ID NO: 827) |
| OSL245A-7 | [mU][mU][mU][mG][mC][mA][mA][mU][mG][mA][mC][mU][mC][mU][mC][mC][mU][mA][mU][mC][mA][mG][mU][mC][mC][dT]*[dT] (SEQ ID NO: 454) | OSL245S-7 | GGACUGAUAGGAGAGUCAUUGCAAA[dT]*[dT] (SEQ ID NO: 828) |
| OSL245A-8 | [mU][2fU][mU][2fG][mC][2fA][mA][2fU][mG][2fA][mC][2fU][mC][2fU][mC][2fC][mU][2fA][mU][2fC][mA][2fG][mU][2fC][mC][dT]*[dT] (SEQ ID NO: 455) | OSL245S-8 | [2fG][mG][2fA][mC][2fU][mG][2fA][mU][2fA][mG][2fG][mA][2fG][mA][2fG][mU][2fC][mA][2fU][mU][2fG][mC][2fA][mA][2fA][dT]*[dT] (SEQ ID NO: 829) |
| OSL245A-9 | [mU][2fU][mU][2fG][mC][2fA][mA][2fU][mG][2fA][mC][2fU][mC][2fU][mC][2fC][mU][2fA][mU][2fC][mA][2fG][mU][2fC][mC] (SEQ ID NO: 456) | OSL245S-9 | [2fG][mG][2fA][mC][2fU][mG][2fA][mU][2fA][mG][2fG][mA][2fG][mA][2fG][mU][2fC][mA][2fU][mU][2fG][mC][2fA][mA][2fA][dT]*[dT] (SEQ ID NO: 830) |
| OSL245A-10 | [mU][2fU][mU][2fG][mC][2fA][mA][2fU][mG][2fA][mC][2fU][mC][2fU][mC][2fC][mU][2fA][mU][2fC][mA][2fG][mU][2fC][mC][dT]*[dT] (SEQ ID NO: 457) | OSL245S-10 | [2fG][mG][2fA][mC][2fU][mG][2fA][mU][2fA][mG][2fG][mA][2fG][mA][2fG][mU][2fC][mA][2fU][mU][2fG][mC][2fA][mA][mA][2fA] (SEQ ID NO: 831) |
| OSL245A-11 | [mU][2fU][mU][2fG][mC][2fA][mA][2fU][mG][2fA][mC][2fU][mC][2fU][mC][2fC][mU][2fA][mU][2fC][mA][2fC][mU][2fC][mC] (SEQ IDNO: 458) | OSL245S-11 | [2fG][mG][2fA][mC][2fU][mG][2fA][mU][2fA][mG][2fG][mA][2fG][mA][2fG][mU][2fC][mA][2fU][mU][2fG][mC][2fA][mA][mA][2fA] (SEQ ID NO: 832) |
| OSL245A-12 | [2fU][mU][2fU][mG][2fC][mA][2fA][mU][2fG][mA][2fC][mU][2fC][mU][2fC][mC][2fU][mA][2fU][mC][2fA][mG][2fU][mC][2fC][dT]*[dT] (SEQ ID NO: 459) | OSL245S-12 | [mG][2fG][mA][2fC][mU][2fG][mA][2fU][mA][2fG][mG][2fA][mG][2fA][mG][2fU][mC][2fA][mU][2fU][mG][2fC][mA][2fA][mA][dT]*[dT] (SEQ ID NO: 833) |
| OSL245A-13 | [mU][2fA][mU][2fC][mC][2fU][mA][2fA][mG][2fU][mC][2fA][mC][2fA][mC][2fG][mU][2fU][mU][2fG][mA][2fC][mU][2fG][mC] (SEQ ID NO: 460) | OSL245S-13 | [2fG][mG][2fA][mC][2fU][mG][2fA][mU][2fA][mG][2fG][mA][2fG][mA][2fG][mU][2fC][mA][2fU][mU][2fG][mC][2fA][mA][mA][2fA] (SEQ ID NO: 834) |
| OSL245A-14 | [mU][2fU][2fU][2fG][2fC][2fA][2fA][2fU][2fG][2fA][2fC][2fU][2fC][2fU][2fC][2fC][2fU][2fA][2fU][2fC][2fA][2fG][2fU][2fC][2fC][dT]*[dT] (SEQ ID NO: 461) | OSL245S-14 | [2fU][mG][2fA][mU][2fA][mG][2fG][mA][2fG][mA][2fG][mU][2fC][mA][2fU][mU][2fG][mC][2fA][mA][2fA][dT]*[dT] (SEQ ID NO: 835) |
| OSL245A-15 | [mU][2fU][2fU][2fG][2fC][2fA][2fA][2fU][2fG][2fA][2fC][2fU][2fC][2fU][2fC][2fC][2fU][2fA][2fU][2fC][2fA][2fG][2fU][2fC][2fC][dT]*[dT] (SEQ ID NO: 462) | OSL245S-15 | [2fG][mA][2fG][mA][2fG][mU][2fC][mA][2fU][mU][2fG][mC][2fA][mA][2fA][dT]*[dT] (SEQ ID NO: 836) |
| OSL245A-16 | [mU][2fU][mU][2fG][mC][2fA][mA][2fU][mG][2fA][mC][2fU][mC][2fU][mC][2fC][mU][2fA][mU][2fC][mA][2fG][mU][2fC][mC][dT]*[dT] (SEQ ID NO: 463) | OSL245S-16 | [2fG][mA][2fG][mA][2fG][mU][2fC][mA][2fU][mU][2fG][mC][2fA][mA][2fA][dT]*[dT] (SEQ ID NO: 837) |
| OSL245A-17 | [mU][2fU][mU][2fG][mC][2fA][mA][2fU][mG][2fA][mC][2fU][mC][2fU][mC][2fC][mU][2fA][mU][2fC][mA][2fG][mU] (SEQ ID NO: 464) | OSL245S-17 | [2fG][mA][2fG][mA][2fG][mU][2fC][mA][2fU][mU][2fG][mC][2fA][mA][2fA] (SEQ ID NO: 838) |
| OSL245A-18 | [mU][2fU][mU][2fG][mC][2fA][mA][2fU][mG][2fA][mC][2fU][mC][2fU][mC][2fC][2fU][2fA][2fU][2fC][2fA][2fG][2fU] (SEQ ID NO: 465) | OSL245S-18 | ACCAGUUAUACUGGAUAUCUA[dT][dT] (SEQ ID NO: 840) |
| OSL246A | UAGAUAUCCAGUAUAACUGGU[dT][dT] (SEQ ID NO: 466) | OSL246S | GGGAGAAGUAUGGAAACAAAA[dT][dT] (SEQ ID NO: 841) |

TABLE 6-continued

LRP2

| OS ID | Antisense Strand (5' TO 3') | OS ID | Sense Strand (5' TO 3') |
|---|---|---|---|
| OSL247A | UUUUGUUCCAUACUUCUCCC[dT][dT](SEQ ID NO: 467) | OSL247S | AGUAUGGAAACAAAAUAAAU[dT][dT] (SEQ ID NO: 842) |
| OSL248A | AUUUAUUUGUUUCCAUACUU[dT][dT](SEQ ID NO: 468) | OSL248S | UUCAUCAACUCAGAUACAAUA[dT][dT] (SEQ ID NO: 843) |
| OSL249A | UAUUGUAUCUGAGUUGAUGAA[dT][dT](SEQ ID NO: 469) | OSL249S | CGGAGGAAAUUGCUAUUUGA[dT][dT] (SEQ ID NO: 844) |
| OSL250A | UCAAAAUAGCAAUUUCCUCCG[dT][dT](SEQ ID NO: 470) | OSL250S | AGGAAAUUGCUAUUUGAUGA[dT][dT] (SEQ ID NO: 845) |
| OSL251A | UCAUCAAAAUAGCAAUUUCCU[dT][dT](SEQ ID NO: 471) | OSL251S | CACCGGAAAAUAUUGUGAAAU[dT][dT] (SEQ ID NO: 846) |
| OSL252A | AUUUCACAAUAUUUCCGGUG[dT][dT](SEQ ID NO: 472) | OSL252S | UUGUGAAAUGGCGUUUUCAAA[dT][dT] (SEQ ID NO: 847) |
| O5L253A | UUUGAAAACGCCAUUUCACAA[dT][dT](SEQ ID NO: 473) | OSL253S | CAGGAUUCUUCCACUAUAGAA[dT][dT] (SEQ ID NO: 848) |
| OSL254A | UUCUAUAGUGGAAGAAUCCUG[dT][dT](SEQ ID NO: 474) | OSL254S | GGCAGAUCUUAACAUGGAUAU[dT][dT] (SEQ ID NO: 849) |
| OSL255A | AUAUCCAUGUUAAGAUCUGCC[dT][dT](SEQ ID NO: 475) | OSL255S | GGCAAUGAGUGAAGACUUUGU[dT][dT] (SEQ ID NO: 850) |
| OSL256A | ACAAAGUCUUCACUCAUUGCC[dT][dT](SEQ ID NO: 476) | OSL256S | AUCUGAAAAUGUGGAUAAUAA[dT][dT] (SEQ ID NO: 851) |
| OSL257A | UUAUUAUCCACAUUUUCAGAU[dT][dT](SEQ ID NO: 477) | OSL257S | ACCAGUUAUACUGGAUAUCUA[dT][dT] (SEQ ID NO: 840) |
| OSL258A | UCUUAUUAUCCACAUUUUCAG[dT][dT](SEQ ID NO: 478) | OSL258S | CUGAAAAUGUGGAUAAUAAGA[dT][dT] (SEQ ID NO: 852) |
| OSL259A | UCCAUAAUUCUUAUUAUCCAC[dT][dT](SEQ ID NO: 479) | OSL259S | GUGGAUAAUAAGAAUUAUGGA[dT][dT] (SEQ ID NO: 853) |
| OSL260A | UUCCAUAAUUCUUAUUAUCCA[dT][dT](SEQ ID NO: 480) | OSL260S | UGGAUAAUAAGAAUUAUGGAA[dT][dT] (SEQ ID NO: 854) |
| OSL261A | UUUUCGUUUGAAGAGAUUCCA[dT][dT](SEQ ID NO: 481) | OSL261S | UGGAAUCUCUUCAAACGAAAA[dT][dT] (SEQ ID NO: 855) |
| OSL262A | UAGAUUUUCGUUUGAAGAGAU[dT][dT](SEQ ID NO: 482) | OSL262S | AUCUCUUCAAACGAAAAUCUA[dT][dT] (SEQ ID NO: 856) |
| OSL263A | UUUAGAUUUUCGUUUGAAGAG[dT][dT](SEQ ID NO: 483) | OSL263S | CUCUUCAAACGAAAAUCUAAA[dT][dT] (SEQ ID NO: 857) |
| OSL264A | UUGUUUAGAUUUUCGUUUGAA[dT][dT](SEQ ID NO: 484) | OSL264S | UUCAAACGAAAAUCUAAACAA[dT][dT] (SEQ ID NO: 858) |
| OSL265A | UAGUUUGUUUAGAUUUUCGUU[dT][dT] (SEQ ID NO: 485) | OSL265S | AACGAAAAUCUAAACAAACUA[dT][dT] (SEQ ID NO: 859) |
| 0SL266A | UUUCAAAGUUGGUAGUUUGUU[dT][dT](SEQ ID NO: 486) | OSL266S | AACAAACUACCAACUUUGAAA[dT][dT] (SEQ ID NO: 860) |
| OSL267A | AUGGAUUUUCAAAGUUGGUA[dT][dT](SEQ ID NO: 487) | OSL267S | UACCAACUUUGAAAAUCCAU[dT][dT] (SEQ ID NO: 861) |
| OSL268A | AUAGAUUGGAUUUUCAAAGUU[dT][dT](SEQ ID NO: 488) | OSL268S | AACUUUGAAAAUCCAAUCUAU[dT][dT] (SEQ ID NO: 862) |
| OSL269A | UUAAAAGUGUCUUCUGUUGCA[dT][dT](SEQ ID NO: 489) | OSL269S | UGCAACAGAAGACACUUUUAA[dT][dT] (SEQ ID NO: 863) |
| OSL270A | UCUUUAACAAGAUUUGCGGUG[dT][dT](SEQ ID NO: 490) | OSL270S | CACCGCAAAUCUUGUUAAAGA[dT][dT] (SEQ ID NO: 864) |
| OSL271A | UCUUCUUUAACAAGAUUUGCG[dT][dT](SEQ ID NO: 491) | OSL271S | CGCAAAUCUUGUUAAAGAAGA[dT][dT] (SEQ ID NO: 865) |

TABLE 6-continued

LRP2

| OS ID | Antisense Strand (5' TO 3') | OS ID | Sense Strand (5' TO 3') |
|---|---|---|---|
| OSL272A | UGGUAUAGCUAUACUUCAGAG[dT][dT](SEQ ID NO: 492) | OSL272S | CUCUGAAGUAUAGCUAUACCA[dT][dT] (SEQ ID NO: 866) |
| OSL273A | AUUAUUCCCUAAAUAGCUGGU[dT][dT](SEQ ID NO: 493) | OSL273S | ACCAGCUAUUUAGGGAAUAAU[dT][dT] (SEQ ID NO: 867) |
| OSL274A | UAAUUAUUCCCUAAAUAGCUG[dT][dT](SEQ ID NO: 494) | OSL274S | CAGCUAUUUAGGGAAUAAUUA[dT][dT] (SEQ ID NO: 868) |
| OSL275A | AUAUAUGUGCAAAAGUGUGUU[dT][dT](SEQ ID NO: 495) | OSL275S | AACACACUUUUGCACAUAUAU[dT][dT] (SEQ ID NO: 869) |
| OSL276A | AAAUAUAUGUGCAAAAGUGUG[dT][dT](SEQ ID NO: 496) | OSL276S | CACACUUUUGCACAUAUAUUU[dT][dT] (SEQ ID NO: 870) |
| OSL277A | AACUUUUUUCAUCUGUUUGUA[dT][dT](SEQ ID NO: 497) | OSL277S | UACAAACAGAUGAAAAAGUU[dT][dT] (SEQ ID NO: 871) |
| OSL278A | UAAAGUACUGAAUGUUAACUU[dT][dT](SEQ ID NO: 498) | OSL278S | AAGUUAACAUUCAGUACUUUA[dT][dT] (SEQ ID NO: 872) |
| OSL279A | UUUUUUUCAUAAAGUACUGAA[dT][dT](SEQ ID NO: 499) | OSL279S | UUCAGUACUUUAUGAAAAAAA[dT][dT] (SEQ ID NO: 873) |
| OSL280A | UAUUUUUUUCAUAAAGUACUG[dT][dT](SEQ ID NO: 500) | OSL280S | CAGUACUUUAUGAAAAAAAUA[dT][dT] (SEQ ID NO: 874) |
| OSL281A | AUUUGUAAAAAUAUGAGACGG[dT][dT](SEQ ID NO: 501) | OSL281S | CCGUCUCAUAUUUUUACAAAU[dT][dT] (SEQ ID NO: 875) |
| OSL282A | ACAUUGUGAUAAUUAUUUGUA[dT][dT](SEQ ID NO: 502) | OSL282S | UACAAAUAAUUAUCACAAUGU[dT][dT] (SEQ ID NO: 876) |
| OSL283A | AUACAUAUAGUACAUUGUGAU[dT][dT](SEQ ID NO: 503) | OSL283S | AUCACAAUGUACUAUAUGUAU[dT][dT] (SEQ ID NO: 877) |
| OSL284A | AUAUACAUAUAGUACAUUGUG[dT][dT](SEQ ID NO: 504) | OSL284S | CACAAUGUACUAUAUGUAUAU[dT][dT] (SEQ ID NO: 878) |
| OSL285A | AAAGAUAUACAUAUAGUACAU[dT][dT](SEQ ID NO: 505) | OSL285S | AUGUACUAUAUGUAUAUCUUU[dT][dT] (SEQ ID NO: 879) |
| OSL286A | AUUACCUUCAGACAACUUCAG[dT][dT](SEQ ID NO: 506) | OSL286S | CUGAAGUUGUCUGAAGGUAAU[dT][dT] (SEQ ID NO: 880) |
| OSL287A | UAUUUAUAGUAUUACCUUCAG[dT][dT](SEQ ID NO: 507) | OSL287S | CUGAAGGUAAUACUAUAAAUA[dT][dT] (SEQ ID NO: 881) |
| OSL288A | UAAUCUUUCCAAAAUUUACAA[dT][dT](SEQ ID NO: 508) | OSL288S | UUGUAAAUUUUGGAAAGAUUA[dT][dT] (SEQ ID NO: 882) |
| OSL289A | AGUAACAGGAUAAUCUUUCCA[dT][dT](SEQ ID NO: 509) | OSL289S | UGGAAAGAUUAUCCUGUUACU[dT][dT] (SEQ ID NO: 883) |
| OSL290A | AUUCAGUAACAGGAUAAUCUU[dT][dT](SEQ ID NO: 510) | OSL290S | AAGAUUAUCCUGUUACUGAAU[dT][dT] (SEQ ID NO: 884) |
| OSL291A | UAGCAAAUUCAGUAACAGGAU[dT][dT](SEQ ID NO: 511) | OSL291S | AUCCUGUUACUGAAUUUGCUA[dT][dT] (SEQ ID NO: 885) |
| OSL292A | UUAGCAAAUUCAGUAACAGGA[dT][dT](SEQ ID NO: 512) | OSL292S | UCCUGUUACUGAAUUUGCUAA[dT][dT] (SEQ ID NO: 886) |
| OSL293A | UCUUUAUUAGCAAAUUCAGUA[dT][dT](SEQ ID NO: 513) | OSL293S | UACUGAAUUUGCUAAUAAAGA[dT][dT] (SEQ ID NO: 887) |
| OSL294A | AUCAUUUACUAUAAUGAUCAC[dT][dT](SEQ ID NO: 514) | OSL294S | GUGAUCAUUAUAGUAAAUGAU[dT][dT] (SEQ ID NO: 888) |
| OSL295A | UUCUUGUUGGAUCAUUUACUA[dT][dT](SEQ ID NO: 515) | OSL295S | UAGUAAAUGAUCCAACAAGAA[dT][dT] (SEQ ID NO: 889) |
| OSL296A | UCAAUUCCUUUUCUUGUUGGA[dT][dT](SEQ ID NO: 516) | OSL296S | UCCAACAAGAAAAGGAAUUGA[dT][dT] (SEQ ID NO: 890) |

TABLE 6-continued

LRP2

| OS ID | Antisense Strand (5' TO 3') | OS ID | Sense Strand (5' TO 3') |
|---|---|---|---|
| OSL297A | AUUUUAUAGGAAAUAUGAGUG[dT][dT](SEQ ID NO: 517) | OSL297S | CACUCAUAUUUCCUAUAAAAU[dT][dT] (SEQ ID NO: 891) |
| OSL298A | UAAUUUUAUAGGAAAUAUGAG[dT][dT](SEQ ID NO: 518) | OSL298S | CUCAUAUUUCCUAUAAAAUUA[dT][dT] (SEQ ID NO: 892) |
| OSL299A | UGCUAAUGUGUAAAAAUGGAC[dT][dT](SEQ ID NO: 519) | OSL299S | GUCCAUUUUUACACAUUAGCA[dT][dT] (SEQ ID NO: 893) |
| OSL300A | UUGAACAUUAAUUAAGUGCUA[dT][dT](SEQ ID NO: 520) | OSL300S | UAGCACUUAAUUAAUGUUCAA[dT][dT] (SEQ ID NO: 894) |
| OSL301A | AUUGAACAUUAAUUAAGUGCU[dT][dT](SEQ ID NO: 521) | OSL301S | AGCACUUAAUUAAUGUUCAAU[dT][dT] (SEQ ID NO: 895) |
| OSL302A | AUAUUGAACAUUAAUUAAGUG[dT][dT](SEQ ID NO: 522) | OSL302S | CACUUAAUUAAUGUUCAAUAU[dT][dT] (SEQ ID NO: 896) |
| OSL303A | AAAUUGACAUGUAAUAUUGAA[dT][dT](SEQ ID NO: 523) | OSL303S | UUCAAUAUUACAUGUCAAUUU[dT][dT] (SEQ ID NO: 897) |
| OSL304A | AUCAACAUAGCCAUUAAUCAA[dT][dT](SEQ ID NO: 524) | OSL304S | UUGAUUAAUGGCUAUGUUGAU[dT][dT] (SEQ ID NO: 898) |
| OSL305A | UCUAUACAACACAUAGUGGCC[dT][dT](SEQ ID NO: 525) | OSL305S | GGCCACUAUGUGUUGUAUAGA[dT][dT] (SEQ ID NO: 899) |
| OSL306A | AUGUCUAUACAACACAUAGUG[dT][dT](SEQ ID NO: 526) | OSL306S | CACUAUGUGUUGUAUAGACAU[dT][dT] (SEQ ID NO: 900) |
| OSL307A | ACUGAAUUGCUUUUCCUACCU[dT][dT](SEQ ID NO: 527) | OSL307S | AGGUAGGAAAAGCAAUUCAGU[dT][dT] (SEQ ID NO: 901) |
| OSL308A | AAAUAAAAAUGUUGUCUUGGC[dT][dT](SEQ ID NO: 528) | OSL308S | GCCAAGACAACAUUUUUAUUU[dT][dT] (SEQ ID NO: 902) |
| OSL309A | AUCACAAAUAAAAAUGUUGUC[dT][dT](SEQ ID NO: 529) | OSL309S | GACAACAUUUUUAUUUGUGAU[dT][dT] (SEQ ID NO: 903) |
| OSL310A | AAUGAUAUGGGAUUUCCUCAU[dT][dT](SEQ ID NO: 530) | OSL310S | AUGAGGAAAUCCCAUAUCAUU[dT][dT] (SEQ ID NO: 904) |
| OSL311A | AUUAACCACAAACUCAAUGCA[dT][dT](SEQ ID NO: 531) | OSL311S | UGCAUUGAGUUUGUGGUUAAU[dT][dT] (SEQ ID NO: 905) |
| OSL312A | UUUAAUUAACCACAAACUCAA[dT][dT](SEQ ID NO: 532) | OSL312S | UUGAGUUUGUGGUUAAUUAAA[dT][dT] (SEQ ID NO: 906) |
| OSL313A | UUUGGUUUCAGAAAUUCAGCU[dT][dT](SEQ ID NO: 533) | OSL313S | AGCUGAAUUUCUGAAACCAAA[dT][dT] (SEQ ID NO: 907) |
| OSL314A | UUAUGAAGACACAGAUUUGGU[dT][dT](SEQ ID NO: 534) | OSL314S | ACCAAAUCUGUGUCUCAUAA[dT][dT] (SEQ ID NO: 908) |
| OSL315A | UUUCAUAGAAACAAAAACCCA[dT][dT](SEQ ID NO: 535) | OSL315S | UGGGUUUUGUUUCUAUGAAA[dT][dT] (SEQ ID NO: 909) |
| OSL316A | AUGAUAUUUCAUAGAAACAA[dT][dT](SEQ ID NO: 536) | OSL316S | UUGUUUCUAUGAAAAUAUCAU[dT][dT] (SEQ ID NO: 910) |
| OSL317A | UAUAAUGAUAUUUCAUAGAA[dT][dT](SEQ ID NO: 537) | OSL317S | UUCUAUGAAAAUAUCAUUAUA[dT][dT] (SEQ ID NO: 911) |
| OSL318A | UGAUUAUAAUGAUAUUUCAU[dT][dT](SEQ ID NO: 538) | OSL318S | AUGAAAAUAUCAUUAUAAUCA[dT][dT] (SEQ ID NO: 912) |
| OSL319A | AUAAAUAGUGAUUAUAAUGAU[dT][dT](SEQ ID NO: 539) | OSL319S | AUCAUUAUAAUCACUAUUUAU[dT][dT] (SEQ ID NO: 913) |
| OSL320A | AAAAGCUUAAUAAGAAUGGUU[dT][dT](SEQ ID NO: 540) | OSL320S | AACCAUUCUUAUUAAGCUUUU[dT][dT] (SEQ ID NO: 914) |
| OSL321A | AAAAAGCUUAAUAAGAAUGGU[dT][dT](SEQ ID NO: 541) | OSL321S | ACCAUUCUUAUUAAGCUUUUU[dT][dT] (SEQ ID NO: 915) |

TABLE 6-continued

LRP2

| OS ID | Antisense Strand (5' TO 3') | OS ID | Sense Strand (5' TO 3') |
|---|---|---|---|
| OSL322A | UAAAUGUACACAUUUAGCCAC[dT][dT](SEQ ID NO: 542) | OSL322S | GUGGCUAAAUGUGUACAUUUA[dT][dT] (SEQ ID NO: 916) |
| OSL323A | AUAAAUGUACACAUUUAGCCA[dT][dT](SEQ ID NO: 543) | OSL323S | UGGCUAAAUGUGUACAUUUAU[dT][dT] (SEQ ID NO: 917) |
| OSL324A | UAUAAAUGUACACAUUUAGCC[dT][dT](SEQ ID NO: 544) | OSL324S | GGCUAAAUGUGUACAUUUAUA[dT][dT] (SEQ ID NO: 918) |
| OSL325A | UUCUAAUAUAAAUGUACACAU[dT][dT](SEQ ID NO: 545) | OSL325S | AUGUGUACAUUUAUAUUAGAA[dT][dT] (SEQ ID NO: 919) |
| OSL326A | AAGAAUUAAAGAAAAGAUCUG[dT][dT](SEQ ID NO: 546) | OSL326S | CAGAUCUUUCUUUAAUUCUU[dT][dT] (SEQ ID NO: 920) |
| OSL327A | AAUAAGAAUUAAAGAAAAGAU[dT][dT](SEQ ID NO: 547) | OSL327S | AUCUUUUCUUUAAUUCUUAUU[dT][dT] (SEQ ID NO: 921) |
| OSL328A | AAACCAAUAAGAAUUAAAGAA[dT][dT](SEQ ID NO: 548) | OSL328S | UUCUUUAAUUCUUAUUGGUUU[dT][dT] (SEQ ID NO: 922) |
| OSL329A | ACUAUACCCACUAUUUAAGAG[dT][dT](SEQ ID NO: 549) | OSL329S | CUCUUAAAUAGUGGGUAUAGU[dT][dT] (SEQ ID NO: 923) |
| OSL330A | ACAAAUGUGCAAUAUUAGCAC[dT][dT](SEQ ID NO: 550) | OSL330S | GUGCUAAUAUUGCACAUUUGU[dT][dT] (SEQ ID NO: 924) |
| OSL331A | AACAAAUGUGCAAUAUUAGCA[dT][dT](SEQ ID NO: 551) | OSL331S | UGCUAAUAUUGCACAUUUGUU[dT][dT] (SEQ ID NO: 925) |
| OSL332A | AUGUUUCAUUCAUUCAUCCAU[dT][dT](SEQ ID NO: 552) | OSL332S | AUGGAUGAAUGAAUGAAACAU[dT][dT] (SEQ ID NO: 926) |
| OSL333A | AGUAGUAUAUGUUUCAUUCAU[dT][dT](SEQ ID NO: 553) | OSL333S | AUGAAUGAAACAUAUACUACU[dT][dT] (SEQ ID NO: 927) |
| OSL334A | AAUCAGUAGUAUAUGUUUCAU[dT][dT](SEQ ID NO: 554) | OSL334S | AUGAAACAUAUACUACUGAUU[dT][dT] (SEQ ID NO: 928) |
| OSL335A | AAAUAAUCAGUAGUAUAUGUU[dT][dT](SEQ ID NO: 555) | OSL335S | AACAUAUACUACUGAUUAUUU[dT][dT] (SEQ ID NO: 929) |
| OSL336A | AAUCAAAGUAAUUACAGUCAG[dT][dT](SEQ ID NO: 556) | OSL336S | CUGACUGUAAUUACUUUGAUU[dT][dT] (SEQ ID NO: 930) |
| OSL337A | AUCUAAUCAAAGUAAUUACAG[dT][dT](SEQ ID NO: 557) | OSL337S | CUGUAAUUACUUUGAUUAGAU[dT][dT] (SEQ ID NO: 931) |
| OSL338A | UUAUUUCCAGUUGUUUAUCUA[dT][dT](SEQ ID NO: 558) | OSL338S | UAGAUAAACAACUGGAAAUAA[dT][dT] (SEQ ID NO: 932) |
| OSL339A | UUAUUAGAACUUUUUCAGCAG[dT][dT](SEQ ID NO: 559) | OSL339S | CUGCUGAAAAAGUUCUAAUAA[dT][dT] (SEQ ID NO: 933) |
| OSL340A | UUUAUUAGAACUUUUUCAGCA[dT][dT](SEQ ID NO: 560) | OSL340S | UGCUGAAAAAGUUCUAAUAAA[dT][dT] (SEQ ID NO: 934) |

TABLE 5A

CD320 ANTISENSE TARGET

| ID | target position | start position | target sequence | Location | Size | SEQ ID NO: |
|---|---|---|---|---|---|---|
| OSC1 | 2-24 | 2 | TGCGCGTGCGCAGGGATAAGAGA | 5' UTR | 21 | 996 |
| OSC2 | 4-26 | 4 | CGCGTGCGCAGGGATAAGAGAGC | 5' UTR | 21 | 997 |
| OSC3 | 48-70 | 48 | GCGCCGCTGTGGGACAGCATGA | 5' UTR | 21 | 998 |
| OSC4 | 63-85 | 63 | CAGCATGAGCGGCGGTTGGATGG | 5' UTR-CDS | 21 | 999 |

TABLE 5A-continued

CD320 ANTISENSE TARGET

| ID | target position | start position | target sequence | Location | Size | SEQ ID NO: |
|---|---|---|---|---|---|---|
| OSC5 | 164-186 | 164 | CCGCCGCGAGCCCGCTTTCCACC | CDS | 21 | 1000 |
| OSC6 | 222-244 | 222 | CTCGTGCCCACCCACCAAGTTCC | CDS | 21 | 1001 |
| OSC7 | 225-247 | 225 | GTGCCCACCCACCAAGTTCCAGT | CDS | 21 | 1002 |
| OSC8 | 227-249 | 227 | GCCCACCCACCAAGTTCCAGTGC | CDS | 21 | 1003 |
| OSC9 | 244-266 | 244 | CAGTGCCGCACCAGTGGCTTATG | CDS | 21 | 1004 |
| OSC10 | 249-271 | 249 | CCGCACCAGTGGCTTATGCGTGC | CDS | 21 | 1005 |
| OSC11 | 282-304 | 282 | GCGCTGCGACAGGGACTTGGACT | CDS | 21 | 1006 |
| OSC12 | 306-328 | 306 | CAGCGATGGCAGCGATGAGGAGG | CDS | 21 | 1007 |
| OSC13 | 390-412 | 390 | CCCCTGCACCGGCGTCAGTGACT | CDS | 21 | 1008 |
| OSC14 | 411-433 | 411 | CTGCTCTGGGGGAACTGACAAGA | CDS | 21 | 1009 |
| OSC15 | 414-436 | 414 | CTCTGGGGGAACTGACAAGAAAC | CDS | 21 | 1010 |
| OSC16 | 417-439 | 417 | TGGGGGAACTGACAAGAAACTGC | CDS | 21 | 1011 |
| OSC17 | 422-466 | 422 | GAACTGACAAGAAACTGCGCAACTG | CDS | 25 | 1012 |
| OSC18 | 483-505 | 483 | CACGCTGAGCGATGACTGCATTC | CDS | 21 | 1013 |
| OSC19 | 484-506 | 484 | ACGCTGAGCGATGACTGCATTCC | CDS | 21 | 1014 |
| OSC20 | 487-509 | 487 | CTGAGCGATGACTGCATTCCACT | CDS | 21 | 1015 |
| OSC21 | 489-511 | 489 | GAGCGATGACTGCATTCCACTCA | CDS | 21 | 1016 |
| OSC22 | 520-542 | 520 | TGCGACGGCCACCCAGACTGTCC | CDS | 21 | 1017 |
| OSC23 | 556-578 | 556 | GAGCTCGGCTGTGGAACCAATGA | CDS | 21 | 1018 |
| OSC24 | 560-582 | 560 | TCGGCTGTGGAACCAATGAGATC | CDS | 21 | 1019 |
| OSC25 | 561-583 | 561 | CGGCTGTGGAACCAATGAGATCC | CDS | 21 | 1020 |
| OSC26 | 564-586 | 564 | CTGTGGAACCAATGAGATCCTCC | CDS | 21 | 1021 |
| OSC27 | 626-648 | 626 | TGGAGAGTGTCACCTCTCTCAGG | CDS | 21 | 1022 |
| OSC28 | 641-663 | 641 | CTCTCAGGAATGCCACAACCATG | CDS | 21 | 1023 |
| OSC29 | 689-711 | 689 | TCCCCTCTGTCGGGAATGCCACA | CDS | 21 | 1024 |
| OSC30 | 695-717 | 695 | CTGTCGGGAATGCCACATCCTCC | CDS | 21 | 1025 |
| OSC31 | 719-741 | 719 | CTGCCGGAGACCAGTCTGGAAGC | CDS | 21 | 1026 |
| OSC32 | 741-763 | 741 | CCCAACTGCCTATGGGGTTATTG | CDS | 21 | 1027 |
| OSC33 | 767-789 | 767 | CTGCTGCGGTGCTCAGTGCAAGC | CDS | 21 | 1028 |
| OSC34 | 795-817 | 795 | CACCGCCACCCTCCTCCTTTTGT | CDS | 21 | 1029 |
| OSC35 | 797-819 | 797 | CCGCCACCCTCCTCCTTTTGTCC | CDS | 21 | 1030 |
| OSC36 | 843-865 | 843 | CCGCCCACTGGGGTTACTGGTGG | CDS | 21 | 1031 |
| OSC37 | 852-874 | 852 | GGGGTTACTGGTGGCCATGAAGG | CDS | 21 | 1032 |
| OSC38 | 857-879 | 857 | TACTGGTGGCCATGAAGGAGTCC | CDS | 21 | 1033 |
| OSC39 | 874-896 | 874 | GAGTCCCTGCTGCTGTCAGAACA | CDS | 21 | 1034 |
| OSC40 | 878-900 | 878 | CCCTGCTGCTGTCAGAACAGAAG | CDS | 21 | 1035 |
| OSC41 | 881-903 | 881 | TGCTGCTGTCAGAACAGAAGACC | CDS | 21 | 1036 |

TABLE 5A-continued

CD320 ANTISENSE TARGET

| ID | target position | start position | target sequence | Location | Size | SEQ ID NO: |
|---|---|---|---|---|---|---|
| OSC42 | 884-906 | 884 | TGCTGTCAGAACAGAAGACCTCG | CDS | 21 | 1037 |
| OSC43 | 901-923 | 901 | ACCTCGCTGCCCTGAGGACAAGC | CDS | 21 | 1038 |
| OSC44 | 907-929 | 907 | CTGCCCTGAGGACAAGCACTTGC | CDS-3' UTR | 21 | 1039 |
| OSC45 | 971-993 | 971 | GAGCAGTGATGCGGATGGGTACC | 3' UTR | 21 | 1040 |
| OSC46 | 995-1017 | 995 | GGGCACACCAGCCCTCAGAGACC | 3' UTR | 21 | 1041 |
| OSC47 | 1006-1026 | 1006 | CCCTCAGAGACCTGAGCTCTT | 3' UTR | 21 | 1393 |
| OSC48 | 1006-1028 | 1006 | CCCTCAGAGACCTGAGCTCTTCT | 3' UTR | 21 | 1042 |
| OSC49 | 1008-1030 | 1008 | CTCAGAGACCTGAGCTCTTCTGG | 3' UTR | 21 | 1043 |
| OSC50 | 1082-1104 | 1082 | GGGTCCCTGGACACTCCCTATGG | 3' UTR | 21 | 1044 |
| OSC51 | 1085-1107 | 1085 | TCCCTGGACACTCCCTATGGAGA | 3' UTR | 21 | 1045 |
| OSC52 | 1088-1110 | 1088 | CTGGACACTCCCTATGGAGATCC | 3' UTR | 21 | 1046 |
| OSC53 | 1129-1151 | 1129 | ACCTGCCACAGCCAGAACTGAGG | 3' UTR | 21 | 1047 |
| OSC54 | 1163-1185 | 1163 | GGCAGCTCCCAGGGGTAGAACG | 3' UTR | 21 | 1048 |
| OSC55 | 1176-1198 | 1176 | GGGTAGAACGGCCCTGTGCTTAA | 3' UTR | 21 | 1049 |
| OSC56 | 1182-1204 | 1182 | AACGGCCCTGTGCTTAAGACACT | 3' UTR | 21 | 1050 |
| OSC57 | 1184-1206 | 1184 | CGGCCCTGTGCTTAAGACACTCC | 3' UTR | 21 | 1051 |
| OSC58 | 1237-1259 | 1237 | TTGCTTCACATCCTCAAAAAAAA | 3' UTR | 21 | 1052 |
| OSC59 | 1238-1260 | 1238 | TGCTTCACATCCTCAAAAAAAA | 3' UTR | 21 | 1053 |

TABLE 6A

LRP2 ANTISENSE TARGET

| ID | Target position | Start position | Target sequence | Location | Size | SEQ ID NO: |
|---|---|---|---|---|---|---|
| OSL1 | 512-534 | 512 | GTCAAGATTGCTCACAAAGTACA | CDS | 21 | 1054 |
| OSL2 | 566-588 | 566 | GTCAGTGTATCCCAAGTGAATAC | CDS | 21 | 1055 |
| OSL3 | 763-785 | 763 | TTGCACAATGAGTTTTCATGTGG | CDS | 21 | 1056 |
| OSL4 | 939-961 | 939 | TGGAGAAGATGACTGTAAAGATA | CDS | 21 | 1057 |
| OSL5 | 941-963 | 941 | GAGAAGATGACTGTAAAGATAAT | CDS | 21 | 1058 |

TABLE 6A-continued

LRP2 ANTISENSE TARGET

| ID | Target position | Start position | Target sequence | Location | Size | SEQ ID NO: |
|---|---|---|---|---|---|---|
| OSL6 | 992-1014 | 992 | CTCATGATGTTCATAAATGTTCC | CDS | 21 | 1059 |
| OSL7 | 1053-1075 | 1053 | CTCCATTTATAAAGTTTGTGATG | CDS | 21 | 1060 |
| OSL8 | 1054-1076 | 1054 | TCCATTTATAAAGTTTGTGATGG | CDS | 21 | 1061 |
| OSL9 | 1119-1141 | 1119 | TACCGGAAAATACTGTAGTATGA | CDS | 21 | 1062 |
| OSL10 | 1121-1143 | 1121 | CCGGAAAATACTGTAGTATGACT | CDS | 21 | 1063 |
| OSL11 | 1267-1289 | 1267 | TGCCAGATATGGGGAATTTGTGA | CDS | 21 | 1064 |
| OSL12 | 1329-1351 | 1329 | CTGTGAAGAAGGGTATATCTTGG | CDS | 21 | 1065 |
| OSL13 | 1356-1378 | 1356 | TGGACAGTATTGCAAAGCTAATG | CDS | 21 | 1066 |
| OSL14 | 1360-1382 | 1360 | CAGTATTGCAAAGCTAATGATTC | CDS | 21 | 1067 |
| OSL15 | 1366-1388 | 1366 | TGCAAAGCTAATGATTCCTTTGG | CDS | 21 | 1068 |
| OSL16 | 1423-1445 | 1423 | TTGTTAATTGGTGATATTCATGG | CDS | 21 | 1069 |
| OSL17 | 1541-1563 | 1541 | CCGTGCAAAATAAGGTTTTTTCA | CDS | 21 | 1070 |
| OSL18 | 1543-1565 | 1543 | GTGCAAAATAAGGTTTTTTCAGT | CDS | 21 | 1071 |
| OSL19 | 1552-1574 | 1552 | AAGGTTTTTTCAGTTGACATTAA | CDS | 21 | 1072 |
| OSL20 | 1553-1575 | 1553 | AGGTTTTTTCAGTTGACATTAAT | CDS | 21 | 1073 |
| OSL21 | 1562-1584 | 1562 | CAGTTGACATTAATGGTTTAAAT | CDS | 21 | 1074 |
| OSL22 | 1565-1587 | 1565 | TTGACATTAATGGTTTAAATATC | CDS | 21 | 1075 |
| OSL23 | 1638-1660 | 1638 | CTGGGTTAATAATAAAATCTATC | CDS | 21 | 1076 |
| OSL24 | 1639-1661 | 1639 | TGGGTTAATAATAAAATCTATCT | CDS | 21 | 1077 |
| OSL25 | 1680-1702 | 1680 | CCGCATAGATATGGTAAATTTGG | CDS | 21 | 1078 |
| OSL26 | 1719-1741 | 1719 | TACCCTTATAACTGAAAACTTGG | CDS | 21 | 1079 |
| OSL27 | 1767-1789 | 1767 | CCCAACTGTTGGTTATTTATTTT | CDS | 21 | 1080 |
| OSL28 | 1772-1794 | 1772 | CTGTTGGTTATTTATTTTTCTCA | CDS | 21 | 1081 |
| OSL29 | 1895-1917 | 1895 | GGGTAACTCTGGATATGATATCG | CDS | 21 | 1082 |

TABLE 6A-continued

LRP2 ANTISENSE TARGET

| ID | Target position | Start position | Target sequence | Location | Size | SEQ ID NO: |
|---|---|---|---|---|---|---|
| OSL30 | 1942-1964 | 1942 | CGGTTTGATTACATTGAAACTGT | CDS | 21 | 1083 |
| OSL31 | 1946-1968 | 1946 | TTGATTACATTGAAACTGTAACT | CDS | 21 | 1084 |
| OSL32 | 1951-1973 | 1951 | TACATTGAAACTGTAACTTATGA | CDS | 21 | 1085 |
| OSL33 | 2187-2209 | 2187 | TGCTACCAATCCGTGTAAAGATA | CDS | 21 | 1086 |
| OSL34 | 2437-2459 | 2437 | TTCTTTGTCGGGATTGATTTTGA | CDS | 21 | 1087 |
| OSL35 | 2469-2491 | 2469 | CAGCACTATCTTTTTTCAGATA | CDS | 21 | 1088 |
| OSL36 | 2470-2492 | 2470 | AGCACTATCTTTTTTCAGATAT | CDS | 21 | 1089 |
| OSL37 | 2491-2513 | 2491 | ATGTCAAAACACATGATTTTAA | CDS | 21 | 1090 |
| OSL38 | 2498-2520 | 2498 | AACACATGATTTTTAAGCAAAAG | CDS | 21 | 1091 |
| OSL39 | 2558-2580 | 2558 | GGGTGGAAAATGTTGAAAGTTTG | CDS | 21 | 1092 |
| OSL40 | 2579-2601 | 2579 | TGGCTTTTGATTGGATTTCAAAG | CDS | 21 | 1093 |
| OSL41 | 2580-2602 | 2580 | GGCTTTTGATTGGATTTCAAAGA | CDS | 21 | 1094 |
| OSL42 | 2589-2611 | 2589 | TTGGATTTCAAAGAATCTCTATT | CDS | 21 | 1095 |
| OSL43 | 2590-2612 | 2590 | TGGATTTCAAAGAATCTCTATTG | CDS | 21 | 1096 |
| OSL44 | 2670-2692 | 2670 | CACAGTAGTTCAGTATTTAAATA | CDS | 21 | 1097 |
| OSL45 | 2672-2694 | 2672 | CAGTAGTTCAGTATTTAAATAAC | CDS | 21 | 1098 |
| OSL46 | 2714-2736 | 2714 | ATCCTTTTGCCGGGTATCTATTC | CDS | 21 | 1099 |
| OSL47 | 2800-2820 | 2800 | CCTGTAATAAACACTACTCTT | CDS | 21 | 1394 |
| OSL48 | 2869-2891 | 2869 | TGGGTAGATGCCTATTTTGATAA | CDS | 21 | 1100 |
| OSL49 | 2877-2899 | 2877 | TGCCTATTTTGATAAAATTGAGC | CDS | 21 | 1101 |
| OSL50 | 2971-2993 | 2971 | GCCATCTTTGGAGAGCATTTATT | CDS | 21 | 1102 |
| OSL51 | 3074-3096 | 3074 | TTGCTTACATACTGCATTTGAAA | CDS | 21 | 1103 |
| OSL52 | 3075-3097 | 3075 | TGCTTACATACTGCATTTGAAAT | CDS | 21 | 1104 |
| OSL53 | 3120-3142 | 3120 | TGGTTCTAACGCCTGTAATCAAC | CDS | 21 | 1105 |

TABLE 6A-continued

LRP2 ANTISENSE TARGET

| ID | Target position | Start position | Target sequence | Location | Size | SEQ ID NO: |
|---|---|---|---|---|---|---|
| OSL54 | 3356-3378 | 3356 | TCGATGATTGTCATGATAACAGT | CDS | 21 | 1106 |
| OSL55 | 3546-3568 | 3546 | CACCCAATACACCTGTGATAATC | CDS | 21 | 1107 |
| OSL56 | 3547-3569 | 3547 | ACCCAATACACCTGTGATAATCA | CDS | 21 | 1108 |
| OSL57 | 3569-3591 | 3569 | ACCAGTGTATCTCAAAGAACTGG | CDS | 21 | 1109 |
| OSL58 | 3629-3651 | 3629 | ATGAAAAGAACTGCAATTCGACA | CDS | 21 | 1110 |
| OSL59 | 3681-3703 | 3681 | CCCCAATCATCGATGTATTGACC | CDS | 21 | 1111 |
| OSL60 | 3690-3712 | 3690 | TCGATGTATTGACCTATCGTTTG | CDS | 21 | 1112 |
| OSL61 | 3693-3715 | 3693 | ATGTATTGACCTATCGTTTGTCT | CDS | 21 | 1113 |
| OSL62 | 3828-3850 | 3828 | TCGTTGTGATGGTGTTTTTGATT | CDS | 21 | 1114 |
| OSL63 | 3945-3967 | 3945 | CCCGAACTTCTGGGAATGTGATG | CDS | 21 | 1115 |
| OSL64 | 3946-3968 | 3946 | CCGAACTTCTGGGAATGTGATGG | CDS | 21 | 1116 |
| OSL65 | 4015-4037 | 4015 | CCCAAGACTTGCCCTTCATCATA | CDS | 21 | 1117 |
| OSL66 | 4348-4370 | 4348 | TTCTTACTTGCCAATGATTCTAA | CDS | 21 | 1118 |
| OSL67 | 4379-4401 | 4379 | AAGACATAGATGAATGTGATATT | CDS | 21 | 1119 |
| OSL68 | 4381-4403 | 4381 | GACATAGATGAATGTGATATTCT | CDS | 21 | 1120 |
| OSL69 | 4455-4477 | 4455 | GTGTGATACAGGCTACATGTTAG | CDS | 21 | 1121 |
| OSL70 | 4464-4486 | 4464 | AGGCTACATGTTAGAAAGTGATG | CDS | 21 | 1122 |
| OSL71 | 4465-4487 | 4465 | GGCTACATGTTAGAAAGTGATGG | CDS | 21 | 1123 |
| OSL72 | 4597-4619 | 4597 | GTCGAGAATGGTTCTTACATTGT | CDS | 21 | 1124 |
| OSL73 | 4600-4622 | 4600 | GAGAATGGTTCTTACATTGTAGC | CDS | 21 | 1125 |
| OSL74 | 4612-4634 | 4612 | TACATTGTAGCTGTTGATTTTGA | CDS | 21 | 1126 |
| OSL75 | 4620-4642 | 4620 | AGCTGTTGATTTTGATTCAATTA | CDS | 21 | 1127 |
| OSL76 | 4622-4644 | 4622 | CTGTTGATTTTGATTCAATTAGT | CDS | 21 | 1128 |
| OSL77 | 4635-4657 | 4635 | TTCAATTAGTGGTCGTATCTTTT | CDS | 21 | 1129 |

TABLE 6A-continued

LRP2 ANTISENSE TARGET

| ID | Target position | Start position | Target sequence | Location | Size | SEQ ID NO: |
|---|---|---|---|---|---|---|
| OSL78 | 4732-4754 | 4732 | AGCATCATCTTGACTGAAACTAT | CDS | 21 | 1130 |
| OSL79 | 4735-4757 | 4735 | ATCATCTTGACTGAAACTATTGC | CDS | 21 | 1131 |
| OSL80 | 4741-4763 | 4741 | TTGACTGAAACTATTGCAATAGA | CDS | 21 | 1132 |
| OSL81 | 4743-4765 | 4743 | GACTGAAACTATTGCAATAGATT | CDS | 21 | 1133 |
| OSL82 | 4745-4767 | 4745 | CTGAAACTATTGCAATAGATTGG | CDS | 21 | 1134 |
| OSL83 | 4806-4828 | 4806 | AACAATTGAAGTCTCCAAAATTG | CDS | 21 | 1135 |
| OSL84 | 4847-4869 | 4847 | TGCTGATTAGTAAAAACCTAACA | CDS | 21 | 1136 |
| OSL85 | 4883-4905 | 4883 | TAGCATTAGATCCCAGAATGAAT | CDS | 21 | 1137 |
| OSL86 | 4884-4906 | 4884 | AGCATTAGATCCCAGAATGAATG | CDS | 21 | 1138 |
| OSL87 | 4896-4918 | 4896 | CAGAATGAATGAGCATCTACTGT | CDS | 21 | 1139 |
| OSL88 | 5077-5099 | 5077 | ATGGACTTTTGTGATTATAATGG | CDS | 21 | 1140 |
| OSL89 | 5080-5102 | 5080 | GACTTTTGTGATTATAATGGACA | CDS | 21 | 1141 |
| OSL90 | 5126-5144 | 5126 | GTGATTTGATTATACGGCA | CDS | 19 | 1142 |
| OSL91 | 5241-5263 | 5241 | GTCAGTTGTAATGTATAATATTC | CDS | 21 | 1143 |
| OSL92 | 5246-5268 | 5246 | TTGTAATGTATAATATTCAATGG | CDS | 21 | 1144 |
| OSL93 | 5291-5313 | 5291 | ATCCTTCGAAACAACCAAATTCC | CDS | 21 | 1145 |
| OSL94 | 5295-5317 | 5295 | TTCGAAACAACCAAATTCCGTGA | CDS | 21 | 1146 |
| OSL95 | 5447-5469 | 5447 | AACCTTTCTTAATAACTGTAAGG | CDS | 21 | 1147 |
| OSL96 | 5467-5489 | 5467 | AGGCAACATATAATTTTTGGAAT | CDS | 21 | 1148 |
| OSL97 | 5468-5490 | 5468 | GGCAACATATAATTTTTGGAATC | CDS | 21 | 1149 |
| OSL98 | 5538-5560 | 5538 | AGGGATACAGAATGGTTTAGATG | CDS | 21 | 1150 |
| OSL99 | 5539-5561 | 5539 | GGGATACAGAATGGTTTAGATGT | CDS | 21 | 1151 |
| OSL100 | 5545-5567 | 5545 | CAGAATGGTTTAGATGTTGAATT | CDS | 21 | 1152 |
| OSL101 | 5584-5606 | 5584 | TACATCTATTGGGTTGAAAATCC | CDS | 21 | 1153 |

TABLE 6A-continued

LRP2 ANTISENSE TARGET

| ID | Target position | Start position | Target sequence | Location | Size | SEQ ID NO: |
|---|---|---|---|---|---|---|
| OSL102 | 5644-5666 | 5644 | AGGACAGTATTTGCTTCTATATC | CDS | 21 | 1154 |
| OSL103 | 5648-5670 | 5648 | CAGTATTTGCTTCTATATCTATG | CDS | 21 | 1155 |
| OSL104 | 5677-5697 | 5677 | CCTTCTATGAACCTGGCCTTA | CDS | 21 | 1156 |
| OSL105 | 5692-5714 | 5692 | GCCTTAGATTGGATTTCAAGAAA | CDS | 21 | 1157 |
| OSL106 | 5701-5723 | 5701 | TGGATTTCAAGAAACCTTTATTC | CDS | 21 | 1158 |
| OSL107 | 5738-5760 | 5738 | CTCAGTCAATCGAGGTTTTGACA | CDS | 21 | 1159 |
| OSL108 | 5765-5787 | 5765 | ACGGAGATATCAGATACAGAAAA | CDS | 21 | 1160 |
| OSL109 | 5766-5788 | 5766 | CGGAGATATCAGATACAGAAAAA | CDS | 21 | 1161 |
| OSL110 | 5768-5790 | 5768 | GAGATATCAGATACAGAAAAACA | CDS | 21 | 1162 |
| OSL111 | 5775-5797 | 5775 | CAGATACAGAAAAACATTGATTG | CDS | 21 | 1163 |
| OSL112 | 6115-6137 | 6115 | GTCCATGATTCTTTCCTTTATTA | CDS | 21 | 1164 |
| OSL113 | 6116-6138 | 6116 | TCCATGATTCTTTCCTTTATTAT | CDS | 21 | 1165 |
| OSL114 | 6123-6145 | 6123 | TTCTTTCCTTTATTATACTGATG | CDS | 21 | 1166 |
| OSL115 | 6146-6168 | 6146 | AACAGTATGAGGTCATTGAAAGA | CDS | 21 | 1167 |
| OSL116 | 6202-6224 | 6202 | TTGAGAGATAATGTTCCAAATCT | CDS | 21 | 1168 |
| OSL117 | 6204-6226 | 6204 | GAGAGATAATGTTCCAAATCTGA | CDS | 21 | 1169 |
| OSL118 | 6206-6228 | 6206 | GAGATAATGTTCCAAATCTGAGG | CDS | 21 | 1170 |
| OSL119 | 6266-6284 | 6266 | CCTCAAATGGCTGTAGCAA | CDS | 19 | 1171 |
| OSL120 | 6387-6409 | 6387 | CTCTCCATATAACTCTTTCATTG | CDS | 21 | 1172 |
| OSL121 | 6390-6412 | 6390 | TCCATATAACTCTTTCATTGTTG | CDS | 21 | 1173 |
| OSL122 | 6397-6419 | 6397 | AACTCTTTCATTGTTGTTTCAAT | CDS | 21 | 1174 |
| OSL123 | 6399-6421 | 6399 | CTCTTTCATTGTTGTTTCAATGC | CDS | 21 | 1175 |
| OSL124 | 6425-6447 | 6425 | CTGCAATCAGAGGCTTTAGCTTG | CDS | 21 | 1176 |
| OSL125 | 6426-6448 | 6426 | TGCAATCAGAGGCTTTAGCTTGG | CDS | 21 | 1177 |

TABLE 6A-continued

LRP2 ANTISENSE TARGET

| ID | Target position | Start position | Target sequence | Location | Size | SEQ ID NO: |
|---|---|---|---|---|---|---|
| OSL126 | 6434-6456 | 6434 | GAGGCTTTAGCTTGGAATTGTCA | CDS | 21 | 1178 |
| OSL127 | 6436-6458 | 6436 | GGCTTTAGCTTGGAATTGTCAGA | CDS | 21 | 1179 |
| OSL128 | 6445-6467 | 6445 | TTGGAATTGTCAGATCATTCAGA | CDS | 21 | 1180 |
| OSL129 | 6603-6625 | 6603 | TGGATCTTCTCTGATGAACATTG | CDS | 21 | 1181 |
| OSL130 | 6619-6641 | 6619 | AACATTGTGACACATGGAATAGG | CDS | 21 | 1182 |
| OSL131 | 6711-6733 | 6711 | TTCTGAAACACTGATAGAAGTTC | CDS | 21 | 1183 |
| OSL132 | 6725-6747 | 6725 | TAGAAGTTCTGCGGATCAATACT | CDS | 21 | 1184 |
| OSL133 | 6797-6819 | 6797 | TTGTTGTAGATCCCAAGAACAGA | CDS | 21 | 1185 |
| OSL134 | 6849-6871 | 6849 | ACCAAAGATTGAGCGTTCTTTCC | CDS | 21 | 1186 |
| OSL135 | 6939-6961 | 6939 | CCGAAGTGATGGCTACGTTTATT | CDS | 21 | 1187 |
| OSL136 | 6961-6983 | 6961 | TGGGTTGATGATTCTTTAGATAT | CDS | 21 | 1188 |
| OSL137 | 6965-6987 | 6965 | TTGATGATTCTTTAGATATAATT | CDS | 21 | 1189 |
| OSL138 | 7062-7084 | 7062 | CACTGTTTTGAAAATTCTATCA | CDS | 21 | 1190 |
| OSL139 | 7064-7086 | 7064 | CTGTTTTGAAAATTCTATCATA | CDS | 21 | 1191 |
| OSL140 | 7087-7109 | 7087 | TGGGTAGATAGGAATTTGAAAAA | CDS | 21 | 1192 |
| OSL141 | 7088-7110 | 7088 | GGGTAGATAGGAATTTGAAAAG | CDS | 21 | 1193 |
| OSL142 | 7152-7174 | 7152 | CACAGTGATAAGAGACAATATCA | CDS | 21 | 1194 |
| OSL143 | 7154-7176 | 7154 | CAGTGATAAGAGACAATATCAAC | CDS | 21 | 1195 |
| OSL144 | 7348-7370 | 7348 | GGCAAGAATTGTGCCATTTCAAC | CDS | 21 | 1196 |
| OSL145 | 7351-7373 | 7351 | AAGAATTGTGCCATTTCAACAGA | CDS | 21 | 1197 |
| OSL146 | 7358-7380 | 7358 | GTGCCATTTCAACAGAAAATTTC | CDS | 21 | 1198 |
| OSL147 | 7359-7381 | 7359 | TGCCATTTCAACAGAAAATTTCC | CDS | 21 | 1199 |
| OSL148 | 7381-7403 | 7381 | CTCATCTTTGCCTTGTCTAATTC | CDS | 21 | 1200 |

TABLE 6A-continued

LRP2 ANTISENSE TARGET

| ID | Target position | Start position | Target sequence | Location | Size | SEQ ID NO: |
|---|---|---|---|---|---|---|
| OSL149 | 7443-7465 | 7443 | ACCTTTCCAAACAATAAATGTGG | CDS | 21 | 1201 |
| OSL150 | 7486-7508 | 7486 | GACTATGACAGTGTAAGTGATAG | CDS | 21 | 1202 |
| OSL151 | 7494-7516 | 7494 | CAGTGTAAGTGATAGAATCTACT | CDS | 21 | 1203 |
| OSL152 | 7496-7518 | 7496 | GTGTAAGTGATAGAATCTACTTC | CDS | 21 | 1204 |
| OSL153 | 7506-7528 | 7506 | TAGAATCTACTTCACACAAAATT | CDS | 21 | 1205 |
| OSL154 | 7510-7532 | 7510 | ATCTACTTCACACAAAATTTAGC | CDS | 21 | 1206 |
| OSL155 | 7627-7649 | 7627 | GCCTTTGACTGGATTACTAGAAG | CDS | 21 | 1207 |
| OSL156 | 7633-7655 | 7633 | GACTGGATTACTAGAAGAATTTA | CDS | 21 | 1208 |
| OSL157 | 7635-7657 | 7635 | CTGGATTACTAGAAGAATTTATT | CDS | 21 | 1209 |
| OSL158 | 7636-7658 | 7636 | TGGATTACTAGAAGAATTTATTA | CDS | 21 | 1210 |
| OSL159 | 8007-8029 | 8007 | GACTCTCTATGGCCAGTATATTT | CDS | 21 | 1211 |
| OSL160 | 8036-8058 | 8036 | CTGACTTGTACACACAAAGAATT | CDS | 21 | 1212 |
| OSL161 | 8038-8060 | 8038 | GACTTGTACACACAAAGAATTTA | CDS | 21 | 1213 |
| OSL162 | 8044-8066 | 8044 | TACACACAAAGAATTTACCGAGC | CDS | 21 | 1214 |
| OSL163 | 8150-8172 | 8150 | ACCAGAAACAACAGTGTAACAAT | CDS | 21 | 1215 |
| OSL164 | 8152-8174 | 8152 | CAGAAACAACAGTGTAACAATCC | CDS | 21 | 1216 |
| OSL165 | 8167-8189 | 8167 | AACAATCCTTGTGAACAGTTTAA | CDS | 21 | 1217 |
| OSL166 | 8293-8315 | 8293 | GTGGACAATGGTGAACGATGTGG | CDS | 21 | 1218 |
| OSL167 | 8564-8586 | 8564 | CGGAGTTTATGTGCAATAACAGA | CDS | 21 | 1219 |
| OSL168 | 8566-8588 | 8566 | GAGTTTATGTGCAATAACAGAAG | CDS | 21 | 1220 |
| OSL169 | 8685-8707 | 8685 | TGGATACACAAAATGTCATAATT | CDS | 21 | 1221 |
| OSL170 | 8689-8711 | 8689 | TACACAAAATGTCATAATTCAAA | CDS | 21 | 1222 |
| OSL171 | 8691-8713 | 8691 | CACAAAATGTCATAATTCAAATA | CDS | 21 | 1223 |
| OSL172 | 8699-8721 | 8699 | GTCATAATTCAAATATTTGTATT | CDS | 21 | 1224 |

TABLE 6A-continued

LRP2 ANTISENSE TARGET

| ID | Target position | Start position | Target sequence | Location | Size | SEQ ID NO: |
|---|---|---|---|---|---|---|
| OSL173 | 8715-8737 | 8715 | TTGTATTCCTCGCGTTTATTTGT | CDS | 21 | 1225 |
| OSL174 | 8768-8790 | 8768 | GTGATGAAAACCCTACTTATTGC | CDS | 21 | 1226 |
| OSL175 | 8844-8866 | 8844 | TCCTCAACATTGGTATTGTGATC | CDS | 21 | 1227 |
| OSL176 | 8854-8876 | 8854 | TGGTATTGTGATCAAGAAACAGA | CDS | 21 | 1228 |
| OSL177 | 8861-8883 | 8861 | GTGATCAAGAAACAGATTGTTTT | CDS | 21 | 1229 |
| OSL178 | 9063-9085 | 9063 | TTCCGAGTTTCTCTGTGTAAATG | CDS | 21 | 1230 |
| OSL179 | 9064-9086 | 9064 | TCCGAGTTTCTCTGTGTAAATGA | CDS | 21 | 1231 |
| OSL180 | 9153-9175 | 9153 | CGGCTACGATGAGAATCAGAATT | CDS | 21 | 1232 |
| OSL181 | 9181-9203 | 9181 | AGGAGAACTTGCTCTGAAAATGA | CDS | 21 | 1233 |
| OSL182 | 9221-9243 | 9221 | GACTGTGTATCCCAAAGATATTC | CDS | 21 | 1234 |
| OSL183 | 9308-9330 | 9308 | GCCAACAGAATCAGTTTACCTGT | CDS | 21 | 1235 |
| OSL184 | 9595-9617 | 9595 | GACACCTTAACCAGTTTCTATTG | CDS | 21 | 1236 |
| OSL185 | 9598-9620 | 9598 | ACCTTAACCAGTTTCTATTGTTC | CDS | 21 | 1237 |
| OSL186 | 9657-9679 | 9657 | GACTTGTGTTGATATTGATGAAT | CDS | 21 | 1238 |
| OSL187 | 9719-9741 | 9719 | ATGTAATAGGCTCCTACATCTGT | CDS | 21 | 1239 |
| OSL188 | 9786-9808 | 9786 | CCGGCAAAACAGTAACATCGAAC | CDS | 21 | 1240 |
| OSL189 | 9807-9829 | 9807 | ACCCTATCTCATTTTTAGCAACC | CDS | 21 | 1241 |
| OSL190 | 9826-9848 | 9826 | AACCGTTACTATTTGAGAAATTT | CDS | 21 | 1242 |
| OSL191 | 9827-9849 | 9827 | ACCGTTACTATTTGAGAAATTTA | CDS | 21 | 1243 |
| OSL192 | 9828-9850 | 9828 | CCGTTACTATTTGAGAAATTTAA | CDS | 21 | 1244 |
| OSL193 | 9832-9854 | 9832 | TACTATTTGAGAAATTTAACTAT | CDS | 21 | 1245 |
| OSL194 | 9838-9860 | 9838 | TTGAGAAATTTAACTATAGATGG | CDS | 21 | 1246 |
| OSL195 | 9849-9871 | 9849 | AACTATAGATGGCTATTTTTACT | CDS | 21 | 1247 |
| OSL196 | 9892-9914 | 9892 | GACAATGTTGTGGCATTAGATTT | CDS | 21 | 1248 |

TABLE 6A-continued

LRP2 ANTISENSE TARGET

| ID | Target position | Start position | Target sequence | Location | Size | SEQ ID NO: |
|---|---|---|---|---|---|---|
| OSL197 | 9925-9947 | 9925 | GAGAAGAGATTGTATTGGATTGA | CDS | 21 | 1249 |
| OSL198 | 9956-9978 | 9956 | GGCAAGTCATTGAGAGAATGTTT | CDS | 21 | 1250 |
| OSL199 | 9987-10009 | 9987 | GACAAACAAGGAGACAATCATAA | CDS | 21 | 1251 |
| OSL200 | 10272-10294 | 10272 | AACCAACAAGTCTGTGATAATCT | CDS | 21 | 1252 |
| OSL201 | 10444-10466 | 10444 | TTCGCTATTACCATTTTTGAAGA | CDS | 21 | 1253 |
| OSL202 | 10446-10468 | 10446 | CGCTATTACCATTTTTGAAGACA | CDS | 21 | 1254 |
| OSL203 | 10499-10521 | 10499 | CAGTGGAAAAGGGAAACAAATAT | CDS | 21 | 1255 |
| OSL204 | 10513-10535 | 10513 | AACAAATATGATGGATCAAATAG | CDS | 21 | 1256 |
| OSL205 | 10574-10596 | 10574 | TCCATGTGTACCATCCATATAGG | CDS | 21 | 1257 |
| OSL206 | 10958-10980 | 10958 | CTGATGAAGACCGTCTTCTTTGT | CDS | 21 | 1258 |
| OSL207 | 11246-11268 | 11246 | GTGACAACTTCACAGAATTCAGC | CDS | 21 | 1259 |
| OSL208 | 11623-11645 | 11623 | CAGTGTACAAGTGGACATTGTGT | CDS | 21 | 1260 |
| OSL209 | 11625-11647 | 11625 | GTGTACAAGTGGACATTGTGTAC | CDS | 21 | 1261 |
| OSL210 | 11745-11767 | 11745 | TACTATGTTCGAATGCAAAAACC | CDS | 21 | 1262 |
| OSL211 | 11749-11771 | 11749 | ATGTTCGAATGCAAAAACCATGT | CDS | 21 | 1263 |
| OSL212 | 11757-11779 | 11757 | ATGCAAAAACCATGTTTGTATCC | CDS | 21 | 1264 |
| OSL213 | 11779-11801 | 11779 | CCGCCATATTGGAAATGTGATGG | CDS | 21 | 1265 |
| OSL214 | 11820-11842 | 11820 | TGGTTCAGATGAAGAACTTCACC | CDS | 21 | 1266 |
| OSL215 | 11887-11909 | 11887 | GACAACAATCGCTGCATTTATAG | CDS | 21 | 1267 |
| OSL216 | 11984-12006 | 11984 | CCCCTAAACCTTGTACAGAATAT | CDS | 21 | 1268 |
| OSL217 | 11985-12007 | 11985 | CCCTAAACCTTGTACAGAATATG | CDS | 21 | 1269 |
| OSL218 | 11990-12012 | 11990 | AACCTTGTACAGAATATGAATAT | CDS | 21 | 1270 |
| OSL219 | 11991-12013 | 11991 | ACCTTGTACAGAATATGAATATA | CDS | 21 | 1271 |
| OSL220 | 11994-12016 | 11994 | TTGTACAGAATATGAATATAAGT | CDS | 21 | 1272 |

TABLE 6A-continued

LRP2 ANTISENSE TARGET

| ID | Target position | Start position | Target sequence | Location | Size | SEQ ID NO: |
|---|---|---|---|---|---|---|
| OSL221 | 12083-12105 | 12083 | CCGATGAACTGGGTTGCAATAAA | CDS | 21 | 1273 |
| OSL222 | 12114-12136 | 12114 | AAGAACATGTGCTGAAAATATAT | CDS | 21 | 1274 |
| OSL223 | 12140-12162 | 12140 | AGCAAAATTGTACCCAATTAAAT | CDS | 21 | 1275 |
| OSL224 | 12193-12215 | 12193 | GGGTTCGAAACCAATGTTTTTGA | CDS | 21 | 1276 |
| OSL225 | 12197-12219 | 12197 | TCGAAACCAATGTTTTTGACAGA | CDS | 21 | 1277 |
| OSL226 | 12389-12411 | 12389 | CTGACAATGTCCGAATTCGAAAA | CDS | 21 | 1278 |
| OSL227 | 12397-12419 | 12397 | GTCCGAATTCGAAAATATAATCT | CDS | 21 | 1279 |
| OSL228 | 12399-12421 | 12399 | CCGAATTCGAAAATATAATCTCT | CDS | 21 | 1280 |
| OSL229 | 12435-12457 | 12435 | CTCAGAGTATCTTCAAGATGAGG | CDS | 21 | 1281 |
| OSL230 | 12443-12465 | 12443 | ATCTTCAAGATGAGGAATATATC | CDS | 21 | 1282 |
| OSL231 | 12537-12561 | 12537 | GGGCTCTAGGTTTGGTGCTATCAAA | CDS | 25 | 1283 |
| OSL232 | 12564-12586 | 12564 | TGCCTACATCCCCAACTTTGAAT | CDS | 21 | 1284 |
| OSL233 | 12608-12630 | 12608 | AGGAAGTTGACCTGAAACTGAAA | CDS | 21 | 1285 |
| OSL234 | 12616-12638 | 12616 | GACCTGAAACTGAAATACGTAAT | CDS | 21 | 1286 |
| OSL235 | 12617-12639 | 12617 | ACCTGAAACTGAAATACGTAATG | CDS | 21 | 1287 |
| OSL236 | 12705-12727 | 12705 | ACGCATTGAGGTGGCTAAACTTG | CDS | 21 | 1288 |
| OSL237 | 12792-12814 | 12792 | TCCCAAACTAGGGCTTATGTTCT | CDS | 21 | 1289 |
| OSL238 | 12825-12847 | 12825 | GGGAAAGGAACCTAAAATCGAGT | CDS | 21 | 1290 |
| OSL239 | 12870-12892 | 12870 | CCGCAACATCCTGGTTTTCGAGG | CDS | 21 | 1291 |
| OSL240 | 12911-12933 | 12911 | GCCTTTCTATCGATTATTTGAAC | CDS | 21 | 1292 |
| OSL241 | 12915-12937 | 12915 | TTCTATCGATTATTTGAACAATG | CDS | 21 | 1293 |
| OSL242 | 12965-12987 | 12965 | AGGACGTTATTGAAACCATAAAA | CDS | 21 | 1294 |
| OSL243 | 12967-12989 | 12967 | GACGTTATTGAAACCATAAAATA | CDS | 21 | 1295 |
| OSL244 | 12968-12990 | 12968 | ACGTTATTGAAACCATAAAATAT | CDS | 21 | 1296 |

TABLE 6A-continued

LRP2 ANTISENSE TARGET

| ID | Target position | Start position | Target sequence | Location | Size | SEQ ID NO: |
|---|---|---|---|---|---|---|
| OSL245 | 12995-13019 | 12995 | GGACTGATAGGAGAGTCATTGCAAA | CDS | 21 | 1297 |
| OSL246 | 13058-13080 | 13058 | ACCAGTTATACTGGATATCTAAG | CDS | 25 | 1298 |
| OSL247 | 13086-13108 | 13086 | GGGAGAAGTATGGAAACAAAATA | CDS | 21 | 1299 |
| OSL248 | 13091-13113 | 13091 | AAGTATGGAAACAAAATAAATTT | CDS | 21 | 1300 |
| OSL249 | 13175-13197 | 13175 | TTCATCAACTCAGATACAATAAG | CDS | 21 | 1301 |
| OSL250 | 13368-13390 | 13368 | CGGAGGAAATTGCTATTTTGATG | CDS | 21 | 1302 |
| OSL251 | 13371-13393 | 13371 | AGGAAATTGCTATTTTGATGAGA | CDS | 21 | 1303 |
| OSL252 | 13428-13450 | 13428 | CACCGGAAAATATTGTGAAATGG | CDS | 21 | 1304 |
| OSL253 | 13440-13462 | 13440 | TTGTGAAATGGCGTTTTCAAAAG | CDS | 21 | 1305 |
| OSL254 | 13541-13563 | 13541 | CAGGATTCTTCCACTATAGAAGG | CDS | 21 | 1306 |
| OSL255 | 13659-13681 | 13659 | GGCAGATCTTAACATGGATATTG | CDS | 21 | 1307 |
| OSL256 | 13725-13747 | 13725 | GGCAATGAGTGAAGACTTTGTCA | CDS | 21 | 1308 |
| OSL257 | 13842-13864 | 13842 | ATCTGAAAATGTGGATAATAAGA | CDS | 21 | 1309 |
| OSL258 | 13844-13866 | 13844 | CTGAAAATGTGGATAATAAGAAT | CDS | 21 | 1310 |
| OSL259 | 13852-13874 | 13852 | GTGGATAATAAGAATTATGGAAG | CDS | 21 | 1311 |
| OSL260 | 13853-13875 | 13853 | TGGATAATAAGAATTATGGAAGT | CDS | 21 | 1312 |
| OSL261 | 13951-13973 | 13951 | TGGAATCTCTTCAAACGAAAATC | CDS | 21 | 1313 |
| OSL262 | 13955-13977 | 13955 | ATCTCTTCAAACGAAAATCTAAA | CDS | 21 | 1314 |
| OSL263 | 13957-13979 | 13957 | CTCTTCAAACGAAAATCTAAACA | CDS | 21 | 1315 |
| OSL264 | 13960-13982 | 13960 | TTCAAACGAAAATCTAAACAAAC | CDS | 21 | 1316 |
| OSL265 | 13964-13986 | 13964 | AACGAAAATCTAAACAAACTACC | CDS | 21 | 1317 |
| OSL266 | 13976-13998 | 13976 | AACAAACTACCAACTTTGAAAAT | CDS | 21 | 1318 |
| OSL267 | 13983-14005 | 13983 | TACCAACTTTGAAAATCCAATCT | CDS | 21 | 1319 |
| OSL268 | 13987-14009 | 13987 | AACTTTGAAAATCCAATCTATGC | CDS | 21 | 1320 |

TABLE 6A-continued

LRP2 ANTISENSE TARGET

| ID | Target position | Start position | Target sequence | Location | Size | SEQ ID NO: |
|---|---|---|---|---|---|---|
| OSL269 | 14121-14143 | 14121 | TGCAACAGAAGACACTTTTAAAG | CDS | 21 | 1321 |
| OSL270 | 14145-14167 | 14145 | CACCGCAAATCTTGTTAAAGAAG | CDS | 21 | 1322 |
| OSL271 | 14148-14170 | 14148 | CGCAAATCTTGTTAAAGAAGACT | CDS | 21 | 1323 |
| OSL272 | 14169-14191 | 14169 | CTCTGAAGTATAGCTATACCAGC | CDS/ 3'-UTR | 21 | 1324 |
| OSL273 | 14186-14208 | 14186 | ACCAGCTATTTAGGGAATAATTA | 3'-UTR | 21 | 1325 |
| OSL274 | 14188-14210 | 14188 | CAGCTATTTAGGGAATAATTAGA | 3'-UTR | 21 | 1326 |
| OSL275 | 14211-14233 | 14211 | AACACACTTTTGCACATATATTT | 3'-UTR | 21 | 1327 |
| OSL276 | 14213-14235 | 14213 | CACACTTTTGCACATATATTTTT | 3'-UTR | 21 | 1328 |
| OSL277 | 14236-14258 | 14236 | TACAAACAGATGAAAAAGTTAA | 3'-UTR | 21 | 1329 |
| OSL278 | 14252-14274 | 14252 | AAGTTAACATTCAGTACTTTATG | 3'-UTR | 21 | 1330 |
| OSL279 | 14261-14283 | 14261 | TTCAGTACTTTATGAAAAAAATA | 3'-UTR | 21 | 1331 |
| OSL280 | 14263-14285 | 14263 | CAGTACTTTATGAAAAAAATATA | 3'-UTR | 21 | 1332 |
| OSL281 | 14341-14363 | 14341 | CCGTCTCATATTTTTACAAATAA | 3'-UTR | 21 | 1333 |
| OSL282 | 14355-14377 | 14355 | TACAAATAATTATCACAATGTAC | 3'-UTR | 21 | 1334 |
| OSL283 | 14366-14388 | 14366 | ATCACAATGTACTATATGTATAT | 3'-UTR | 21 | 1335 |
| OSL284 | 14368-14390 | 14368 | CACAATGTACTATATGTATATCT | 3'-UTR | 21 | 1336 |
| OSL285 | 14372-14394 | 14372 | ATGTACTATATGTATATCTTTGC | 3'-UTR | 21 | 1337 |
| OSL286 | 14396-14418 | 14396 | CTGAAGTTGTCTGAAGGTAATAC | 3'-UTR | 21 | 1338 |
| OSL287 | 14406-14428 | 14406 | CTGAAGGTAATACTATAAATATA | 3'-UTR | 21 | 1339 |
| OSL288 | 14437-14459 | 14437 | TTGTAAATTTTGGAAAGATTATC | 3'-UTR | 21 | 1340 |
| OSL289 | 14447-14469 | 14447 | TGGAAAGATTATCCTGTTACTGA | 3'-UTR | 21 | 1341 |
| OSL290 | 14451-14473 | 14451 | AAGATTATCCTGTTACTGAATTT | 3'-UTR | 21 | 1342 |
| OSL291 | 14457-14479 | 14457 | ATCCTGTTACTGAATTTGCTAAT | 3'-UTR | 21 | 1343 |
| OSL292 | 14458-14480 | 14458 | TCCTGTTACTGAATTTGCTAATA | 3'-UTR | 21 | 1344 |

TABLE 6A-continued

LRP2 ANTISENSE TARGET

| ID | Target position | Start position | Target sequence | Location | Size | SEQ ID NO: |
|---|---|---|---|---|---|---|
| OSL293 | 14464-14486 | 14464 | TACTGAATTTGCTAATAAAGATG | 3'-UTR | 21 | 1345 |
| OSL294 | 14503-14525 | 14503 | GTGATCATTATAGTAAATGATCC | 3'-UTR | 21 | 1346 |
| OSL295 | 14513-14535 | 14513 | TAGTAAATGATCCAACAAGAAAA | 3'-UTR | 21 | 1347 |
| OSL296 | 14523-14545 | 14523 | TCCAACAAGAAAAGGAATTGACT | 3'-UTR | 21 | 1348 |
| OSL297 | 14579-14601 | 14579 | CACTCATATTTCCTATAAAATTA | 3'-UTR | 21 | 1349 |
| OSL298 | 14581-14603 | 14581 | CTCATATTTCCTATAAAATTATC | 3'-UTR | 21 | 1350 |
| OSL299 | 14633-14655 | 14633 | GTCCATTTTTACACATTAGCACT | 3'-UTR | 21 | 1351 |
| OSL300 | 14649-14671 | 14649 | TAGCACTTAATTAATGTTCAATA | 3'-UTR | 21 | 1352 |
| OSL301 | 14650-14672 | 14650 | AGCACTTAATTAATGTTCAATAT | 3'-UTR | 21 | 1353 |
| OSL302 | 14652-14674 | 14652 | CACTTAATTAATGTTCAATATTA | 3'-UTR | 21 | 1354 |
| OSL303 | 14665-14687 | 14665 | TTCAATATTACATGTCAATTTGA | 3'-UTR | 21 | 1355 |
| OSL304 | 14684-14706 | 14684 | TTGATTAATGGCTATGTTGATAG | 3'-UTR | 21 | 1356 |
| OSL305 | 14708-14730 | 14708 | GGCCACTATGTGTTGTATAGACA | 3'-UTR | 21 | 1357 |
| OSL306 | 14711-14733 | 14711 | CACTATGTGTTGTATAGACATCT | 3'-UTR | 21 | 1358 |
| OSL307 | 14767-14789 | 14767 | AGGTAGGAAAAGCAATTCAGTTT | 3'-UTR | 21 | 1359 |
| OSL308 | 14856-14878 | 14856 | GCCAAGACAACATTTTTATTTGT | 3'-UTR | 21 | 1360 |
| OSL309 | 14861-14883 | 14861 | GACAACATTTTTATTTGTGATGT | 3'-UTR | 21 | 1361 |
| OSL310 | 14886-14908 | 14886 | ATGAGGAAATCCCATATCATTAA | 3'-UTR | 21 | 1362 |
| OSL311 | 14921-14943 | 14921 | TGCATTGAGTTTGTGGTTAATTA | 3'-UTR | 21 | 1363 |
| OSL312 | 14925-14947 | 14925 | TTGAGTTTGTGGTTAATTAAATG | 3'-UTR | 21 | 1364 |
| OSL313 | 15034-15056 | 15034 | AGCTGAATTTCTGAAACCAAATC | 3'-UTR | 21 | 1365 |
| OSL314 | 15049-15071 | 15049 | ACCAAATCTGTGTCTTCATAAAA | 3'-UTR | 21 | 1366 |
| OSL315 | 15115-15137 | 15115 | TGGGTTTTGTTTCTATGAAAAT | 3'-UTR | 21 | 1367 |
| OSL316 | 15122-15144 | 15122 | TTGTTTCTATGAAAATATCATTA | 3'-UTR | 21 | 1368 |
| OSL317 | 15126-15148 | 15126 | TTCTATGAAAATATCATTATAAT | 3'-UTR | 21 | 1369 |

TABLE 6A-continued

LRP2 ANTISENSE TARGET

| ID | Target position | Start position | Target sequence | Location | Size | SEQ ID NO: |
|---|---|---|---|---|---|---|
| OSL318 | 15130-15152 | 15130 | ATGAAAATATCATTATAATCACT | 3'-UTR | 21 | 1370 |
| OSL319 | 15138-15160 | 15138 | ATCATTATAATCACTATTTATTT | 3'-UTR | 21 | 1371 |
| OSL320 | 15188-15210 | 15188 | AACCATTCTTATTAAGCTTTTTA | 3'-UTR | 21 | 1372 |
| OSL321 | 15189-15211 | 15189 | ACCATTCTTATTAAGCTTTTTAT | 3'-UTR | 21 | 1373 |
| OSL322 | 15220-15242 | 15220 | GTGGCTAAATGTGTACATTTATA | 3'-UTR | 21 | 1374 |
| OSL323 | 15221-15243 | 15221 | TGGCTAAATGTGTACATTTATAT | 3'-UTR | 21 | 1375 |
| OSL324 | 15222-15244 | 15222 | GGCTAAATGTGTACATTTATATT | 3'-UTR | 21 | 1376 |
| OSL325 | 15228-15250 | 15228 | ATGTGTACATTTATATTAGAATG | 3'-UTR | 21 | 1377 |
| OSL326 | 15263-15285 | 15263 | CAGATCTTTTCTTTAATTCTTAT | 3'-UTR | 21 | 1378 |
| OSL327 | 15266-15288 | 15266 | ATCTTTTCTTTAATTCTTATTGG | 3'-UTR | 21 | 1379 |
| OSL328 | 15271-15293 | 15271 | TTCTTTAATTCTTATTGGTTTTT | 3'-UTR | 21 | 1380 |
| OSL329 | 15438-15460 | 15438 | CTCTTAAATAGTGGGTATAGTCT | 3'-UTR | 21 | 1381 |
| OSL330 | 15524-15546 | 15524 | GTGCTAATATTGCACATTTGTTA | 3'-UTR | 21 | 1382 |
| OSL331 | 15525-15547 | 15525 | TGCTAATATTGCACATTTGTTAA | 3'-UTR | 21 | 1383 |
| OSL332 | 15575-15597 | 15575 | ATGGATGAATGAATGAAACATAT | 3'-UTR | 21 | 1384 |
| OSL333 | 15583-15605 | 15583 | ATGAATGAAACATATACTACTGA | 3'-UTR | 21 | 1385 |
| OSL334 | 15587-15609 | 15587 | ATGAAACATATACTACTGATTAT | 3'-UTR | 21 | 1386 |
| OSL335 | 15591-15613 | 15591 | AACATATACTACTGATTATTTTA | 3'-UTR | 21 | 1387 |
| OSL336 | 15655-15677 | 15655 | CTGACTGTAATTACTTTGATTAG | 3'-UTR | 21 | 1388 |
| OSL337 | 15659-15681 | 15659 | CTGTAATTACTTTGATTAGATAA | 3'-UTR | 21 | 1389 |
| OSL338 | 15675-15697 | 15675 | TAGATAAACAACTGGAAATAATG | 3'-UTR | 21 | 1390 |
| OSL339 | 15698-15720 | 15698 | CTGCTGAAAAAGTTCTAATAAAT | 3'-UTR | 21 | 1391 |
| OSL340 | 15699-15721 | 15699 | TGCTGAAAAAGTTCTAATAAATG | 3'-UTR | 21 | 1392 |

TABLE 11

Additional table of siRNA sequences

| SEQ ID | OSID | antisense sequence (5' to 3') | OSID | sense sequence (3' to 5') | SEQ ID NOS: |
|---|---|---|---|---|---|
| 957 | OSC17C-1 | CAGUUGCGCAGUUUCUUGUCAGUUC[dT][dT] | OSC17B-1 | [dT][dT]GUCAACGCGUCAAGAACAGUCAAG | 973 |
| 958 | OSC17C-2 | CAGUUGCGCAGUUUCUUGU[mC][mA]GUUC[dT][dT] | OSC17B-2 | [dT][dT]*G*UCAACGCGUCAAAGAACAGUCAAG | 974 |
| 959 | OSC17C-3 | CAGUUGCGCAGUUUCU[mU][mG]UCAGUUC[dT][dT] | OSC17B-3 | [dT][dT]*G*UCAACGCGUCAAAGAACAG[mU]CAAG | 975 |
| 960 | OSC17C-4 | CAGUUGCGCAGUUUCU[mU][mG]U[mC][mA]GUUC[dT][dT] | OSC17B-4 | [dT][dT]*G*UCAACGCGUCAAAGAA[mC]AGUCAAG | 976 |
| | | | OSC17B-5 | [dT][dT]*G*UCAACGCGUCAAAGAA[mC]AG[mU]CAAG | 977 |
| | | | OSC17B-6 | [dT][dT]*G*UCAA[mC]GCGUCAAAGAA[mC]AG[mU]CAAG | 978 |
| 961 | OSC47C-1 | AAGAGCUCAGGUCUCUGAGGG[dT][dT] | OSC47B-1 | [dT][dT]UUCUCGAGUCCAGAGACUCCC | 979 |
| 962 | OSC47C-2 | AAGAGCUCAGGUCUC[mU]GAGGG[dT][dT] | OSC47B-2 | [dT][dT]*U*UCUCGAGUCCAGAGACUCCC | 980 |
| 963 | OSC47C-3 | AAGAGCUCAGGUCUC[mU][mG]AGGG[dT][dT] | OSC47B-3 | [dT][dT]*U*UCUCGAGUCCAGAGA[mC]UCCC | 981 |
| | | | OSC47B-4 | [dT][dT]*U*UCUCGAGUCCAGAG[mA][mC]UCCC | 982 |
| | | | OSC47B-5 | [dT][dT]*U*UCUCGAG[mU]CCAGAG[mA][mC]UCCC | 983 |
| 964 | OSL231C-1 | UUUGAUAGCACCAAACCUAGAGCCC[dT][dT] | OSL231B-1 | [dT][dT]AAACUAUCGUGGUUUGGAUCUCGGG | 984 |
| 965 | OSL231C-2 | UUUGA[mU]AG[mC]ACCAAACC[mU]AGAGCCC[dT][dT] | OSL231B-2 | [dT][dT]*A*AACUAUCGUGGUUUGGAUCUCGGG | 985 |
| 966 | OSL231C-3 | UUUGAUAGCACCAAACC[mU][mA]GAGCCC[dT][dT] | OSL231B-3 | [dT][dT]*A*AACUA[mU]CG[mU]9 GGUUUGGA[mU]CUCGGG | 986 |
| 967 | OSL231C-4 | UUUGAUAG[mC]ACCAAACC[mU]AGAGCCC[dT][dT] | OSL231B-4 | [dT][dT]*A*AACU[mA][mU]C[mG][mU]GGUUUGG[mA][mU]CUCGGG | 987 |
| 968 | OSL231C-5 | UUUGAUAGCACCAAACC[mU]AGAGCCC[dT][dT] | OSL231B-5 | [dT][dT]*A*AACUGUCGUGGUUUGGA[mU]CUCGGG | 988 |
| | | | OSL231B-6 | [dT][dT]*A*AACUGUCG[mU]GGUUUGGA[mU]CUCGGG | 989 |
| | | | OSL231B-7 | [dT][dT]*A*AACUAUCGUGG[mU]UUGGAUCUCGGG | 990 |
| 969 | OSL245C-1 | UUUGCAAUGACUCUCCUAUCAGUCC[dT][dT] | OSL245B-1 | [dT][dT]AAACGUUACUGAGGAUAGUCAGG | 991 |
| 970 | OSL245C-2 | UUUGCAA[mU][mG]ACUCUCC[mU][mA]UCAGUCC[dT][dT] | OSL245B-2 | [dT][dT]*A*AACG[mU]UA[mC]UGAGAGGA[mU]AGUCAGG | 992 |
| 971 | OSL245C-3 | UUUGCAAUGACUCUCC[mU][mA]UCAGUCC[dT][dT] | OSL245B-3 | [dT][dT]*A*AACGUUACUGAGGA[mU]AGUCAGG | 993 |
| 972 | OSL245C-4 | UUUGCAA[mU][mG]ACUCUCCUAUCAGUCC[dT][dT] | OSL245B-4 | [dT][dT]*A*AACGUUA[mC]UGAGGA[mU]AGUCAGG | 994 |
| | | | OSL245B-5 | [dT][dT]*A*AACGUUACUGAGGAUAGUCAGG | 995 |

Key to modifications
[dT] = DNA base (T) within RNA oligo
[mA], [mG], [mC], [mU] = 2'O-Methyl RNA
* = Phosphorothioate linkages In one embodiment, an RNAi (e.g., a dsRNA) featured herein includes a first sequence of a dsRNA that is selected from the group including the sense sequences of any table herein and a second sequence that is selected from the group consisting of the corresponding antisense sequences of any table herein. A corresponding antisense sequence is a nucleotide sequence within the OSID family for example OSC17. In those instances when we refer to an siRNA with no suffix (e.g., OSC17), we mean that to indicate the dsRNA comprised of the antisense and sense strands corresponding to that number (e.g., OSC17A paired with OSC17S or OSC17C-(n) paired with OSC17B-(n) where "n" is any number of the OSC17 family).

Unless otherwise specified, the compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation. It is understood that the phosphorothioate group, designated by an asterisk (*), constitutes a stereogenic center, and the presence of each such group in a sequence engenders two diastereoisomers. The number of such diastereoisomers in a double stranded RNAi agent may be calculated by the formula 2^n, wherein n represents the number of phosphorothioate groups in a sequence comprised of a double stranded siRNA.

In some embodiments, the antisense strand (identified with "A" in the OS ID name) and/or the sense strand (identified with "S" in the OS ID name) of an RNAi agent comprises or consists of a nucleobase sequence, for example, "OSC17A-1" CAGUUGCGCAGUUUCUUGUCAGUUC[dT][dT] (SEQ ID NO: 17), and the nucleobase sequence may include at least one or more nucleotides as a modified nucleotide, and wherein SEQ ID NO: 17 is located at positions 1 to 25 (5'→3') of the antisense strand and forms a duplex with the corresponding sense strand (identified as OSC17S-1. In some embodiments, the antisense strand of an RNAi agent comprises or consists of a nucleobase sequence for example CAGUUGCGCAGUUUCUUGUCAGUUC[dT][dT] (SEQ ID NO: 17), wherein all or substantially all or 1, 2, 3, 4 or 5 of the nucleotides are modified nucleotides (see for example SEQ ID NO. 24), and wherein SEQ ID NO: 24 is located at positions 1 to 27 (5'→3') of the antisense strand. For any antisense or sense strand disclosed herein, in some embodiments, the antisense strand of an RNAi agent comprises or consists of the sequence (5'→3') wherein * is a phosphorothioate linkage between deoxy thymine [dT]; and/or wherein mC, mA, mG, mU are 2'-O-methyl cytidine, 2'-O-methyl adenine, 2'-O-methyl guanosine, 2'-O-methyl uridine respectively; and/or wherein 2fA, 2fU, 2fG, 2fC are 2'-fluoro adenine, 2'-fluoro uridine, 2'-fluoro guanosine, and 2'-fluoro cytosine respectively. The antisense target on the mRNA is identified with the same name but without the notation of "A" or "S" after the name. An antisense sequence with the same name, for example OSC17A-1 through OSC17A-18 binds to the same nucleotide target sequence.

Sequences shown in Table 4 were transfected into HEK 293 (human embryonic kidney) and MDA-MB-435S (human melanoma) cell lines to determine their ability to reduce the protein expression of LRP2 and CD320 gene/protein. These two cell lines were chosen because of their relatively high expression levels of LRP2 as noted in the Human Protein Atlas at world wide web.proteinatlas.org and the NCI-60 gene expression profiles at discover.nci.nih.gov/cellminer/ so that a change in protein expression for LRP2 was easy to detect.

Referring now to FIGS. 3A-B and FIGS. 3D-E, HEK293 and MDA-MB-231 cells were transfected with 20 nM of indicated siRNAs and incubated for 48 hours. Whole cell lysates were prepared and immunoblotted for CD320 and LRP2 protein levels. The protein levels were normalized to a housekeeping control gene unaffected by the siRNA transfection. The graphs represent the fold change of protein levels compared to the scrambled siRNA control (OSS1). (Average −/+ SEM is shown, n=3).

CD320 and LRP2 protein levels were determined by western blot and quantified by Image Studio Software (LiCor Company), relative to a control protein that is not affected by CD320 or LRP2 knockdown. To determine the efficacy of knockdown, protein levels of CD320 (FIGS. 3 A-B) and LRP2 (FIGS. 3 D-E) on the samples that were exposed to siRNA sequences against the mRNA of either gene, were compared to that in the untreated and scrambled controls (black and gray bars, respectively, in all graphs of FIG. 3). We found that both siRNA sequences directed against CD320 (OSC17 and OSC47) almost completely abrogated CD320 expression (circles in FIGS. 3 A-B). siLRP2 sequences resulted in variable efficiency in reducing LRP2 protein. Two sequences (05L231 and OSL245) consistently reduced LRP2 levels 75% or more in both cell lines (circles FIGS. 3 B, E).

Figure 6:
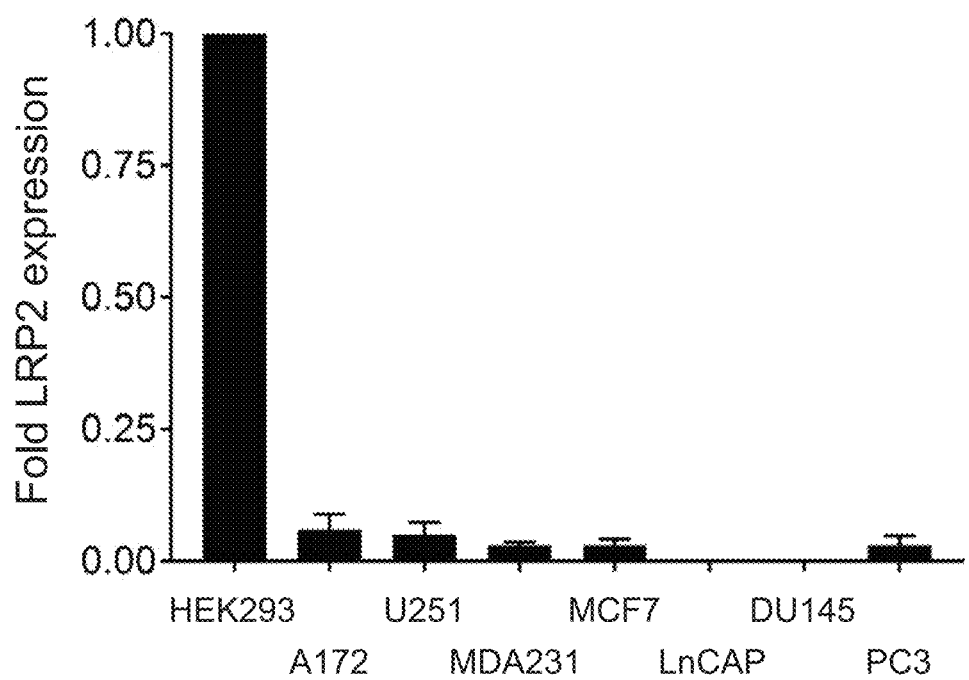
FIG. 6 illustrates a graph of relative LRP2 protein expression in various cell lines—Lysates were made from the cell lines indicated on the x-axis, and western blot was performed to determine LRP2 protein levels. The results represent the averages +/−SEM of three independent lysates.

Referring now to FIG. 6, lysates were made from transformed (HEK293) and representative cancer cell lines, and western blot was performed to determine LRP2 protein levels. The cancer cells screened have low levels of LRP2 expression. The results represent the averages +SEM of three independent lysates. The data suggests that the cancer cells screened have very low levels of LRP2 expression.

We transfected a panel of LRP2 and CD320 siRNAs into cancer cell lines derived from multiple tissues and analyzed the levels of LRP2 protein and CD320 protein in the cell line. Representative cell lines from prostate, breast and glioblastoma, and normal fibroblasts were exposed to CD320 and LRP2 siRNAs in an experimental set-up similar to that described for HEK293 and MDA-MB-435S cells. The results are shown in FIGS. 3 C, F, and FIG. 4.

Referring now to FIGS. 3 C, F; and FIG. 4, MDA-MB-231 LnCAP, MCF-7 and U251 cells were exposed to siRNA sequences to knockdown CD320 (FIG. 3C, and FIGS. 4 A-C) and LRP2 (FIG. 3 F, and FIGS. 4 D-F), in a similar fashion as described for the data represented in FIGS. 3 A, B, D, and E. CD320 protein knockdown FIG. 3C, and FIGS. 4 A-C, compared to the untreated or scrambled controls, is more than 90% for all cell lines tested. LRP2 knockdown is accomplished in all cell lines too. However, the level of knockdown is less in the LnCAP cells compared to the other cell lines and the sequences that are effective may differ as well (FIG. 3 F, and FIGS. 4 D-F).

Figure 5A:
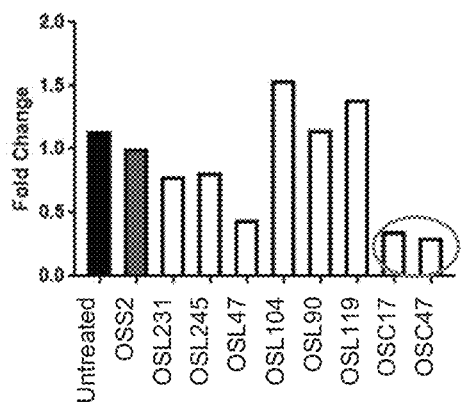
FIG. 5A-C illustrate graphs of protein levels after transfection of A172, DU145 and GM05659 cells with siRNA to LRP2 and CD320. A172, DU145 and GM05659 cells were transfected with 20 nM of indicated siRNAs and incubated for 48 hours. siRNAs targeting CD320 are designated OSC17 and OSC47. siRNAs targeting LRP2 are designated OSL245, OSL47, OSL104, OSL90 and OSL119). Whole cell lysates were prepared and immunoblotted for CD320. The protein levels were normalized to a housekeeping control gene unaffected by the siRNA transfection. The graphs
Figure 5B:
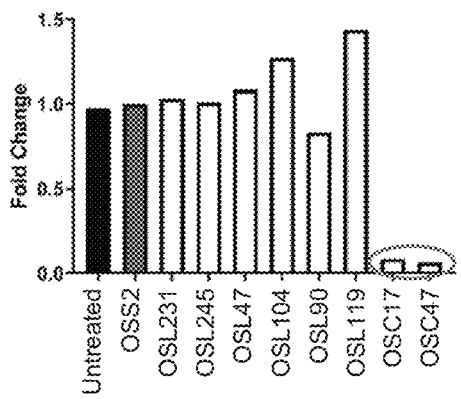
Figure 5C:
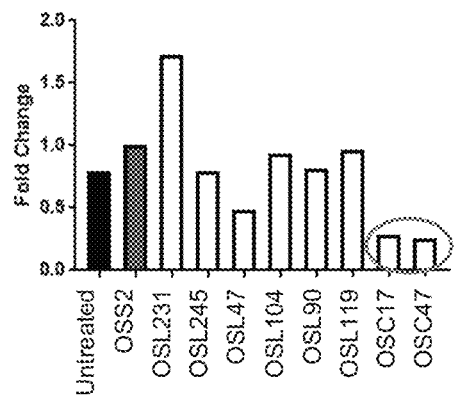

Referring now to FIG. 5, an experimental set up similar to that described in FIG. 3 was employed. Additional prostate and brain cancer cell lines, as well as normal fibroblast, were exposed to siRNAs directed against CD320. Levels of CD320 were nearly abrogated in DU-145 (prostate) cells, whereas the levels of knockdown in A172 brain cells and normal fibroblasts were 21%-33% and 25%-28%, respectively (FIGS. 5 A-C).

From these studies we can conclude that two siRNAs to CD320 (OSC17 and OSC47) are very effective in knocking down CD320 protein levels (80% or more), in nearly every cell line tested. While LRP2 is theoretically harder to knock down because of its size, we have identified two siRNAs, OSL231 and OSL245, that consistently knock down LRP2 in most cell lines in which we can detect LRP2.

In addition, LRP2 protein expression levels are very high in HEK 293 cells and easily detectable by western blot. Cancer cell lines have much lower expression of LRP2 compared to HEK293 cells as measured by western blot (FIG. 6), and some cell lines may contain LRP2 at levels below reliable detection.

Figures 7A, 7B:
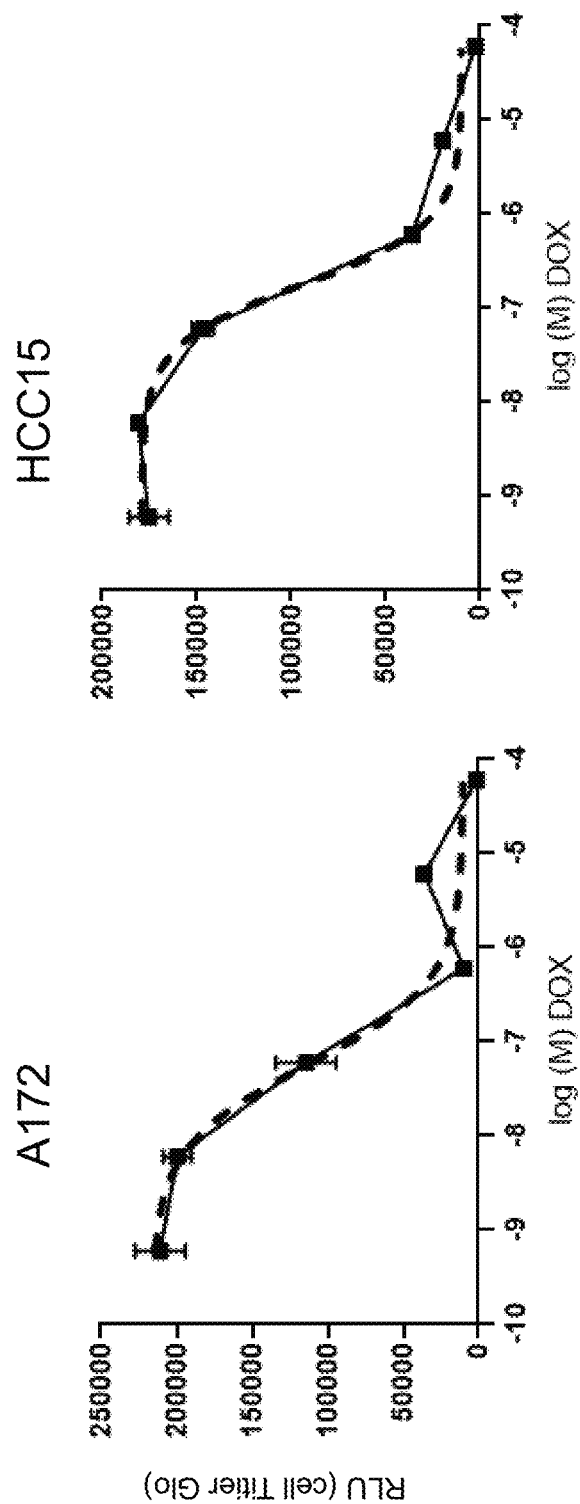
FIGS. 7 A-B illustrates graphs of the effect of doxorubicin treatment on cell viability, as measured by the CTG assay. A172 and HCC15 cells were plated at 1200 cells/well in a 96 well plate. The next day, cells were treated with doxorubicin at the indicated concentrations. Four days after doxorubicin treatment was initiated, the cells were assayed for viability using the CTG assay. The dashed line indicates the non-linear fitting of the data to calculate an $IC_{50}$ value.

Referring now to FIG. 7, the effects of doxorubicin treatment on cell viability, as measured by the CTG assay, are illustrated. A172 and HCC15 cells were plated at 1200 cells/well in a 96 well plate. The next day, cells were treated with doxorubicin at the indicated concentrations. Four days after the doxorubicin exposure was initiated, the cells were assayed for viability using the CTG assay. The line indicates the non-linear fitting of the data to calculate an $IC_{50}$ value. Instead of visually assessing the effect of CD320/LRP2 gene expression knockdown on cell proliferation (as shown for shRNA-mediated CD320/LRP2 knockdown in FIG. 2), a functional assay for quantitating the effect on cell viability of the simultaneous knockdown of LRP2 and CD320 by siRNA was developed. A widely used assay for the measurement of cell viability is the Promega Cell-titer GLO® platform (CTG), which quantifies ATP levels in the cell (live cells produce ATP, dead cells do not). After incubating the cells with the CTG reagent, ATP levels can be indirectly measured as light production using the TECAN luminescence plate reader. As a first step, toxicity of a known chemotherapeutic drug, doxorubicin, was assayed on the cell lines of interest. Doxorubicin was used as a positive control for cell toxicity in our assay. Representative data from A172 brain cancer cells (FIG. 7A) and HCC15 lung cancer cells (FIG. 7B) exposed to doxorubicin are shown in FIG. 7. From this data, the $IC_{50}$ of doxorubicin treatment on these cell lines was determined: 132 nm for A172 cells and 167 nm for HCC15 cells. Based upon these findings, a larger screen was initiated to determine the $IC_{50}$ of doxorubicin in several cancer and non-cancer cell lines, to determine the doxorubicin dose to use when cell lines are used in the viability assay to test the simultaneous knockdown of CD320 and LRP2. The results of the cell lines tested are summarized in Table 8 $IC_{50}$ determination of doxorubicin.

To quantify the effects of knocking down CD320 and LRP2 on cell proliferation, cells are plated in a 24-well plate. The next day, the cells are transfected with siRNAs to CD320 and/or LRP2. The cell lines may require repeated transfections and/or time for efficient toxicity (cell line dependent). In this experimental set-up there is room for repeat infection should some cell lines require that for efficient toxicity. At the end of the study, the cell lines are analyzed for cell growth by the CTG assay. A schematic of this experimental setup is presented in FIG. 8.

TABLE 8

| Cancer type | Cell line | $IC_{50}$ (nM) |
| --- | --- | --- |
| Glioblastoma | A172 | 132 |
|  | U251 | 24 |
| Breast | MDA-MB-231 | 43 |
|  | MCF7 | 121 |

TABLE 8-continued

| Cancer type | Cell line | $IC_{50}$ (nM) |
| --- | --- | --- |
| Prostate | DU145 | 248 |
|  | PC3 | 387 |
| Lung | NCI-H460 | 56 |
|  | A549 | 126 |
|  | HCC15 | 167 |
| Melanoma | MDA-MB-435S | 325 |
| Other | GM05659 | 267 |
|  | HEK293 | 29 |

The cells lines were plated at 1,000 to 4,000 cells/well in a 96-well plate and treated with doxorubicin the following day. CTG activity was measured 4 days after treatment. $IC_{50}$ values were calculated by GraphPad Prism Software. Results are tabulated in Table 8.

These data show that doxorubicin works efficiently on this CTG platform (i.e., doxorubicin kills cancer cells) and can thus be used as a positive control in the in vitro assay to compare the cytotoxic effects of siRNA-knockdown of CD320 and LRP2. In this latter assay, normal or cancer cells are transfected with individual or combinations of siRNAs sequences that are targeting CD320 or LRP2 specifically or control siRNAs, similar to the experiments that provided the data for FIGS. 3, 4, and 5. In FIGS. 3, 4, and 5, protein levels are measured, but in the in vitro assay, cell viability is measured.

Figure 8:
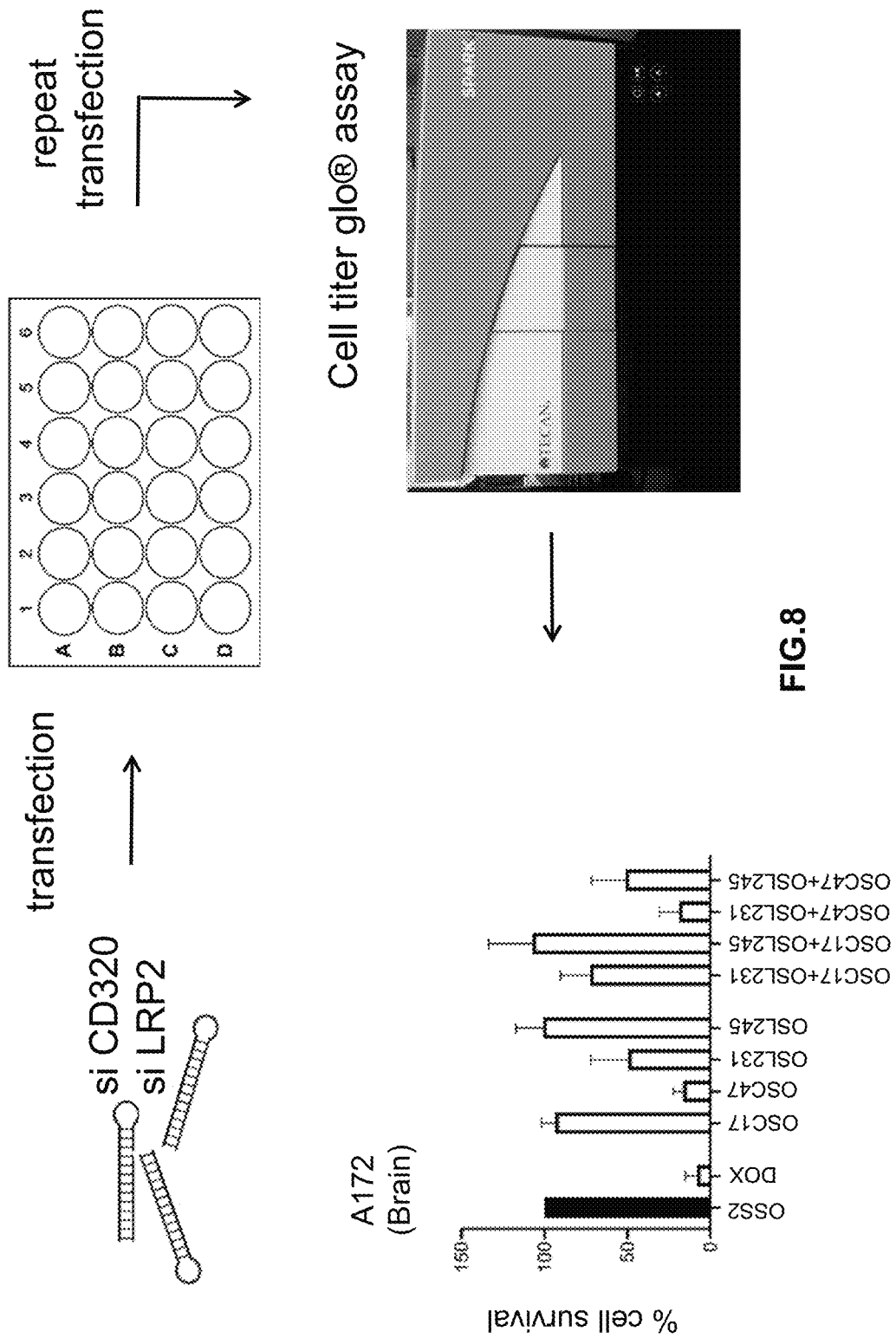
FIG. 8 is a schematic overview of the functional assay for screening siRNA effects on cell proliferation to facilitate quantification of the effects of knocking down CD320 and LRP2 on cell proliferation. Cells were plated in a 24-well plate. The next day, the cells were transfected with siRNAs targeting CD320 (OSC17, OSC47) and/or targeting LRP2 (05L231, OSL245), or a control siRNA (OSS2). The cell lines may require repeated transfections and/or time for efficient toxicity (cell line dependent). In this experimental set-up there is room for repeat infection should some cell lines require that for efficient toxicity. In addition, in a small subset of the wells, cells were only treated with doxorubicin as a positive control for toxicity. At the end of the study, the cell lines are analyzed for cell growth by the CTG assay.

Referring now to FIG. 8, an overview of a functional assay for screening (ds) siRNA effects on cell proliferation is illustrated. To quantify the effects of knocking down CD320 and LRP2 on cell proliferation, cells are plated in a 24-well plate. The next day, the cells are transfected with siRNAs to CD320 and/or LRP2. The cell lines may require repeated transfections and/or time for efficient toxicity (cell line dependent). In this experimental set-up there is room for repeat infection should some cell lines require that for efficient toxicity. At the end of the study, the cell lines were analyzed for cell growth by the CTG assay.

Now, referring to FIG. 10B, MDA-MB-231 triple negative breast cancer cells were plated in a 24-well plate at 20,000 cells/well. Cells were transfected the next day with an siRNA selected from the group of OSC17, OSC47, OSL231, and OSL245 at 20 nM. Cells were also transfected with combinations of two siRNAs each of 10 nM, one of these targeting CD320 and the other LRP2, with the siRNAs targeting CD320 selected from the group of OSC17 and OSC47, and the LRP2 targeting siRNAs selected from the group of OSL231 and OSL245, each dosed at 10 nM. Cells were repeated transfected 4 times over the course of 11 days as indicated in Table 9. At day 11, cells were analyzed for cell growth by the CTG assay. The percent cell survival compared to the non-targeting control (OSS2) is shown. The data represented is the average of 6 experiments −/+ SEM.

Figures 11A, 11B:
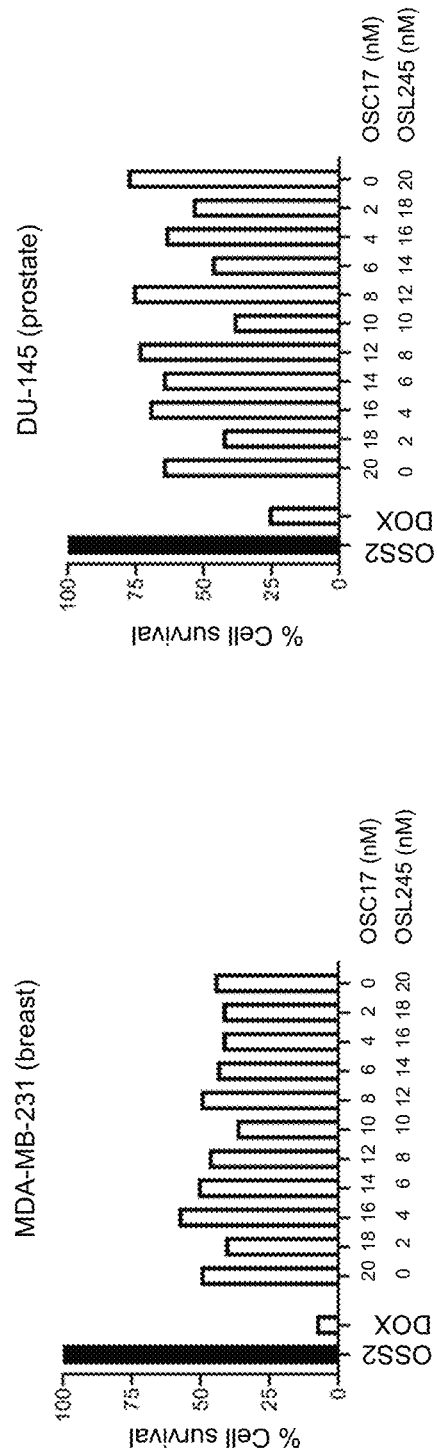
FIGS. 11A-B illustrate the effects of siCD320 and siLRP2 molar proportions on cell proliferation with different molar proportions of siRNA targeting CD320 and siRNA targeting LRP2. Cell lines representative of two types of cancers (breast, prostate) were transfected with different proportions of siRNAs targeting CD320 (OSC17) or LRP2 (05L245) (0-20 nM) or a negative control siRNA (OSS2) as indicated. Cells were repeatedly transfected for efficient toxicity then assayed for viability by the CTG assay. Doxorubicin-treated cells served as a positive control for cell toxicity in our assays (Table 8).

Now, referring to FIG. 11, MDA-MB-231 and DU-145 cells were transfected with 20 nM of the negative control siRNA (OSS2), 20 nM siRNA targeting CD320 (OSC17), or 20 nM siRNA targeting LRP2 (05L245). Cells were also transfected with a combination of a CD320 targeting siRNA (OSC17) and LRP2 targeting siRNA (05L24), over a range of concentrations (2-20 nM), so the concentration of the two siRNAs equaled 20 nM total siRNA transfected, as indicated in FIG. 11. Cells were repeatedly transfected as indicated in Table 9, and the percent cell survival is shown.

Now, referring to FIG. 12, MDA-MB-231 breast cancer cells were transfected with 20 nM of the negative control siRNA (OSS2), 20 nM siRNA targeting CD320 (OSC17), or 20 nM siRNA targeting LRP2 (05L245). Each day, over five days, lysates were prepared. Western blotting was performed on the lysates for CD320 protein levels (FIG. 12A) or LRP2 protein levels (FIG. 12B).

Referring now to FIG. 9 and FIG. 10, data quantifying the effects of knocking down CD320 and LRP2 in various cell lines is represented. Cell lines representative of several types of cancers or normal fibroblasts were transfected with individual or combinations of siRNAs to CD320 or LRP2 as indicated. Cells were repeatedly transfected as outlined in Table 9 for efficient toxicity, then assayed for viability by the CTG assay. Doxorubicin treated cells served as a positive control for cell toxicity in our assays.

The data of the individual experiments presented in FIG. 9 and FIG. 10 and additional cell lines we have screened are summarized in Table 9. These experiments show the broad applicability of siCD320 and siLRP2 toxicity in a variety of cancer types.

Figure 13:
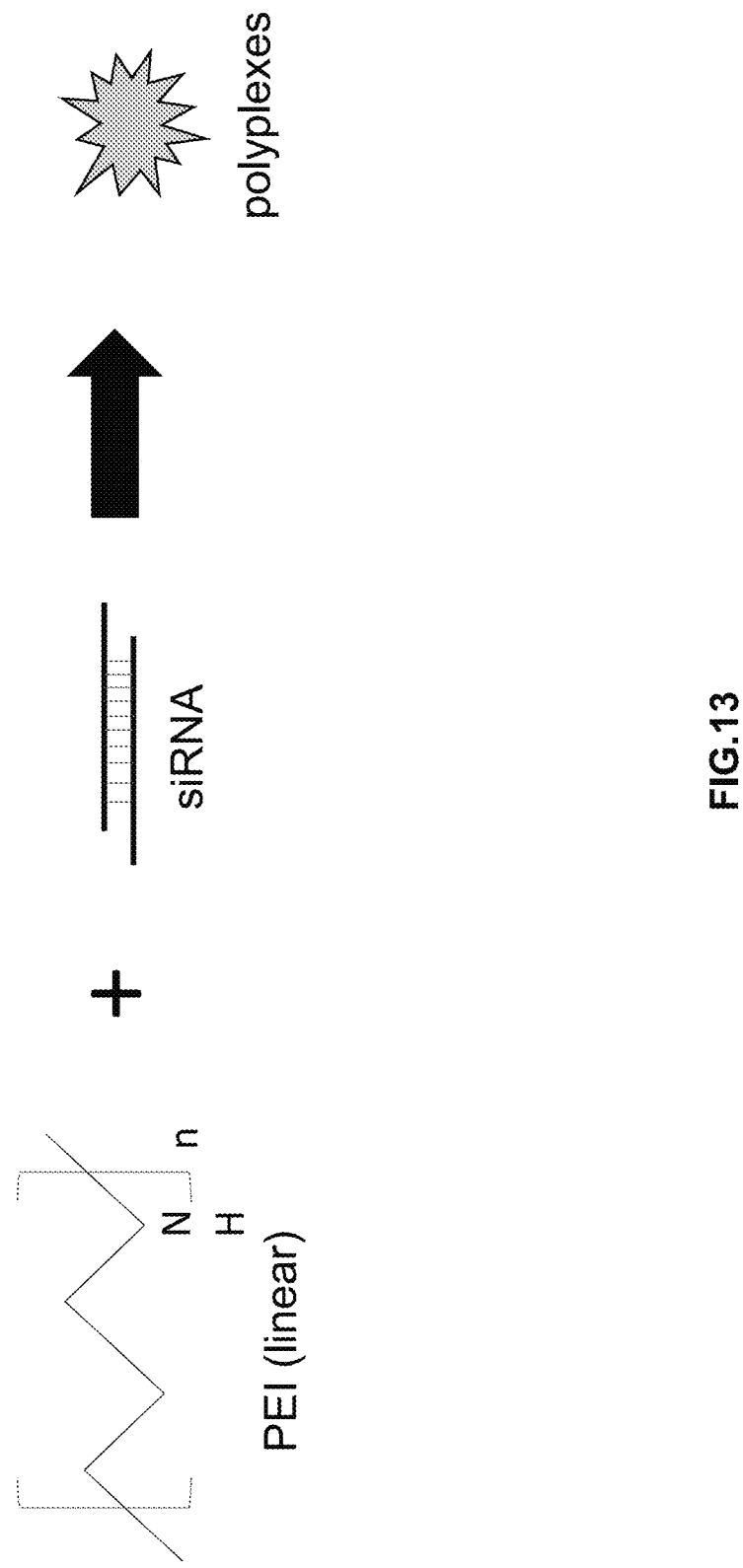
FIG. 13 is a schematic of polyethylinimine (PEI) and siRNA complexation. PEI and siRNAs are mixed together. Subsequently, polyplexes (a nanoparticle, broadly speaking) of the PEI-siRNA complex form, which are able to enter the cell.

Referring now to FIG. 13, a schematic of PEI and siRNA complexes is illustrated. PEI and siRNAs are mixed together. Subsequently, polyplexes (a nanoparticle, broadly speaking) form of the PEI-siRNA complex, which are able to enter the cell via an endocytotic or pinocytotic mechanism.

Referring now to FIG. 14, siRNAs are short RNA duplexes of generally 16 to 30 nucleotides; the sequence of the siRNA is complementary to a mRNA expressed in the cell. Exogenous siRNA duplexes are introduced into the cell via a method of transfection. The siRNA duplexes are unwound via the RISC (RNA-induced silencing complex) complex, whereby the guide strand of the siRNA hybridizes with its complementary mRNA molecule. The mRNA is degraded by the RISC/AGO complex, which has RNAse cleave activity. The end result is that the mRNA targeted by the siRNA is degraded, and the protein encoded by the mRNA is not produced. This causes the "knockdown" effect or reduced protein levels of the gene targeted by the siRNA compared to control-treated cells.

Figure 15B:
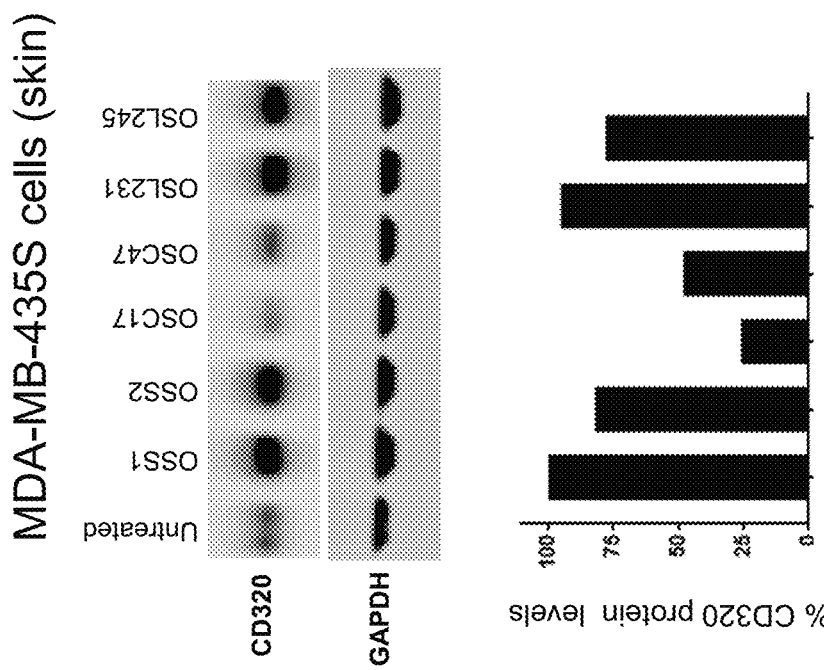
FIGS. 15 A-B illustrate graphs of A172 cell line or MDA-MD-435S cell lines treated with control siRNA (OSS1, OSS2) and siRNA directed to CD320 mRNA (OSC17, OSC47) and siRNA directed to LRP2 mRNA (05L231, OSL245) to determine the effectiveness of INTERFERin, a polyethanolamine transfection reagent, in delivering siRNAs to cancer cells.
Figure 15A:
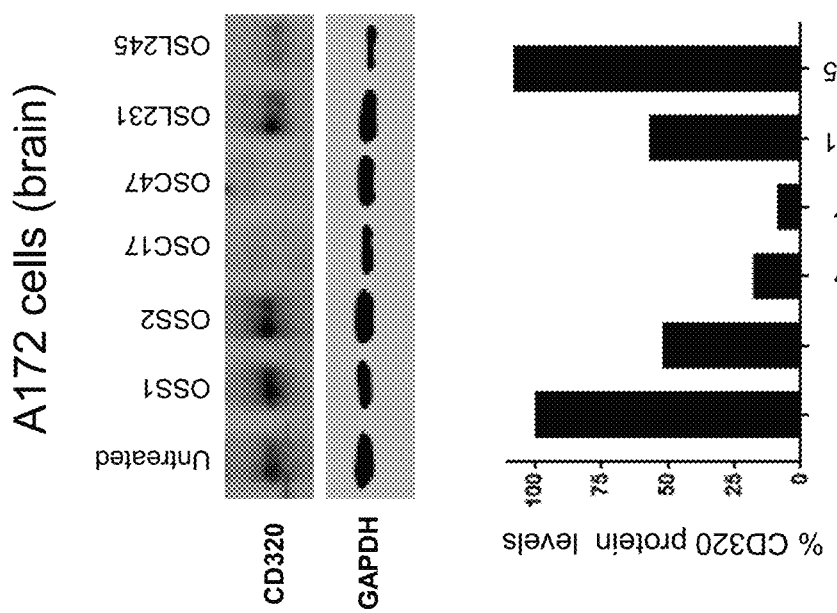

Referring now to FIG. 15 effectiveness of INTERFERin in delivering siRNAs to cancer cells is illustrated. 2 nM of indicated siRNAs were transfected into A172 and MDA-MB-435S cells as per the manufacturers protocol. Cell lysates were prepared 3 days post-infection and analyzed by western blot for CD320 protein levels. OSS1 and OSS2 are non-targeting siRNA controls. In this experiment, both sequences were tested. CD320 protein levels were knocked down to 9% to 18% for A172 cells and 26% to 48% for MDA-MB-435S cells, compared to OSS1. Much more efficient knockdown of CD320 is observed when the siRNAs were delivered with other transfection reagents (e.g. RNAiMAX, Viromer Blue) that were used in the experiments described previously particularly for MDA-MB-435S cells. The Polyplus INTERFERin platform has been tested in vitro in our laboratory in a proof of principle experiment, whereby the platform is able to deliver siRNAs to the target cells in vitro.

Referring now to FIG. 16, treatment of breast, prostate, and skin cancer cells with an inhibitor of CD320 receptor or an inhibitor of LRP2 receptor or a combination of both in an amount effective to inhibit proliferation of the cancer cells as compared to the control cells treated with control siRNA is illustrated. MDA-MB-231, DU145, LnCAP, and MDA-MB-435S cells were plated at 20,000 cells per well in a 24-well plate. The next day, the cells were transected with 20 nM of indicated siRNAs to knock down CD320, LRP2, or scrambled control. For the combination of siRNAs, cells were treated with 10 nM of each siRNA for 20 nM total treatments. Cells were repeatedly transfected as in Table 9 for the length of time indicated in Table 9. The indicated pictures of the cells were taken at the end of the experiment.

TABLE 9

Summary of functional siRNA data screening

| Cell line | n | # of txns | Days expt | Single siRNA knockdown | | | | Double siRNA knockdown | | | | DOX |
|---|---|---|---|---|---|---|---|---|---|---|---|---|
| | | | | (siCD320) | | (siLRP2) | | OSC17+ | | OSC47+ | | |
| | | | | OSC-17 | OSO-47 | OSL-231 | OSL-245 | OSL 231 | OSL 245 | OSL 231 | OSL 245 | |
| Normal | | | | | | | | | | | | |
| GM05659 | 3 | 4 | 7 | 133 | 104 | 96 | 103 | 111 | 129 | 97 | 107 | 39 |
| Lung | | | | | | | | | | | | |
| HCC15 | 3 | 2 | 7 | 86 | 109 | 68 | 92 | 81 | 93 | 38 | 105 | 2 |
| H157 | 3 | 5 | 8 | 7 | 9 | 116 | 33 | 119 | 39 | 31 | 15 | 20 |
| Melanoma | | | | | | | | | | | | |
| MDA-MB-435S | 4 | 5 | 10 | 119 | 108 | 92 | 31 | 122 | 56 | 103 | 70 | 51 |
| Prostate | | | | | | | | | | | | |
| LnCAP | 3 | 4 | 7 | 52 | 42 | 72 | 60 | 68 | 51 | 52 | 57 | 38 |
| DU-145 | 6 | 4 | 7 | 39 | 82 | 71 | 44 | 80 | 44 | 90 | 76 | 40 |
| Glioblastoma | | | | | | | | | | | | |
| A172 | 3 | 5 | 7 | 94 | 17 | 50 | 101 | 73 | 107 | 19 | 51 | 8 |
| U251 | 4 | 6 | 8 | 94 | 50 | 77 | 97 | 99 | 94 | 66 | 87 | 51 |
| Breast | | | | | | | | | | | | |
| MCF-7 | 3 | 2 | 7 | 61 | 69 | 32 | 68 | 31 | 52 | 26 | 48 | 5 |
| MDA-MB-231 | 6 | 4 | 11 | 66 | 81 | 130 | 77 | 71 | 44 | 81 | 61 | 7 |

Note:
The numbers represent percent survival compared to negative control OSS2.

A murine human tumor xenograft model was established using triple-negative breast cancer cells (MDA-MB-231) injected into the flanks of nude mice to test the efficacy of combined dosing of OSC17 and OSL245. The administration of the drug is by repeated dosing over a range of drug concentrations using intratumoral, iv, ip or specialized route of administration. The dosing schedule is based on pilot studies to determine the tolerability of the delivery vehicle and the drug and will incorporate ranges that are taught in the art. Among the delivery platforms are nanoparticles, liposomes, micelles, polymers, small molecule conjugates, aptamers and antibody conjugates. Hybrid technologies containing elements of the aforementioned delivery systems are also known.

The manufacturing process consists of synthesizing the two single strand oligonucleotides of the duplex by conventional solid phase oligonucleotide synthesis. After purification, the two oligonucleotides are annealed into the duplex.

In vivo JetPEI® is a cationic polymer delivery system that binds the negatively charged siRNA molecules to the cationic polyamine polymer. Its use has been reported in xenograft models using MCF-7 (breast), MDA-MB-231 (breast) and A549 (lung) cell lines both ip and intratumoral. This delivery system is currently used in seven human clinical trials (Table 10). The formulated siRNAs are reported to be very stable.

TABLE 10

Clinical trial use of in vivo-jetPEI ®

| Organization | Type of study | Phase |
|---|---|---|
| Cancer Targeting Systems | Imaging and cancer therapy | Pre-clinical |
| Benitec | Lung metastases | Pre-clinical |
| Avena | Blood-brain barrier | Pre-clinical |
| BiOncoTech | Melanoma immunotherapy | Phase 1 |
| Ottawa Hospital Research Institute | Acute myocardial infarction gene therapy | Phase 1 |
| CHU-Toulouse, Rangueil Hospital | Pancreatic cancer gene therapy | Phase 2 |
| BioCancell | Bladder cancer gene therapy | Phase 3 |

Note that in the specification and claims, "about" or "approximately" means within twenty percent (20%) of the numerical amount cited. Although the invention has been described in detail with particular reference to these embodiments, other embodiments can achieve the same results. For example, antisense oligonucleotides that are complimentary to the target mRNA can inhibit expression of the protein of interest even though the antisense oligonucleotide is not provided as a dsRNA and may not bind to RISC/AGO complex. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A double stranded RNA interference (RNAi) agent comprising:
a combination of (i) a first double-stranded ribonucleic acid (dsRNA) for inhibiting expression of a CD320 gene wherein the first dsRNA comprises a sense strand and an antisense strand forming a duplex, and (ii) a second dsRNA for inhibiting expression of a LRP2 gene wherein the second dsRNA comprises a sense strand and an antisense strand forming a duplex, and wherein the sense strand of the first dsRNA is at least substantially complementary to the antisense strand of the first dsRNA and the sense strand of the second dsRNA is at least substantially complementary to the antisense strand of the second dsRNA wherein the antisense strand of (i) the first dsRNA is selected from SEQ ID NO:1-93 and the antisense strand of (ii) the second dsRNA is selected from SEQ ID NO: 187-560.

2. The double stranded RNAi agent of claim 1 wherein the antisense strand of (i) the first dsRNA includes a region of complementarity to a CD320 RNA transcript.

3. The double stranded RNAi agent of claim 1 wherein the antisense strand of (i) the first dsRNA, comprises the nucleotide sequence selected from (5'→3')

```
                                              (SEQ ID NO: 17)
CAGUUGCGCAGUUUCUUGUCAGUUCdTdT;

(SEQ ID NO 18)
CAGUUGCGCAGUUUCUUGUCAGUUCdT*dT;

(SEQ ID NO 19)
mCmAmGmUmUmGmCmGmCmAmGmUmUmUmCmUmUmGmUmCmAmGmUmUmCd
T*dT;

(SEQ ID NO 21)
mCmAmGmUmUmGmCmGmCmAmGmUmUmUmCmUmUmGmUmCmAmGmUmUmC;

(SEQ ID NO 23)
mCmAmGmUmUmGmCmGmCmAmGmUmUmUmCmUmUmGmUmCmAmGmUmUmCd
T*dT;

(SEQ ID NO 24)
mC2fAmG2fUmU2fGmC2fGmC2fAmG2fUmU2fUmC2fUmU2fGmU2fCm
A2fGmU2fUmCdT*dT;

(SEQ ID NO 25)
mC2fAmG2fUmU2fGmC2fGmC2fAmG2fUmU2fUmC2fUmU2fGmU2fCm
A2fGmU2fUmC;

(SEQ ID NO 28)
2fCmA2fGmU2fUmG2fCmG2fCmA2fGmU2fUmU2fCmU2fUmG2fUmC2
fAmG2fUmU2fCdT*dT;

(SEQ ID NO 29)
2fCmA2fGmU2fUmG2fCmG2fCmA2fGmU2fUmU2fCmU2fUmG2fUmC2
fAmG2fUmU2fC;

(SEQ ID NO 30)
mC2fA2fG2fU2fU2fG2fC2fG2fC2fA2fG2fU2fU2fU2fC2fU2fU2
fG2fU2fC2fA2fG2fU2fU2fCdT*dT;

(SEQ ID NO 32)
mC2fAmG2fUmU2fGmC2fGmC2fAmG2fUmU2fUmC2fUmU2fGmU2fCm
A2fGmU2fUmCdT*dT;

(SEQ ID NO 33)
mC2fAmG2fUmU2fGmC2fGmC2fAmG2fUmU2fUmC2fUmU2fGmU2fCm
A2fGmU;

(SEQ ID NO 34)
mC2fAmG2fUmU2fGmC2fGmC2fAmG2fUmU2fUmC2fU2fU2fG2fU2f
C2fA2fG2fU;
``` wherein, mA, mC, mG, and mU are 2'-O-methyl adenosine, cytidine, guanosine, or uridine, respectively; 2fA, 2fC, 2fG, and 2fU are 2'-fluoro adenosine, cytidine, guanosine, or uridine, respectively; and * is a phosphorothioate linkage.

4. The double stranded RNAi agent of claim 1 wherein the antisense strand of (i) the first dsRNA, comprises the nucleotide sequence selected from (5'→3')

```
                                              (SEQ ID NO 64)
AAGAGCUCAGGUCUCUGAGGGdTdT;

(SEQ ID NO 65)
AAGAGCUCAGGUCUCUGAGGGdT*dT;

(SEQ ID NO 66)
mAmAmGmAmGmCmUmCmAmGmGmUmCmUmCmUmGmAmGmGmGdT*dT;
```

-continued
```
                                              (SEQ ID NO 68)
mAmAmGmAmGmCmUmCmAmGmGmUmCmUmCmUmGmAmGmGmG;

(SEQ ID NO 71)
mA2fAmG2fAmG2fCmU2fCmA2fGmG2fUmC2fUmC2fUmG2fAmG2fGm
GdT*dT;

(SEQ ID NO 72)
mA2fAmG2fAmG2fCmU2fCmA2fGmG2fUmC2fUmC2fUmG2fAmG2fGm
G;

(SEQ ID NO 75)
2fAmA2fGmA2fGmC2fUmC2fAmG2fGmU2fCmU2fCmU2fGmA2fGmG2
fGdT*dT;

(SEQ ID NO 76)
2fAmA2fGmA2fGmC2fUmC2fAmG2fGmU2fCmU2fCmU2fGmA2fGmG2
fG;

(SEQ ID NO 77)
mA2fA2fGmA2fGmC2fUmC2fAmG2fGmU2fCmU2fCmU2fGmA2fGmG2
fG;

(SEQ ID NO 78)
mA2fA2fGmA2fGmC2fUmC2fAmG2fGmU2fCmU2fCmU2fGmA2fGmG2
fGdT*dT;

(SEQ ID NO 79)
2fAmA2fGmA2fGmC2fUmC2fAmG2fGmU2fCmU2fCmU2fGmA2fGmG2
fGdT*dT;

(SEQ ID NO 81)
2fAmA2fGmA2fGmC2fl JmC2fAmG2fGmU2fCmU2fC2fl J2fG2fA2f
G2fG2fG;
``` wherein, mA, mC, mG, and mU are 2'-O-methyl adenosine, cytidine, guanosine, or uridine, respectively; 2fA, 2fC, 2fG, and 2fU are 2'-fluoro adenosine, cytidine, guanosine, or uridine, respectively; and * is a phosphorothioate linkage.

5. The double stranded RNAi agent of claim 1 wherein the sense strand of (i) the first dsRNA is no more than 30 nucleotides in length, and the antisense strand of (i) the first dsRNA is no more than 30 nucleotides in length.

6. The double stranded RNAi agent of claim 1 wherein the antisense strand of (ii) the second dsRNA includes a region of complementarity to an LRP2 RNA transcript.

7. The double stranded RNAi agent of claim 1, wherein the antisense strand of (ii) the second dsRNA comprises the nucleotide sequence selected from (5'→3')

```
                                              (SEQ ID NO: 417)
UUUGAUAGCACCAAACCUAGAGCCCdTdT;

(SEQ ID NO: 418)
UUUGAUAGCACCAAACCUAGAGCCCdT*dT;

(SEQ ID NO: 419)
mUm[mUmGmAmUmAmGmCmAmCmCmAmAmAmCmCmUmAmGmAmGmCmCmCd
T*dT;

(SEQ ID NO: 421)
mUmUmGmAmUmAmGmCmAmCmCmAmAmAmCmCmUmAmGmAmGmCmCmC;
```

```
                                      (SEQ ID NO: 424)
mU2fUmU2fGmA2fUmA2fGmC2fAmC2fCmA2fAmA2fCmC2fUmA2fGm

A2fGmC2fCmCdT*dT];

(SEQ ID NO: 425)
mU2fUmU2fGmA2fUmA2fGmC2fAmC2fCmA2fAmA2fCmC2fUmA2fGm

A2fGmC2fCmC;

(SEQ ID NO: 429)
mU2fAmU2fCmA2fAmA2fCmC2fUmC2fGmA2fUmA2fGmC2fAmA2fCm

A2fCmC2fGmC;

(SEQ ID NO: 430)
mU2fU2fU2fG2fA2fU2fA2fG2fC2fA2fC2fC2fA2fA2fA2fC2fC2 fU2fA2fG2fA2fG2fC2fC2fCdT*dT;

(SEQ ID NO: 432)
mU2fUmU2fGmA2fUmA2fGmC2fAmC2fCmA2fAmA2fCmC2fUmA2fGm

A2fGmC2fCmCdT*dT;

(SEQ ID NO: 433)
mU2fUmU2fGmA2fUmA2fGmC2fAmC2fCmA2fAmA2fCmC2fUmA2fGm

A2fGmC;
and (SEQ ID NO: 434)
mU2fUmU2fGmA2fUmA2fGmC2fAmC2fCmA2fAmA2fC2fC2fU2fA2f G2fA2fG2fC
```

```
                                      (SEQ ID NO: 459)
2fUmU2fUmG2fCmA2fAmU2fGmA2fCmU2fCmU2fCmC2fUmA2fUmC2 fAmG2fUmC2fCdT*dT;

(SEQ ID NO: 460)
mU2fAmU2fCmC2fUmA2fAmG2fUmC2fAmC2fAmC2fGmU2fUmU2fGm

A2fCmU2fGmC;

(SEQ ID NO: 461)
mU2fU2fU2fG2fC2fA2fA2fU2fG2fA2fC2fU2fC2fU2fC2fC2fU2 fA2fU2fC2fA2fG2fU2fC2fCdT*dT;

(SEQ ID NO: 463)
mU2fUmU2fGmC2fAmA2fUmG2fAmC2fUmC2fUmC2fCmU2fAmU2fCm

A2fGmU2fCmCdT*dT;

(SEQ ID NO: 464)
mU2fUmU2fGmC2fAmA2fUmG2fAmC2fUmC2fUmC2fCmU2fAmU2fCm

A2fGmU;

(SEQ ID NO: 465)
mU2fUmU2fGmC2fAmA2fUmG2fAmC2fUmC2fUmC2fC2fU2fA2fU2f

C2fA2fG2fU
``` wherein, mA, mC, mG, and mU are 2'-O-methyl adenosine, cytidine, guanosine, or uridine, respectively; 2fA, 2fC, 2fG, and 2fU are 2'-fluoro adenosine, cytidine, guanosine, or uridine, respectively; and * is a phosphorothioate linkage.

8. The double stranded RNAi agent of claim 1, wherein the antisense strand of (ii) the second dsRNA comprises the nucleotide sequence selected from (5'→3')

```
                                      (SEQ ID NO: 448)
UUUGCAAUGACUCUCCUAUCAGUCCdTdT;

(SEQ ID NO: 449)
UUUGCAAUGACUCUCCUAUCAGUCCdT*dT;

(SEQ ID NO: 450)
mUmUmUmGmCmAmAmUmGmAmCmUmCmUmCmCmUmAmUmCmAmGmUmCmCd

T*dT;

(SEQ ID NO: 452)
mUmUmUmGmCmAmAmUmGmAmCmUmCmUmCmCmUmAmUmCmAmGmUmCmC;

(SEQ ID NO: 455)
mU2fUmU2fGmC2fAmA2fUmG2fAmC2fUmC2fUmC2fCmU2fAmU2fCm

A2fGmU2fCmCdT*dT;

(SEQ ID NO: 456)
mU2fUmU2fGmC2fAmA2fUmG2fAmC2fUmC2fUmC2fCmU2fAmU2fCm

A2fGmU2fCmC;

(SEQ ID NO: 458)
mU2fUmU2fGmC2fAmA2fUmG2fAmC2fUmC2fUmC2fCmU2fAmU2fCm

A2fCmU2fCmc;
``` wherein, mA, mC, mG, and mU are 2'-O-methyl adenosine, cytidine, guanosine, or uridine, respectively; 2fA, 2fC, 2fG, and 2fU are 2'-fluoro adenosine, cytidine, guanosine, or uridine, respectively; and * is a phosphorothioate linkage.

9. A double stranded RNA interference (RNAi) agent comprising:

a combination of (i) a first double-stranded ribonucleic acid (dsRNA) for inhibiting the expression of a CD320 gene wherein the first dsRNA comprises a sense strand and an antisense strand forming a duplex, and (ii) a second dsRNA for inhibiting the expression of a LRP2 gene wherein the second dsRNA comprises a sense strand and an antisense strand forming a duplex, and wherein the sense strand of the first dsRNA is at least substantially complementary to the antisense strand of the first dsRNA and the sense strand of the second dsRNA is at least substantially complementary to the antisense strand of the second dsRNA wherein the antisense strand of (i) the first dsRNA is selected from

```
                                      (SEQ ID NO: 17)
CAGUUGCGCAGUUUCUUGUCAGUUCdTdT;

(SEQ ID NO 18)
CAGUUGCGCAGUUUCUUGUCAGUUCdT*dT;

(SEQ ID NO 64)
AAGAGCUCAGGUCUCUGAGGGdTdT;
and (SEQ ID NO 65)
AAGAGCUCAGGUCUCUGAGGGdT*dT;
``` and the antisense strand of (ii) the second dsRNA is selected from

UUUGAUAGCACCAAACCUAGAGCCCdTdT;  (SEQ ID NO: 417)

UUUGAUAGCACCAAACCUAGAGCCCdT*dT;  (SEQ ID NO: 418)

UUUGCAAUGACUCUCCUAUCAGUCCdTdT; and  (SEQ ID NO: 448)

UUUGCAAUGACUCUCCUAUCAGUCCdT*dT;  (SEQ ID NO: 449)

wherein * is a phosphorothioate linkage.

10. The double stranded RNAi agent of claim 9 wherein (i) the first dsRNA has the duplex structure of (SEQ ID NOs: 17 and 110) or (SEQ ID NOs: 18 and 111).

11. The double stranded RNAi agent of claim 9 wherein (ii) the second dsRNA has the duplex structure of (SEQ ID NOs: 417 and 791) or (SEQ ID NOs: 448 and 822).

12. An isolated cell comprising a double stranded RNAi agent of claim 9.

13. A pharmaceutical composition for inhibiting expression of a CD320 gene and a LRP2 gene, the pharmaceutical composition comprising a double stranded RNAi agent (i) of claim 1 and a doubled stranded RNAi agent (ii) of claim 1 and an excipient.

14. A method for inhibiting proliferation of a cancer cell (CC) comprising contacting of the CC with an inhibitor of CD320 expression of claim 9 and an inhibitor of LRP2 expression of claim 9, wherein the inhibitor of CD320 expression is a first double-stranded ribonucleic acid (dsRNA) comprising a sense strand and an antisense strand forming a duplex, and the inhibitor of LRP2 expression is a second dsRNA comprising a sense strand and an antisense strand forming a duplex, wherein the sense strand of the first dsRNA is at least substantially complementary to the antisense strand of the first dsRNA and the sense strand of the second dsRNA is at least substantially complementary to the antisense strand of the second dsRNA wherein the CC is from a cancer selected from melanoma, glioblastoma, lung carcinoma, breast carcinoma, triple negative breast carcinoma, and prostate carcinoma.

15. A method for treating cancer in a subject who has recurring or relapsed cancer comprising administering to a subject an inhibitor of CD320 expression of claim 9 and an inhibitor of LRP2 expression of claim 9 in an amount effective to inhibit proliferation or kill cancer cells (CC) of the cancer wherein the CC is from the cancer selected from melanoma, glioblastoma, lung carcinoma, breast carcinoma, triple negative breast carcinoma, and prostate carcinoma.

* * * * *

SEQUENCE LISTING

```
<160> NUMBER OF SEQ ID NOS: 1394

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
ucuuaucccu gcgcacgcgc att                                            23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
ucucuuaucc cugcgcacgc gtt                                            23
```

```
<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
augcuguccc cacagcggcg ctt                                                 23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
auccaaccgc cgcucaugcu gtt                                                 23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
uggaaagcgg gcucgcggcg gtt                                                 23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
aacuuggugg gugggcacga gtt                                                 23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
uggaacuugg ugggugggca ctt                                                 23
```

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
acuggaacuu ggugggtggg ctt                                              23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
uaagccacug gugcggcacu gtt                                              23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
acgcauaagc cacuggugcg gtt                                              23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
uccaagcccc ugucgcagcg ctt                                              23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
uccucaucgc ugccaucgcu gtt                                             23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
ucacugacgc cggugcaggg gtt                                             23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
uugucaguuc ccccagagca gtt                                             23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
uucuugucag uuccccaga gtt                                              23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
aguuucuugu caguccccc att                                              23

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17

```
caguugcgca guucuuguc aguuctt                                              27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
caguugcgca guucuuguc aguuctt                                              27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
caguugcgca guucuuguc aguuctt                                              27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
caguugcgca guucuuguc aguuctt                                              27

<210> SEQ ID NO 21
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
caguugcgca guucuuguc aguuc                                                25

<210> SEQ ID NO 22
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
caguugcgca guucuuguc aguuc                                                25

<210> SEQ ID NO 23
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
caguugcgca guucuuguc aguucuu                                             27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
caguugcgca guucuuguc aguucuu                                             27

<210> SEQ ID NO 25
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
caguugcgca guucuuguc aguuc                                               25

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
caguugcgca guucuuguc aguucuu                                             27

<210> SEQ ID NO 27
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
caguugcgca guucuuguc aguuc                                               25

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
```

```
     oligonucleotide
<220> FEATURE:
<223> OTHER INFORMATION: Description of Combined DNA/RNA Molecule:
      Synthetic oligonucleotide

<400> SEQUENCE: 28
caguugcgca guucuuguc aguuctt                                          27

<210> SEQ ID NO 29
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
caguugcgca guucuuguc aguuc                                            25

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
caguugcgca guucuuguc aguuctt                                          27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
caguugcgca guucuuguc aguuctt                                          27

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 32
caguugcgca guucuuguc aguuctt                                          27

<210> SEQ ID NO 33
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 33
caguugcgca guucuuguc agu                                              23

<210> SEQ ID NO 34
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
caguugcgca guucuuguc agu                                              23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
augcagucau cgcucagcgu gtt                                             23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
aaugcaguca ucgcucagcg utt                                             23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37
uggaaugcag ucaucgcuca gtt                                             23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
```
aguggaaugc agucaucgcu ctt                                          23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
acagucuggg uggccgucgc att                                          23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
auugguucca cagccgagcu ctt                                          23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
ucucauuggu uccacagccg att                                          23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
aucucauugg uuccacagcc gtt                                          23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43

-continued aggaucucau ugguuccaca gtt                                              23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
ugagagaggu gacacucucc att                                              23

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
ugguuguggc auuccugaga gtt                                              23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
uggcauuccc gacagagggg att                                              23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
aggauguggc auucccgaca gtt                                              23

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<400> SEQUENCE: 48
uuccagacug gucuccggca gtt                                          23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
auaaccccau aggcaguugg gtt                                          23

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
uugcacugag caccgcagca gtt                                          23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
aaaaggagga ggguggcggu gtt                                          23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
acaaaaggag gaggguggcg gtt                                          23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 53
accaguaacc ccagugggcg gtt                                          23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
uucauggcca ccaguaaccc ctt                                          23

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
acuccuucau ggccaccagu att                                          23

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
uucugacagc agcagggacu ctt                                          23

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
ucuguucuga cagcagcagg gtt                                          23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 58
ucuucuguuc ugacagcagc att                                              23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
aggucuucug uucugacagc att                                              23

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
uuguccucag ggcagcgagg utt                                              23

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
aagugcuugu ccucagggca gtt                                              23

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
uacccauccg caucacugcu ctt                                              23

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 63
ucucugaggg cuggugugcc ctt                                           23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 64
aagagcucag gucucugagg gtt                                           23

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 65
aagagcucag gucucugagg gtt                                           23

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 66
aagagcucag gucucugagg gtt                                           23

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
aagagcucag gucucugagg gtt                                           23

<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
aagagcucag gucucugagg g                                              21

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
aagagcucag gucucugagg g                                              21

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
aagagcucag gucucugagg gtt                                            23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
aagagcucag gucucugagg gtt                                            23

<210> SEQ ID NO 72
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
aagagcucag gucucugagg g                                              21

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
aagagcucag gucucugagg gtt                                            23

```
<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
aagagcucag gucucugagg g                                             21

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
aagagcucag gucucugagg gtt                                           23

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
aagagcucag gucucugagg g                                             21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
aagagcucag gucucugagg g                                             21

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 78
aagagcucag gucucugagg gtt                                           23

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 79
aagagcucag gucucugagg gtt                                               23

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 80
aagagcucag gucucugagg gtt                                               23

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
aagagcucag gucucugagg g                                                 21

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
aagagcucag gucucugagg gtt                                               23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
agaagagcuc aggucucuga gtt                                               23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 84
auagggagug uccagggacc ctt                                          23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
uccauaggga guguccaggg att                                          23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 86
aucuccauag ggagugucca gtt                                          23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
ucaguucugg cuguggcagg utt                                          23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
uucuaccccc ugggagcugc ctt                                          23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 89
aagcacaggg ccguucuacc ctt                                           23

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 90
ugucuuaagc acagggccgu utt                                           23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 91
agugucuuaa gcacagggcc gtt                                           23

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92
uuuuuugagg augugaagca att                                           23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
uuuuuuugag gaugugaagc att                                           23

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 94
ugcgcgugcg cagggauaag att                                                23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
cgcgugcgca gggauaagag att                                                23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 96
gcgccgcugu ggggacagca utt                                                23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
cagcaugagc ggcgguugga utt                                                23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
ccgccgcgag cccgcuuucc att                                                23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
       oligonucleotide
<220> FEATURE:
<223> OTHER INFORMATION: Description of Combined DNA/RNA Molecule:
      Synthetic oligonucleotide

<400> SEQUENCE: 99
cucgugccca cccaccaagu utt                                              23

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 100
gugcccaccc accaaguucc att                                              23

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 101
gcccacccac caaguccag utt                                               23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 102
cagugccgca ccaguggcuu att                                              23

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 103
ccgcaccagu ggcuuaugcg utt                                              23

<210> SEQ ID NO 104
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 104
gcgcugcgac agggacuugg att                                         23

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
cagcgauggc agcgaugagg att                                         23

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
ccccugcacc ggcgucagug att                                         23

<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
cugcucuggg ggaacugaca att                                         23

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 108
cucuggggga acugacaaga att                                         23

<210> SEQ ID NO 109
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109 uggggggaacu gacaagaaac utt                                                 23

<210> SEQ ID NO 110
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
gaacugacaa gaaacugcgc aacugtt                                              27

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
gaacugacaa gaaacugcgc aacugtt                                              27

<210> SEQ ID NO 112
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
gaacugacaa gaaacugcgc aacugtt                                              27

<210> SEQ ID NO 113
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
gaacugacaa gaaacugcgc aacug                                                25

<210> SEQ ID NO 114
<211> LENGTH: 27
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 114
gaacugacaa gaaacugcgc aacugtt                                           27

<210> SEQ ID NO 115
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
gaacugacaa gaaacugcgc aacug                                             25

<210> SEQ ID NO 116
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
gaacugacaa gaaacugcgc aacugtt                                           27

<210> SEQ ID NO 117
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
gaacugacaa gaaacugcgc aacugtt                                           27

<210> SEQ ID NO 118
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
gaacugacaa gaaacugcgc aacugtt                                           27

<210> SEQ ID NO 119
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 119
gaacugacaa gaaacugcgc aacug                                    25

<210> SEQ ID NO 120
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
gaacugacaa gaaacugcgc aacug                                    25

<210> SEQ ID NO 121
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121
gaacugacaa gaaacugcgc aacugtt                                  27

<210> SEQ ID NO 122
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gaacugacaa gaaacugcgc aacug                                    25

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 123
ugacaagaaa cugcgcaacu gtt                                      23

<210> SEQ ID NO 124
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 124
gaaacugcgc aacugtt                                             17

```
<210> SEQ ID NO 125
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125
gaaacugcgc aacugtt                                                       17

<210> SEQ ID NO 126
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
gaaacugcgc aacug                                                         15

<210> SEQ ID NO 127
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gaaacugcgc aacug                                                         15

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
cacgcugagc gaugacugca utt                                                23

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
acgcugagcg augacugcau utt                                                23

<210> SEQ ID NO 130
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
cugagcgaug acugcauucc att                                              23

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
gagcgaugac ugcauccac utt                                               23

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
ugcgacggcc acccagacug utt                                              23

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 133
gagcucggcu guggaaccaa utt                                              23

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134
ucggcugugg aaccaaugag att                                              23

<210> SEQ ID NO 135
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
cggcugugga accaaugaga utt                                              23

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 136
cuguggaacc aaugagaucc utt                                              23

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 137
uggagagugu caccucucuc att                                              23

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 138
cucucaggaa ugccacaacc att                                              23

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 139
uccccucugu cgggaaugcc att                                              23

<210> SEQ ID NO 140
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 140
cugucgggaa ugccacaucc utt                                            23

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 141
cugccggaga ccagucugga att                                            23

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 142
cccaacugcc uaugggguua utt                                            23

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 143
cugcugcggu gcucagugca att                                            23

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 144
caccgccacc cuccuccuuu utt                                            23

<210> SEQ ID NO 145
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 145
ccgccacccu ccuccuuuug utt                                               23

<210> SEQ ID NO 146
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 146
ccgcccacug ggguuacugg utt                                               23

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 147
gggguuacug guggccauga att                                               23

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 148
uacugguggc caugaaggag utt                                               23

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 149
gagucccugc ugcugucaga att                                               23

<210> SEQ ID NO 150
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 150
ggcugcugcu gucagaacag att                                          23

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 151
ugcugcuguc agaacagaag att                                          23

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 152
ugcugucaga acagaagacc utt                                          23

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 153
accucgcugc ccugaggaca att                                          23

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 154
cugcccugag gacaagcacu utt                                          23
```

```
<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 155
gagcagugau gcggaugggu att                                              23

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 156
gggcacacca gcccucagag att                                              23

<210> SEQ ID NO 157
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 157
cccucagaga ccugagcucu utt                                              23

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 158
cccucagaga ccugagcucu utt                                              23

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 159
cccucagaga ccugagcucu utt                                              23
```

-continued

```
<210> SEQ ID NO 160
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
cccucagaga ccugagcucu u                                            21

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 161
cccucagaga ccugagcucu utt                                          23

<210> SEQ ID NO 162
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
cccucagaga ccugagcucu u                                            21

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 163
cccucagaga ccugagcucu utt                                          23

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 164
cccucagaga ccugagcucu utt                                          23

<210> SEQ ID NO 165
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 165
cccucagaga ccugagcucu utt                                               23

<210> SEQ ID NO 166
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
cccucagaga ccugagcucu u                                                 21

<210> SEQ ID NO 167
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
cccucagaga ccugagcucu u                                                 21

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 168
cccucagaga ccugagcucu utt                                               23

<210> SEQ ID NO 169
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
cccucagaga ccugagcucu u                                                 21

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 170
```
cccucagaga ccugagcucu utt                                       23

<210> SEQ ID NO 171
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 171
gagaccugag cucuutt                                              17

<210> SEQ ID NO 172
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 172
gagaccugag cucuutt                                              17

<210> SEQ ID NO 173
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
gagaccugag cucuu                                                15

<210> SEQ ID NO 174
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
gagaccugag cucuu                                                15

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 175
cccucagaga ccugagcucu utt                                       23

<210> SEQ ID NO 176

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 176
cucagagacc ugagcucuuc utt                                              23

<210> SEQ ID NO 177
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 177
gggucccugg acacucccua utt                                              23

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 178
ucccuggaca cucccuaugg att                                              23

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 179
cuggacacuc ccuauggaga utt                                              23

<210> SEQ ID NO 180
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 180
accugccaca gccagaacug att                                              23
```

```
<210> SEQ ID NO 181
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 181
ggcagcuccc aggggguaga att                                              23

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 182
ggguagaacg gcccugugcu utt                                              23

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 183
aacggcccug ugcuuaagac att                                              23

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 184
cggcccugug cuuaagacac utt                                              23

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 185
uugcuucaca uccucaaaaa att                                              23
```

```
<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 186
ugcuucacau ccucaaaaaa att                                              23

<210> SEQ ID NO 187
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 187
uacuuuguga gcaaucuuga ctt                                              23

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 188
auucacuugg gauacacuga ctt                                              23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 189
acaugaaaac ucauugugca att                                              23

<210> SEQ ID NO 190
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 190
ucuuuacagu caucuucucc att                                              23
```

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 191
uaucuuuaca gucaucuucu ctt                                            23

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 192
aacauuuaug aacaucauga gtt                                            23

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 193
ucacaaacuu uauaaaugga gtt                                            23

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 194
aucacaaacu uuauaaaugg att                                            23

<210> SEQ ID NO 195
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 195
auacuacagu auuuuccggu att                          23

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 196
ucauacuaca guauuuccg gtt                           23

<210> SEQ ID NO 197
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 197
acaaauuccc cauaucuggc att                          23

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 198
aagauauacc cuucuucaca gtt                          23

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 199
uuagcuuugc aauacugucc att                          23

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 200
aucauuagcu uugcaauacu gtt                                          23

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 201
aaaggaauca uuagcuuugc att                                          23

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 202
augaauauca ccaauuaaca att                                          23

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 203
aaaaaaccuu auuuugcacg gtt                                          23

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 204
ugaaaaaacc uuauuuugca ctt                                          23

<210> SEQ ID NO 205
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 205
aaugucaacu gaaaaaaccu utt                                              23

<210> SEQ ID NO 206
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 206
uaaugucaac ugaaaaaacc utt                                              23

<210> SEQ ID NO 207
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 207
uuaaaccauu aaugucaacu gtt                                              23

<210> SEQ ID NO 208
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 208
uauuuaaacc auuaauguca att                                              23

<210> SEQ ID NO 209
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 209
uagauuuuau uauuaaccca gtt                                              23

<210> SEQ ID NO 210
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 210
auagauuuua uuauuaaccc att                                                23

<210> SEQ ID NO 211
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 211
aaauuuacca uaucuaugcg gtt                                                23

<210> SEQ ID NO 212
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 212 aaguuucag uuauaagggu att                                                 23

<210> SEQ ID NO 213
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 213
aauaaauaac caacaguugg gtt                                                23

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 214
agaaaaauaa auaaccaaca gtt                                                23

<210> SEQ ID NO 215
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 215
auaucauauc cagaguuacc ctt                                           23

<210> SEQ ID NO 216
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 216
aguuucaaug uaaucaaacc gtt                                           23

<210> SEQ ID NO 217
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 217
uuacaguuuc aauguaauca att                                           23

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 218
auaaguuaca guucaaugu att                                            23

<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 219
ucuuuacacg gauugguagc att                                           23

<210> SEQ ID NO 220
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 220
aaaaucaauc ccgacaaaga att                                                 23

<210> SEQ ID NO 221
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 221
ucugaaaaaa agauagugcu gtt                                                 23

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 222
aucugaaaaa aagauagugc utt                                                 23

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 223
aaaaaucaug uguuuugaca utt                                                 23

<210> SEQ ID NO 224
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 224
uuugcuuaaa aaucaugugu utt                                                 23

<210> SEQ ID NO 225
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 225
aacuuucaac auuuuccacc ctt                                                23

<210> SEQ ID NO 226
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 226
uugaaaucca aucaaaagcc att                                                23

<210> SEQ ID NO 227
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 227
uuugaaaucc aaucaaaagc ctt                                                23

<210> SEQ ID NO 228
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 228
uagagauucu uugaaaucca att                                                23

<210> SEQ ID NO 229
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 229
auagagauuc uuugaaaucc att                                                23

<210> SEQ ID NO 230
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<223> OTHER INFORMATION: Description of Combined DNA/RNA Molecule:
      Synthetic oligonucleotide

<400> SEQUENCE: 230
uuuaaauacu gaacuacugu gtt                                                 23

<210> SEQ ID NO 231
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 231
uauuuaaaua cugaacuacu gtt                                                 23

<210> SEQ ID NO 232
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 232
auagauaccc ggcaaaagga utt                                                 23

<210> SEQ ID NO 233
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 233
aagaguagug uuuauuacag gtt                                                 23

<210> SEQ ID NO 234
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 234
aucaaaauag gcaucuaccc att                                                 23

<210> SEQ ID NO 235
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 235
ucaauuuuau caaauaggc att                                                  23

<210> SEQ ID NO 236
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 236
uaaaugcucu ccaaagaugg ctt                                                 23

<210> SEQ ID NO 237
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 237
ucaaaugcag uauguaagca att                                                 23

<210> SEQ ID NO 238
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 238
uucaaaugca guauguaagc att                                                 23

<210> SEQ ID NO 239
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 239
ugauuacagg cguuagaacc att                                                 23

<210> SEQ ID NO 240
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 240 uguaucaug acaaucaucg att                                              23

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 241
uuaucacagg uguauugggu gtt                                             23

<210> SEQ ID NO 242
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 242
auuaucacag guguauuggg utt                                             23

<210> SEQ ID NO 243
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 243
aguucuuuga gauacacugg utt                                             23

<210> SEQ ID NO 244
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 244
ucgaauugca guucuuuuca utt                                             23

<210> SEQ ID NO 245
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 245
ucaauacauc gaugauuggg gtt                                            23

<210> SEQ ID NO 246
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 246
aacgauaggu caauacaucg att                                            23

<210> SEQ ID NO 247
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 247
acaaacgaua ggucaauaca utt                                            23

<210> SEQ ID NO 248
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 248
ucaaaaacac caucacaacg att                                            23

<210> SEQ ID NO 249
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 249
ucacauuccc agaaguucgg gtt                                            23

<210> SEQ ID NO 250
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 250
aucacauucc cagaaguucg gtt                                            23

<210> SEQ ID NO 251
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 251
ugaugaaggg caagucuugg gtt                                            23

<210> SEQ ID NO 252
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 252
agaaucauug gcaaguaaga att                                            23

<210> SEQ ID NO 253
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 253
uaucacauuc aucuaugucu utt                                            23

<210> SEQ ID NO 254
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 254
aauaucacau ucaucuaugu ctt                                            23

<210> SEQ ID NO 255
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 255
aacauguagc cuguaucaca ctt                                            23

<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 256
ucacuuucua acauguagcc utt                                            23

<210> SEQ ID NO 257
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 257
aucacuuucu aacauguagc ctt                                            23

<210> SEQ ID NO 258
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 258
aauguaagaa ccauucucga ctt                                            23

<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 259
uacaauguaa gaaccauucu ctt                                            23
```

```
<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 260
aaaaucaaca gcuacaaugu att                                            23

<210> SEQ ID NO 261
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 261
auugaaucaa aaucaacagc utt                                            23

<210> SEQ ID NO 262
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 262
uaauugaauc aaaaucaaca gtt                                            23

<210> SEQ ID NO 263
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 263
aagauacgac cacuaauuga att                                            23

<210> SEQ ID NO 264
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 264
aguuucaguc aagaugaugc utt                                            23
```

<210> SEQ ID NO 265
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 265
aauaguuuca gucaagauga utt                                              23

<210> SEQ ID NO 266
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 266
uauugcaaua guuucaguca att                                              23

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 267
ucuauugcaa uaguuucagu ctt                                              23

<210> SEQ ID NO 268
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 268
aaucuauugc aauaguuuca gtt                                              23

<210> SEQ ID NO 269
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 269
auuuuggaga cuucaauugu utt                                              23

<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 270
uuagguuuuu acuaaucagc att                                              23

<210> SEQ ID NO 271
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 271
ucauucuggg aucuaaugcu att                                              23

<210> SEQ ID NO 272
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 272
uucauucugg gaucuaaugc utt                                              23

<210> SEQ ID NO 273
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 273
aguagaugcu cauucauucu gtt                                              23

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 274
auuauaauca caaaagucca utt                                        23

<210> SEQ ID NO 275
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 275
uccauuauaa ucacaaaagu ctt                                        23

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 276
ugccguauaa ucaaaucact t                                          21

<210> SEQ ID NO 277
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 277
auauuauaca uuacaacuga ctt                                        23

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 278
auugaauauu auacauuaca att                                        23

<210> SEQ ID NO 279
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 279
aauuugguug uuucgaagga utt         23

<210> SEQ ID NO 280
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 280
acggaauuug guuguuucga att         23

<210> SEQ ID NO 281
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 281
uuacaguuau uaagaaaggu utt         23

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 282
uccaaaaauu auauguugcc utt         23

<210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 283
uuccaaaaau uauauguugc ctt         23

<210> SEQ ID NO 284
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<400> SEQUENCE: 284
ucuaaaccau ucuguauccc utt                                          23

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 285
aucuaaacca uucuguaucc ctt                                          23

<210> SEQ ID NO 286
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 286
uucaacaucu aaaccauucu gtt                                          23

<210> SEQ ID NO 287
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 287
auuuucaacc caauagaugu att                                          23

<210> SEQ ID NO 288
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 288
uauagaagca aauacugucc utt                                          23

<210> SEQ ID NO 289
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 289
uagauauaga agcaaauacu gtt                                              23

<210> SEQ ID NO 290
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 290
uaaggccagg uucauagaag gtt                                              23

<210> SEQ ID NO 291
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 291
ucuugaaauc caaucuaagg ctt                                              23

<210> SEQ ID NO 292
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 292
auaaagguuu cuugaaaucc att                                              23

<210> SEQ ID NO 293
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 293
ucaaaaccuc gauugacuga gtt                                              23

<210> SEQ ID NO 294
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 294
uucuguaucu gauaucuccg utt                                             23

<210> SEQ ID NO 295
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 295
uuucuguauc ugauaucucc gtt                                             23

<210> SEQ ID NO 296
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 296
uuuuucugua ucugauaucu ctt                                             23

<210> SEQ ID NO 297
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 297
aucaauguuu uucuguaucu gtt                                             23

<210> SEQ ID NO 298
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 298
auaaaggaaa gaaucaugga ctt                                             23

<210> SEQ ID NO 299
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 299
aauaaaggaa agaaucaugg att                                               23

<210> SEQ ID NO 300
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 300
ucaguauaau aaaggaaaga att                                               23

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 301
uuucaaugac cucauacugu utt                                               23

<210> SEQ ID NO 302
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 302
auuuggaaca uuaucucuca att                                               23

<210> SEQ ID NO 303
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 303
agauuuggaa cauuaucucu ctt                                               23

<210> SEQ ID NO 304
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 304
ucagauuugg aacauuaucu ctt                                              23

<210> SEQ ID NO 305
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 305
uugcuacagc cauuugaggt t                                                21

<210> SEQ ID NO 306
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 306
augaaagagu uauauggaga gtt                                              23

<210> SEQ ID NO 307
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 307
acaaugaaag aguuauaugg att                                              23

<210> SEQ ID NO 308
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 308
ugaaacaaca augaaagagu utt                                              23

<210> SEQ ID NO 309
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<223> OTHER INFORMATION: Description of Combined DNA/RNA Molecule:
      Synthetic oligonucleotide

<400> SEQUENCE: 309
auugaaacaa caaugaaaga gtt                                              23

<210> SEQ ID NO 310
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 310
agcuaaagcc ucugauugca gtt                                              23

<210> SEQ ID NO 311
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 311
aagcuaaagc cucugauugc att                                              23

<210> SEQ ID NO 312
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 312
acaauuccaa gcuaaagccu ctt                                              23

<210> SEQ ID NO 313
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 313
ugacaauucc aagcuaaagc ctt                                              23

<210> SEQ ID NO 314
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 314
ugaaugaucu gacaauucca att                                           23

<210> SEQ ID NO 315
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 315
auguucauca gagaagaucc att                                           23

<210> SEQ ID NO 316
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 316
uauuccaugu gucacaaugu utt                                           23

<210> SEQ ID NO 317
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 317
acuucuauca guguuucaga att                                           23

<210> SEQ ID NO 318
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 318
uauugauccg cagaacuucu att                                           23

<210> SEQ ID NO 319
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 319
uguucuuggg aucuacaaca att                                            23

<210> SEQ ID NO 320
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 320
aaagaacgcu caaucuuugg utt                                            23

<210> SEQ ID NO 321
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 321
uaaacguagc caucacuucg gtt                                            23

<210> SEQ ID NO 322
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 322
aucuaaagaa ucaucaaccc att                                            23

<210> SEQ ID NO 323
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 323
uuauaucuaa agaaucauca att                                            23

<210> SEQ ID NO 324
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 324
auagaauuuu caaaaacagu gtt                                              23

<210> SEQ ID NO 325
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 325
ugauagaauu ucaaaaaca gtt                                               23

<210> SEQ ID NO 326
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 326
uuucaaauuc cuaucuaccc att                                              23

<210> SEQ ID NO 327
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 327
uuuucaaauu ccuaucuacc ctt                                              23

<210> SEQ ID NO 328
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 328
auauugucuc uuaucacugu gtt                                              23

<210> SEQ ID NO 329
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 329
ugauauuguc ucuuaucacu gtt                                              23

<210> SEQ ID NO 330
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 330
ugaaauggca caauucuugc ctt                                              23

<210> SEQ ID NO 331
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 331
uguugaaaug gcacaauucu utt                                              23

<210> SEQ ID NO 332
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 332
aauuuucugu ugaaauggca ctt                                              23

<210> SEQ ID NO 333
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 333
aaauuuucug uugaaauggc att                                              23

<210> SEQ ID NO 334
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 334
auuagacaag gcaaagauga gtt                                              23

<210> SEQ ID NO 335
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 335
acauuuauug uuuggaaagg utt                                              23

<210> SEQ ID NO 336
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 336
aucacuuaca cugucauagu ctt                                              23

<210> SEQ ID NO 337
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 337
uagauucuau cacuuacacu gtt                                              23

<210> SEQ ID NO 338
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 338
aguagauucu aucacuuaca ctt                                              23
```

```
<210> SEQ ID NO 339
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 339
uuuuguguga aguagauucu att                                              23

<210> SEQ ID NO 340
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 340
uaaauuuugu gugaaguaga utt                                              23

<210> SEQ ID NO 341
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 341
ucuaguaauc cagucaaagg ctt                                              23

<210> SEQ ID NO 342
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 342
aauucuucua guaauccagu ctt                                              23

<210> SEQ ID NO 343
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 343
uaaauucuuc uaguaaucca gtt                                              23
```

```
<210> SEQ ID NO 344
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 344
auaaauucuu cuaguaaucc att                                              23

<210> SEQ ID NO 345
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 345
auauacuggc cauagagagu ctt                                              23

<210> SEQ ID NO 346
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 346
uucuuugugu guacaaguca gtt                                              23

<210> SEQ ID NO 347
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 347
aauucuuugu guguacaagu ctt                                              23

<210> SEQ ID NO 348
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 348
ucgguaaauu cuuugugugu att                                              23
```

<210> SEQ ID NO 349
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 349
uguuacacug uuguuucugg utt                                              23

<210> SEQ ID NO 350
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 350
auuguuacac uguuguuucu gtt                                              23

<210> SEQ ID NO 351
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 351
aaacuguuca caaggauugu utt                                              23

<210> SEQ ID NO 352
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 352
acaucguuca ccauugucca ctt                                              23

<210> SEQ ID NO 353
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 353
uguuauugca cauaaacucc gtt                                           23

<210> SEQ ID NO 354
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 354
ucuguuauug cacauaaacu ctt                                           23

<210> SEQ ID NO 355
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 355
uuaugacauu uuguguaucc att                                           23

<210> SEQ ID NO 356
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 356
ugaauuauga cauuuugugu att                                           23

<210> SEQ ID NO 357
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 357
uuugaauuau gacauuuugu gtt                                           23

<210> SEQ ID NO 358
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 358

```
uacaaauauu ugaauuauga ctt                                            23

<210> SEQ ID NO 359
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 359
aaauaaacgc gaggaauaca att                                            23

<210> SEQ ID NO 360
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 360
aauaaguagg guuuucauca ctt                                            23

<210> SEQ ID NO 361
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 361
ucacaauacc aauguugagg att                                            23

<210> SEQ ID NO 362
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 362
uguuucuuga ucacaauacc att                                            23

<210> SEQ ID NO 363
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

```
<400> SEQUENCE: 363
aacaaucugu uucuugauca ctt                                            23

<210> SEQ ID NO 364
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 364
uuuacacaga gaaacucgga att                                            23

<210> SEQ ID NO 365
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 365
auuuacacag agaaacucgg att                                            23

<210> SEQ ID NO 366
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 366
uucugauucu caucguagcc gtt                                            23

<210> SEQ ID NO 367
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 367
auuuucagag caaguucucc utt                                            23

<210> SEQ ID NO 368
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 368
auaucuuugg gauacacagu ctt                                              23

<210> SEQ ID NO 369
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 369
agguaaacug auucuguugg ctt                                              23

<210> SEQ ID NO 370
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 370
auagaaacug guuaaggugu ctt                                              23

<210> SEQ ID NO 371
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 371
acaauagaaa cugguuaagg utt                                              23

<210> SEQ ID NO 372
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 372
ucaucaauau caacacaagu ctt                                              23

<210> SEQ ID NO 373
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 373
agauguagga gccuauuaca utt                                              23

<210> SEQ ID NO 374
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 374
ucgauguuac uguuugccg gtt                                               23

<210> SEQ ID NO 375
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 375
uugcuaaaaa ugagauaggg utt                                              23

<210> SEQ ID NO 376
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 376
auuucucaaa uaguaacggu utt                                              23

<210> SEQ ID NO 377
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 377
aauuucucaa auaguaacgg utt                                              23

<210> SEQ ID NO 378
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 378
aaauuucuca aauaguaacg gtt                                          23

<210> SEQ ID NO 379
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 379
aguuaaauuu cucaaauagu att                                          23

<210> SEQ ID NO 380
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 380
aucuauaguu aaauuucuca att                                          23

<210> SEQ ID NO 381
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 381
uaaaaauagc caucuauagu utt                                          23

<210> SEQ ID NO 382
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 382
aucuaaugcc acaacauugu ctt                                          23

<210> SEQ ID NO 383
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 383
aauccaauac aaucucuucu ctt                                             23

<210> SEQ ID NO 384
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 384
acauucucuc aaugacuugc ctt                                             23

<210> SEQ ID NO 385
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 385
augauugucu ccuuguuugu ctt                                             23

<210> SEQ ID NO 386
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 386
auuaucacag acuuguuggu utt                                             23

<210> SEQ ID NO 387
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 387
uucaaaaaug guaauagcga att                                             23

<210> SEQ ID NO 388
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
         oligonucleotide
<220> FEATURE:
<223> OTHER INFORMATION: Description of Combined DNA/RNA Molecule:
      Synthetic oligonucleotide

<400> SEQUENCE: 388
ucuucaaaaa ugguaauagc gtt                                           23

<210> SEQ ID NO 389
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 389
auuuguuucc cuuuuccacu gtt                                           23

<210> SEQ ID NO 390
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 390
auuugaucca ucauauuugu utt                                           23

<210> SEQ ID NO 391
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 391
uauauggaug guacacaugg att                                           23

<210> SEQ ID NO 392
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 392
aaagaagacg gucuucauca gtt                                           23

<210> SEQ ID NO 393
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 393
ugaauucugu gaaguuguca ctt                                          23

<210> SEQ ID NO 394
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 394
acaaugucca cuuguacacu gtt                                          23

<210> SEQ ID NO 395
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 395
acacaauguc cacuuguaca ctt                                          23

<210> SEQ ID NO 396
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 396
uuuuugcauu cgaacauagu att                                          23

<210> SEQ ID NO 397
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 397
augguuuuug cauucgaaca utt                                          23

<210> SEQ ID NO 398
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 398
auacaaacau gguuuugca utt                                             23

<210> SEQ ID NO 399
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 399
aucacauuuc caauauggcg gtt                                            23

<210> SEQ ID NO 400
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 400
ugaaguucuu caucugaacc att                                            23

<210> SEQ ID NO 401
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 401
auaaaugcag cgauuguugu ctt                                            23

<210> SEQ ID NO 402
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 402
auucuguaca agguuuaggg gtt                                            23

<210> SEQ ID NO 403
<211> LENGTH: 23
<212> TYPE: DNA
```

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 403
uauucuguac aagguuuagg gtt                                           23

<210> SEQ ID NO 404
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 404
auucauauuc uguacaaggu utt                                           23

<210> SEQ ID NO 405
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 405
uauucauauu cuguacaagg utt                                           23

<210> SEQ ID NO 406
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 406
uuauauucau auucuguaca att                                           23

<210> SEQ ID NO 407
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 407
uauugcaacc caguucaucg gtt                                           23

<210> SEQ ID NO 408
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 408
auauuuucag cacauguucu utt                                            23

<210> SEQ ID NO 409
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 409
uuaauugggu acaauuuugc utt                                            23

<210> SEQ ID NO 410
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 410
aaaaacauug guuucgaacc ctt                                            23

<210> SEQ ID NO 411
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 411
ugucaaaaac auugguuucg att                                            23

<210> SEQ ID NO 412
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 412
uucgaauucg gacauuguca gtt                                            23

<210> SEQ ID NO 413
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 413
auuauauuuu cgaauucgga ctt                                            23

<210> SEQ ID NO 414
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 414
agauuauauu uucgaauucg gtt                                            23

<210> SEQ ID NO 415
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 415
ucaucuugaa gauacucuga gtt                                            23

<210> SEQ ID NO 416
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 416
uauauuccuc aucuugaaga utt                                            23

<210> SEQ ID NO 417
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 417
uuugauagca ccaaaccuag agcccuu                                        27
```

```
<210> SEQ ID NO 418
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 418
uuugauagca ccaaaccuag agccctt                                        27

<210> SEQ ID NO 419
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 419
uuugauagca ccaaaccuag agccctt                                        27

<210> SEQ ID NO 420
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 420
uuugauagca ccaaaccuag agccctt                                        27

<210> SEQ ID NO 421
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
uuugauagca ccaaaccuag agccc                                          25

<210> SEQ ID NO 422
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
uuugauagca ccaaaccuag agccc                                          25

<210> SEQ ID NO 423
<211> LENGTH: 27
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 423
uuugauagca ccaaaccuag agcccuu                                         27

<210> SEQ ID NO 424
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 424
uuugauagca ccaaaccuag agcccuu                                         27

<210> SEQ ID NO 425
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
uuugauagca ccaaaccuag agccc                                           25

<210> SEQ ID NO 426
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 426
uuugauagca ccaaaccuag agcccuu                                         27

<210> SEQ ID NO 427
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
uuugauagca ccaaaccuag acccc                                           25

<210> SEQ ID NO 428
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 428
uuugauagca ccaaaccuag agcccuu                                            27

<210> SEQ ID NO 429
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
uaucaaaccu cgauagcaac accgc                                              25

<210> SEQ ID NO 430
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 430
uuugauagca ccaaaccuag agcccuu                                            27

<210> SEQ ID NO 431
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 431
uuugauagca ccaaaccuag agcccuu                                            27

<210> SEQ ID NO 432
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 432
uuugauagca ccaaaccuag agcccuu                                            27

<210> SEQ ID NO 433
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
uuugauagca ccaaaccuag agc                                                23
```

<210> SEQ ID NO 434
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 434
uuugauagca ccaaaccuag agc                                              23

<210> SEQ ID NO 435
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 435
ucaaaguugg ggauguaggc att                                              23

<210> SEQ ID NO 436
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 436
ucaguuucag gucaacuucc utt                                              23

<210> SEQ ID NO 437
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 437
uacguauuuc aguucaggu ctt                                               23

<210> SEQ ID NO 438
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 438
uuacguauuu caguucagg utt                                               23

<210> SEQ ID NO 439

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 439
aguuuagcca ccucaaugcg utt                                              23

<210> SEQ ID NO 440
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 440
aacauaagcc cuaguuuggg att                                              23

<210> SEQ ID NO 441
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 441
ucgauuuuag guuccuuucc ctt                                              23

<210> SEQ ID NO 442
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 442
ucgaaaacca ggauguugcg gtt                                              23

<210> SEQ ID NO 443
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 443
ucaaauaauc gauagaaagg ctt                                              23
```

-continued

```
<210> SEQ ID NO 444
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 444
uuguucaaau aaucgauaga att                                              23

<210> SEQ ID NO 445
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 445
uuaugguuuc aauaacgucc utt                                              23

<210> SEQ ID NO 446
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 446
uuuuaugguu ucaauaacgu ctt                                              23

<210> SEQ ID NO 447
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 447
auuuuauggu ucaauaacg utt                                               23

<210> SEQ ID NO 448
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 448
uuugcaauga cucuccuauc agucctt                                          27
```

<210> SEQ ID NO 449
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 449
uuugcaauga cucuccuauc agucctt                                    27

<210> SEQ ID NO 450
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 450
uuugcaauga cucuccuauc agucctt                                    27

<210> SEQ ID NO 451
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 451
uuugcaauga cucuccuauc agucctt                                    27

<210> SEQ ID NO 452
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 452
uuugcaauga cucuccuauc agucc                                      25

<210> SEQ ID NO 453
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 453
uuugcaauga cucuccuauc agucc                                      25

<210> SEQ ID NO 454
<211> LENGTH: 27
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 454
uuugcaauga cucuccuauc agucctt                                           27

<210> SEQ ID NO 455
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 455
uuugcaauga cucuccuauc agucctt                                           27

<210> SEQ ID NO 456
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
uuugcaauga cucuccuauc agucc                                             25

<210> SEQ ID NO 457
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 457
uuugcaauga cucuccuauc agucctt                                           27

<210> SEQ ID NO 458
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
uuugcaauga cucuccuauc acucc                                             25

<210> SEQ ID NO 459
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

```
            Synthetic oligonucleotide

<400> SEQUENCE: 459
uuugcaauga cucuccuauc agucctt                                              27

<210> SEQ ID NO 460
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
uauccuaagu cacacguuug acugc                                                25

<210> SEQ ID NO 461
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 461
uuugcaauga cucuccuauc agucctt                                              27

<210> SEQ ID NO 462
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 462
uuugcaauga cucuccuauc agucctt                                              27

<210> SEQ ID NO 463
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 463
uuugcaauga cucuccuauc agucctt                                              27

<210> SEQ ID NO 464
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
uuugcaauga cucuccuauc agu                                                  23
```

<210> SEQ ID NO 465
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 465
uuugcaauga cucuccuauc agu                                             23

<210> SEQ ID NO 466
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 466
uagauaucca guauaacugg utt                                             23

<210> SEQ ID NO 467
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 467
uuuuguuucc auacuucucc ctt                                             23

<210> SEQ ID NO 468
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 468
auuuauuuug uuuccauacu utt                                             23

<210> SEQ ID NO 469
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 469
uauuguaucu gaguugauga att                                             23

```
<210> SEQ ID NO 470
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 470
ucaaaauagc aauuccucc gtt                                            23

<210> SEQ ID NO 471
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 471
ucaucaaaau agcaauuucc utt                                           23

<210> SEQ ID NO 472
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 472
auuucacaau auuuccggu gtt                                            23

<210> SEQ ID NO 473
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 473
uuugaaaacg ccauuucaca att                                           23

<210> SEQ ID NO 474
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 474
uucuauagug gaagaauccu gtt                                           23
```

```
<210> SEQ ID NO 475
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 475
auauccaugu uaagaucugc ctt                                               23

<210> SEQ ID NO 476
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 476
acaaagucuu cacucauugc ctt                                               23

<210> SEQ ID NO 477
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 477
uuauuaucca cauuucaga utt                                                23

<210> SEQ ID NO 478
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 478
ucuuauuauc cacauuuuca gtt                                               23

<210> SEQ ID NO 479
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 479
uccauaauuc uuauuaucca ctt                                               23
```

```
<210> SEQ ID NO 480
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 480
uuccauaauu cuuauuaucc att                                              23

<210> SEQ ID NO 481
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 481
uuuucguuug aagagauucc att                                              23

<210> SEQ ID NO 482
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 482
uagauuuucg uuugaagaga utt                                              23

<210> SEQ ID NO 483
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 483
uuuagauuuu cguuugaaga gtt                                              23

<210> SEQ ID NO 484
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 484
```
uuguuuagau uuucguuuga att                                          23

<210> SEQ ID NO 485
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 485
uaguuuguuu agauuuucgu utt                                          23

<210> SEQ ID NO 486
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 486
uuucaaaguu gguaguuugu utt                                          23

<210> SEQ ID NO 487
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 487
auuggauuuu caaaguuggu att                                          23

<210> SEQ ID NO 488
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 488
auagauugga uuucaaagu utt                                           23

<210> SEQ ID NO 489
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 489
uuaaaagugu cuucuguugc att                                           23

<210> SEQ ID NO 490
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 490
ucuuuaacaa gauuugcggu gtt                                           23

<210> SEQ ID NO 491
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 491
ucuucuuuaa caagauuugc gtt                                           23

<210> SEQ ID NO 492
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 492
ugguauagcu auacuucaga gtt                                           23

<210> SEQ ID NO 493
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 493
auuauucccu aaauagcugg utt                                           23

<210> SEQ ID NO 494
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<400> SEQUENCE: 494
uaauuauucc cuaaauagcu gtt                                              23

<210> SEQ ID NO 495
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 495
auauaugugc aaaagugugu utt                                              23

<210> SEQ ID NO 496
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 496
aaauauaugu gcaaaagugu gtt                                              23

<210> SEQ ID NO 497
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 497
aacuuuuuuc aucuguuugu att                                              23

<210> SEQ ID NO 498
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 498
uaaaguacug aauguuaacu utt                                              23

<210> SEQ ID NO 499
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 499
uuuuuuucau aaaguacuga att                                          23

<210> SEQ ID NO 500
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 500 uauuuuuuc auaaaguacu gtt                                           23

<210> SEQ ID NO 501
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 501
auuuguaaaa auaugagacg gtt                                          23

<210> SEQ ID NO 502
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 502
acauugugau aauuauuugu att                                          23

<210> SEQ ID NO 503
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 503
auacauauag uacauuguga utt                                          23

<210> SEQ ID NO 504
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 504
auauacauau aguacauugu gtt                                              23

<210> SEQ ID NO 505
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 505
aaagauauac auauaguaca utt                                              23

<210> SEQ ID NO 506
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 506
auuaccuuca gacaacuuca gtt                                              23

<210> SEQ ID NO 507
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 507
uauuuauagu auuaccuuca gtt                                              23

<210> SEQ ID NO 508
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 508
uaaucuuccc aaaauuuaca att                                              23

<210> SEQ ID NO 509
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 509
aguaacagga uaaucuuucc att                                                23

<210> SEQ ID NO 510
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 510
auucaguaac aggauaaucu utt                                                23

<210> SEQ ID NO 511
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 511
uagcaaauuc aguaacagga utt                                                23

<210> SEQ ID NO 512
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 512
uuagcaaauu caguaacagg att                                                23

<210> SEQ ID NO 513
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 513
ucuuuauuag caaauucagu att                                                23

<210> SEQ ID NO 514
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 514
aucauuuacu auaaugauca ctt                                           23

<210> SEQ ID NO 515
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 515
uucuuguugg aucauuuacu att                                           23

<210> SEQ ID NO 516
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 516
ucaauuccuu uucuuguugg att                                           23

<210> SEQ ID NO 517
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 517
auuuuauagg aaauaugagu gtt                                           23

<210> SEQ ID NO 518
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 518
uaauuuuaua ggaaauauga gtt                                           23

<210> SEQ ID NO 519
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 519
ugcuaaugug uaaaaaugga ctt                                             23

<210> SEQ ID NO 520
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 520
uugaacauua auuaagugcu att                                             23

<210> SEQ ID NO 521
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 521
auugaacauu aauuaagugc utt                                             23

<210> SEQ ID NO 522
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 522
auauugaaca uuaauuaagu gtt                                             23

<210> SEQ ID NO 523
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 523
aaauugacau guaauauuga att                                             23

<210> SEQ ID NO 524
<211> LENGTH: 23
<212> TYPE: DNA
<213> ORGANISM: Artificial Sequence
<220> FEATURE:
```

<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 524
aucaacauag ccauuaauca att                                             23

<210> SEQ ID NO 525
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 525
ucuauacaac acauaguggc ctt                                             23

<210> SEQ ID NO 526
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 526
augucuauac aacacauagu gtt                                             23

<210> SEQ ID NO 527
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 527
acugaauugc uuuuccuacc utt                                             23

<210> SEQ ID NO 528
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 528
aaauaaaaau guugucuugg ctt                                             23

<210> SEQ ID NO 529
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 529
aucacaaaua aaauguugu ctt                                              23

<210> SEQ ID NO 530
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 530
aaugauaugg gauuccuca utt                                              23

<210> SEQ ID NO 531
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 531
auuaaccaca aacucaaugc att                                             23

<210> SEQ ID NO 532
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 532
uuuaauuaac cacaaacuca att                                             23

<210> SEQ ID NO 533
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 533
uuugguuuca gaaauucagc utt                                             23

<210> SEQ ID NO 534
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 534
uuaugaagac acagauuugg utt                                           23

<210> SEQ ID NO 535
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 535
uuucauagaa acaaaaaccc att                                           23

<210> SEQ ID NO 536
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 536
augauauuuu cauagaaaca att                                           23

<210> SEQ ID NO 537
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 537
uauaaugaua uuuucauaga att                                           23

<210> SEQ ID NO 538
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 538
ugauuauaau gauauuuuca utt                                           23

<210> SEQ ID NO 539
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 539
auaaauagug auuauaauga utt                                            23

<210> SEQ ID NO 540
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 540
aaaagcuuaa uaagaauggu utt                                            23

<210> SEQ ID NO 541
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541
aaaaagcuua auaagaaugg utt                                            23

<210> SEQ ID NO 542
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 542
uaaauguaca cauuuagcca ctt                                            23

<210> SEQ ID NO 543
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 543
auaaauguac acauuuagcc att                                            23

<210> SEQ ID NO 544
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 544
uauaaaugua cacauuuagc ctt                                            23

<210> SEQ ID NO 545
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 545
uucuaauaua aauguacaca utt                                            23

<210> SEQ ID NO 546
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 546
aagaauuaaa gaaaagaucu gtt                                            23

<210> SEQ ID NO 547
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 547
aauaagaauu aaagaaaaga utt                                            23

<210> SEQ ID NO 548
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 548
aaaccaauaa gaauuaaaga att                                            23
```

```
<210> SEQ ID NO 549
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 549
acuauaccca cuauuuaaga gtt                                              23

<210> SEQ ID NO 550
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 550
acaaaugugc aauauuagca ctt                                              23

<210> SEQ ID NO 551
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 551
aacaaaugug caauauuagc att                                              23

<210> SEQ ID NO 552
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 552
auguuucauu cauucaucca utt                                              23

<210> SEQ ID NO 553
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 553
aguaguauau guuucauuca utt                                              23
```

<210> SEQ ID NO 554
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 554
aaucaguagu auauguuuca utt                                            23

<210> SEQ ID NO 555
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 555
aaauaaucag uaguauaugu utt                                            23

<210> SEQ ID NO 556
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 556
aaucaaagua auuacaguca gtt                                            23

<210> SEQ ID NO 557
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 557
aucuaaucaa aguaauuaca gtt                                            23

<210> SEQ ID NO 558
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 558
uuauuuccag uuguuuaucu att                                            23

```
<210> SEQ ID NO 559
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 559
uuauuagaac uuuuucagca gtt                                               23

<210> SEQ ID NO 560
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 560
uuuauuagaa cuuuuucagc att                                               23

<210> SEQ ID NO 561
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 561
gucaagauug cucacaaagu att                                               23

<210> SEQ ID NO 562
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 562
gucaguguau cccaagugaa utt                                               23

<210> SEQ ID NO 563
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 563
```
uugcacaaug aguuuucaug utt                          23

<210> SEQ ID NO 564
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 564
uggagaagau gacuguaaag auatt                        25

<210> SEQ ID NO 565
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 565
gagaagauga cuguaaagau att                          23

<210> SEQ ID NO 566
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 566
cucaugaugu ucauaaaugu utt                          23

<210> SEQ ID NO 567
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 567
cuccauuuau aaaguuugug att                          23

<210> SEQ ID NO 568
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 568
uccauuuaua aaguuuguga utt                                23

<210> SEQ ID NO 569
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 569
uaccggaaaa uacuguagua utt                                23

<210> SEQ ID NO 570
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 570
ccggaaaaua cuguaguaug att                                23

<210> SEQ ID NO 571
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 571
ugccagauau ggggaauuug utt                                23

<210> SEQ ID NO 572
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 572
cugugaagaa ggguauaucu utt                                23

<210> SEQ ID NO 573
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 573
uggacaguau ugcaaagcua att    23

<210> SEQ ID NO 574
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 574
caguauugca aagcuaauga utt    23

<210> SEQ ID NO 575
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 575
ugcaaagcua augauuccuu utt    23

<210> SEQ ID NO 576
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 576
uuguuaauug gugauauuca utt    23

<210> SEQ ID NO 577
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 577
ccgugcaaaa uaagguuuuu utt    23

<210> SEQ ID NO 578
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 578
gugcaaaaua agguuuuuc att                                          23

<210> SEQ ID NO 579
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 579
aagguuuuuu caguugacau utt                                         23

<210> SEQ ID NO 580
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 580 agguuuuuc aguugacauu att                                          23

<210> SEQ ID NO 581
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 581
caguugacau uaaugguuua att                                         23

<210> SEQ ID NO 582
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 582
uugacauuaa ugguuuaaau att                                         23

<210> SEQ ID NO 583
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 583
cuggguuaau aauaaaaucu att                                              23

<210> SEQ ID NO 584
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 584
uggguuaaua auaaaaucua utt                                              23

<210> SEQ ID NO 585
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 585
ccgcauagau augguaaauu utt                                              23

<210> SEQ ID NO 586
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 586
uacccuuaua acugaaaacu utt                                              23

<210> SEQ ID NO 587
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 587
cccaacuguu gguuauuuau utt                                              23

<210> SEQ ID NO 588
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 588
cguuggguua uuuauuuuuc utt                                              23

<210> SEQ ID NO 589
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 589
ggguaacucu ggauaugaua utt                                              23

<210> SEQ ID NO 590
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 590
cgguuugauu acauugaaac utt                                              23

<210> SEQ ID NO 591
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 591
uugauuacau ugaaacugua att                                              23

<210> SEQ ID NO 592
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 592
uacauugaaa cuguaacuua utt                                              23

<210> SEQ ID NO 593
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 593
ugcuaccaau ccguguaaag att                                              23

<210> SEQ ID NO 594
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 594
uucuuugucg ggauugauuu utt                                              23

<210> SEQ ID NO 595
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 595
cagcacuauc uuuuuuucag att                                              23

<210> SEQ ID NO 596
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 596
agcacuaucu uuuuucaga utt                                               23

<210> SEQ ID NO 597
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 597
augucaaaac acaugauuuu utt                                              23

<210> SEQ ID NO 598
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
                              oligonucleotide
<220> FEATURE:
<223> OTHER INFORMATION: Description of Combined DNA/RNA Molecule:
      Synthetic oligonucleotide

<400> SEQUENCE: 598
aacacaugau uuuuaagcaa att                                                 23

<210> SEQ ID NO 599
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 599
ggguggaaaa uguugaaagu utt                                                 23

<210> SEQ ID NO 600
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 600
uggcuuuuga uuggauuuca att                                                 23

<210> SEQ ID NO 601
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 601
ggcuuuugau uggauuucaa att                                                 23

<210> SEQ ID NO 602
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 602
uuggauuuca aagaaucucu att                                                 23

<210> SEQ ID NO 603
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 603
uggauuucaa agaaucucua utt                                              23

<210> SEQ ID NO 604
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 604
cacaguaguu caguauuuaa att                                              23

<210> SEQ ID NO 605
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 605
caguaguuca guauuuaaau att                                              23

<210> SEQ ID NO 606
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 606
auccuuuugc cggguaucua utt                                              23

<210> SEQ ID NO 607
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 607
ccccuguaau aaacacuacu ctt                                              23

<210> SEQ ID NO 608
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 608
uggguagaug ccuauuuuga utt                                              23

<210> SEQ ID NO 609
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 609
ugccuauuuu gauaaaauug att                                              23

<210> SEQ ID NO 610
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 610
gccaucuuug gagagcauuu att                                              23

<210> SEQ ID NO 611
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 611
uugcuuacau acugcauuug att                                              23

<210> SEQ ID NO 612
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 612
ugcuuacaua cugcauuuga att                                              23

<210> SEQ ID NO 613
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 613
ugguucuaac gccuguaauc att                                             23

<210> SEQ ID NO 614
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 614
ucgaugauug ucaugauaac att                                             23

<210> SEQ ID NO 615
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 615
cacccaauac accugugaua att                                             23

<210> SEQ ID NO 616
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 616
acccaauaca ccugugauaa utt                                             23

<210> SEQ ID NO 617
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 617
accaguguau cucaaagaac utt                                             23

<210> SEQ ID NO 618
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 618
augaaaagaa cugcaauucg att                                               23

<210> SEQ ID NO 619
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 619
ccccaaucau cgauguauug att                                               23

<210> SEQ ID NO 620
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 620
ucgauguauu gaccuaucgu utt                                               23

<210> SEQ ID NO 621
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 621
auguauugac cuaucguuug utt                                               23

<210> SEQ ID NO 622
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 622
ucguugugau ggguguuuug att                                               23

<210> SEQ ID NO 623
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 623
cccgaacuuc ugggaaugug att                                            23

<210> SEQ ID NO 624
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 624
ccgaacuucu gggaauguga utt                                            23

<210> SEQ ID NO 625
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 625
cccaagacuu gcccuucauc att                                            23

<210> SEQ ID NO 626
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 626
uucuuacuug ccaaugauuc utt                                            23

<210> SEQ ID NO 627
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 627
aagacauaga ugaaugugau att                                            23
```

```
<210> SEQ ID NO 628
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 628
gacauagaug aaugugauau utt                                               23

<210> SEQ ID NO 629
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 629
gugugauaca ggcuacaugu utt                                               23

<210> SEQ ID NO 630
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 630
aggcuacaug uuagaaagug att                                               23

<210> SEQ ID NO 631
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 631
ggcuacaugu uagaaaguga utt                                               23

<210> SEQ ID NO 632
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 632
gucgagaaug guucuuacau utt                                               23
```

<210> SEQ ID NO 633
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 633
gagaaugguu cuuacauugu att                                              23

<210> SEQ ID NO 634
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 634
uacauuguag cguugauuu utt                                               23

<210> SEQ ID NO 635
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 635
agcuguugau uuugauucaa utt                                              23

<210> SEQ ID NO 636
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 636 cguugauuu ugauucaauu att                                               23

<210> SEQ ID NO 637
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 637
uucaauuagu ggucguaucu utt                                              23

<210> SEQ ID NO 638
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 638
agcaucaucu ugacugaaac utt                                              23

<210> SEQ ID NO 639
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 639
aucaucuuga cugaaacuau utt                                              23

<210> SEQ ID NO 640
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 640
uugacugaaa cuauugcaau att                                              23

<210> SEQ ID NO 641
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 641
gacugaaacu auugcaauag att                                              23

<210> SEQ ID NO 642
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 642
cugaaacuau ugcaauagau utt                              23

<210> SEQ ID NO 643
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 643
aacaauugaa gucuccaaaa utt                              23

<210> SEQ ID NO 644
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 644
ugcugauuag uaaaaaccua att                              23

<210> SEQ ID NO 645
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 645
uagcauuaga ucccagaaug att                              23

<210> SEQ ID NO 646
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 646
agcauuagau cccagaauga att                              23

<210> SEQ ID NO 647
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 647
cagaaugaau gagcaucuac utt                                           23

<210> SEQ ID NO 648
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 648
auggacuuuu gugauuauaa utt                                           23

<210> SEQ ID NO 649
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 649
gacuuuugug auuauaaugg att                                           23

<210> SEQ ID NO 650
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 650
gugugauuug auuauacggc att                                           23

<210> SEQ ID NO 651
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 651
gucaguugua auguauaaua utt                                           23

<210> SEQ ID NO 652
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 652
uuguaaugua uaauauucaa utt                                                23

<210> SEQ ID NO 653
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 653
auccuucgaa acaaccaaau utt                                                23

<210> SEQ ID NO 654
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 654
uucgaaacaa ccaaauuccg utt                                                23

<210> SEQ ID NO 655
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 655
aaccuuucuu aauaacugua att                                                23

<210> SEQ ID NO 656
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 656
aggcaacaua uaauuuuugg att                                                23

<210> SEQ ID NO 657
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 657
ggcaacauau aauuuuugga att                                              23

<210> SEQ ID NO 658
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 658
agggauacag aaugguuuag att                                              23

<210> SEQ ID NO 659
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 659
gggauacaga augguuuaga utt                                              23

<210> SEQ ID NO 660
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 660
cagaaugguu uagauguuga att                                              23

<210> SEQ ID NO 661
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 661
uacaucuauu ggguugaaaa utt                                              23

<210> SEQ ID NO 662
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 662
aggacaguau uugcuucuau att        23

<210> SEQ ID NO 663
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 663
caguauuugc uucuauaucu att        23

<210> SEQ ID NO 664
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 664
ccuucuauga accuggccut t        21

<210> SEQ ID NO 665
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 665
gccuuagauu ggauuucaag att        23

<210> SEQ ID NO 666
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 666
uggauuucaa gaaaccuuua utt        23

<210> SEQ ID NO 667
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 667
cucagucaau cgagguuuug att                                             23

<210> SEQ ID NO 668
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 668
acggagauau cagauacaga att                                             23

<210> SEQ ID NO 669
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 669
cggagauauc agauacagaa att                                             23

<210> SEQ ID NO 670
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 670
gagauaucag auacagaaaa att                                             23

<210> SEQ ID NO 671
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 671
cagauacaga aaaacauuga utt                                             23

<210> SEQ ID NO 672
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 672
guccaugauu cuuccuuua utt                                                  23

<210> SEQ ID NO 673
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 673
uccaugauuc uuccuuuau utt                                                  23

<210> SEQ ID NO 674
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 674
uucuuuccuu uauuauacug att                                                 23

<210> SEQ ID NO 675
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 675
aacaguauga ggucauugaa att                                                 23

<210> SEQ ID NO 676
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 676
uugagagaua auguccaaa utt                                                  23

<210> SEQ ID NO 677
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 677
gagagauaau guuccaaauc utt                                                 23

<210> SEQ ID NO 678
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 678
gagauaaugu uccaaaucug att                                                 23

<210> SEQ ID NO 679
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 679
ccucaaaugg cuguagcaat t                                                   21

<210> SEQ ID NO 680
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 680
cucuccauau aacucuuuca utt                                                 23

<210> SEQ ID NO 681
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 681
uccauauaac cuuucauug utt                                                  23

<210> SEQ ID NO 682
<211> LENGTH: 23
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 682
aacucuuuca uguuguuuc att                                              23

<210> SEQ ID NO 683
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 683
cucuuucauu guuguuucaa utt                                             23

<210> SEQ ID NO 684
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 684
cugcaaucag aggcuuuagc utt                                             23

<210> SEQ ID NO 685
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 685
ugcaaucaga ggcuuuagcu utt                                             23

<210> SEQ ID NO 686
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 686
gaggcuuuag cuuggaauug utt                                             23

<210> SEQ ID NO 687
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 687
ggcuuuagcu uggaauuguc att                                          23

<210> SEQ ID NO 688
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 688
uuggaauugu cagaucauuc att                                          23

<210> SEQ ID NO 689
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 689
uggaucuucu cugaugaaca utt                                          23

<210> SEQ ID NO 690
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 690
aacauuguga cacauggaau att                                          23

<210> SEQ ID NO 691
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 691
uucugaaaca cugauagaag utt                                          23

<210> SEQ ID NO 692
<211> LENGTH: 23
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 692
uagaaguucu gcggaucaau att                                          23

<210> SEQ ID NO 693
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 693
uuguuguaga ucccaagaac att                                          23

<210> SEQ ID NO 694
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 694
accaaagauu gagcguucuu utt                                          23

<210> SEQ ID NO 695
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 695
ccgaagugau ggcuacguuu att                                          23

<210> SEQ ID NO 696
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 696
uggguugaug auucuuuaga utt                                          23

<210> SEQ ID NO 697
<211> LENGTH: 23
```

```
-continued

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 697
uugaugauuc uuuagauaua att                                              23

<210> SEQ ID NO 698
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 698
cacuguuuuu gaaaauucua utt                                              23

<210> SEQ ID NO 699
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 699
cuguuuuuga aaauucuauc att                                              23

<210> SEQ ID NO 700
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 700
uggguagaua ggaauuugaa att                                              23

<210> SEQ ID NO 701
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 701
ggguagauag gaauuugaaa att                                              23

<210> SEQ ID NO 702
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 702
cacagugaua agagacaaua utt                                           23

<210> SEQ ID NO 703
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 703
cagugauaag agacaauauc att                                           23

<210> SEQ ID NO 704
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 704
ggcaagaauu gugccauuuc att                                           23

<210> SEQ ID NO 705
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 705
aagaauugug ccauuucaac att                                           23

<210> SEQ ID NO 706
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 706
gugccauuuc aacagaaaau utt                                           23
```

```
<210> SEQ ID NO 707
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 707
ugccauuuca acagaaaauu utt                                               23

<210> SEQ ID NO 708
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 708
cucaucuuug ccuugcuaa utt                                                23

<210> SEQ ID NO 709
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 709
accuuuccaa acaauaaaug utt                                               23

<210> SEQ ID NO 710
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 710
gacuaugaca guguaaguga utt                                               23

<210> SEQ ID NO 711
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 711
caguguaagu gauagaaucu att                                               23
```

<210> SEQ ID NO 712
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 712
guguaaguga uagaaucuac utt                                              23

<210> SEQ ID NO 713
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 713
uagaaucuac uucacacaaa att                                              23

<210> SEQ ID NO 714
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 714
aucuacuuca cacaaaauuu att                                              23

<210> SEQ ID NO 715
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 715
gccuuugacu ggauuacuag att                                              23

<210> SEQ ID NO 716
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 716
gacuggauua cuagaagaau utt                                              23

<210> SEQ ID NO 717
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 717
cuggauuacu agaagaauuu att                                              23

<210> SEQ ID NO 718
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 718
uggauuacua gaagaauuua utt                                              23

<210> SEQ ID NO 719
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 719
gacucucuau ggccaguaua utt                                              23

<210> SEQ ID NO 720
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 720
cugacuugua cacacaaaga att                                              23

<210> SEQ ID NO 721
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 721

-continued gacuuguaca cacaaagaau utt    23

<210> SEQ ID NO 722
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 722
uacacacaaa gaauuuaccg att    23

<210> SEQ ID NO 723
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 723
accagaaaca acaguguaac att    23

<210> SEQ ID NO 724
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 724
cagaaacaac aguguaacaa utt    23

<210> SEQ ID NO 725
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 725
aacaauccuu gugaacaguu utt    23

<210> SEQ ID NO 726
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 726
guggacaaug gugaacgaug utt                                          23

<210> SEQ ID NO 727
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 727
cggaguuuau gugcaauaac att                                          23

<210> SEQ ID NO 728
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 728
gaguuuaugu gcaauaacag att                                          23

<210> SEQ ID NO 729
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 729
uggauacaca aaaugucaua att                                          23

<210> SEQ ID NO 730
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 730
uacacaaaau gucauaauuc att                                          23

<210> SEQ ID NO 731
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 731
cacaaaaugu cauaauucaa att                                           23

<210> SEQ ID NO 732
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 732
gucauaauuc aaauauuugu att                                           23

<210> SEQ ID NO 733
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 733
uuguauuccu cgcguuuauu utt                                           23

<210> SEQ ID NO 734
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 734
gugaugaaaa cccuacuuau utt                                           23

<210> SEQ ID NO 735
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 735
uccucaacau ugguauugug att                                           23

<210> SEQ ID NO 736
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 736
ugguauugug aucaagaaac att                                              23

<210> SEQ ID NO 737
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 737
gugaucaaga aacagauugu utt                                              23

<210> SEQ ID NO 738
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 738
uuccgaguuu cucuguguaa att                                              23

<210> SEQ ID NO 739
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 739
uccgaguuuc ucuguguaaa utt                                              23

<210> SEQ ID NO 740
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 740
cggcuacgau gagaaucaga att                                              23

<210> SEQ ID NO 741
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 741
aggagaacuu gcucugaaaa utt                                          23

<210> SEQ ID NO 742
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 742
gacuguguau cccaaagaua utt                                          23

<210> SEQ ID NO 743
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 743
gccaacagaa ucaguuuacc utt                                          23

<210> SEQ ID NO 744
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 744
gacaccuuaa ccaguuucua utt                                          23

<210> SEQ ID NO 745
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 745
accuuaacca guuucuauug utt                                          23

<210> SEQ ID NO 746
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

-continued

```
<223> OTHER INFORMATION: Description of Combined DNA/RNA Molecule:
      Synthetic oligonucleotide

<400> SEQUENCE: 746
gacuuguguu gauauugaug att                                                  23

<210> SEQ ID NO 747
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 747
auguaauagg cuccuacauc utt                                                  23

<210> SEQ ID NO 748
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 748
ccggcaaaac aguaacaucg att                                                  23

<210> SEQ ID NO 749
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 749
acccuaucuc auuuuuagca att                                                  23

<210> SEQ ID NO 750
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 750
aaccguuacu auuugagaaa utt                                                  23

<210> SEQ ID NO 751
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 751
accguuacua uuugagaaau utt                                               23

<210> SEQ ID NO 752
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 752
ccguuacuau uugagaaauu utt                                               23

<210> SEQ ID NO 753
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 753
uacuauuuga gaaauuuaac utt                                               23

<210> SEQ ID NO 754
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 754
uugagaaauu uaacuauaga utt                                               23

<210> SEQ ID NO 755
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 755
aacuauagau ggcuauuuuu att                                               23

<210> SEQ ID NO 756
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 756
gacaauguug uggcauuaga utt                                           23

<210> SEQ ID NO 757
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 757
gagaagagau uguauuggau utt                                           23

<210> SEQ ID NO 758
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 758
ggcaagucau ugagagaaug utt                                           23

<210> SEQ ID NO 759
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 759
gacaaacaag gagacaauca utt                                           23

<210> SEQ ID NO 760
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 760
aaccaacaag ucugugauaa utt                                           23

<210> SEQ ID NO 761
<211> LENGTH: 23
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 761
uucgcuauua ccauuuuga att                                              23

<210> SEQ ID NO 762
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 762
cgcuauuacc auuuugaag att                                              23

<210> SEQ ID NO 763
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 763
caguggaaaa gggaaacaaa utt                                             23

<210> SEQ ID NO 764
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 764
aacaaauaug auggaucaaa utt                                             23

<210> SEQ ID NO 765
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 765
uccaugugua ccauccauau att                                             23

<210> SEQ ID NO 766
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 766
cugaugaaga ccgucuucuu utt                                          23

<210> SEQ ID NO 767
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 767
gugacaacuu cacagaauuc att                                          23

<210> SEQ ID NO 768
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 768
cgguguacaa guggacauug utt                                          23

<210> SEQ ID NO 769
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 769
guguacaagu ggacauugug utt                                          23

<210> SEQ ID NO 770
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 770
uacuauguuc gaaugcaaaa att                                          23

<210> SEQ ID NO 771
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 771
auguucgaau gcaaaaacca utt                                              23

<210> SEQ ID NO 772
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 772
augcaaaaac cauguuugua utt                                              23

<210> SEQ ID NO 773
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 773
ccgccauauu ggaaauguga utt                                              23

<210> SEQ ID NO 774
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 774
ugguucagau gaagaacuuc att                                              23

<210> SEQ ID NO 775
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 775
gacaacaauc gcugcauuua utt                                              23

<210> SEQ ID NO 776
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 776
ccccuaaacc uuguacagaa utt                                               23

<210> SEQ ID NO 777
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 777
cccuaaaccu uguacagaau att                                               23

<210> SEQ ID NO 778
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 778
aaccuuguac agaauaugaa utt                                               23

<210> SEQ ID NO 779
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 779
accuuguaca gaauaugaau att                                               23

<210> SEQ ID NO 780
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 780
uuguacagaa uaugaauaua att                                               23

<210> SEQ ID NO 781
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 781
ccgaugaacu ggguugcaau att                                              23

<210> SEQ ID NO 782
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 782
aagaacaugu gcugaaaaua utt                                              23

<210> SEQ ID NO 783
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 783
agcaaaauug uacccaauua att                                              23

<210> SEQ ID NO 784
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 784
ggguucgaaa ccaauguuuu utt                                              23

<210> SEQ ID NO 785
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 785
ucgaaaccaa uguuuuugac att                                              23
```

```
<210> SEQ ID NO 786
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 786
cugacaaugu ccgaauucga att                                              23

<210> SEQ ID NO 787
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 787
guccgaauuc gaaaauauaa utt                                              23

<210> SEQ ID NO 788
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 788
ccgaauucga aaauauaauc utt                                              23

<210> SEQ ID NO 789
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 789
cucagaguau cuucaagaug att                                              23

<210> SEQ ID NO 790
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 790
aucuucaaga ugaggaauau att                                              23
```

<210> SEQ ID NO 791
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 791
gggcucuagg uuuggugcua ucaaatt                                              27

<210> SEQ ID NO 792
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 792
gggcucuagg uuuggugcua ucaaatt                                              27

<210> SEQ ID NO 793
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 793
gggcucuagg uuuggugcua ucaaatt                                              27

<210> SEQ ID NO 794
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 794
gggcucuagg uuuggugcua ucaaa                                                25

<210> SEQ ID NO 795
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 795
gggcucuagg uuuggugcua ucaaatt                                              27

<210> SEQ ID NO 796

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 796
gggcucuagg uuggugcua ucaaa                                              25

<210> SEQ ID NO 797
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 797
gggcucuagg uuggugcua ucaaatt                                            27

<210> SEQ ID NO 798
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 798
gggcucuagg uuggugcua ucaaatt                                            27

<210> SEQ ID NO 799
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 799
gggcucuagg uuggugcua ucaaatt                                            27

<210> SEQ ID NO 800
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 800
gggcucuagg uuggugcua ucaaa                                              25

<210> SEQ ID NO 801
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 801
gggcucuagg uuuggugcua ucaaa                                    25

<210> SEQ ID NO 802
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 802
gggcucuagg uuuggugcua ucaaatt                                  27

<210> SEQ ID NO 803
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 803
gggcucuagg uuuggugcua ucaaa                                    25

<210> SEQ ID NO 804
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 804
ucuagguuug gugcuaucaa att                                      23

<210> SEQ ID NO 805
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 805
uuuggugcua ucaaatt                                             17

<210> SEQ ID NO 806
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<400> SEQUENCE: 806
uuuggugcua ucaaatt                                                  17

<210> SEQ ID NO 807
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 807
uuuggugcua ucaaa                                                    15

<210> SEQ ID NO 808
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 808
uuuggugcua ucaaa                                                    15

<210> SEQ ID NO 809
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 809
ugccuacauc cccaacuuug att                                           23

<210> SEQ ID NO 810
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 810
aggaaguuga ccugaaacug att                                           23

<210> SEQ ID NO 811
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 811
gaccugaaac ugaaauacgu att                                           23
```

```
<210> SEQ ID NO 812
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 812
accugaaacu gaaauacgua att                                           23

<210> SEQ ID NO 813
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 813
acgcauugag guggcuaaac utt                                           23

<210> SEQ ID NO 814
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 814
ucccaaacua gggcuuaugu utt                                           23

<210> SEQ ID NO 815
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 815
gggaaaggaa ccuaaaaucg att                                           23

<210> SEQ ID NO 816
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 816
ccgcaacauc cugguuuucg att                                           23
```

<210> SEQ ID NO 817
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 817
gccuuucuau cgauuauuug att                                            23

<210> SEQ ID NO 818
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 818
uucuaucgau uauuugaaca att                                            23

<210> SEQ ID NO 819
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 819
aggacguuau ugaaaccaua att                                            23

<210> SEQ ID NO 820
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 820
gacguuauug aaaccauaaa att                                            23

<210> SEQ ID NO 821
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 821
acguuauuga aaccauaaaa utt                                            23

<210> SEQ ID NO 822
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 822
ggacugauag gagagucauu gcaaatt 27

<210> SEQ ID NO 823
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 823
ggacugauag gagagucauu gcaaatt 27

<210> SEQ ID NO 824
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 824
ggacugauag gagagucauu gcaaatt 27

<210> SEQ ID NO 825
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 825
ggacugauag gagagucauu gcaaa 25

<210> SEQ ID NO 826
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 826
ggacugauag gagagucauu gcaaatt 27

```
<210> SEQ ID NO 827
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 827
ggacugauag gagagucauu gcaaa                                               25

<210> SEQ ID NO 828
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 828
ggacugauag gagagucauu gcaaatt                                             27

<210> SEQ ID NO 829
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 829
ggacugauag gagagucauu gcaaatt                                             27

<210> SEQ ID NO 830
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 830
ggacugauag gagagucauu gcaaatt                                             27

<210> SEQ ID NO 831
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 831
ggacugauag gagagucauu gcaaa                                               25

<210> SEQ ID NO 832
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 832
ggacugauag gagagucauu gcaaa                                              25

<210> SEQ ID NO 833
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 833
ggacugauag gagagucauu gcaaatt                                            27

<210> SEQ ID NO 834
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 834
ggacugauag gagagucauu gcaaa                                              25

<210> SEQ ID NO 835
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 835
ugauaggaga gucauugcaa att                                                23

<210> SEQ ID NO 836
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 836
gagagucauu gcaaatt                                                       17

<210> SEQ ID NO 837
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

```
<400> SEQUENCE: 837
gagagucauu gcaaatt                                                    17

<210> SEQ ID NO 838
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 838
gagagucauu gcaaa                                                      15

<210> SEQ ID NO 839

<400> SEQUENCE: 839

000

<210> SEQ ID NO 840
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 840
accaguuaua cuggauaucu att                                             23

<210> SEQ ID NO 841
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 841
gggagaagua uggaaacaaa att                                             23

<210> SEQ ID NO 842
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 842
aaguauggaa acaaaauaaa utt                                             23

<210> SEQ ID NO 843
<211> LENGTH: 23
<212> TYPE: DNA
<213> ORGANISM: Artificial Sequence
<220> FEATURE:
```

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 843
uucaucaacu cagauacaau att                                              23

<210> SEQ ID NO 844
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 844
cggaggaaau ugcuauuuug att                                              23

<210> SEQ ID NO 845
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 845
aggaaauugc uauuuugaug att                                              23

<210> SEQ ID NO 846
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 846
caccggaaaa uauugugaaa utt                                              23

<210> SEQ ID NO 847
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 847
uugugaaaug gcguuuucaa att                                              23

<210> SEQ ID NO 848
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 848
caggauucuu ccacuauaga att                                           23

<210> SEQ ID NO 849
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 849
ggcagaucuu aacauggaua utt                                           23

<210> SEQ ID NO 850
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 850
ggcaaugagu gaagacuuug utt                                           23

<210> SEQ ID NO 851
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 851
aucugaaaau guggauaaua att                                           23

<210> SEQ ID NO 852
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 852
cugaaaaugu ggauaauaag att                                           23

<210> SEQ ID NO 853
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 853
guggauaaua agaauuaugg att                                              23

<210> SEQ ID NO 854
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 854
uggauaauaa gaauuaugga att                                              23

<210> SEQ ID NO 855
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 855
uggaaucucu ucaaacgaaa att                                              23

<210> SEQ ID NO 856
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 856
aucucuucaa acgaaaaucu att                                              23

<210> SEQ ID NO 857
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 857
cucuucaaac gaaaaucuaa att                                              23

<210> SEQ ID NO 858
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 858
uucaaacgaa aaucuaaaca att                                           23

<210> SEQ ID NO 859
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 859
aacgaaaauc uaaacaaacu att                                           23

<210> SEQ ID NO 860
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 860
aacaaacuac caacuugaa att                                            23

<210> SEQ ID NO 861
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 861
uaccaacuuu gaaauccaa utt                                            23

<210> SEQ ID NO 862
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 862
aacuuugaaa auccaaucua utt                                           23

<210> SEQ ID NO 863
```

-continued

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 863
ugcaacagaa gacacuuuua att                                         23

<210> SEQ ID NO 864
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 864
caccgcaaau cuuguuaaag att                                         23

<210> SEQ ID NO 865
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 865
cgcaaaucuu guuaaagaag att                                         23

<210> SEQ ID NO 866
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 866
cucugaagua uagcuauacc att                                         23

<210> SEQ ID NO 867
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 867
accagcuauu uagggaauaa utt                                         23
```

```
<210> SEQ ID NO 868
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 868
cagcuauuua gggaauaauu att                                                23

<210> SEQ ID NO 869
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 869
aacacacuuu ugcacauaua utt                                                23

<210> SEQ ID NO 870
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 870
cacacuuuug cacauauauu utt                                                23

<210> SEQ ID NO 871
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 871
uacaaacaga ugaaaaagu utt                                                 23

<210> SEQ ID NO 872
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 872
aaguuaacau ucaguacuuu att                                                23
```

```
<210> SEQ ID NO 873
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 873
uucaguacuu uaugaaaaaa att                                              23

<210> SEQ ID NO 874
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 874
caguacuuua ugaaaaaau att                                               23

<210> SEQ ID NO 875
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 875
ccgucucaua uuuuuacaaa utt                                              23

<210> SEQ ID NO 876
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 876
uacaaauaau uaucacaaug utt                                              23

<210> SEQ ID NO 877
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 877
aucacaaugu acuauaugua utt                                              23
```

<210> SEQ ID NO 878
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 878
cacaauguac uauauguaua utt                                              23

<210> SEQ ID NO 879
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 879
auguacuaua uguauaucuu utt                                              23

<210> SEQ ID NO 880
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 880
cugaaguugu cugaagguaa utt                                              23

<210> SEQ ID NO 881
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 881
cugaagguaa uacuauaaau att                                              23

<210> SEQ ID NO 882
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 882
uuguaaauuu uggaaagauu att                                            23

<210> SEQ ID NO 883
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 883
uggaaagauu auccuguuac utt                                            23

<210> SEQ ID NO 884
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 884
aagauuaucc uguuacugaa utt                                            23

<210> SEQ ID NO 885
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 885
auccuguuac ugaauuugcu att                                            23

<210> SEQ ID NO 886
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 886
uccuguuacu gaauuugcua att                                            23

<210> SEQ ID NO 887
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 887
uacugaauuu gcuaauaaag att                                               23

<210> SEQ ID NO 888
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 888
gugaucauua uaguaaauga utt                                               23

<210> SEQ ID NO 889
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 889
uaguaaauga uccaacaaga att                                               23

<210> SEQ ID NO 890
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 890
uccaacaaga aaaggaauug att                                               23

<210> SEQ ID NO 891
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 891
cacucauauu uccuauaaaa utt                                               23

<210> SEQ ID NO 892
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 892
cucauauuuc cuauaaaauu att                                              23

<210> SEQ ID NO 893
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 893
guccauuuuu acacauuagc att                                              23

<210> SEQ ID NO 894
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 894
uagcacuuaa uuaauguuca att                                              23

<210> SEQ ID NO 895
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 895
agcacuuaau uaauguucaa utt                                              23

<210> SEQ ID NO 896
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 896
cacuuaauua auguucaaua utt                                              23

<210> SEQ ID NO 897
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

<400> SEQUENCE: 897
uucaauauua caugucaauu utt                                          23

<210> SEQ ID NO 898
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 898
uugauuaaug gcuauguuga utt                                          23

<210> SEQ ID NO 899
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 899
ggccacuaug uguuguauag att                                          23

<210> SEQ ID NO 900
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 900
cacuaugugu uguauagaca utt                                          23

<210> SEQ ID NO 901
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 901
agguaggaaa agcaauucag utt                                          23

<210> SEQ ID NO 902
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

-continued

Synthetic oligonucleotide

<400> SEQUENCE: 902
gccaagacaa cauuuuauu utt                                      23

<210> SEQ ID NO 903
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 903
gacaacauuu uuauuguga utt                                      23

<210> SEQ ID NO 904
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 904
augaggaaau cccauaucau utt                                     23

<210> SEQ ID NO 905
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 905
ugcauugagu uugugguuaa utt                                     23

<210> SEQ ID NO 906
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 906
uugaguuugu gguuaauuaa att                                     23

<210> SEQ ID NO 907
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

-continued

<223> OTHER INFORMATION: Description of Combined DNA/RNA Molecule:
       Synthetic oligonucleotide

<400> SEQUENCE: 907
agcugaauuu cugaaaccaa att                                           23

<210> SEQ ID NO 908
<211> LENGTH: 23
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 908
accaaaucug ugucuucaua att                                           23

<210> SEQ ID NO 909
<211> LENGTH: 23
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 909
uggguuuuug uuucuaugaa att                                           23

<210> SEQ ID NO 910
<211> LENGTH: 23
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 910
uuguuucuau gaaauauca utt                                            23

<210> SEQ ID NO 911
<211> LENGTH: 23
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 911
uucuaugaaa auaucauuau att                                           23

<210> SEQ ID NO 912
<211> LENGTH: 23
<212> TYPE: DNA
<213> ORGANISM: Artificial Sequence
<220> FEATURE:
<223> OTHER INFORMATION: Description of Artificial Sequence: Synthetic
       oligonucleotide

```
<220> FEATURE:
<223> OTHER INFORMATION: Description of Combined DNA/RNA Molecule:
      Synthetic oligonucleotide

<400> SEQUENCE: 912
augaaaauau cauuauaauc att                                              23

<210> SEQ ID NO 913
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 913
aucauuauaa ucacuauuua utt                                              23

<210> SEQ ID NO 914
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 914
aaccauucuu auuaagcuuu utt                                              23

<210> SEQ ID NO 915
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 915
accauucuua uuaagcuuuu utt                                              23

<210> SEQ ID NO 916
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 916
guggcuaaau guguacauuu att                                              23

<210> SEQ ID NO 917
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<223> OTHER INFORMATION: Description of Combined DNA/RNA Molecule:
      Synthetic oligonucleotide

<400> SEQUENCE: 917
uggcuaaaug uguacauuua utt                                         23

<210> SEQ ID NO 918
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 918
ggcuaaaugu guacauuuau att                                         23

<210> SEQ ID NO 919
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 919
auguguacau uuauauuaga att                                         23

<210> SEQ ID NO 920
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 920
cagaucuuuu cuuuaauucu utt                                         23

<210> SEQ ID NO 921
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 921
aucuuuucuu uaauucuuau utt                                         23

<210> SEQ ID NO 922
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 922
uucuuuaauu cuuauugguu utt                                              23

<210> SEQ ID NO 923
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 923
cucuuaaaua guggguauag utt                                              23

<210> SEQ ID NO 924
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 924
gugcuaauau ugcacauuug utt                                              23

<210> SEQ ID NO 925
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 925
ugcuaauauu gcacauuugu utt                                              23

<210> SEQ ID NO 926
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 926
auggaugaau gaaugaaaca utt                                              23

<210> SEQ ID NO 927
<211> LENGTH: 23
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 927
augaaugaaa cauauacuac utt                                            23

<210> SEQ ID NO 928
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 928
augaaacaua uacuacugau utt                                            23

<210> SEQ ID NO 929
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 929
aacauauacu acugauuauu utt                                            23

<210> SEQ ID NO 930
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 930
cugacuguaa uuacuuugau utt                                            23

<210> SEQ ID NO 931
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 931
cuguaauuac uuugauuaga utt                                            23

<210> SEQ ID NO 932
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 932
uagauaaaca acuggaaaua att                                               23

<210> SEQ ID NO 933
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 933
cugcugaaaa aguucuaaua att                                               23

<210> SEQ ID NO 934
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 934
ugcugaaaaa guucuaauaa att                                               23

<210> SEQ ID NO 935
<211> LENGTH: 1283
<212> TYPE: DNA
<213> ORGANISM: Homo sapiens

<400> SEQUENCE: 935
gtgcgcgtgc gcagggataa gagagcggtc tggacagcgc gtggccggcg ccgctgtggg     60
gacagcatga gcggcggttg gatggcgcag gttggagcgt ggcgaacagg ggctctgggc    120
ctggcgctgc tgctgctgct cggcctcgga ctaggcctgg aggccgccgc gagcccgctt    180
tccaccccga cctctgccca ggccgcaggc cccagctcag gctcgtgccc acccaccaag    240
ttccagtgcc gcaccagtgg cttatgcgtg cccctcacct ggcgctgcga cagggacttg    300
gactgcagcg atggcagcga tgaggaggag tgcaggattg agccatgtac ccagaaaggg    360
caatgcccac cgcccctgg cctcccctgc cctgcaccg cgtcagtga ctgtctggg    420 ggaactgaca agaaactgcg caactgcagc cgcctggcct gctagcagg cgagctccgt    480 tgcacgctga gcgatgactg cattccactc acgtggcgct gcgacggcca cccagactgt    540
cccgactcca gcgacgagct cggctgtgga accaatgaga tcctcccgga agggatgcc    600 acaaccatgg ggccccctgt gaccctggag agtgtcacct ctctcaggaa tgccacaacc    660
atggggcccc ctgtgaccct ggagagtgtc cctctgtcg ggaatgccac atcctcctct    720
gccggagacc agtctggaag cccaactgcc tatgggtta ttgcagctgc tgcggtgctc    780
agtgcaagcc tggtcaccgc caccctcctc cttttgtcct ggctccgagc ccaggagcgc    840

```
ctccgcccac tgggggttact ggtggccatg aaggagtccc tgctgctgtc agaacagaag      900
acctcgctgc cctgaggaca agcacttgcc accaccgtca ctcagccctg ggcgtagccg      960
gacaggagga gagcagtgat gcggatgggt acccgggcac accagccctc agagacctga     1020
gctcttctgg ccacgtggaa cctcgaaccc gagctcctgc agaagtggcc ctggagattg     1080
agggtccctg gacactccct atggagatcc ggggagctag gatggggaac ctgccacagc     1140
cagaactgag gggctggccc caggcagctc ccagggggta gaacggccct gtgcttaaga     1200
cactcctgct gccccgtctg agggtggcga ttaaagttgc ttcacatcct caaaaaaaaa     1260
aaaaaaaaaa aaaaaaaaaa aaa                                             1283
```

<210> SEQ ID NO 936
<211> LENGTH: 282
<212> TYPE: PRT
<213> ORGANISM: Homo sapiens

<400> SEQUENCE: 936

```
Met Ser Gly Gly Trp Met Ala Gln Val Gly Ala Trp Arg Thr Gly Ala
1               5                   10                  15
Leu Gly Leu Ala Leu Leu Leu Leu Gly Leu Gly Leu Glu
            20                  25                  30
Ala Ala Ala Ser Pro Leu Ser Thr Pro Thr Ser Ala Gln Ala Ala Gly
            35                  40                  45
Pro Ser Ser Gly Ser Cys Pro Pro Thr Lys Phe Gln Cys Arg Thr Ser
        50                  55                  60
Gly Leu Cys Val Pro Leu Thr Trp Arg Cys Asp Arg Asp Leu Asp Cys
65                  70                  75                  80
Ser Asp Gly Ser Asp Glu Glu Cys Arg Ile Glu Pro Cys Thr Gln
                85                  90                  95
Lys Gly Gln Cys Pro Pro Pro Gly Leu Pro Cys Pro Cys Thr Gly
                100                 105                 110
Val Ser Asp Cys Ser Gly Gly Thr Asp Lys Lys Leu Arg Asn Cys Ser
            115                 120                 125
Arg Leu Ala Cys Leu Ala Gly Glu Leu Arg Cys Thr Leu Ser Asp Asp
        130                 135                 140
Cys Ile Pro Leu Thr Trp Arg Cys Asp Gly His Pro Asp Cys Pro Asp
145                 150                 155                 160
Ser Ser Asp Glu Leu Gly Cys Gly Thr Asn Glu Ile Leu Pro Glu Gly
                165                 170                 175
Asp Ala Thr Thr Met Gly Pro Pro Val Thr Leu Glu Ser Val Thr Ser
                180                 185                 190
Leu Arg Asn Ala Thr Thr Met Gly Pro Pro Val Thr Leu Glu Ser Val
            195                 200                 205
Pro Ser Val Gly Asn Ala Thr Ser Ser Ala Gly Asp Gln Ser Gly
        210                 215                 220
Ser Pro Thr Ala Tyr Gly Val Ile Ala Ala Ala Val Leu Ser Ala
225                 230                 235                 240
Ser Leu Val Thr Ala Thr Leu Leu Leu Ser Trp Leu Arg Ala Gln
                245                 250                 255
Glu Arg Leu Arg Pro Leu Gly Leu Leu Val Ala Met Lys Glu Ser Leu
            260                 265                 270
Leu Leu Ser Glu Gln Lys Thr Ser Leu Pro
        275                 280
```

<210> SEQ ID NO 937
<211> LENGTH: 1127
<212> TYPE: DNA
<213> ORGANISM: Homo sapiens

<400> SEQUENCE: 937

```
gcgtgcgcgt gcgcagggat aagagagcgg tctggacagc gcgtggccgg cgccgctgtg      60
gggacagcat gagcggcggt tggatggcgc aggttggagc gtggcgaaca ggggctctgg     120
gcctggcgct gctgctgctg ctcggcctcg gactaggcct ggaggccgcc gcgagcccgc     180
tttccacccc gacctctgcc caggccgcag ggattgagcc atgtacccag aaagggcaat     240
gcccaccgcc ccctggcctc ccctgcccct gcaccggcgt cagtgactgc tctgggggaa     300
ctgacaagaa actgcgcaac tgcagccgcc tggcctgcct agcaggcgag ctccgttgca     360
cgctgagcga tgactgcatt ccactcacgt ggcgctgcga cggccaccca gactgtcccg     420
actccagcga cgagctcggc tgtgaaccaa tgagatcctc cccggaaggg atgccacaa      480
ccatggggcc ccctgtgacc ctggagagtg tcacctctct caggaatgcc acaaccatgg     540
ggccccctgt gacctggag agtgtcccct ctgtcgggaa tgccacatcc tcctctgccg      600
gagaccagtc tggaagccca actgcctatg gggttattgc agctgctgcg gtgctcagtg     660
caagcctggt caccgccacc ctcctccttt tgtcctggct ccgagccag gagcgcctcc      720
gcccactggg gttactggtg gccatgaagg agtccctgct gctgtcagaa cagaagacct     780
cgctgccctg aggacaagca cttgccacca ccgtcactca gccctgggcg tagccggaca     840
ggaggagagc agtgatgcgg atgggtaccc gggcacacca gccctcagag acctgagctc     900
ttctggccac gtggaacctc gaacccgagc tcctgcagaa gtggccctgg agattgaggg     960
tccctggaca ctccctatgg agatccgggg agctaggatg gggaacctgc cacagccaga    1020
actgaggggc tggccccagg cagctcccag ggggtagaac ggccctgtgc ttaagacact    1080
cctgctgccc cgtctgaggg tggcaattaa agttgcttca catcctc                  1127
```

<210> SEQ ID NO 938
<211> LENGTH: 240
<212> TYPE: PRT
<213> ORGANISM: Homo sapiens

<400> SEQUENCE: 938

```
Met Ser Gly Gly Trp Met Ala Gln Val Gly Ala Trp Arg Thr Gly Ala
1               5                   10                  15

Leu Gly Leu Ala Leu Leu Leu Leu Gly Leu Gly Leu Glu
            20                  25                  30

Ala Ala Ala Ser Pro Leu Ser Thr Pro Thr Ser Ala Gln Ala Ala Gly
            35                  40                  45

Ile Glu Pro Cys Thr Gln Lys Gly Gln Cys Pro Pro Pro Gly Leu
    50                  55                  60

Pro Cys Pro Cys Thr Gly Val Ser Asp Cys Ser Gly Thr Asp Lys
65                  70                  75                  80

Lys Leu Arg Asn Cys Ser Arg Leu Ala Cys Leu Ala Gly Glu Leu Arg
                85                  90                  95

Cys Thr Leu Ser Asp Asp Cys Ile Pro Leu Thr Trp Arg Cys Asp Gly
            100                 105                 110

His Pro Asp Cys Pro Asp Ser Ser Asp Glu Leu Gly Cys Gly Thr Asn
        115                 120                 125

Glu Ile Leu Pro Glu Gly Asp Ala Thr Thr Met Gly Pro Pro Val Thr
```

|   |   | 130 |   |   |   | 135 |   |   |   | 140 |   |
|---|---|---|---|---|---|---|---|---|---|---|---|

Leu Glu Ser Val Thr Ser Leu Arg Asn Ala Thr Thr Met Gly Pro Pro
145                 150                 155                 160

Val Thr Leu Glu Ser Val Pro Ser Val Gly Asn Ala Thr Ser Ser Ser
                165                 170                 175

Ala Gly Asp Gln Ser Gly Ser Pro Thr Ala Tyr Gly Val Ile Ala Ala
            180                 185                 190

Ala Ala Val Leu Ser Ala Ser Leu Val Thr Ala Thr Leu Leu Leu Leu
        195                 200                 205

Ser Trp Leu Arg Ala Gln Glu Arg Leu Arg Pro Leu Gly Leu Leu Val
    210                 215                 220

Ala Met Lys Glu Ser Leu Leu Leu Ser Glu Gln Lys Thr Ser Leu Pro
225                 230                 235                 240

<210> SEQ ID NO 939
<211> LENGTH: 15735
<212> TYPE: DNA
<213> ORGANISM: Homo sapiens

<400> SEQUENCE: 939

| | | | | | |
|---|---|---|---|---|---|
| ggtctaaagg | gctttatgca | ctgtctggag | ggtggggact | ggcgcgggta | gaaaacggga | 60 |
| tgcctcgggc | gtggggcag | gcttttggcc | actaggagct | ggcggaggtg | cagacctaaa | 120 |
| ggagcgttcg | ctagcagagg | cgctgccggt | gcggtgtgct | acgcgcgccc | acctcccggg | 180 |
| gaaggaacgg | cgaggccggg | gaccgtcgcg | gagatggatc | gcgggccggc | agcagtggcg | 240 |
| tgcacgctgc | tcctggctct | cgtcgcctgc | ctagcgccgg | ccagtggcca | agaatgtgac | 300 |
| agtgcgcatt | ttcgctgtgg | aagtgggcat | tgcatccctg | cagactggag | gtgtgatggg | 360 |
| accaaagact | gttcagatga | cgcggatgaa | attggctgcg | ctgttgtgac | ctgccagcag | 420 |
| ggctatttca | gtgccagag | tgagggacaa | tgcatcccca | actcctgggt | gtgtgaccaa | 480 |
| gatcaagact | gtgatgatgg | ctcagatgaa | cgtcaagatt | gctcacaaag | tacatgctca | 540 |
| agtcatcaga | taacatgctc | caatggtcag | tgtatcccaa | gtgaatacag | gtgcgaccac | 600 |
| gtcagagact | gccccgatgg | agctgatgag | aatgactgcc | agtacccaac | atgtgagcag | 660 |
| cttacttgtg | acaatggggc | ctgctataac | accagtcaga | agtgtgattg | gaaagttgat | 720 |
| tgcagggact | cctcagatga | aatcaactgc | actgagatat | gcttgcacaa | tgagttttca | 780 |
| tgtggcaatg | gagagtgtat | ccctcgtgct | tatgtctgtg | accatgacaa | tgattgccaa | 840 |
| gacggcagtg | acgaacatgc | ttgcaactat | ccgacctgcg | gtggttacca | gttcacttgc | 900 |
| cccagtggcc | gatgcatttta | tcaaaactgg | gtttgtgatg | gagaagatga | ctgtaaagat | 960 |
| aatggagatg | aagatggatg | tgaaagcggt | cctcatgatg | ttcataaatg | ttccccaaga | 1020 |
| gaatggtctt | gcccagagtc | gggacgatgc | atctccattt | ataaagtttg | tgatgggatt | 1080 |
| ttagattgcc | caggaagaga | agatgaaaac | aacactagta | ccggaaaata | ctgtagtatg | 1140 |
| actctgtgct | ctgccttgaa | ctgccagtac | cagtgccatg | agacgccgta | tggaggagcg | 1200 |
| tgttttttgtc | ccccaggtta | tatcatcaac | cacaatgaca | gccgtacctg | tgttgagttt | 1260 |
| gatgattgcc | agatatgggg | aatttgtgac | cagaagtgtg | aaagccgacc | tggccgtcac | 1320 |
| ctgtgccact | gtgaagaagg | gtatatcttg | gagcgtggac | agtattgcaa | agctaatgat | 1380 |
| tccctttggcg | aggcctccat | tatcttctcc | aatggtcggg | atttgttaat | tggtgatatt | 1440 |
| catgaagga | gcttccggat | cctagtgag | tctcagaatc | gtggagtggc | cgtgggtgtg | 1500 |
| gctttccact | atcacctgca | aagagttttt | tggacagaca | ccgtgcaaaa | taaggttttt | 1560 |

-continued

```
tcagttgaca ttaatggttt aaatatccaa gaggttctca atgtttctgt tgaaacccca    1620
gagaacctgg ctgtggactg ggttaataat aaaatctatc tagtggaaac caaggtcaac    1680
cgcatagata tggtaaattt ggatggaagc tatcgggtta cccttataac tgaaaacttg    1740
gggcatccta gaggaattgc cgtggaccca actgttggtt atttattttt ctcagattgg    1800
gagagccttt ctggggaacc taagctggaa agggcattca tggatggcag caaccgtaaa    1860
gacttggtga aaacaaagct gggatggcct gctggggtaa ctctggatat gatatcgaag    1920
cgtgtttact gggttgactc tcggtttgat tacattgaaa ctgtaactta tgatggaatt    1980
caaaggaaga ctgtagttca tggaggctcc ctcattcctc atcccttttgg agtaagctta   2040 tttgaaggtc aggtgttctt tacagattgg acaaagatgg ccgtgctgaa ggcaaacaag    2100
ttcacagaga ccaacccaca agtgtactac caggcttccc tgaggcccta tggagtgact    2160
gtttaccatt ccctcagaca gccctatgct accaatccgt gtaaagataa caatgggggc    2220
tgtgagcagg tctgtgtcct cagccacaga acagataatg atggtttggg tttccgttgc    2280
aagtgcacat tcggcttcca actggataca gatgagcgcc actgcattgc tgttcagaat    2340
ttcctcattt tttcatccca agttgctatt cgtgggatcc cgttcacctt gtctacccag    2400
gaagatgtca tggttccagt ttcggggaat ccttcttttct ttgtcgggat tgattttgac   2460
gcccaggaca gcactatctt tttttcagat atgtcaaaac acatgatttt taagcaaaag    2520
attgatggca caggaagaga aattctcgca gctaacaggg tggaaaatgt tgaaagtttg    2580
gcttttgatt ggatttcaaa gaatctctat tggacagact ctcattacaa gagtatcagt    2640
gtcatgaggc tagctgataa aacgagacgc acagtagttc agtatttaaa taacccacgg    2700
tcggtggtag ttcatccttt tgccgggtat ctattcttca ctgattggtt ccgtcctgct    2760
aaaattatga gagcatggag tgacggatct cacctcttgc ctgtaataaa cactactctt    2820
ggatggccca atggcttggc catcgattgg gctgcttcac gattgtactg ggtagatgcc    2880
tattttgata aaattgagca cagcaccttt gatggtttag acagaagaag actgggccat    2940
atagagcaga tgacacatcc gtttggactt gccatctttg gagagcattt atttttttact    3000 gactggagac tgggtgccat tattcgagtc aggaaagcag atggtggaga atgacagtt     3060 atccgaagtg gcattgctta catactgcat ttgaaatcgt atgatgtcaa catccagact    3120
ggttctaacg cctgtaatca acccacgcat cctaacggtg actgcagcca cttctgcttc    3180
ccggtgccaa atttccagcg agtgtgtggg tgcccttatg gaatgaggct ggcttccaat    3240
cacttgacat gcgaggggga cccaaccaat gaaccaccca cagagcagtg tggcttattt    3300
tccttcccct gtaaaaatgg cagatgtgtg cccaattact atctctgtga tggagtcgat    3360
gattgtcatg ataacagtga tgagcaacta tgtggcacac ttaataatac ctgttcatct    3420
tcggcgttca cctgtggcca tggggagtgc attcctgcac actggcgctg tgacaaacgc    3480
aacgactgtg tggatggcag tgatgagcac aactgcccca cccacgcacc tgcttcctgc    3540
cttgacaccc aatacacctg tgataatcac cagtgtatct caaagaactg ggtctgtgac    3600
acagacaatg attgtgggga tggatctgat gaaaagaact gcaattcgac agagacatgc    3660
caacctagtc agtttaattg ccccaatcat cgatgtattg acctatcgtt tgtctgtgat    3720
ggtgacaagg attgtgttga tggatctgat gaggttggtt gtgtattaaa ctgtactgct    3780
tctcaattca gtgtgccag tggggataaa tgtattggcg tcacaaatcg ttgtgatggt     3840
gtttttgatt gcagtgacaa ctcggatgaa gcaggctgtc aaccaggcc tcctggtatg     3900
```

```
tgccactcag atgaatttca gtgccaagaa gatggtatct gcatcccgaa cttctgggaa    3960
tgtgatgggc atccagactg cctctatgga tctgatgagc acaatgcctg tgtccccaag    4020
acttgccctt catcatattt ccactgtgac aacggaaact gcatccacag ggcatggctc    4080
tgtgatcggg acaatgactg cggggatatg agtgatgaga aggactgccc tactcagccc    4140
tttcgctgtc ctagttggca atggcagtgt cttggccata acatctgtgt gaatctgagt    4200
gtagtgtgtg atggcatctt tgactgcccc aatgggacag atgagtcccc actttgcaat    4260
gggaacagct gctcagattt caatggtggt tgtactcacg agtgtgttca agagcccttt    4320
ggggctaaat gcctatgtcc attgggattc ttacttgcca atgattctaa gacctgtgaa    4380
gacatagatg aatgtgatat tctaggctct tgtagccagc actgttacaa tatgagaggt    4440
tctttccggt gctcgtgtga tacaggctac atgttagaaa gtgatgggag acttgcaaa     4500 gttacagcat ctgagagtct gctgttactt gtggcaagtc agaacaaaat tattgccgac    4560
agtgtcacct cccaggtcca caatatctat tcattggtcg agaatggttc ttacattgta    4620
gctgttgatt ttgattcaat tagtggtcgt atcttttggt ctgatgcaac tcagggtaaa    4680
acctggagtg cgtttcaaaa tggaacggac agaagagtgg tatttgacag tagcatcatc    4740
ttgactgaaa ctattgcaat agattgggta ggtcgtaatc tttactggac agactatgct    4800
ctggaaacaa ttgaagtctc caaaattgat gggagccaca ggactgtgct gattagtaaa    4860
aacctaacaa atccaagagg actagcatta gatcccagaa tgaatgagca tctactgttc    4920
tggtctgact ggggccacca ccctcgcatc gagcgagcca gcatggacgg cagcatgcgc    4980
actgtcattg tccaggacaa gatcttctgg ccctgcggct taactattga ctaccccaac    5040
agactgctct acttcatgga ctcctatctt gattacatgg acttttgtga ttataatgga    5100
caccatcgga gacaggtgat agccagtgat ttgattatac ggcaccccta tgccctaact    5160
ctctttgaag actctgtgta ctggactgac cgtgctactc gtcgggttat gcgagccaac    5220
aagtggcatg gagggaacca gtcagttgta atgtataata ttcaatggcc ccttgggatt    5280
gttgcggttc atccttcgaa acaaccaaat tccgtgaatc catgtgcctt ttcccgctgc    5340
agccatctct gcctgctttc ctcacagggg cctcattttt actcctgtgt ttgtcccttca   5400 ggatggagtc tgtctcctga tctcctgaat tgcttgagag atgatcaacc tttcttaata    5460
actgtaaggc aacatataat ttttggaatc tcccttaatc ctgaggtgaa gagcaatgat    5520
gctatggtcc ccatagcagg gatacagaat ggtttagatg ttgaatttga tgatgctgag    5580
caatacatct attgggttga aaatccaggt gaaattcaca gagtgaagac agatggcacc    5640
aacaggacag tatttgcttc tatatctatg gtggggcctt ctatgaacct ggccttagat    5700
tggatttcaa gaacccttta ttctaccaat cctagaactc agtcaatcga ggttttgaca    5760
ctccacggag atatcagata cagaaaaaca ttgattgcca atgatgggac agctcttgga    5820
gttggctttc caattggcat aactgttgat cctgctcgtg ggaagctgta ctggtcagac    5880
caaggaactg acagtggggt tcctgccaag atcgccagtg ctaacatgga tggcacatct    5940
gtgaaaactc tctttactgg gaacctcgaa cacctggagt gtgtcactct tgacatcgaa    6000
gagcagaaac tctactgggc agtcactgga agaggagtga ttgaaagagg aaacgtggat    6060
ggaacagatc gaatgatcct ggtacaccag cttccccacc cctggggaat tgcagtccat    6120 gattcttcc tttattatac tgatgaacag tatgaggtca ttgaaagagt tgataaggcc     6180
actggggcca acaaaatagt cttgagagat aatgttccaa atctgagggg tcttcaagtt    6240
tatcacagac gcaatgccgc cgaatcctca aatggctgta gcaacaacat gaatgcctgt    6300
```

```
cagcagattt gcctgcctgt accaggagga ttgttttcct gcgcctgtgc cactggattt    6360
aaactcaatc ctgataatcg gtcctgctct ccatataact ctttcattgt tgtttcaatg    6420
ctgtctgcaa tcagaggctt tagcttggaa ttgtcagatc attcagaaac catggtgccg    6480
gtggcaggcc aaggacgaaa cgcactgcat gtggatgtgg atgtgtcctc tggctttatt    6540
tattggtgtg attttagcag ctcagtggca tctgataatg cgatccgtag aattaaacca    6600
gatggatctt ctctgatgaa cattgtgaca catggaatag gagaaaatgg agtccggggt    6660
attgcagtgg attgggtagc aggaaatctt tatttcacca atgcctttgt ttctgaaaca    6720
ctgatagaag ttctgcggat caatactact taccgccgtg ttcttcttaa agtcacagtg    6780
gacatgccta ggcatattgt tgtagatccc aagaacagat acctcttctg ggctgactat    6840
gggcagagac caaagattga gcgttctttc cttgactgta ccaatcgaac agtgcttgtg    6900
tcagagggca ttgtcacacc acggggcttg gcagtggacc gaagtgatgg ctacgtttat    6960
tgggttgatg attctttaga tataattgca aggattcgta tcaatggaga gaactctgaa    7020
gtgattcgtt atggcagtcg ttacccaact ccttatggca tcactgtttt tgaaaattct    7080
atcatatggg tagataggaa tttgaaaaag atcttccaag ccagcaagga accagagaac    7140
acagagccac ccacagtgat aagagacaat atcaactggc taagagatgt gaccatcttt    7200
gacaagcaag tccagccccg gtcaccagca gaggtcaaca caaacccttg cttgaaaaac    7260
aatggtgggt gctctcatct ctgctttgct ctgcctggat tgcacacccc aaaatgtgac    7320
tgtgcctttg ggaccctgca aagtgatggc aagaattgtg ccatttcaac agaaaatttc    7380
ctcatctttg ccttgtctaa ttccttgaga gcttacact tggaccctga aaaccatagc     7440
ccacctttcc aaacaataaa tgtggaaaga actgtcatgt ctctagacta tgacagtgta    7500
agtgatagaa tctacttcac acaaaattta gcctctggag ttggacagat ttcctatgcc    7560
accctgtctt cagggatcca tactccaact gtcattgctt caggtatagg gactgctgat    7620
ggcattgcct ttgactggat tactagaaga atttattaca gtgactacct caaccagatg    7680
attaattcca tggctgaaga tgggtctaac cgcactgtga tagcccgcgt tccaaaacca    7740
agagcaattg tgttagatcc ctgccaaggg tacctgtact gggctgactg ggatacacat    7800
gccaaaatcg agagagccac attgggagga aacttccgcg tacccattgt gaacagcagt    7860
ctggtcatgc ccagtgggct gactctgac tatgaagagg accttctcta ctgggtggat    7920
gctagtctgc agaggattga acgcagcact ctgacgggcg tggatcgtga agtcattgtc    7980
aatgcagccg ttcatgcttt tggcttgact ctctatggcc agtatattta ctggactgac    8040
ttgtacacac aaagaattta ccgagctaac aaatatgacg ggtcaggtca gattgcaatg    8100
accacaaatt tgctctccca gcccagggga atcaacactg ttgtgaagaa ccagaaacaa    8160
cagtgtaaca atccttgtga acagtttaat ggggctgca gccatatctg tgcaccaggt    8220
ccaaatggtg ccgagtgcca gtgtccacat gagggcaact ggtatttggc caacaacagg    8280
aagcactgca ttgtggacaa tggtgaacga tgtggtgcat cttccttcac ctgctccaat    8340
gggcgctgca tctcggaaga gtggaagtgt gataatgaca cgactgtgg ggatggcagt     8400 gatgagatgg aaagtgtctg tgcacttcac acctgctcac cgacagcctt cacctgtgcc    8460
aatgggcgat gtgtccaata ctcttaccgc tgtgattact acaatgactg tggtgatggc    8520
agtgatgagg cagggtgcct gttcagggac tgcaatgcca ccacggagtt tatgtgcaat    8580
aacagaaggt gcatacctcg tgagtttatc tgcaatggtg tagacaactg ccatgataat    8640
```

```
aacacttcag atgagaaaaa ttgccctgat cgcacttgcc agtctggata cacaaaatgt   8700
cataattcaa atatttgtat tcctcgcgtt tatttgtgtg acggagacaa tgactgtgga   8760
gataacagtg atgaaaaccc tacttattgc accactcaca cgtgcagcag cagtgagttc   8820
caatgcgcat ctgggcgctg tattcctcaa cattggtatt gtgatcaaga aacagattgt   8880
tttgatgcct ctgatgaacc tgcctcttgt ggtcactctg agcgaacatg cctagctgat   8940
gagttcaagt gtgatggtgg gaggtgcatc ccaagcgaat ggatctgtga cggtgataat   9000
gactgtgggg atatgagtga cgaggataaa aggcaccagt gtcagaatca aaactgctcg   9060
gattccgagt ttctctgtgt aaatgacaga cctccggaca ggaggtgcat tccccagtct   9120
tgggtctgtg atggcgatgt ggattgtact gacggctacg atgagaatca gaattgcacc   9180
aggagaactt gctctgaaaa tgaattcacc tgtggttacg gactgtgtat cccaaagata   9240
ttcaggtgtg accggcacaa tgactgtggt gactatagcg acgagagggg ctgcttatac   9300
cagacttgcc aacagaatca gtttacctgt cagaacgggc gctgcattag taaaaccttc   9360
gtctgtgatg aggataatga ctgtggagac ggatctgatg agctgatgca cctgtgccac   9420
accccagaac ccacgtgtcc acctcacgag ttcaagtgtg acaatgggcg ctgcatcgag   9480
atgatgaaac tctgcaacca cctagatgac tgtttggaca cagcgatga gaaaggctgt   9540 ggcattaatg aatgccatga cccttcaatc agtggctgcg atcacaactg cacagacacc   9600
ttaaccagtt tctattgttc ctgtcgtcct ggttacaagc tcatgtctga caagcggact   9660
tgtgttgata ttgatgaatg cacagagatg cctttttgtct gtagccagaa gtgtgagaat   9720
gtaataggct cctacatctg taagtgtgcc ccaggctacc tccgagaacc agatggaaag   9780
acctgccggc aaaacagtaa catcgaaccc tatctcattt ttagcaaccg ttactatttg   9840
agaaatttaa ctatagatgg ctattttttac tccctcatct tggaaggact ggacaatgtt   9900
gtggcattag attttgaccg agtagagaag agattgtatt ggattgatac acagaggcaa   9960
gtcattgaga gaatgtttct gaataagaca aacaaggaga caatcataaa ccacagacta  10020
ccagctgcag aaagtctggc tgtagactgg gtttccagaa agctctactg gttggatgcc  10080
cgcctggatg gcctctttgt ctctgacctc aatggtggac accgccgcat gctggcccag  10140
cactgtgtgg atgccaacaa caccttctgc tttgataatc ccagaggact tgcccttcac  10200
cctcaatatg ggtacctcta ctgggcagac tggggtcacc gcgcatacat gggagagta  10260 ggcatggatg gaaccaacaa gtctgtgata atctccacca agttagagtg gcctaatggc  10320
atcaccattg attacaccaa tgatctactc tactgggcag atgcccacct gggttacata  10380
gagtactctg atttggaggg ccaccatcga cacacggtgt atgatggggc actgcctcac  10440
cctttcgcta ttaccatttt tgaagacact atttattgga cagattggaa tacaaggaca  10500
gtggaaaagg gaaacaaata tgatggatca aatagacaga cactggtgaa cacaacacac  10560
agaccatttg acatccatgt gtaccatcca tataggcagc ccattgtgag caatcctgt  10620 ggtaccaaca tggtggctg ttctcatctc tgcctcatca agccaggagg aaaagggttc  10680
acttgcgagt gtccagatga cttccgcacc cttcagctga gtggcagcac ctactgcatg  10740
cccatgtgct ccagcaccca gttcctgtgc gctaacaatg aaaagtgcat tcctatctgg  10800
tggaaatgtg atggacagaa agactgctca gatggctctg atgaactggc cctttgcccg  10860
cagcgcttct gccgactggg acagttccag tgcagtgacg gcaactgcac cagcccgcag  10920
actttatgca atgctcacca aaattgccct gatgggtctg atgaagaccg tcttctttgt  10980
gagaatcacc actgtgactc caatgaatgg cagtgcgcca acaaacgttg catcccagaa  11040
```

```
tcctggcagt gtgacacatt taacgactgt gaggataact cagatgaaga cagttcccac    11100
tgtgccagca ggacctgccg gccgggccag tttcggtgtg ctaatggccg ctgcatcccg    11160
caggcctgga agtgtgatgt ggataatgat tgtggagacc actcggatga gcccattgaa    11220
gaatgcatga gctctgccca tctctgtgac aacttcacag aattcagctg caaaacaaat    11280
taccgctgca tcccaaagtg ggccgtgtgc aatggtgtag atgactgcag ggacaacagt    11340
gatgagcaag gctgtgagga gaggacatgc catcctgtgg gggatttccg ctgtaaaaat    11400
caccactgca tccctcttcg ttggcagtgt gatgggcaaa atgactgtgg agataactca    11460
gatgaggaaa actgtgctcc ccgggagtgc acagagagcg agtttcgatg tgtcaatcag    11520
cagtgcattc cctcgcgatg gatctgtgac cattacaacg actgtgggga caactcagat    11580
gaacgggact gtgagatgag gacctgccat cctgaatatt ttcagtgtac aagtggacat    11640
tgtgtacaca gtgaactgaa atgcgatgga tccgctgact gtttggatgc gtctgatgaa    11700
gctgattgtc ccacacgctt tcctgatggt gcatactgcc aggctactat gttcgaatgc    11760
aaaaaccatg tttgtatccc gccatattgg aaatgtgatg gcgatgatga ctgtggcgat    11820
ggttcagatg aagaacttca cctgtgcttg gatgttccct gtaattcacc aaaccgtttc    11880
cggtgtgaca acaatcgctg catttatagt catgaggtgt gcaatggtgt ggatgactgt    11940
ggagatggaa ctgatgagac agaggagcac tgtagaaaac cgaccccaa accttgtaca     12000
gaatatgaat ataagtgtgg caatgggcat tgcattccac atgacaatgt gtgtgatgat    12060
gccgatgact gtggtgactg gtccgatgaa ctgggttgca ataaaggaaa agaaagaaca    12120
tgtgctgaaa atatatgcga gcaaaattgt acccaattaa atgaaggagg atttatctgc    12180
tcctgtacag ctgggttcga aaccaatgtt tttgacagaa cctcctgtct agatatcaat    12240
gaatgtgaac aatttgggac ttgtccccag cactgcagaa ataccaaagg aagttatgag    12300
tgtgtctgtg ctgatggctt cacgtctatg agtgaccgcc ctggaaaacg atgtgcagct    12360
gagggtagct ctcctttgtt gctactgcct gacaatgtcc gaattcgaaa atataatctc    12420
tcatctgaga ggttctcaga gtatcttcaa gatgaggaat atatccaagc tgttgattat    12480
gattgggatc ccaaggacat aggcctcagt gttgtgtatt acactgtgcg aggggagggc    12540
tctaggtttg gtgctatcaa acgtgcctac atccccaact ttgaatccgg ccgcaataat    12600
cttgtgcagg aagttgacct gaaactgaaa tacgtaatgc agccagatgg aatagcagtg    12660
gactgggttg gaaggcatat ttactggtca gatgtcaaga ataaacgcat tgaggtggct    12720
aaacttgatg gaaggtacag aaagtggctg atttccactg acctggacca accagctgct    12780
attgctgtga atcccaaact agggcttatg ttctggactg actgggaaa ggaacctaaa      12840
atcgagtctg cctggatgaa tggagaggac cgcaacatcc tggttttcga ggaccttggt    12900
tggccaactg gcctttctat cgattatttg aacaatgacc gaatctactg gagtgacttc    12960
aaggaggacg ttattgaaac cataaaatat gatgggactg ataggagagt cattgcaaag    13020
gaagcaatga acccttacag cctggacatc tttgaagacc agttatactg gatatctaag    13080
gaaaagggag aagtatggaa acaaaataaa tttgggcaag aaagaaaga gaaaacgctg    13140
gtagtgaacc cttggctcac tcaagttcga atctttcatc aactcagata caataagtca    13200
gtgcccaacc tttgcaaaca gatctgcagc cacctctgcc ttctgagacc tggaggatac    13260
agctgtgcct gtcccccaagg ctccagcttt atagagggga gcaccactga gtgtgatgca    13320
gccatcgaac tgcctatcaa cctgccccc ccatgcaggt gcatgcacgg aggaaattgc    13380
```

```
tattttgatg agactgacct ccccaaatgc aagtgtccta gcggctacac cggaaaatat   13440
tgtgaaatgg cgttttcaaa aggcatctct ccaggaacaa ccgcagtagc tgtgctgttg   13500
acaatcctct tgatcgtcgt aattggagct ctggcaattg caggattctt ccactataga   13560
aggaccggct ccctttgcc tgctctgccc aagctgccaa gcttaagcag tctcgtcaag   13620
ccctctgaaa atgggaatgg ggtgaccttc agatcagggg cagatcttaa catggatatt   13680
ggagtgtctg gttttggacc tgagactgct attgacaggt caatggcaat gagtgaagac   13740
tttgtcatgg aaatggggaa gcagcccata atatttgaaa acccaatgta ctcagccaga   13800
gacagtgctg tcaaagtggt tcagccaatc caggtgactg tatctgaaaa tgtggataat   13860
aagaattatg gaagtcccat aaaccttct gagatagttc cagagacaaa cccaacttca   13920
ccagctgctg atggaactca ggtgacaaaa tggaatctct tcaaacgaaa atctaaacaa   13980
actaccaact ttgaaaatcc aatctatgca cagatggaga acgagcaaaa ggaaagtgtt   14040
gctgcgacac cacctccatc accttcgctc cctgctaagc ctaagcctcc ttcgagaaga   14100
gacccaactc caacctattc tgcaacagaa gacacttta aagacaccgc aaatcttgtt   14160
aaagaagact ctgaagtata gctataccag ctatttaggg aataattaga aacacacttt   14220
tgcacatata ttttttacaa acagatgaaa aaagttaaca ttcagtactt tatgaaaaaa   14280
atatattttt ccctgtttgc ctatagttgg aggtatcctg tgtgtctttt tttacttatg   14340
ccgtctcata tttttacaaa taattatcac aatgtactat atgtatatct ttgcactgaa   14400
gttgtctgaa ggtaatacta taaatatatt gtatatttgt aaattttgga aagattatcc   14460
tgttactgaa tttgctaata aagatgtctg ctgatttggt tggtgatcat tatagtaaat   14520
gatccaacaa gaaaaggaat tgactgggga cctttagccg tgtctaaaga agaggcacca   14580
ctcatatttc ctataaaatt atctaggaaa ggaatccagg ccccgctctt gggtccattt   14640
ttacacatta gcacttaatt aatgttcaat attacatgtc aatttgatta atggctatgt   14700
tgataggggc cactatgtgt tgtatagaca tctggacttg actgtagact cctcagataa   14760
tacagaaggt aggaaaagca attcagtttg gcccttctgt gtgttggcat tgtctaacca   14820
gaactctctg tttcatgtgt gttctctcac tagctgccaa gacaacattt ttatttgtga   14880
tgtctatgag gaaatcccat atcattaagt gccagtgtcc tgcattgagt ttgtggttaa   14940
ttaaatgagc tcttctgctg atggaccctg gagcaattc tccctcacc tgacattcaa   15000
ggtggtcacc tgccctagta gttggagctc agtagctgaa tttctgaaac caaatctgtg   15060
tcttcataaa ataaggtgca aaaaaaaaa ataccagtta agtaaagcct caactggtt   15120
tttgttctta tgaaaatatc attataatca ctattattt cctaagttga acctgaatag   15180
aaagggaaac cattcttatt aagctttta ttaggcctg tggctaaatg tgtacattta   15240
tattagaatg tactgtacag tccagatctt ttctttaatt cttattggtt ttttttttt   15300
ttttttttt agagatggag tcttgctata ttgccaaggc tgatcttgaa gtcctgggct   15360
caagtgatcc tcccacctca gcctcctgag tggttgggt tacgggcgtg agccactgtg   15420
cctggcttcc agctctcctc ttaaatagtg ggtatagtct gcacaacagg aaccatggca   15480
ggaatataca ctttcccata gcaaatagca tacctgactc tctgtgctaa tattgcacat   15540
ttgttaaaca atgaatgaat ggatggatgg atggatggat gaatgaatga acatatact   15600
actgattatt ttattccaga gttctcaaaa tatttgttgc tgatattttg agtgctgact   15660
gtaattactt tgattagata aacaactgga aataatgctg ctgaaaaagt tctaataaat   15720
gtgtattta tcaga                                                    15735
```

<210> SEQ ID NO 940
<211> LENGTH: 4655
<212> TYPE: PRT
<213> ORGANISM: Homo sapiens

<400> SEQUENCE: 940

```
Met Asp Arg Gly Pro Ala Ala Val Ala Cys Thr Leu Leu Ala Leu
1               5                   10                  15

Val Ala Cys Leu Ala Pro Ala Ser Gly Gln Glu Cys Asp Ser Ala His
            20                  25                  30

Phe Arg Cys Gly Ser Gly His Cys Ile Pro Ala Asp Trp Arg Cys Asp
        35                  40                  45

Gly Thr Lys Asp Cys Ser Asp Ala Asp Glu Ile Gly Cys Ala Val
    50                  55                  60

Val Thr Cys Gln Gln Gly Tyr Phe Lys Cys Gln Ser Glu Gly Gln Cys
65                  70                  75                  80

Ile Pro Asn Ser Trp Val Cys Asp Gln Asp Gln Cys Asp Asp Gly
                85                  90                  95

Ser Asp Glu Arg Gln Asp Cys Ser Gln Ser Thr Cys Ser Ser His Gln
            100                 105                 110

Ile Thr Cys Ser Asn Gly Gln Cys Ile Pro Ser Glu Tyr Arg Cys Asp
        115                 120                 125

His Val Arg Asp Cys Pro Asp Gly Ala Asp Glu Asn Asp Cys Gln Tyr
    130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
            180                 185                 190

Gly Glu Cys Ile Pro Arg Ala Tyr Val Cys Asp His Asp Asn Asp Cys
        195                 200                 205

Gln Asp Gly Ser Asp Glu His Ala Cys Asn Tyr Pro Thr Cys Gly Gly
    210                 215                 220

Tyr Gln Phe Thr Cys Pro Ser Gly Arg Cys Ile Tyr Gln Asn Trp Val
225                 230                 235                 240

Cys Asp Gly Glu Asp Asp Cys Lys Asp Asn Gly Asp Glu Asp Gly Cys
                245                 250                 255

Glu Ser Gly Pro His Asp Val His Lys Cys Ser Pro Arg Glu Trp Ser
            260                 265                 270

Cys Pro Glu Ser Gly Arg Cys Ile Ser Ile Tyr Lys Val Cys Asp Gly
        275                 280                 285

Ile Leu Asp Cys Pro Gly Arg Glu Asp Glu Asn Asn Thr Ser Thr Gly
    290                 295                 300

Lys Tyr Cys Ser Met Thr Leu Cys Ser Ala Leu Asn Cys Gln Tyr Gln
305                 310                 315                 320

Cys His Glu Thr Pro Tyr Gly Gly Ala Cys Phe Cys Pro Pro Gly Tyr
                325                 330                 335

Ile Ile Asn His Asn Asp Ser Arg Thr Cys Val Glu Phe Asp Asp Cys
            340                 345                 350

Gln Ile Trp Gly Ile Cys Asp Gln Lys Cys Glu Ser Arg Pro Gly Arg
        355                 360                 365

His Leu Cys His Cys Glu Glu Gly Tyr Ile Leu Glu Arg Gly Gln Tyr
```

```
        370                 375                 380
Cys Lys Ala Asn Asp Ser Phe Gly Glu Ala Ser Ile Ile Phe Ser Asn
385                 390                 395                 400

Gly Arg Asp Leu Leu Ile Gly Asp Ile His Gly Arg Ser Phe Arg Ile
                405                 410                 415

Leu Val Glu Ser Gln Asn Arg Gly Val Ala Val Gly Val Ala Phe His
                420                 425                 430

Tyr His Leu Gln Arg Val Phe Trp Thr Asp Thr Val Gln Asn Lys Val
                435                 440                 445

Phe Ser Val Asp Ile Asn Gly Leu Asn Ile Gln Glu Val Leu Asn Val
450                 455                 460

Ser Val Glu Thr Pro Glu Asn Leu Ala Val Asp Trp Val Asn Asn Lys
465                 470                 475                 480

Ile Tyr Leu Val Glu Thr Lys Val Asn Arg Ile Asp Met Val Asn Leu
                485                 490                 495

Asp Gly Ser Tyr Arg Val Thr Leu Ile Thr Glu Asn Leu Gly His Pro
                500                 505                 510

Arg Gly Ile Ala Val Asp Pro Thr Val Gly Tyr Leu Phe Phe Ser Asp
                515                 520                 525

Trp Glu Ser Leu Ser Gly Glu Pro Lys Leu Glu Arg Ala Phe Met Asp
                530                 535                 540

Gly Ser Asn Arg Lys Asp Leu Val Lys Thr Lys Leu Gly Trp Pro Ala
545                 550                 555                 560

Gly Val Thr Leu Asp Met Ile Ser Lys Arg Val Tyr Trp Val Asp Ser
                565                 570                 575

Arg Phe Asp Tyr Ile Glu Thr Val Thr Tyr Asp Gly Ile Gln Arg Lys
                580                 585                 590

Thr Val His Gly Gly Ser Leu Ile Pro His Pro Phe Gly Val Ser
                595                 600                 605

Leu Phe Glu Gly Gln Val Phe Phe Thr Asp Trp Thr Lys Met Ala Val
                610                 615                 620

Leu Lys Ala Asn Lys Phe Thr Glu Thr Asn Pro Gln Val Tyr Tyr Gln
625                 630                 635                 640

Ala Ser Leu Arg Pro Tyr Gly Val Thr Val Tyr His Ser Leu Arg Gln
                645                 650                 655

Pro Tyr Ala Thr Asn Pro Cys Lys Asp Asn Asn Gly Gly Cys Glu Gln
                660                 665                 670

Val Cys Val Leu Ser His Arg Thr Asp Asn Asp Gly Leu Gly Phe Arg
                675                 680                 685

Cys Lys Cys Thr Phe Gly Phe Gln Leu Asp Thr Asp Glu Arg His Cys
                690                 695                 700

Ile Ala Val Gln Asn Phe Leu Ile Phe Ser Gln Val Ala Ile Arg
705                 710                 715                 720

Gly Ile Pro Phe Thr Leu Ser Thr Gln Glu Asp Val Met Val Pro Val
                725                 730                 735

Ser Gly Asn Pro Ser Phe Phe Val Gly Ile Asp Phe Asp Ala Gln Asp
                740                 745                 750

Ser Thr Ile Phe Phe Ser Asp Met Ser Lys His Met Ile Phe Lys Gln
                755                 760                 765

Lys Ile Asp Gly Thr Gly Arg Glu Ile Leu Ala Ala Asn Arg Val Glu
                770                 775                 780

Asn Val Glu Ser Leu Ala Phe Asp Trp Ile Ser Lys Asn Leu Tyr Trp
785                 790                 795                 800
```

```
Thr Asp Ser His Tyr Lys Ser Ile Ser Val Met Arg Leu Ala Asp Lys
            805                 810                 815

Thr Arg Arg Thr Val Val Gln Tyr Leu Asn Asn Pro Arg Ser Val Val
        820                 825                 830

Val His Pro Phe Ala Gly Tyr Leu Phe Phe Thr Asp Trp Phe Arg Pro
        835                 840                 845

Ala Lys Ile Met Arg Ala Trp Ser Asp Gly Ser His Leu Leu Pro Val
850                 855                 860

Ile Asn Thr Thr Leu Gly Trp Pro Asn Gly Leu Ala Ile Asp Trp Ala
865                 870                 875                 880

Ala Ser Arg Leu Tyr Trp Val Asp Ala Tyr Phe Asp Lys Ile Glu His
            885                 890                 895

Ser Thr Phe Asp Gly Leu Asp Arg Arg Arg Leu Gly His Ile Glu Gln
            900                 905                 910

Met Thr His Pro Phe Gly Leu Ala Ile Phe Gly Glu His Leu Phe Phe
            915                 920                 925

Thr Asp Trp Arg Leu Gly Ala Ile Ile Arg Val Arg Lys Ala Asp Gly
    930                 935                 940

Gly Glu Met Thr Val Ile Arg Ser Gly Ile Ala Tyr Ile Leu His Leu
945                 950                 955                 960

Lys Ser Tyr Asp Val Asn Ile Gln Thr Gly Ser Asn Ala Cys Asn Gln
                965                 970                 975

Pro Thr His Pro Asn Gly Asp Cys Ser His Phe Cys Phe Pro Val Pro
            980                 985                 990

Asn Phe Gln Arg Val Cys Gly Cys Pro Tyr Gly Met Arg Leu Ala Ser
        995                 1000                1005

Asn His Leu Thr Cys Glu Gly Asp Pro Thr Asn Glu Pro Pro Thr
    1010                1015                1020

Glu Gln Cys Gly Leu Phe Ser Phe Pro Cys Lys Asn Gly Arg Cys
    1025                1030                1035

Val Pro Asn Tyr Tyr Leu Cys Asp Gly Val Asp Asp Cys His Asp
    1040                1045                1050

Asn Ser Asp Glu Gln Leu Cys Gly Thr Leu Asn Asn Thr Cys Ser
    1055                1060                1065

Ser Ser Ala Phe Thr Cys His Gly Glu Cys Ile Pro Ala His
    1070                1075                1080

Trp Arg Cys Asp Lys Arg Asn Asp Cys Val Asp Gly Ser Asp Glu
    1085                1090                1095

His Asn Cys Pro Thr His Ala Pro Ala Ser Cys Leu Asp Thr Gln
    1100                1105                1110

Tyr Thr Cys Asp Asn His Gln Cys Ile Ser Lys Asn Trp Val Cys
    1115                1120                1125

Asp Thr Asp Asn Asp Cys Gly Asp Gly Ser Asp Glu Lys Asn Cys
    1130                1135                1140

Asn Ser Thr Glu Thr Cys Gln Pro Ser Gln Phe Asn Cys Pro Asn
    1145                1150                1155

His Arg Cys Ile Asp Leu Ser Phe Val Cys Asp Gly Asp Lys Asp
    1160                1165                1170

Cys Val Asp Gly Ser Asp Glu Val Gly Cys Val Leu Asn Cys Thr
    1175                1180                1185

Ala Ser Gln Phe Lys Cys Ala Ser Gly Asp Lys Cys Ile Gly Val
    1190                1195                1200
```

```
Thr  Asn  Arg  Cys  Asp  Gly  Val  Phe  Asp  Cys  Ser  Asp  Asn  Ser  Asp
1205                1210                1215

Glu  Ala  Gly  Cys  Pro  Thr  Arg  Pro  Pro  Gly  Met  Cys  His  Ser  Asp
1220                1225                1230

Glu  Phe  Gln  Cys  Gln  Glu  Asp  Gly  Ile  Cys  Ile  Pro  Asn  Phe  Trp
1235                1240                1245

Glu  Cys  Asp  Gly  His  Pro  Asp  Cys  Leu  Tyr  Gly  Ser  Asp  Glu  His
1250                1255                1260

Asn  Ala  Cys  Val  Pro  Lys  Thr  Cys  Pro  Ser  Ser  Tyr  Phe  His  Cys
1265                1270                1275

Asp  Asn  Gly  Asn  Cys  Ile  His  Arg  Ala  Trp  Leu  Cys  Asp  Arg  Asp
1280                1285                1290

Asn  Asp  Cys  Gly  Asp  Met  Ser  Asp  Glu  Lys  Asp  Cys  Pro  Thr  Gln
1295                1300                1305

Pro  Phe  Arg  Cys  Pro  Ser  Trp  Gln  Trp  Gln  Cys  Leu  Gly  His  Asn
1310                1315                1320

Ile  Cys  Val  Asn  Leu  Ser  Val  Val  Cys  Asp  Gly  Ile  Phe  Asp  Cys
1325                1330                1335

Pro  Asn  Gly  Thr  Asp  Glu  Ser  Pro  Leu  Cys  Asn  Gly  Asn  Ser  Cys
1340                1345                1350

Ser  Asp  Phe  Asn  Gly  Gly  Cys  Thr  His  Glu  Cys  Val  Gln  Glu  Pro
1355                1360                1365

Phe  Gly  Ala  Lys  Cys  Leu  Cys  Pro  Leu  Gly  Phe  Leu  Leu  Ala  Asn
1370                1375                1380

Asp  Ser  Lys  Thr  Cys  Glu  Asp  Ile  Asp  Glu  Cys  Asp  Ile  Leu  Gly
1385                1390                1395

Ser  Cys  Ser  Gln  His  Cys  Tyr  Asn  Met  Arg  Gly  Ser  Phe  Arg  Cys
1400                1405                1410

Ser  Cys  Asp  Thr  Gly  Tyr  Met  Leu  Glu  Ser  Asp  Gly  Arg  Thr  Cys
1415                1420                1425

Lys  Val  Thr  Ala  Ser  Glu  Ser  Leu  Leu  Leu  Leu  Val  Ala  Ser  Gln
1430                1435                1440

Asn  Lys  Ile  Ile  Ala  Asp  Ser  Val  Thr  Ser  Gln  Val  His  Asn  Ile
1445                1450                1455

Tyr  Ser  Leu  Val  Glu  Asn  Gly  Ser  Tyr  Ile  Val  Ala  Val  Asp  Phe
1460                1465                1470

Asp  Ser  Ile  Ser  Gly  Arg  Ile  Phe  Trp  Ser  Asp  Ala  Thr  Gln  Gly
1475                1480                1485

Lys  Thr  Trp  Ser  Ala  Phe  Gln  Asn  Gly  Thr  Asp  Arg  Arg  Val  Val
1490                1495                1500

Phe  Asp  Ser  Ser  Ile  Ile  Leu  Thr  Glu  Thr  Ile  Ala  Ile  Asp  Trp
1505                1510                1515

Val  Gly  Arg  Asn  Leu  Tyr  Trp  Thr  Asp  Tyr  Ala  Leu  Glu  Thr  Ile
1520                1525                1530

Glu  Val  Ser  Lys  Ile  Asp  Gly  Ser  His  Arg  Thr  Val  Leu  Ile  Ser
1535                1540                1545

Lys  Asn  Leu  Thr  Asn  Pro  Arg  Gly  Leu  Ala  Leu  Asp  Pro  Arg  Met
1550                1555                1560

Asn  Glu  His  Leu  Leu  Phe  Trp  Ser  Asp  Trp  Gly  His  His  Pro  Arg
1565                1570                1575

Ile  Glu  Arg  Ala  Ser  Met  Asp  Gly  Ser  Met  Arg  Thr  Val  Ile  Val
1580                1585                1590

Gln  Asp  Lys  Ile  Phe  Trp  Pro  Cys  Gly  Leu  Thr  Ile  Asp  Tyr  Pro
```

-continued

```
            1595                1600                1605
Asn Arg Leu Leu Tyr Phe Met Asp Ser Tyr Leu Asp Tyr Met Asp
    1610                1615                1620
Phe Cys Asp Tyr Asn Gly His His Arg Arg Gln Val Ile Ala Ser
    1625                1630                1635
Asp Leu Ile Ile Arg His Pro Tyr Ala Leu Thr Leu Phe Glu Asp
    1640                1645                1650
Ser Val Tyr Trp Thr Asp Arg Ala Thr Arg Arg Val Met Arg Ala
    1655                1660                1665
Asn Lys Trp His Gly Gly Asn Gln Ser Val Val Met Tyr Asn Ile
    1670                1675                1680
Gln Trp Pro Leu Gly Ile Val Ala Val His Pro Ser Lys Gln Pro
    1685                1690                1695
Asn Ser Val Asn Pro Cys Ala Phe Ser Arg Cys Ser His Leu Cys
    1700                1705                1710
Leu Leu Ser Ser Gln Gly Pro His Phe Tyr Ser Cys Val Cys Pro
    1715                1720                1725
Ser Gly Trp Ser Leu Ser Pro Asp Leu Leu Asn Cys Leu Arg Asp
    1730                1735                1740
Asp Gln Pro Phe Leu Ile Thr Val Arg Gln His Ile Ile Phe Gly
    1745                1750                1755
Ile Ser Leu Asn Pro Glu Val Lys Ser Asn Asp Ala Met Val Pro
    1760                1765                1770
Ile Ala Gly Ile Gln Asn Gly Leu Asp Val Glu Phe Asp Asp Ala
    1775                1780                1785
Glu Gln Tyr Ile Tyr Trp Val Glu Asn Pro Gly Glu Ile His Arg
    1790                1795                1800
Val Lys Thr Asp Gly Thr Asn Arg Thr Val Phe Ala Ser Ile Ser
    1805                1810                1815
Met Val Gly Pro Ser Met Asn Leu Ala Leu Asp Trp Ile Ser Arg
    1820                1825                1830
Asn Leu Tyr Ser Thr Asn Pro Arg Thr Gln Ser Ile Glu Val Leu
    1835                1840                1845
Thr Leu His Gly Asp Ile Arg Tyr Arg Lys Thr Leu Ile Ala Asn
    1850                1855                1860
Asp Gly Thr Ala Leu Gly Val Gly Phe Pro Ile Gly Ile Thr Val
    1865                1870                1875
Asp Pro Ala Arg Gly Lys Leu Tyr Trp Ser Asp Gln Gly Thr Asp
    1880                1885                1890
Ser Gly Val Pro Ala Lys Ile Ala Ser Ala Asn Met Asp Gly Thr
    1895                1900                1905
Ser Val Lys Thr Leu Phe Thr Gly Asn Leu Glu His Leu Glu Cys
    1910                1915                1920
Val Thr Leu Asp Ile Glu Glu Gln Lys Leu Tyr Trp Ala Val Thr
    1925                1930                1935
Gly Arg Gly Val Ile Glu Arg Gly Asn Val Asp Gly Thr Asp Arg
    1940                1945                1950
Met Ile Leu Val His Gln Leu Ser His Pro Trp Gly Ile Ala Val
    1955                1960                1965
His Asp Ser Phe Leu Tyr Tyr Thr Asp Glu Gln Tyr Glu Val Ile
    1970                1975                1980
Glu Arg Val Asp Lys Ala Thr Gly Ala Asn Lys Ile Val Leu Arg
    1985                1990                1995
```

-continued

```
Asp Asn Val Pro Asn Leu Arg Gly Leu Gln Val Tyr His Arg Arg
2000                2005                2010

Asn Ala Ala Glu Ser Ser Asn Gly Cys Ser Asn Asn Met Asn Ala
2015                2020                2025

Cys Gln Gln Ile Cys Leu Pro Val Pro Gly Gly Leu Phe Ser Cys
2030                2035                2040

Ala Cys Ala Thr Gly Phe Lys Leu Asn Pro Asp Asn Arg Ser Cys
2045                2050                2055

Ser Pro Tyr Asn Ser Phe Ile Val Val Ser Met Leu Ser Ala Ile
2060                2065                2070

Arg Gly Phe Ser Leu Glu Leu Ser Asp His Ser Glu Thr Met Val
2075                2080                2085

Pro Val Ala Gly Gln Gly Arg Asn Ala Leu His Val Asp Val Asp
2090                2095                2100

Val Ser Ser Gly Phe Ile Tyr Trp Cys Asp Phe Ser Ser Ser Val
2105                2110                2115

Ala Ser Asp Asn Ala Ile Arg Arg Ile Lys Pro Asp Gly Ser Ser
2120                2125                2130

Leu Met Asn Ile Val Thr His Gly Ile Gly Glu Asn Gly Val Arg
2135                2140                2145

Gly Ile Ala Val Asp Trp Val Ala Gly Asn Leu Tyr Phe Thr Asn
2150                2155                2160

Ala Phe Val Ser Glu Thr Leu Ile Glu Val Leu Arg Ile Asn Thr
2165                2170                2175

Thr Tyr Arg Arg Val Leu Leu Lys Val Thr Val Asp Met Pro Arg
2180                2185                2190

His Ile Val Val Asp Pro Lys Asn Arg Tyr Leu Phe Trp Ala Asp
2195                2200                2205

Tyr Gly Gln Arg Pro Lys Ile Glu Arg Ser Phe Leu Asp Cys Thr
2210                2215                2220

Asn Arg Thr Val Leu Val Ser Glu Gly Ile Val Thr Pro Arg Gly
2225                2230                2235

Leu Ala Val Asp Arg Ser Asp Gly Tyr Val Tyr Trp Val Asp Asp
2240                2245                2250

Ser Leu Asp Ile Ile Ala Arg Ile Arg Ile Asn Gly Glu Asn Ser
2255                2260                2265

Glu Val Ile Arg Tyr Gly Ser Arg Tyr Pro Thr Pro Tyr Gly Ile
2270                2275                2280

Thr Val Phe Glu Asn Ser Ile Ile Trp Val Asp Arg Asn Leu Lys
2285                2290                2295

Lys Ile Phe Gln Ala Ser Lys Glu Pro Glu Asn Thr Glu Pro Pro
2300                2305                2310

Thr Val Ile Arg Asp Asn Ile Asn Trp Leu Arg Asp Val Thr Ile
2315                2320                2325

Phe Asp Lys Gln Val Gln Pro Arg Ser Pro Ala Glu Val Asn Asn
2330                2335                2340

Asn Pro Cys Leu Glu Asn Asn Gly Gly Cys Ser His Leu Cys Phe
2345                2350                2355

Ala Leu Pro Gly Leu His Thr Pro Lys Cys Asp Cys Ala Phe Gly
2360                2365                2370

Thr Leu Gln Ser Asp Gly Lys Asn Cys Ala Ile Ser Thr Glu Asn
2375                2380                2385
```

-continued

| | | | | | | | | | | | |
|---|---|---|---|---|---|---|---|---|---|---|---|
|Phe|Leu|Ile|Phe|Ala|Leu|Ser|Asn|Ser|Leu|Arg|Ser|Leu|His|Leu|
| |2390| | | |2395| | | |2400| | | | | |
|Asp|Pro|Glu|Asn|His|Ser|Pro|Pro|Phe|Gln|Thr|Ile|Asn|Val|Glu|
| |2405| | | |2410| | | |2415| | | | | |
|Arg|Thr|Val|Met|Ser|Leu|Asp|Tyr|Asp|Ser|Val|Ser|Asp|Arg|Ile|
| |2420| | | |2425| | | |2430| | | | | |
|Tyr|Phe|Thr|Gln|Asn|Leu|Ala|Ser|Gly|Val|Gly|Gln|Ile|Ser|Tyr|
| |2435| | | |2440| | | |2445| | | | | |
|Ala|Thr|Leu|Ser|Ser|Gly|Ile|His|Thr|Pro|Thr|Val|Ile|Ala|Ser|
| |2450| | | |2455| | | |2460| | | | | |
|Gly|Ile|Gly|Thr|Ala|Asp|Gly|Ile|Ala|Phe|Asp|Trp|Ile|Thr|Arg|
| |2465| | | |2470| | | |2475| | | | | |
|Arg|Ile|Tyr|Tyr|Ser|Asp|Tyr|Leu|Asn|Gln|Met|Ile|Asn|Ser|Met|
| |2480| | | |2485| | | |2490| | | | | |
|Ala|Glu|Asp|Gly|Ser|Asn|Arg|Thr|Val|Ile|Ala|Arg|Val|Pro|Lys|
| |2495| | | |2500| | | |2505| | | | | |
|Pro|Arg|Ala|Ile|Val|Leu|Asp|Pro|Cys|Gln|Gly|Tyr|Leu|Tyr|Trp|
| |2510| | | |2515| | | |2520| | | | | |
|Ala|Asp|Trp|Asp|Thr|His|Ala|Lys|Ile|Glu|Arg|Ala|Thr|Leu|Gly|
| |2525| | | |2530| | | |2535| | | | | |
|Gly|Asn|Phe|Arg|Val|Pro|Ile|Val|Asn|Ser|Ser|Leu|Val|Met|Pro|
| |2540| | | |2545| | | |2550| | | | | |
|Ser|Gly|Leu|Thr|Leu|Asp|Tyr|Glu|Glu|Asp|Leu|Leu|Tyr|Trp|Val|
| |2555| | | |2560| | | |2565| | | | | |
|Asp|Ala|Ser|Leu|Gln|Arg|Ile|Glu|Arg|Ser|Thr|Leu|Thr|Gly|Val|
| |2570| | | |2575| | | |2580| | | | | |
|Asp|Arg|Glu|Val|Ile|Val|Asn|Ala|Ala|Val|His|Ala|Phe|Gly|Leu|
| |2585| | | |2590| | | |2595| | | | | |
|Thr|Leu|Tyr|Gly|Gln|Tyr|Ile|Tyr|Trp|Thr|Asp|Leu|Tyr|Thr|Gln|
| |2600| | | |2605| | | |2610| | | | | |
|Arg|Ile|Tyr|Arg|Ala|Asn|Lys|Tyr|Asp|Gly|Ser|Gly|Gln|Ile|Ala|
| |2615| | | |2620| | | |2625| | | | | |
|Met|Thr|Thr|Asn|Leu|Leu|Ser|Gln|Pro|Arg|Gly|Ile|Asn|Thr|Val|
| |2630| | | |2635| | | |2640| | | | | |
|Val|Lys|Asn|Gln|Lys|Gln|Gln|Cys|Asn|Asn|Pro|Cys|Glu|Gln|Phe|
| |2645| | | |2650| | | |2655| | | | | |
|Asn|Gly|Gly|Cys|Ser|His|Ile|Cys|Ala|Pro|Gly|Pro|Asn|Gly|Ala|
| |2660| | | |2665| | | |2670| | | | | |
|Glu|Cys|Gln|Cys|Pro|His|Glu|Gly|Asn|Trp|Tyr|Leu|Ala|Asn|Asn|
| |2675| | | |2680| | | |2685| | | | | |
|Arg|Lys|His|Cys|Ile|Val|Asp|Asn|Gly|Glu|Arg|Cys|Gly|Ala|Ser|
| |2690| | | |2695| | | |2700| | | | | |
|Ser|Phe|Thr|Cys|Ser|Asn|Gly|Arg|Cys|Ile|Ser|Glu|Glu|Trp|Lys|
| |2705| | | |2710| | | |2715| | | | | |
|Cys|Asp|Asn|Asp|Asn|Asp|Cys|Gly|Asp|Gly|Ser|Asp|Glu|Met|Glu|
| |2720| | | |2725| | | |2730| | | | | |
|Ser|Val|Cys|Ala|Leu|His|Thr|Cys|Ser|Pro|Thr|Ala|Phe|Thr|Cys|
| |2735| | | |2740| | | |2745| | | | | |
|Ala|Asn|Gly|Arg|Cys|Val|Gln|Tyr|Ser|Tyr|Arg|Cys|Asp|Tyr|Tyr|
| |2750| | | |2755| | | |2760| | | | | |
|Asn|Asp|Cys|Gly|Asp|Gly|Ser|Asp|Glu|Ala|Gly|Cys|Leu|Phe|Arg|
| |2765| | | |2770| | | |2775| | | | | |
|Asp|Cys|Asn|Ala|Thr|Thr|Glu|Phe|Met|Cys|Asn|Asn|Arg|Arg|Cys|

```
             2780                2785                2790
Ile Pro Arg Glu Phe Ile Cys Asn Gly Val Asp Asn Cys His Asp
    2795                2800                2805

Asn Asn Thr Ser Asp Glu Lys Asn Cys Pro Asp Arg Thr Cys Gln
    2810                2815                2820

Ser Gly Tyr Thr Lys Cys His Asn Ser Asn Ile Cys Ile Pro Arg
    2825                2830                2835

Val Tyr Leu Cys Asp Gly Asp Asn Asp Cys Gly Asp Asn Ser Asp
    2840                2845                2850

Glu Asn Pro Thr Tyr Cys Thr Thr His Thr Cys Ser Ser Ser Glu
    2855                2860                2865

Phe Gln Cys Ala Ser Gly Arg Cys Ile Pro Gln His Trp Tyr Cys
    2870                2875                2880

Asp Gln Glu Thr Asp Cys Phe Asp Ala Ser Asp Glu Pro Ala Ser
    2885                2890                2895

Cys Gly His Ser Glu Arg Thr Cys Leu Ala Asp Glu Phe Lys Cys
    2900                2905                2910

Asp Gly Gly Arg Cys Ile Pro Ser Glu Trp Ile Cys Asp Gly Asp
    2915                2920                2925

Asn Asp Cys Gly Asp Met Ser Asp Glu Asp Lys Arg His Gln Cys
    2930                2935                2940

Gln Asn Gln Asn Cys Ser Asp Ser Glu Phe Leu Cys Val Asn Asp
    2945                2950                2955

Arg Pro Pro Asp Arg Arg Cys Ile Pro Gln Ser Trp Val Cys Asp
    2960                2965                2970

Gly Asp Val Asp Cys Thr Asp Gly Tyr Asp Glu Asn Gln Asn Cys
    2975                2980                2985

Thr Arg Arg Thr Cys Ser Glu Asn Glu Phe Thr Cys Gly Tyr Gly
    2990                2995                3000

Leu Cys Ile Pro Lys Ile Phe Arg Cys Asp Arg His Asn Asp Cys
    3005                3010                3015

Gly Asp Tyr Ser Asp Glu Arg Gly Cys Leu Tyr Gln Thr Cys Gln
    3020                3025                3030

Gln Asn Gln Phe Thr Cys Gln Asn Gly Arg Cys Ile Ser Lys Thr
    3035                3040                3045

Phe Val Cys Asp Glu Asp Asn Asp Cys Gly Asp Gly Ser Asp Glu
    3050                3055                3060

Leu Met His Leu Cys His Thr Pro Glu Pro Thr Cys Pro Pro His
    3065                3070                3075

Glu Phe Lys Cys Asp Asn Gly Arg Cys Ile Glu Met Met Lys Leu
    3080                3085                3090

Cys Asn His Leu Asp Asp Cys Leu Asp Asn Ser Asp Glu Lys Gly
    3095                3100                3105

Cys Gly Ile Asn Glu Cys His Asp Pro Ser Ile Ser Gly Cys Asp
    3110                3115                3120

His Asn Cys Thr Asp Thr Leu Thr Ser Phe Tyr Cys Ser Cys Arg
    3125                3130                3135

Pro Gly Tyr Lys Leu Met Ser Asp Lys Arg Thr Cys Val Asp Ile
    3140                3145                3150

Asp Glu Cys Thr Glu Met Pro Phe Val Cys Ser Gln Lys Cys Glu
    3155                3160                3165

Asn Val Ile Gly Ser Tyr Ile Cys Lys Cys Ala Pro Gly Tyr Leu
    3170                3175                3180
```

-continued

Arg Glu Pro Asp Gly Lys Thr Cys Arg Gln Asn Ser Asn Ile Glu
3185                3190                3195

Pro Tyr Leu Ile Phe Ser Asn Arg Tyr Tyr Leu Arg Asn Leu Thr
3200                3205                3210

Ile Asp Gly Tyr Phe Tyr Ser Leu Ile Leu Glu Gly Leu Asp Asn
3215                3220                3225

Val Val Ala Leu Asp Phe Asp Arg Val Glu Lys Arg Leu Tyr Trp
3230                3235                3240

Ile Asp Thr Gln Arg Gln Val Ile Glu Arg Met Phe Leu Asn Lys
3245                3250                3255

Thr Asn Lys Glu Thr Ile Ile Asn His Arg Leu Pro Ala Ala Glu
3260                3265                3270

Ser Leu Ala Val Asp Trp Val Ser Arg Lys Leu Tyr Trp Leu Asp
3275                3280                3285

Ala Arg Leu Asp Gly Leu Phe Val Ser Asp Leu Asn Gly Gly His
3290                3295                3300

Arg Arg Met Leu Ala Gln His Cys Val Asp Ala Asn Asn Thr Phe
3305                3310                3315

Cys Phe Asp Asn Pro Arg Gly Leu Ala Leu His Pro Gln Tyr Gly
3320                3325                3330

Tyr Leu Tyr Trp Ala Asp Trp Gly His Arg Ala Tyr Ile Gly Arg
3335                3340                3345

Val Gly Met Asp Gly Thr Asn Lys Ser Val Ile Ile Ser Thr Lys
3350                3355                3360

Leu Glu Trp Pro Asn Gly Ile Thr Ile Asp Tyr Thr Asn Asp Leu
3365                3370                3375

Leu Tyr Trp Ala Asp Ala His Leu Gly Tyr Ile Glu Tyr Ser Asp
3380                3385                3390

Leu Glu Gly His His Arg His Thr Val Tyr Asp Gly Ala Leu Pro
3395                3400                3405

His Pro Phe Ala Ile Thr Ile Phe Glu Asp Thr Ile Tyr Trp Thr
3410                3415                3420

Asp Trp Asn Thr Arg Thr Val Glu Lys Gly Asn Lys Tyr Asp Gly
3425                3430                3435

Ser Asn Arg Gln Thr Leu Val Asn Thr Thr His Arg Pro Phe Asp
3440                3445                3450

Ile His Val Tyr His Pro Tyr Arg Gln Pro Ile Val Ser Asn Pro
3455                3460                3465

Cys Gly Thr Asn Asn Gly Gly Cys Ser His Leu Cys Leu Ile Lys
3470                3475                3480

Pro Gly Gly Lys Gly Phe Thr Cys Glu Cys Pro Asp Asp Phe Arg
3485                3490                3495

Thr Leu Gln Leu Ser Gly Ser Thr Tyr Cys Met Pro Met Cys Ser
3500                3505                3510

Ser Thr Gln Phe Leu Cys Ala Asn Asn Glu Lys Cys Ile Pro Ile
3515                3520                3525

Trp Trp Lys Cys Asp Gly Gln Lys Asp Cys Ser Asp Gly Ser Asp
3530                3535                3540

Glu Leu Ala Leu Cys Pro Gln Arg Phe Cys Arg Leu Gly Gln Phe
3545                3550                3555

Gln Cys Ser Asp Gly Asn Cys Thr Ser Pro Gln Thr Leu Cys Asn
3560                3565                3570

Ala His Gln Asn Cys Pro Asp Gly Ser Asp Glu Asp Arg Leu Leu
3575                3580                3585

Cys Glu Asn His His Cys Asp Ser Asn Glu Trp Gln Cys Ala Asn
3590                3595                3600

Lys Arg Cys Ile Pro Glu Ser Trp Gln Cys Asp Thr Phe Asn Asp
3605                3610                3615

Cys Glu Asp Asn Ser Asp Glu Asp Ser Ser His Cys Ala Ser Arg
3620                3625                3630

Thr Cys Arg Pro Gly Gln Phe Arg Cys Ala Asn Gly Arg Cys Ile
3635                3640                3645

Pro Gln Ala Trp Lys Cys Asp Val Asp Asn Asp Cys Gly Asp His
3650                3655                3660

Ser Asp Glu Pro Ile Glu Glu Cys Met Ser Ser Ala His Leu Cys
3665                3670                3675

Asp Asn Phe Thr Glu Phe Ser Cys Lys Thr Asn Tyr Arg Cys Ile
3680                3685                3690

Pro Lys Trp Ala Val Cys Asn Gly Val Asp Asp Cys Arg Asp Asn
3695                3700                3705

Ser Asp Glu Gln Gly Cys Glu Glu Arg Thr Cys His Pro Val Gly
3710                3715                3720

Asp Phe Arg Cys Lys Asn His His Cys Ile Pro Leu Arg Trp Gln
3725                3730                3735

Cys Asp Gly Gln Asn Asp Cys Gly Asp Asn Ser Asp Glu Glu Asn
3740                3745                3750

Cys Ala Pro Arg Glu Cys Thr Glu Ser Glu Phe Arg Cys Val Asn
3755                3760                3765

Gln Gln Cys Ile Pro Ser Arg Trp Ile Cys Asp His Tyr Asn Asp
3770                3775                3780

Cys Gly Asp Asn Ser Asp Glu Arg Asp Cys Glu Met Arg Thr Cys
3785                3790                3795

His Pro Glu Tyr Phe Gln Cys Thr Ser Gly His Cys Val His Ser
3800                3805                3810

Glu Leu Lys Cys Asp Gly Ser Ala Asp Cys Leu Asp Ala Ser Asp
3815                3820                3825

Glu Ala Asp Cys Pro Thr Arg Phe Pro Asp Gly Ala Tyr Cys Gln
3830                3835                3840

Ala Thr Met Phe Glu Cys Lys Asn His Val Cys Ile Pro Pro Tyr
3845                3850                3855

Trp Lys Cys Asp Gly Asp Asp Cys Gly Asp Gly Ser Asp Glu
3860                3865                3870

Glu Leu His Leu Cys Leu Asp Val Pro Cys Asn Ser Pro Asn Arg
3875                3880                3885

Phe Arg Cys Asp Asn Asn Arg Cys Ile Tyr Ser His Glu Val Cys
3890                3895                3900

Asn Gly Val Asp Asp Cys Gly Asp Gly Thr Asp Glu Thr Glu Glu
3905                3910                3915

His Cys Arg Lys Pro Thr Pro Lys Pro Cys Thr Glu Tyr Glu Tyr
3920                3925                3930

Lys Cys Gly Asn Gly His Cys Ile Pro His Asp Asn Val Cys Asp
3935                3940                3945

Asp Ala Asp Asp Cys Gly Asp Trp Ser Asp Glu Leu Gly Cys Asn
3950                3955                3960

Lys Gly Lys Glu Arg Thr Cys Ala Glu Asn Ile Cys Glu Gln Asn

```
                3965                3970                3975

Cys Thr Gln Leu Asn Glu Gly Gly Phe Ile Cys Ser Cys Thr Ala
        3980                3985                3990

Gly Phe Glu Thr Asn Val Phe Asp Arg Thr Ser Cys Leu Asp Ile
        3995                4000                4005

Asn Glu Cys Glu Gln Phe Gly Thr Cys Pro Gln His Cys Arg Asn
        4010                4015                4020

Thr Lys Gly Ser Tyr Glu Cys Val Cys Ala Asp Gly Phe Thr Ser
        4025                4030                4035

Met Ser Asp Arg Pro Gly Lys Arg Cys Ala Ala Glu Gly Ser Ser
        4040                4045                4050

Pro Leu Leu Leu Pro Asp Asn Val Arg Ile Arg Lys Tyr Asn
        4055                4060                4065

Leu Ser Ser Glu Arg Phe Ser Glu Tyr Leu Gln Asp Glu Glu Tyr
        4070                4075                4080

Ile Gln Ala Val Asp Tyr Asp Trp Asp Pro Lys Asp Ile Gly Leu
        4085                4090                4095

Ser Val Val Tyr Tyr Thr Val Arg Gly Glu Gly Ser Arg Phe Gly
        4100                4105                4110

Ala Ile Lys Arg Ala Tyr Ile Pro Asn Phe Glu Ser Gly Arg Asn
        4115                4120                4125

Asn Leu Val Gln Glu Val Asp Leu Lys Leu Lys Tyr Val Met Gln
        4130                4135                4140

Pro Asp Gly Ile Ala Val Asp Trp Val Gly Arg His Ile Tyr Trp
        4145                4150                4155

Ser Asp Val Lys Asn Lys Arg Ile Glu Val Ala Lys Leu Asp Gly
        4160                4165                4170

Arg Tyr Arg Lys Trp Leu Ile Ser Thr Asp Leu Asp Gln Pro Ala
        4175                4180                4185

Ala Ile Ala Val Asn Pro Lys Leu Gly Leu Met Phe Trp Thr Asp
        4190                4195                4200

Trp Gly Lys Glu Pro Lys Ile Glu Ser Ala Trp Met Asn Gly Glu
        4205                4210                4215

Asp Arg Asn Ile Leu Val Phe Glu Asp Leu Gly Trp Pro Thr Gly
        4220                4225                4230

Leu Ser Ile Asp Tyr Leu Asn Asn Asp Arg Ile Tyr Trp Ser Asp
        4235                4240                4245

Phe Lys Glu Asp Val Ile Glu Thr Ile Lys Tyr Asp Gly Thr Asp
        4250                4255                4260

Arg Arg Val Ile Ala Lys Glu Ala Met Asn Pro Tyr Ser Leu Asp
        4265                4270                4275

Ile Phe Glu Asp Gln Leu Tyr Trp Ile Ser Lys Glu Lys Gly Glu
        4280                4285                4290

Val Trp Lys Gln Asn Lys Phe Gly Gln Gly Lys Lys Glu Lys Thr
        4295                4300                4305

Leu Val Val Asn Pro Trp Leu Thr Gln Val Arg Ile Phe His Gln
        4310                4315                4320

Leu Arg Tyr Asn Lys Ser Val Pro Asn Leu Cys Lys Gln Ile Cys
        4325                4330                4335

Ser His Leu Cys Leu Leu Arg Pro Gly Gly Tyr Ser Cys Ala Cys
        4340                4345                4350

Pro Gln Gly Ser Ser Phe Ile Glu Gly Ser Thr Thr Glu Cys Asp
        4355                4360                4365
```

```
Ala Ala Ile Glu Leu Pro Ile Asn Leu Pro Pro Cys Arg Cys
    4370            4375            4380

Met His Gly Gly Asn Cys Tyr Phe Asp Glu Thr Asp Leu Pro Lys
    4385            4390            4395

Cys Lys Cys Pro Ser Gly Tyr Thr Gly Lys Tyr Cys Glu Met Ala
    4400            4405            4410

Phe Ser Lys Gly Ile Ser Pro Gly Thr Thr Ala Val Ala Val Leu
    4415            4420            4425

Leu Thr Ile Leu Leu Ile Val Val Ile Gly Ala Leu Ala Ile Ala
    4430            4435            4440

Gly Phe Phe His Tyr Arg Arg Thr Gly Ser Leu Leu Pro Ala Leu
    4445            4450            4455

Pro Lys Leu Pro Ser Leu Ser Ser Leu Val Lys Pro Ser Glu Asn
    4460            4465            4470

Gly Asn Gly Val Thr Phe Arg Ser Gly Ala Asp Leu Asn Met Asp
    4475            4480            4485

Ile Gly Val Ser Gly Phe Gly Pro Glu Thr Ala Ile Asp Arg Ser
    4490            4495            4500

Met Ala Met Ser Glu Asp Phe Val Met Glu Met Gly Lys Gln Pro
    4505            4510            4515

Ile Ile Phe Glu Asn Pro Met Tyr Ser Ala Arg Asp Ser Ala Val
    4520            4525            4530

Lys Val Val Gln Pro Ile Gln Val Thr Val Ser Glu Asn Val Asp
    4535            4540            4545

Asn Lys Asn Tyr Gly Ser Pro Ile Asn Pro Ser Glu Ile Val Pro
    4550            4555            4560

Glu Thr Asn Pro Thr Ser Pro Ala Ala Asp Gly Thr Gln Val Thr
    4565            4570            4575

Lys Trp Asn Leu Phe Lys Arg Lys Ser Lys Gln Thr Thr Asn Phe
    4580            4585            4590

Glu Asn Pro Ile Tyr Ala Gln Met Glu Asn Glu Gln Lys Glu Ser
    4595            4600            4605

Val Ala Ala Thr Pro Pro Pro Ser Pro Ser Leu Pro Ala Lys Pro
    4610            4615            4620

Lys Pro Pro Ser Arg Arg Asp Pro Thr Pro Thr Tyr Ser Ala Thr
    4625            4630            4635

Glu Asp Thr Phe Lys Asp Thr Ala Asn Leu Val Lys Glu Asp Ser
    4640            4645            4650

Glu Val
    4655

<210> SEQ ID NO 941
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 941
cctaaggtta agtcgccctc g                                          21

<210> SEQ ID NO 942
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 942
cgagggcgac ttaaccttag g                                              21

<210> SEQ ID NO 943
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 943
ccctcagaga cctgagctct t                                              21

<210> SEQ ID NO 944
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 944
aagagctcag gtctctgagg g                                              21

<210> SEQ ID NO 945
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 945
cctgtaataa acactactct t                                              21

<210> SEQ ID NO 946
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 946
aagagtagtg tttattacag g                                              21

<210> SEQ ID NO 947
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 947
ccuaagguua agucgcccuc g                                              21

<210> SEQ ID NO 948
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 948
ugguuuacau guuguguga                                                       19

<210> SEQ ID NO 949
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 949
gggcucuagg uuuggugcua ucaaa                                                25

<210> SEQ ID NO 950
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 950
ggacugauag gagagucauu gcaaa                                                25

<210> SEQ ID NO 951
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 951
ccuguaauaa acacuacucu u                                                    21

<210> SEQ ID NO 952
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 952
ccuucuauga accuggccuu a                                                    21

<210> SEQ ID NO 953
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 953
gugauuugau uauacggca                                                       19

<210> SEQ ID NO 954
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 954
ccucaaaugg cuguagcaa                                                   19

<210> SEQ ID NO 955
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 955
gaacugacaa gaaacugcgc aacug                                            25

<210> SEQ ID NO 956
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 956
cccucagaga ccugagcucu u                                                21

<210> SEQ ID NO 957
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 957
caguugcgca guucuuguc aguuctt                                           27

<210> SEQ ID NO 958
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 958
caguugcgca guucuuguc aguuctt                                           27

<210> SEQ ID NO 959
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 959
caguugcgca guucuuguc aguuctt                                           27

<210> SEQ ID NO 960
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 960
caguugcgca guucuuguc aguuctt                                            27

<210> SEQ ID NO 961
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 961
aagagcucag gucucugagg gtt                                               23

<210> SEQ ID NO 962
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 962
aagagcucag gucucugagg gtt                                               23

<210> SEQ ID NO 963
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 963
aagagcucag gucucugagg gtt                                               23

<210> SEQ ID NO 964
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 964

-continued uuugauagca ccaaaccuag agcccuu 27

<210> SEQ ID NO 965
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 965
uuugauagca ccaaaccuag agcccuu 27

<210> SEQ ID NO 966
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 966
uuugauagca ccaaaccuag agcccuu 27

<210> SEQ ID NO 967
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 967
uuugauagca ccaaaccuag agcccuu 27

<210> SEQ ID NO 968
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 968
uuugauagca ccaaaccuag agcccuu 27

<210> SEQ ID NO 969
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 969
uuugcaauga cucuccuauc agucctt                                  27

<210> SEQ ID NO 970
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 970
uuugcaauga cucuccuauc agucctt                                  27

<210> SEQ ID NO 971
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 971
uuugcaauga cucuccuauc agucctt                                  27

<210> SEQ ID NO 972
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 972
uuugcaauga cucuccuauc agucctt                                  27

<210> SEQ ID NO 973
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 973
ttgucaacgc gucaaagaac agucaag                                  27

<210> SEQ ID NO 974
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 974
ttgucaacgc gucaaagaac agucaag                                          27

<210> SEQ ID NO 975
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 975
ttgucaacgc gucaaagaac agucaag                                          27

<210> SEQ ID NO 976
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 976
ttgucaacgc gucaaagaac agucaag                                          27

<210> SEQ ID NO 977
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 977
ttgucaacgc gucaaagaac agucaag                                          27

<210> SEQ ID NO 978
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 978
ttgucaacgc gucaaagaac agucaag                                          27

<210> SEQ ID NO 979
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 979
ttuucucgag uccagagacu ccc                                          23

<210> SEQ ID NO 980
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 980
ttuucucgag uccagagacu ccc                                          23

<210> SEQ ID NO 981
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 981
ttuucucgag uccagagacu ccc                                          23

<210> SEQ ID NO 982
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 982
ttuucucgag uccagagacu ccc                                          23

<210> SEQ ID NO 983
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 983
ttuucucgag uccagagacu ccc                                          23

<210> SEQ ID NO 984
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

```
<210> SEQ ID NO 985
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 985
ttaaacuauc gugguuugga ucucggg                                         27

<210> SEQ ID NO 986
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 986
ttaaacuauc gugguuugga ucucggg                                         27

<210> SEQ ID NO 987
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 987
ttaaacuauc gugguuugga ucucggg                                         27

<210> SEQ ID NO 988
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 988
ttaaacuguc gugguuugga ucucggg                                         27

<210> SEQ ID NO 989
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

(Synthetic oligonucleotide)

<400> SEQUENCE: 984
ttaaacuauc gugguuugga ucucggg                                         27

```
<223> OTHER INFORMATION: Description of Combined DNA/RNA Molecule:
      Synthetic oligonucleotide

<400> SEQUENCE: 989
ttaaacuguc gugguuugga ucucggg                                          27

<210> SEQ ID NO 990
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 990
ttaaacuauc gugguuugga ucucggg                                          27

<210> SEQ ID NO 991
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 991
ttaaacguua cugagaggau agucagg                                          27

<210> SEQ ID NO 992
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 992
ttaaacguua cugagaggau agucagg                                          27

<210> SEQ ID NO 993
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 993
ttaaacguua cugagaggau agucagg                                          27

<210> SEQ ID NO 994
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: Description of Combined DNA/RNA Molecule:
      Synthetic oligonucleotide

<400> SEQUENCE: 994
ttaaacguua cugagaggau agucagg                                        27

<210> SEQ ID NO 995
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 995
ttaaacguua cugagaggau agucagg                                        27

<210> SEQ ID NO 996
<211> LENGTH: 23
<212> TYPE: DNA
<213> ORGANISM: Homo sapiens

<400> SEQUENCE: 996
tgcgcgtgcg cagggataag aga                                            23

<210> SEQ ID NO 997
<211> LENGTH: 23
<212> TYPE: DNA
<213> ORGANISM: Homo sapiens

<400> SEQUENCE: 997
cgcgtgcgca gggataagag agc                                            23

<210> SEQ ID NO 998
<211> LENGTH: 23
<212> TYPE: DNA
<213> ORGANISM: Homo sapiens

<400> SEQUENCE: 998
gcgccgctgt ggggacagca tga                                            23

<210> SEQ ID NO 999
<211> LENGTH: 23
<212> TYPE: DNA
<213> ORGANISM: Homo sapiens

<400> SEQUENCE: 999
cagcatgagc ggcggttgga tgg                                            23

<210> SEQ ID NO 1000
<211> LENGTH: 23
<212> TYPE: DNA
<213> ORGANISM: Homo sapiens

<400> SEQUENCE: 1000
ccgccgcgag cccgctttcc acc                                            23

<210> SEQ ID NO 1001
<211> LENGTH: 23
<212> TYPE: DNA
<213> ORGANISM: Homo sapiens

```
<400> SEQUENCE: 1001
ctcgtgccca cccaccaagt tcc                                              23

<210> SEQ ID NO 1002
<211> LENGTH: 23
<212> TYPE: DNA
<213> ORGANISM: Homo sapiens

<400> SEQUENCE: 1002
gtgcccaccc accaagttcc agt                                              23

<210> SEQ ID NO 1003
<211> LENGTH: 23
<212> TYPE: DNA
<213> ORGANISM: Homo sapiens

<400> SEQUENCE: 1003
gcccacccac caagttccag tgc                                              23

<210> SEQ ID NO 1004
<211> LENGTH: 23
<212> TYPE: DNA
<213> ORGANISM: Homo sapiens

<400> SEQUENCE: 1004
cagtgccgca ccagtggctt atg                                              23

<210> SEQ ID NO 1005
<211> LENGTH: 23
<212> TYPE: DNA
<213> ORGANISM: Homo sapiens

<400> SEQUENCE: 1005
ccgcaccagt ggcttatgcg tgc                                              23

<210> SEQ ID NO 1006
<211> LENGTH: 23
<212> TYPE: DNA
<213> ORGANISM: Homo sapiens

<400> SEQUENCE: 1006
gcgctgcgac agggacttgg act                                              23

<210> SEQ ID NO 1007
<211> LENGTH: 23
<212> TYPE: DNA
<213> ORGANISM: Homo sapiens

<400> SEQUENCE: 1007
cagcgatggc agcgatgagg agg                                              23

<210> SEQ ID NO 1008
<211> LENGTH: 23
<212> TYPE: DNA
<213> ORGANISM: Homo sapiens

<400> SEQUENCE: 1008
cccctgcacc ggcgtcagtg act                                              23

<210> SEQ ID NO 1009
<211> LENGTH: 23
<212> TYPE: DNA
```

```
<213> ORGANISM: Homo sapiens

<400> SEQUENCE: 1009
ctgctctggg ggaactgaca aga                                              23

<210> SEQ ID NO 1010
<211> LENGTH: 23
<212> TYPE: DNA
<213> ORGANISM: Homo sapiens

<400> SEQUENCE: 1010
ctctggggga actgacaaga aac                                              23

<210> SEQ ID NO 1011
<211> LENGTH: 23
<212> TYPE: DNA
<213> ORGANISM: Homo sapiens

<400> SEQUENCE: 1011
tgggggaact gacaagaaac tgc                                              23

<210> SEQ ID NO 1012
<211> LENGTH: 25
<212> TYPE: DNA
<213> ORGANISM: Homo sapiens

<400> SEQUENCE: 1012
gaactgacaa gaaactgcgc aactg                                            25

<210> SEQ ID NO 1013
<211> LENGTH: 23
<212> TYPE: DNA
<213> ORGANISM: Homo sapiens

<400> SEQUENCE: 1013
cacgctgagc gatgactgca ttc                                              23

<210> SEQ ID NO 1014
<211> LENGTH: 23
<212> TYPE: DNA
<213> ORGANISM: Homo sapiens

<400> SEQUENCE: 1014
acgctgagcg atgactgcat tcc                                              23

<210> SEQ ID NO 1015
<211> LENGTH: 23
<212> TYPE: DNA
<213> ORGANISM: Homo sapiens

<400> SEQUENCE: 1015
ctgagcgatg actgcattcc act                                              23

<210> SEQ ID NO 1016
<211> LENGTH: 23
<212> TYPE: DNA
<213> ORGANISM: Homo sapiens

<400> SEQUENCE: 1016
gagcgatgac tgcattccac tca                                              23

<210> SEQ ID NO 1017
<211> LENGTH: 23
```

<212> TYPE: DNA
<213> ORGANISM: Homo sapiens

<400> SEQUENCE: 1017
tgcgacggcc acccagactg tcc                                              23

<210> SEQ ID NO 1018
<211> LENGTH: 23
<212> TYPE: DNA
<213> ORGANISM: Homo sapiens

<400> SEQUENCE: 1018
gagctcggct gtggaaccaa tga                                              23

<210> SEQ ID NO 1019
<211> LENGTH: 23
<212> TYPE: DNA
<213> ORGANISM: Homo sapiens

<400> SEQUENCE: 1019
tcggctgtgg aaccaatgag atc                                              23

<210> SEQ ID NO 1020
<211> LENGTH: 23
<212> TYPE: DNA
<213> ORGANISM: Homo sapiens

<400> SEQUENCE: 1020
cggctgtgga accaatgaga tcc                                              23

<210> SEQ ID NO 1021
<211> LENGTH: 23
<212> TYPE: DNA
<213> ORGANISM: Homo sapiens

<400> SEQUENCE: 1021
ctgtggaacc aatgagatcc tcc                                              23

<210> SEQ ID NO 1022
<211> LENGTH: 23
<212> TYPE: DNA
<213> ORGANISM: Homo sapiens

<400> SEQUENCE: 1022
tggagagtgt cacctctctc agg                                              23

<210> SEQ ID NO 1023
<211> LENGTH: 23
<212> TYPE: DNA
<213> ORGANISM: Homo sapiens

<400> SEQUENCE: 1023
ctctcaggaa tgccacaacc atg                                              23

<210> SEQ ID NO 1024
<211> LENGTH: 23
<212> TYPE: DNA
<213> ORGANISM: Homo sapiens

<400> SEQUENCE: 1024 tccctctgt cgggaatgcc aca                                              23

<210> SEQ ID NO 1025

```
<211> LENGTH: 23
<212> TYPE: DNA
<213> ORGANISM: Homo sapiens

<400> SEQUENCE: 1025
ctgtcgggaa tgccacatcc tcc                                            23

<210> SEQ ID NO 1026
<211> LENGTH: 23
<212> TYPE: DNA
<213> ORGANISM: Homo sapiens

<400> SEQUENCE: 1026
ctgccggaga ccagtctgga agc                                            23

<210> SEQ ID NO 1027
<211> LENGTH: 23
<212> TYPE: DNA
<213> ORGANISM: Homo sapiens

<400> SEQUENCE: 1027
cccaactgcc tatggggtta ttg                                            23

<210> SEQ ID NO 1028
<211> LENGTH: 23
<212> TYPE: DNA
<213> ORGANISM: Homo sapiens

<400> SEQUENCE: 1028
ctgctgcggt gctcagtgca agc                                            23

<210> SEQ ID NO 1029
<211> LENGTH: 23
<212> TYPE: DNA
<213> ORGANISM: Homo sapiens

<400> SEQUENCE: 1029
caccgccacc ctcctccttt tgt                                            23

<210> SEQ ID NO 1030
<211> LENGTH: 23
<212> TYPE: DNA
<213> ORGANISM: Homo sapiens

<400> SEQUENCE: 1030
ccgccaccct cctcctttg tcc                                             23

<210> SEQ ID NO 1031
<211> LENGTH: 23
<212> TYPE: DNA
<213> ORGANISM: Homo sapiens

<400> SEQUENCE: 1031
ccgcccactg gggttactgg tgg                                            23

<210> SEQ ID NO 1032
<211> LENGTH: 23
<212> TYPE: DNA
<213> ORGANISM: Homo sapiens

<400> SEQUENCE: 1032
ggggttactg gtggccatga agg                                            23
```

```
<210> SEQ ID NO 1033
<211> LENGTH: 23
<212> TYPE: DNA
<213> ORGANISM: Homo sapiens

<400> SEQUENCE: 1033
tactggtggc catgaaggag tcc                                              23

<210> SEQ ID NO 1034
<211> LENGTH: 23
<212> TYPE: DNA
<213> ORGANISM: Homo sapiens

<400> SEQUENCE: 1034
gagtccctgc tgctgtcaga aca                                              23

<210> SEQ ID NO 1035
<211> LENGTH: 23
<212> TYPE: DNA
<213> ORGANISM: Homo sapiens

<400> SEQUENCE: 1035
ccctgctgct gtcagaacag aag                                              23

<210> SEQ ID NO 1036
<211> LENGTH: 23
<212> TYPE: DNA
<213> ORGANISM: Homo sapiens

<400> SEQUENCE: 1036
tgctgctgtc agaacagaag acc                                              23

<210> SEQ ID NO 1037
<211> LENGTH: 23
<212> TYPE: DNA
<213> ORGANISM: Homo sapiens

<400> SEQUENCE: 1037
tgctgtcaga acagaagacc tcg                                              23

<210> SEQ ID NO 1038
<211> LENGTH: 23
<212> TYPE: DNA
<213> ORGANISM: Homo sapiens

<400> SEQUENCE: 1038
acctcgctgc cctgaggaca agc                                              23

<210> SEQ ID NO 1039
<211> LENGTH: 23
<212> TYPE: DNA
<213> ORGANISM: Homo sapiens

<400> SEQUENCE: 1039
ctgccctgag gacaagcact tgc                                              23

<210> SEQ ID NO 1040
<211> LENGTH: 23
<212> TYPE: DNA
<213> ORGANISM: Homo sapiens

<400> SEQUENCE: 1040
gagcagtgat gcggatgggt acc                                              23
```

```
<210> SEQ ID NO 1041
<211> LENGTH: 23
<212> TYPE: DNA
<213> ORGANISM: Homo sapiens

<400> SEQUENCE: 1041
gggcacacca gccctcagag acc                                          23

<210> SEQ ID NO 1042
<211> LENGTH: 23
<212> TYPE: DNA
<213> ORGANISM: Homo sapiens

<400> SEQUENCE: 1042
ccctcagaga cctgagctct tct                                          23

<210> SEQ ID NO 1043
<211> LENGTH: 23
<212> TYPE: DNA
<213> ORGANISM: Homo sapiens

<400> SEQUENCE: 1043
ctcagagacc tgagctcttc tgg                                          23

<210> SEQ ID NO 1044
<211> LENGTH: 23
<212> TYPE: DNA
<213> ORGANISM: Homo sapiens

<400> SEQUENCE: 1044
gggtccctgg acactcccta tgg                                          23

<210> SEQ ID NO 1045
<211> LENGTH: 23
<212> TYPE: DNA
<213> ORGANISM: Homo sapiens

<400> SEQUENCE: 1045
tccctggaca ctccctatgg aga                                          23

<210> SEQ ID NO 1046
<211> LENGTH: 23
<212> TYPE: DNA
<213> ORGANISM: Homo sapiens

<400> SEQUENCE: 1046
ctggacactc cctatggaga tcc                                          23

<210> SEQ ID NO 1047
<211> LENGTH: 23
<212> TYPE: DNA
<213> ORGANISM: Homo sapiens

<400> SEQUENCE: 1047
acctgccaca gccagaactg agg                                          23

<210> SEQ ID NO 1048
<211> LENGTH: 23
<212> TYPE: DNA
<213> ORGANISM: Homo sapiens

<400> SEQUENCE: 1048
ggcagctccc aggggggtaga acg                                         23
```

<210> SEQ ID NO 1049
<211> LENGTH: 23
<212> TYPE: DNA
<213> ORGANISM: Homo sapiens

<400> SEQUENCE: 1049
gggtagaacg gccctgtgct taa                                          23

<210> SEQ ID NO 1050
<211> LENGTH: 23
<212> TYPE: DNA
<213> ORGANISM: Homo sapiens

<400> SEQUENCE: 1050
aacggccctg tgcttaagac act                                          23

<210> SEQ ID NO 1051
<211> LENGTH: 23
<212> TYPE: DNA
<213> ORGANISM: Homo sapiens

<400> SEQUENCE: 1051
cggccctgtg cttaagacac tcc                                          23

<210> SEQ ID NO 1052
<211> LENGTH: 23
<212> TYPE: DNA
<213> ORGANISM: Homo sapiens

<400> SEQUENCE: 1052
ttgcttcaca tcctcaaaaa aaa                                          23

<210> SEQ ID NO 1053
<211> LENGTH: 23
<212> TYPE: DNA
<213> ORGANISM: Homo sapiens

<400> SEQUENCE: 1053
tgcttcacat cctcaaaaaa aaa                                          23

<210> SEQ ID NO 1054
<211> LENGTH: 23
<212> TYPE: DNA
<213> ORGANISM: Homo sapiens

<400> SEQUENCE: 1054
gtcaagattg ctcacaaagt aca                                          23

<210> SEQ ID NO 1055
<211> LENGTH: 23
<212> TYPE: DNA
<213> ORGANISM: Homo sapiens

<400> SEQUENCE: 1055
gtcagtgtat cccaagtgaa tac                                          23

<210> SEQ ID NO 1056
<211> LENGTH: 23
<212> TYPE: DNA
<213> ORGANISM: Homo sapiens

<400> SEQUENCE: 1056

```
ttgcacaatg agttttcatg tgg                                           23

<210> SEQ ID NO 1057
<211> LENGTH: 23
<212> TYPE: DNA
<213> ORGANISM: Homo sapiens

<400> SEQUENCE: 1057
tggagaagat gactgtaaag ata                                           23

<210> SEQ ID NO 1058
<211> LENGTH: 23
<212> TYPE: DNA
<213> ORGANISM: Homo sapiens

<400> SEQUENCE: 1058
gagaagatga ctgtaaagat aat                                           23

<210> SEQ ID NO 1059
<211> LENGTH: 23
<212> TYPE: DNA
<213> ORGANISM: Homo sapiens

<400> SEQUENCE: 1059
ctcatgatgt tcataaatgt tcc                                           23

<210> SEQ ID NO 1060
<211> LENGTH: 23
<212> TYPE: DNA
<213> ORGANISM: Homo sapiens

<400> SEQUENCE: 1060
ctccatttat aaagtttgtg atg                                           23

<210> SEQ ID NO 1061
<211> LENGTH: 23
<212> TYPE: DNA
<213> ORGANISM: Homo sapiens

<400> SEQUENCE: 1061
tccatttata aagtttgtga tgg                                           23

<210> SEQ ID NO 1062
<211> LENGTH: 23
<212> TYPE: DNA
<213> ORGANISM: Homo sapiens

<400> SEQUENCE: 1062
taccggaaaa tactgtagta tga                                           23

<210> SEQ ID NO 1063
<211> LENGTH: 23
<212> TYPE: DNA
<213> ORGANISM: Homo sapiens

<400> SEQUENCE: 1063
ccggaaaata ctgtagtatg act                                           23

<210> SEQ ID NO 1064
<211> LENGTH: 23
<212> TYPE: DNA
<213> ORGANISM: Homo sapiens

<400> SEQUENCE: 1064
```
tgccagatat ggggaatttg tga                      23

<210> SEQ ID NO 1065
<211> LENGTH: 23
<212> TYPE: DNA
<213> ORGANISM: Homo sapiens

<400> SEQUENCE: 1065
ctgtgaagaa gggtatatct tgg                      23

<210> SEQ ID NO 1066
<211> LENGTH: 23
<212> TYPE: DNA
<213> ORGANISM: Homo sapiens

<400> SEQUENCE: 1066
tggacagtat tgcaaagcta atg                      23

<210> SEQ ID NO 1067
<211> LENGTH: 23
<212> TYPE: DNA
<213> ORGANISM: Homo sapiens

<400> SEQUENCE: 1067
cagtattgca aagctaatga ttc                      23

<210> SEQ ID NO 1068
<211> LENGTH: 23
<212> TYPE: DNA
<213> ORGANISM: Homo sapiens

<400> SEQUENCE: 1068
tgcaaagcta atgattcctt tgg                      23

<210> SEQ ID NO 1069
<211> LENGTH: 23
<212> TYPE: DNA
<213> ORGANISM: Homo sapiens

<400> SEQUENCE: 1069
ttgttaattg gtgatattca tgg                      23

<210> SEQ ID NO 1070
<211> LENGTH: 23
<212> TYPE: DNA
<213> ORGANISM: Homo sapiens

<400> SEQUENCE: 1070
ccgtgcaaaa taaggttttt tca                      23

<210> SEQ ID NO 1071
<211> LENGTH: 23
<212> TYPE: DNA
<213> ORGANISM: Homo sapiens

<400> SEQUENCE: 1071
gtgcaaaata aggttttttc agt                      23

<210> SEQ ID NO 1072
<211> LENGTH: 23
<212> TYPE: DNA
<213> ORGANISM: Homo sapiens

```
<400> SEQUENCE: 1072
aaggtttttt cagttgacat taa                                              23

<210> SEQ ID NO 1073
<211> LENGTH: 23
<212> TYPE: DNA
<213> ORGANISM: Homo sapiens

<400> SEQUENCE: 1073
aggttttttc agttgacatt aat                                              23

<210> SEQ ID NO 1074
<211> LENGTH: 23
<212> TYPE: DNA
<213> ORGANISM: Homo sapiens

<400> SEQUENCE: 1074
cagttgacat taatggttta aat                                              23

<210> SEQ ID NO 1075
<211> LENGTH: 23
<212> TYPE: DNA
<213> ORGANISM: Homo sapiens

<400> SEQUENCE: 1075
ttgacattaa tggtttaaat atc                                              23

<210> SEQ ID NO 1076
<211> LENGTH: 23
<212> TYPE: DNA
<213> ORGANISM: Homo sapiens

<400> SEQUENCE: 1076
ctgggttaat aataaaatct atc                                              23

<210> SEQ ID NO 1077
<211> LENGTH: 23
<212> TYPE: DNA
<213> ORGANISM: Homo sapiens

<400> SEQUENCE: 1077
tgggttaata ataaaatcta tct                                              23

<210> SEQ ID NO 1078
<211> LENGTH: 23
<212> TYPE: DNA
<213> ORGANISM: Homo sapiens

<400> SEQUENCE: 1078
ccgcatagat atggtaaatt tgg                                              23

<210> SEQ ID NO 1079
<211> LENGTH: 23
<212> TYPE: DNA
<213> ORGANISM: Homo sapiens

<400> SEQUENCE: 1079 taccctata actgaaaact tgg                                               23

<210> SEQ ID NO 1080
<211> LENGTH: 23
<212> TYPE: DNA
<213> ORGANISM: Homo sapiens
```

```
<400> SEQUENCE: 1080
cccaactgtt ggttatttat ttt                                              23

<210> SEQ ID NO 1081
<211> LENGTH: 23
<212> TYPE: DNA
<213> ORGANISM: Homo sapiens

<400> SEQUENCE: 1081
ctgttggtta tttatttttc tca                                              23

<210> SEQ ID NO 1082
<211> LENGTH: 23
<212> TYPE: DNA
<213> ORGANISM: Homo sapiens

<400> SEQUENCE: 1082
gggtaactct ggatatgata tcg                                              23

<210> SEQ ID NO 1083
<211> LENGTH: 23
<212> TYPE: DNA
<213> ORGANISM: Homo sapiens

<400> SEQUENCE: 1083
cggtttgatt acattgaaac tgt                                              23

<210> SEQ ID NO 1084
<211> LENGTH: 23
<212> TYPE: DNA
<213> ORGANISM: Homo sapiens

<400> SEQUENCE: 1084
ttgattacat tgaaactgta act                                              23

<210> SEQ ID NO 1085
<211> LENGTH: 23
<212> TYPE: DNA
<213> ORGANISM: Homo sapiens

<400> SEQUENCE: 1085
tacattgaaa ctgtaactta tga                                              23

<210> SEQ ID NO 1086
<211> LENGTH: 23
<212> TYPE: DNA
<213> ORGANISM: Homo sapiens

<400> SEQUENCE: 1086
tgctaccaat ccgtgtaaag ata                                              23

<210> SEQ ID NO 1087
<211> LENGTH: 23
<212> TYPE: DNA
<213> ORGANISM: Homo sapiens

<400> SEQUENCE: 1087
ttctttgtcg ggattgattt tga                                              23

<210> SEQ ID NO 1088
<211> LENGTH: 23
<212> TYPE: DNA
```

<213> ORGANISM: Homo sapiens

<400> SEQUENCE: 1088
cagcactatc tttttttcag ata                                       23

<210> SEQ ID NO 1089
<211> LENGTH: 23
<212> TYPE: DNA
<213> ORGANISM: Homo sapiens

<400> SEQUENCE: 1089
agcactatct tttttcaga tat                                        23

<210> SEQ ID NO 1090
<211> LENGTH: 23
<212> TYPE: DNA
<213> ORGANISM: Homo sapiens

<400> SEQUENCE: 1090
atgtcaaaac acatgatttt taa                                       23

<210> SEQ ID NO 1091
<211> LENGTH: 23
<212> TYPE: DNA
<213> ORGANISM: Homo sapiens

<400> SEQUENCE: 1091
aacacatgat ttttaagcaa aag                                       23

<210> SEQ ID NO 1092
<211> LENGTH: 23
<212> TYPE: DNA
<213> ORGANISM: Homo sapiens

<400> SEQUENCE: 1092
gggtggaaaa tgttgaaagt ttg                                       23

<210> SEQ ID NO 1093
<211> LENGTH: 23
<212> TYPE: DNA
<213> ORGANISM: Homo sapiens

<400> SEQUENCE: 1093
tggcttttga ttggatttca aag                                       23

<210> SEQ ID NO 1094
<211> LENGTH: 23
<212> TYPE: DNA
<213> ORGANISM: Homo sapiens

<400> SEQUENCE: 1094
ggcttttgat tggatttcaa aga                                       23

<210> SEQ ID NO 1095
<211> LENGTH: 23
<212> TYPE: DNA
<213> ORGANISM: Homo sapiens

<400> SEQUENCE: 1095
ttggatttca aagaatctct att                                       23

<210> SEQ ID NO 1096
<211> LENGTH: 23

```
<212> TYPE: DNA
<213> ORGANISM: Homo sapiens

<400> SEQUENCE: 1096
tggatttcaa agaatctcta ttg                                              23

<210> SEQ ID NO 1097
<211> LENGTH: 23
<212> TYPE: DNA
<213> ORGANISM: Homo sapiens

<400> SEQUENCE: 1097
cacagtagtt cagtatttaa ata                                              23

<210> SEQ ID NO 1098
<211> LENGTH: 23
<212> TYPE: DNA
<213> ORGANISM: Homo sapiens

<400> SEQUENCE: 1098
cagtagttca gtatttaaat aac                                              23

<210> SEQ ID NO 1099
<211> LENGTH: 23
<212> TYPE: DNA
<213> ORGANISM: Homo sapiens

<400> SEQUENCE: 1099 atcctttgc cgggtatcta ttc                                               23

<210> SEQ ID NO 1100
<211> LENGTH: 23
<212> TYPE: DNA
<213> ORGANISM: Homo sapiens

<400> SEQUENCE: 1100
tgggtagatg cctattttga taa                                              23

<210> SEQ ID NO 1101
<211> LENGTH: 23
<212> TYPE: DNA
<213> ORGANISM: Homo sapiens

<400> SEQUENCE: 1101
tgcctatttt gataaaattg agc                                              23

<210> SEQ ID NO 1102
<211> LENGTH: 23
<212> TYPE: DNA
<213> ORGANISM: Homo sapiens

<400> SEQUENCE: 1102
gccatctttg gagagcattt att                                              23

<210> SEQ ID NO 1103
<211> LENGTH: 23
<212> TYPE: DNA
<213> ORGANISM: Homo sapiens

<400> SEQUENCE: 1103
ttgcttacat actgcatttg aaa                                              23

<210> SEQ ID NO 1104
```

```
<211> LENGTH: 23
<212> TYPE: DNA
<213> ORGANISM: Homo sapiens

<400> SEQUENCE: 1104
tgcttacata ctgcatttga aat                                              23

<210> SEQ ID NO 1105
<211> LENGTH: 23
<212> TYPE: DNA
<213> ORGANISM: Homo sapiens

<400> SEQUENCE: 1105
tggttctaac gcctgtaatc aac                                              23

<210> SEQ ID NO 1106
<211> LENGTH: 23
<212> TYPE: DNA
<213> ORGANISM: Homo sapiens

<400> SEQUENCE: 1106
tcgatgattg tcatgataac agt                                              23

<210> SEQ ID NO 1107
<211> LENGTH: 23
<212> TYPE: DNA
<213> ORGANISM: Homo sapiens

<400> SEQUENCE: 1107
cacccaatac acctgtgata atc                                              23

<210> SEQ ID NO 1108
<211> LENGTH: 23
<212> TYPE: DNA
<213> ORGANISM: Homo sapiens

<400> SEQUENCE: 1108
acccaataca cctgtgataa tca                                              23

<210> SEQ ID NO 1109
<211> LENGTH: 23
<212> TYPE: DNA
<213> ORGANISM: Homo sapiens

<400> SEQUENCE: 1109
accagtgtat ctcaaagaac tgg                                              23

<210> SEQ ID NO 1110
<211> LENGTH: 23
<212> TYPE: DNA
<213> ORGANISM: Homo sapiens

<400> SEQUENCE: 1110
atgaaaagaa ctgcaattcg aca                                              23

<210> SEQ ID NO 1111
<211> LENGTH: 23
<212> TYPE: DNA
<213> ORGANISM: Homo sapiens

<400> SEQUENCE: 1111
ccccaatcat cgatgtattg acc                                              23
```

```
<210> SEQ ID NO 1112
<211> LENGTH: 23
<212> TYPE: DNA
<213> ORGANISM: Homo sapiens

<400> SEQUENCE: 1112
tcgatgtatt gacctatcgt ttg                                            23

<210> SEQ ID NO 1113
<211> LENGTH: 23
<212> TYPE: DNA
<213> ORGANISM: Homo sapiens

<400> SEQUENCE: 1113
atgtattgac ctatcgtttg tct                                            23

<210> SEQ ID NO 1114
<211> LENGTH: 23
<212> TYPE: DNA
<213> ORGANISM: Homo sapiens

<400> SEQUENCE: 1114
tcgttgtgat ggtgttttg att                                             23

<210> SEQ ID NO 1115
<211> LENGTH: 23
<212> TYPE: DNA
<213> ORGANISM: Homo sapiens

<400> SEQUENCE: 1115
cccgaacttc tgggaatgtg atg                                            23

<210> SEQ ID NO 1116
<211> LENGTH: 23
<212> TYPE: DNA
<213> ORGANISM: Homo sapiens

<400> SEQUENCE: 1116
ccgaacttct gggaatgtga tgg                                            23

<210> SEQ ID NO 1117
<211> LENGTH: 23
<212> TYPE: DNA
<213> ORGANISM: Homo sapiens

<400> SEQUENCE: 1117
cccaagactt gcccttcatc ata                                            23

<210> SEQ ID NO 1118
<211> LENGTH: 23
<212> TYPE: DNA
<213> ORGANISM: Homo sapiens

<400> SEQUENCE: 1118
ttcttacttg ccaatgattc taa                                            23

<210> SEQ ID NO 1119
<211> LENGTH: 23
<212> TYPE: DNA
<213> ORGANISM: Homo sapiens

<400> SEQUENCE: 1119
aagacataga tgaatgtgat att                                            23
```

<210> SEQ ID NO 1120
<211> LENGTH: 23
<212> TYPE: DNA
<213> ORGANISM: Homo sapiens

<400> SEQUENCE: 1120
gacatagatg aatgtgatat tct                                              23

<210> SEQ ID NO 1121
<211> LENGTH: 23
<212> TYPE: DNA
<213> ORGANISM: Homo sapiens

<400> SEQUENCE: 1121
gtgtgataca ggctacatgt tag                                              23

<210> SEQ ID NO 1122
<211> LENGTH: 23
<212> TYPE: DNA
<213> ORGANISM: Homo sapiens

<400> SEQUENCE: 1122
aggctacatg ttagaaagtg atg                                              23

<210> SEQ ID NO 1123
<211> LENGTH: 23
<212> TYPE: DNA
<213> ORGANISM: Homo sapiens

<400> SEQUENCE: 1123
ggctacatgt tagaaagtga tgg                                              23

<210> SEQ ID NO 1124
<211> LENGTH: 23
<212> TYPE: DNA
<213> ORGANISM: Homo sapiens

<400> SEQUENCE: 1124
gtcgagaatg gttcttacat tgt                                              23

<210> SEQ ID NO 1125
<211> LENGTH: 23
<212> TYPE: DNA
<213> ORGANISM: Homo sapiens

<400> SEQUENCE: 1125
gagaatggtt cttacattgt agc                                              23

<210> SEQ ID NO 1126
<211> LENGTH: 23
<212> TYPE: DNA
<213> ORGANISM: Homo sapiens

<400> SEQUENCE: 1126
tacattgtag ctgttgattt tga                                              23

<210> SEQ ID NO 1127
<211> LENGTH: 23
<212> TYPE: DNA
<213> ORGANISM: Homo sapiens

<400> SEQUENCE: 1127
agctgttgat tttgattcaa tta                                              23

<210> SEQ ID NO 1128
<211> LENGTH: 23
<212> TYPE: DNA
<213> ORGANISM: Homo sapiens

<400> SEQUENCE: 1128
ctgttgattt tgattcaatt agt                                             23

<210> SEQ ID NO 1129
<211> LENGTH: 23
<212> TYPE: DNA
<213> ORGANISM: Homo sapiens

<400> SEQUENCE: 1129
ttcaattagt ggtcgtatct ttt                                             23

<210> SEQ ID NO 1130
<211> LENGTH: 23
<212> TYPE: DNA
<213> ORGANISM: Homo sapiens

<400> SEQUENCE: 1130
agcatcatct tgactgaaac tat                                             23

<210> SEQ ID NO 1131
<211> LENGTH: 23
<212> TYPE: DNA
<213> ORGANISM: Homo sapiens

<400> SEQUENCE: 1131
atcatcttga ctgaaactat tgc                                             23

<210> SEQ ID NO 1132
<211> LENGTH: 23
<212> TYPE: DNA
<213> ORGANISM: Homo sapiens

<400> SEQUENCE: 1132
ttgactgaaa ctattgcaat aga                                             23

<210> SEQ ID NO 1133
<211> LENGTH: 23
<212> TYPE: DNA
<213> ORGANISM: Homo sapiens

<400> SEQUENCE: 1133
gactgaaact attgcaatag att                                             23

<210> SEQ ID NO 1134
<211> LENGTH: 23
<212> TYPE: DNA
<213> ORGANISM: Homo sapiens

<400> SEQUENCE: 1134
ctgaaactat tgcaatagat tgg                                             23

<210> SEQ ID NO 1135
<211> LENGTH: 23
<212> TYPE: DNA
<213> ORGANISM: Homo sapiens

<400> SEQUENCE: 1135

```
aacaattgaa gtctccaaaa ttg                                              23

<210> SEQ ID NO 1136
<211> LENGTH: 23
<212> TYPE: DNA
<213> ORGANISM: Homo sapiens

<400> SEQUENCE: 1136
tgctgattag taaaaaccta aca                                              23

<210> SEQ ID NO 1137
<211> LENGTH: 23
<212> TYPE: DNA
<213> ORGANISM: Homo sapiens

<400> SEQUENCE: 1137
tagcattaga tcccagaatg aat                                              23

<210> SEQ ID NO 1138
<211> LENGTH: 23
<212> TYPE: DNA
<213> ORGANISM: Homo sapiens

<400> SEQUENCE: 1138
agcattagat cccagaatga atg                                              23

<210> SEQ ID NO 1139
<211> LENGTH: 23
<212> TYPE: DNA
<213> ORGANISM: Homo sapiens

<400> SEQUENCE: 1139
cagaatgaat gagcatctac tgt                                              23

<210> SEQ ID NO 1140
<211> LENGTH: 23
<212> TYPE: DNA
<213> ORGANISM: Homo sapiens

<400> SEQUENCE: 1140
atggactttt gtgattataa tgg                                              23

<210> SEQ ID NO 1141
<211> LENGTH: 23
<212> TYPE: DNA
<213> ORGANISM: Homo sapiens

<400> SEQUENCE: 1141 gactttgtg attataatgg aca                                               23

<210> SEQ ID NO 1142
<211> LENGTH: 19
<212> TYPE: DNA
<213> ORGANISM: Homo sapiens

<400> SEQUENCE: 1142
gtgatttgat tatacggca                                                   19

<210> SEQ ID NO 1143
<211> LENGTH: 23
<212> TYPE: DNA
<213> ORGANISM: Homo sapiens

<400> SEQUENCE: 1143
```
gtcagttgta atgtataata ttc											23

<210> SEQ ID NO 1144
<211> LENGTH: 23
<212> TYPE: DNA
<213> ORGANISM: Homo sapiens

<400> SEQUENCE: 1144
ttgtaatgta taatattcaa tgg											23

<210> SEQ ID NO 1145
<211> LENGTH: 23
<212> TYPE: DNA
<213> ORGANISM: Homo sapiens

<400> SEQUENCE: 1145
atccttcgaa acaaccaaat tcc											23

<210> SEQ ID NO 1146
<211> LENGTH: 23
<212> TYPE: DNA
<213> ORGANISM: Homo sapiens

<400> SEQUENCE: 1146
ttcgaaacaa ccaaattccg tga											23

<210> SEQ ID NO 1147
<211> LENGTH: 23
<212> TYPE: DNA
<213> ORGANISM: Homo sapiens

<400> SEQUENCE: 1147
aacctttctt aataactgta agg											23

<210> SEQ ID NO 1148
<211> LENGTH: 23
<212> TYPE: DNA
<213> ORGANISM: Homo sapiens

<400> SEQUENCE: 1148
aggcaacata taatttttgg aat											23

<210> SEQ ID NO 1149
<211> LENGTH: 23
<212> TYPE: DNA
<213> ORGANISM: Homo sapiens

<400> SEQUENCE: 1149
ggcaacatat aatttttgga atc											23

<210> SEQ ID NO 1150
<211> LENGTH: 23
<212> TYPE: DNA
<213> ORGANISM: Homo sapiens

<400> SEQUENCE: 1150
agggatacag aatggtttag atg											23

<210> SEQ ID NO 1151
<211> LENGTH: 23
<212> TYPE: DNA
<213> ORGANISM: Homo sapiens

```
<400> SEQUENCE: 1151
gggatacaga atggtttaga tgt                                          23

<210> SEQ ID NO 1152
<211> LENGTH: 23
<212> TYPE: DNA
<213> ORGANISM: Homo sapiens

<400> SEQUENCE: 1152
cagaatggtt tagatgttga att                                          23

<210> SEQ ID NO 1153
<211> LENGTH: 23
<212> TYPE: DNA
<213> ORGANISM: Homo sapiens

<400> SEQUENCE: 1153
tacatctatt gggttgaaaa tcc                                          23

<210> SEQ ID NO 1154
<211> LENGTH: 23
<212> TYPE: DNA
<213> ORGANISM: Homo sapiens

<400> SEQUENCE: 1154
aggacagtat ttgcttctat atc                                          23

<210> SEQ ID NO 1155
<211> LENGTH: 23
<212> TYPE: DNA
<213> ORGANISM: Homo sapiens

<400> SEQUENCE: 1155
cagtatttgc ttctatatct atg                                          23

<210> SEQ ID NO 1156
<211> LENGTH: 21
<212> TYPE: DNA
<213> ORGANISM: Homo sapiens

<400> SEQUENCE: 1156
ccttctatga acctggcctt a                                            21

<210> SEQ ID NO 1157
<211> LENGTH: 23
<212> TYPE: DNA
<213> ORGANISM: Homo sapiens

<400> SEQUENCE: 1157
gccttagatt ggatttcaag aaa                                          23

<210> SEQ ID NO 1158
<211> LENGTH: 23
<212> TYPE: DNA
<213> ORGANISM: Homo sapiens

<400> SEQUENCE: 1158
tggatttcaa gaaacctta ttc                                           23

<210> SEQ ID NO 1159
<211> LENGTH: 23
<212> TYPE: DNA
<213> ORGANISM: Homo sapiens
```

```
<400> SEQUENCE: 1159
ctcagtcaat cgaggttttg aca                                          23

<210> SEQ ID NO 1160
<211> LENGTH: 23
<212> TYPE: DNA
<213> ORGANISM: Homo sapiens

<400> SEQUENCE: 1160
acggagatat cagatacaga aaa                                          23

<210> SEQ ID NO 1161
<211> LENGTH: 23
<212> TYPE: DNA
<213> ORGANISM: Homo sapiens

<400> SEQUENCE: 1161
cggagatatc agatacagaa aaa                                          23

<210> SEQ ID NO 1162
<211> LENGTH: 23
<212> TYPE: DNA
<213> ORGANISM: Homo sapiens

<400> SEQUENCE: 1162
gagatatcag atacagaaaa aca                                          23

<210> SEQ ID NO 1163
<211> LENGTH: 23
<212> TYPE: DNA
<213> ORGANISM: Homo sapiens

<400> SEQUENCE: 1163
cagatacaga aaacattga ttg                                           23

<210> SEQ ID NO 1164
<211> LENGTH: 23
<212> TYPE: DNA
<213> ORGANISM: Homo sapiens

<400> SEQUENCE: 1164
gtccatgatt ctttccttta tta                                          23

<210> SEQ ID NO 1165
<211> LENGTH: 23
<212> TYPE: DNA
<213> ORGANISM: Homo sapiens

<400> SEQUENCE: 1165
tccatgattc tttcctttat tat                                          23

<210> SEQ ID NO 1166
<211> LENGTH: 23
<212> TYPE: DNA
<213> ORGANISM: Homo sapiens

<400> SEQUENCE: 1166
ttctttcctt tattatactg atg                                          23

<210> SEQ ID NO 1167
<211> LENGTH: 23
<212> TYPE: DNA
```

```
<213> ORGANISM: Homo sapiens

<400> SEQUENCE: 1167
aacagtatga ggtcattgaa aga                                           23

<210> SEQ ID NO 1168
<211> LENGTH: 23
<212> TYPE: DNA
<213> ORGANISM: Homo sapiens

<400> SEQUENCE: 1168
ttgagagata atgttccaaa tct                                           23

<210> SEQ ID NO 1169
<211> LENGTH: 23
<212> TYPE: DNA
<213> ORGANISM: Homo sapiens

<400> SEQUENCE: 1169
gagagataat gttccaaatc tga                                           23

<210> SEQ ID NO 1170
<211> LENGTH: 23
<212> TYPE: DNA
<213> ORGANISM: Homo sapiens

<400> SEQUENCE: 1170
gagataatgt tccaaatctg agg                                           23

<210> SEQ ID NO 1171
<211> LENGTH: 19
<212> TYPE: DNA
<213> ORGANISM: Homo sapiens

<400> SEQUENCE: 1171
cctcaaatgg ctgtagcaa                                                19

<210> SEQ ID NO 1172
<211> LENGTH: 23
<212> TYPE: DNA
<213> ORGANISM: Homo sapiens

<400> SEQUENCE: 1172
ctctccatat aactctttca ttg                                           23

<210> SEQ ID NO 1173
<211> LENGTH: 23
<212> TYPE: DNA
<213> ORGANISM: Homo sapiens

<400> SEQUENCE: 1173
tccatataac tctttcattg ttg                                           23

<210> SEQ ID NO 1174
<211> LENGTH: 23
<212> TYPE: DNA
<213> ORGANISM: Homo sapiens

<400> SEQUENCE: 1174
aactctttca ttgttgtttc aat                                           23

<210> SEQ ID NO 1175
<211> LENGTH: 23
```

<212> TYPE: DNA
<213> ORGANISM: Homo sapiens

<400> SEQUENCE: 1175
ctctttcatt gttgtttcaa tgc                                              23

<210> SEQ ID NO 1176
<211> LENGTH: 23
<212> TYPE: DNA
<213> ORGANISM: Homo sapiens

<400> SEQUENCE: 1176
ctgcaatcag aggctttagc ttg                                              23

<210> SEQ ID NO 1177
<211> LENGTH: 23
<212> TYPE: DNA
<213> ORGANISM: Homo sapiens

<400> SEQUENCE: 1177
tgcaatcaga ggctttagct tgg                                              23

<210> SEQ ID NO 1178
<211> LENGTH: 23
<212> TYPE: DNA
<213> ORGANISM: Homo sapiens

<400> SEQUENCE: 1178
gaggctttag cttggaattg tca                                              23

<210> SEQ ID NO 1179
<211> LENGTH: 23
<212> TYPE: DNA
<213> ORGANISM: Homo sapiens

<400> SEQUENCE: 1179
ggctttagct tggaattgtc aga                                              23

<210> SEQ ID NO 1180
<211> LENGTH: 23
<212> TYPE: DNA
<213> ORGANISM: Homo sapiens

<400> SEQUENCE: 1180
ttggaattgt cagatcattc aga                                              23

<210> SEQ ID NO 1181
<211> LENGTH: 23
<212> TYPE: DNA
<213> ORGANISM: Homo sapiens

<400> SEQUENCE: 1181
tggatcttct ctgatgaaca ttg                                              23

<210> SEQ ID NO 1182
<211> LENGTH: 23
<212> TYPE: DNA
<213> ORGANISM: Homo sapiens

<400> SEQUENCE: 1182
aacattgtga cacatggaat agg                                              23

<210> SEQ ID NO 1183

```
<211> LENGTH: 23
<212> TYPE: DNA
<213> ORGANISM: Homo sapiens

<400> SEQUENCE: 1183
ttctgaaaca ctgatagaag ttc                                          23

<210> SEQ ID NO 1184
<211> LENGTH: 23
<212> TYPE: DNA
<213> ORGANISM: Homo sapiens

<400> SEQUENCE: 1184
tagaagttct gcggatcaat act                                          23

<210> SEQ ID NO 1185
<211> LENGTH: 23
<212> TYPE: DNA
<213> ORGANISM: Homo sapiens

<400> SEQUENCE: 1185
ttgttgtaga tcccaagaac aga                                          23

<210> SEQ ID NO 1186
<211> LENGTH: 23
<212> TYPE: DNA
<213> ORGANISM: Homo sapiens

<400> SEQUENCE: 1186
accaaagatt gagcgttctt tcc                                          23

<210> SEQ ID NO 1187
<211> LENGTH: 23
<212> TYPE: DNA
<213> ORGANISM: Homo sapiens

<400> SEQUENCE: 1187
ccgaagtgat ggctacgttt att                                          23

<210> SEQ ID NO 1188
<211> LENGTH: 23
<212> TYPE: DNA
<213> ORGANISM: Homo sapiens

<400> SEQUENCE: 1188
tgggttgatg attctttaga tat                                          23

<210> SEQ ID NO 1189
<211> LENGTH: 23
<212> TYPE: DNA
<213> ORGANISM: Homo sapiens

<400> SEQUENCE: 1189
ttgatgattc tttagatata att                                          23

<210> SEQ ID NO 1190
<211> LENGTH: 23
<212> TYPE: DNA
<213> ORGANISM: Homo sapiens

<400> SEQUENCE: 1190
cactgttttt gaaaattcta tca                                          23
```

```
<210> SEQ ID NO 1191
<211> LENGTH: 23
<212> TYPE: DNA
<213> ORGANISM: Homo sapiens

<400> SEQUENCE: 1191 ctgttttga aaattctatc ata                                               23

<210> SEQ ID NO 1192
<211> LENGTH: 23
<212> TYPE: DNA
<213> ORGANISM: Homo sapiens

<400> SEQUENCE: 1192
tgggtagata ggaatttgaa aaa                                              23

<210> SEQ ID NO 1193
<211> LENGTH: 23
<212> TYPE: DNA
<213> ORGANISM: Homo sapiens

<400> SEQUENCE: 1193
gggtagatag gaatttgaaa aag                                              23

<210> SEQ ID NO 1194
<211> LENGTH: 23
<212> TYPE: DNA
<213> ORGANISM: Homo sapiens

<400> SEQUENCE: 1194
cacagtgata agagacaata tca                                              23

<210> SEQ ID NO 1195
<211> LENGTH: 23
<212> TYPE: DNA
<213> ORGANISM: Homo sapiens

<400> SEQUENCE: 1195
cagtgataag agacaatatc aac                                              23

<210> SEQ ID NO 1196
<211> LENGTH: 23
<212> TYPE: DNA
<213> ORGANISM: Homo sapiens

<400> SEQUENCE: 1196
ggcaagaatt gtgccatttc aac                                              23

<210> SEQ ID NO 1197
<211> LENGTH: 23
<212> TYPE: DNA
<213> ORGANISM: Homo sapiens

<400> SEQUENCE: 1197
aagaattgtg ccatttcaac aga                                              23

<210> SEQ ID NO 1198
<211> LENGTH: 23
<212> TYPE: DNA
<213> ORGANISM: Homo sapiens

<400> SEQUENCE: 1198
gtgccatttc aacagaaaat ttc                                              23
```

-continued

```
<210> SEQ ID NO 1199
<211> LENGTH: 23
<212> TYPE: DNA
<213> ORGANISM: Homo sapiens

<400> SEQUENCE: 1199
tgccatttca acagaaaatt tcc                                              23

<210> SEQ ID NO 1200
<211> LENGTH: 23
<212> TYPE: DNA
<213> ORGANISM: Homo sapiens

<400> SEQUENCE: 1200
ctcatctttg ccttgtctaa ttc                                              23

<210> SEQ ID NO 1201
<211> LENGTH: 23
<212> TYPE: DNA
<213> ORGANISM: Homo sapiens

<400> SEQUENCE: 1201
acctttccaa acaataaatg tgg                                              23

<210> SEQ ID NO 1202
<211> LENGTH: 23
<212> TYPE: DNA
<213> ORGANISM: Homo sapiens

<400> SEQUENCE: 1202
gactatgaca gtgtaagtga tag                                              23

<210> SEQ ID NO 1203
<211> LENGTH: 23
<212> TYPE: DNA
<213> ORGANISM: Homo sapiens

<400> SEQUENCE: 1203
cagtgtaagt gatagaatct act                                              23

<210> SEQ ID NO 1204
<211> LENGTH: 23
<212> TYPE: DNA
<213> ORGANISM: Homo sapiens

<400> SEQUENCE: 1204
gtgtaagtga tagaatctac ttc                                              23

<210> SEQ ID NO 1205
<211> LENGTH: 23
<212> TYPE: DNA
<213> ORGANISM: Homo sapiens

<400> SEQUENCE: 1205
tagaatctac ttcacacaaa att                                              23

<210> SEQ ID NO 1206
<211> LENGTH: 23
<212> TYPE: DNA
<213> ORGANISM: Homo sapiens

<400> SEQUENCE: 1206
atctacttca cacaaaattt agc                                              23
```

```
<210> SEQ ID NO 1207
<211> LENGTH: 23
<212> TYPE: DNA
<213> ORGANISM: Homo sapiens

<400> SEQUENCE: 1207
gcctttgact ggattactag aag                                          23

<210> SEQ ID NO 1208
<211> LENGTH: 23
<212> TYPE: DNA
<213> ORGANISM: Homo sapiens

<400> SEQUENCE: 1208
gactggatta ctagaagaat tta                                          23

<210> SEQ ID NO 1209
<211> LENGTH: 23
<212> TYPE: DNA
<213> ORGANISM: Homo sapiens

<400> SEQUENCE: 1209
ctggattact agaagaattt att                                          23

<210> SEQ ID NO 1210
<211> LENGTH: 23
<212> TYPE: DNA
<213> ORGANISM: Homo sapiens

<400> SEQUENCE: 1210
tggattacta gaagaattta tta                                          23

<210> SEQ ID NO 1211
<211> LENGTH: 23
<212> TYPE: DNA
<213> ORGANISM: Homo sapiens

<400> SEQUENCE: 1211
gactctctat ggccagtata ttt                                          23

<210> SEQ ID NO 1212
<211> LENGTH: 23
<212> TYPE: DNA
<213> ORGANISM: Homo sapiens

<400> SEQUENCE: 1212
ctgacttgta cacacaaaga att                                          23

<210> SEQ ID NO 1213
<211> LENGTH: 23
<212> TYPE: DNA
<213> ORGANISM: Homo sapiens

<400> SEQUENCE: 1213
gacttgtaca cacaaagaat tta                                          23

<210> SEQ ID NO 1214
<211> LENGTH: 23
<212> TYPE: DNA
<213> ORGANISM: Homo sapiens

<400> SEQUENCE: 1214
```

```
tacacacaaa gaatttaccg agc                                              23

<210> SEQ ID NO 1215
<211> LENGTH: 23
<212> TYPE: DNA
<213> ORGANISM: Homo sapiens

<400> SEQUENCE: 1215
accagaaaca acagtgtaac aat                                              23

<210> SEQ ID NO 1216
<211> LENGTH: 23
<212> TYPE: DNA
<213> ORGANISM: Homo sapiens

<400> SEQUENCE: 1216
cagaaacaac agtgtaacaa tcc                                              23

<210> SEQ ID NO 1217
<211> LENGTH: 23
<212> TYPE: DNA
<213> ORGANISM: Homo sapiens

<400> SEQUENCE: 1217
aacaatcctt gtgaacagtt taa                                              23

<210> SEQ ID NO 1218
<211> LENGTH: 23
<212> TYPE: DNA
<213> ORGANISM: Homo sapiens

<400> SEQUENCE: 1218
gtggacaatg gtgaacgatg tgg                                              23

<210> SEQ ID NO 1219
<211> LENGTH: 23
<212> TYPE: DNA
<213> ORGANISM: Homo sapiens

<400> SEQUENCE: 1219
cggagtttat gtgcaataac aga                                              23

<210> SEQ ID NO 1220
<211> LENGTH: 23
<212> TYPE: DNA
<213> ORGANISM: Homo sapiens

<400> SEQUENCE: 1220
gagtttatgt gcaataacag aag                                              23

<210> SEQ ID NO 1221
<211> LENGTH: 23
<212> TYPE: DNA
<213> ORGANISM: Homo sapiens

<400> SEQUENCE: 1221
tggatacaca aaatgtcata att                                              23

<210> SEQ ID NO 1222
<211> LENGTH: 23
<212> TYPE: DNA
<213> ORGANISM: Homo sapiens

<400> SEQUENCE: 1222
```
tacacaaaat gtcataattc aaa        23

<210> SEQ ID NO 1223
<211> LENGTH: 23
<212> TYPE: DNA
<213> ORGANISM: Homo sapiens

<400> SEQUENCE: 1223
cacaaaatgt cataattcaa ata        23

<210> SEQ ID NO 1224
<211> LENGTH: 23
<212> TYPE: DNA
<213> ORGANISM: Homo sapiens

<400> SEQUENCE: 1224
gtcataattc aaatatttgt att        23

<210> SEQ ID NO 1225
<211> LENGTH: 23
<212> TYPE: DNA
<213> ORGANISM: Homo sapiens

<400> SEQUENCE: 1225
ttgtattcct cgcgtttatt tgt        23

<210> SEQ ID NO 1226
<211> LENGTH: 23
<212> TYPE: DNA
<213> ORGANISM: Homo sapiens

<400> SEQUENCE: 1226
gtgatgaaaa ccctacttat tgc        23

<210> SEQ ID NO 1227
<211> LENGTH: 23
<212> TYPE: DNA
<213> ORGANISM: Homo sapiens

<400> SEQUENCE: 1227
tcctcaacat tggtattgtg atc        23

<210> SEQ ID NO 1228
<211> LENGTH: 23
<212> TYPE: DNA
<213> ORGANISM: Homo sapiens

<400> SEQUENCE: 1228
tggtattgtg atcaagaaac aga        23

<210> SEQ ID NO 1229
<211> LENGTH: 23
<212> TYPE: DNA
<213> ORGANISM: Homo sapiens

<400> SEQUENCE: 1229
gtgatcaaga aacagattgt ttt        23

<210> SEQ ID NO 1230
<211> LENGTH: 23
<212> TYPE: DNA
<213> ORGANISM: Homo sapiens

```
<400> SEQUENCE: 1230
ttccgagttt ctctgtgtaa atg                                          23

<210> SEQ ID NO 1231
<211> LENGTH: 23
<212> TYPE: DNA
<213> ORGANISM: Homo sapiens

<400> SEQUENCE: 1231
tccgagtttc tctgtgtaaa tga                                          23

<210> SEQ ID NO 1232
<211> LENGTH: 23
<212> TYPE: DNA
<213> ORGANISM: Homo sapiens

<400> SEQUENCE: 1232
cggctacgat gagaatcaga att                                          23

<210> SEQ ID NO 1233
<211> LENGTH: 23
<212> TYPE: DNA
<213> ORGANISM: Homo sapiens

<400> SEQUENCE: 1233
aggagaactt gctctgaaaa tga                                          23

<210> SEQ ID NO 1234
<211> LENGTH: 23
<212> TYPE: DNA
<213> ORGANISM: Homo sapiens

<400> SEQUENCE: 1234
gactgtgtat cccaaagata ttc                                          23

<210> SEQ ID NO 1235
<211> LENGTH: 23
<212> TYPE: DNA
<213> ORGANISM: Homo sapiens

<400> SEQUENCE: 1235
gccaacagaa tcagtttacc tgt                                          23

<210> SEQ ID NO 1236
<211> LENGTH: 23
<212> TYPE: DNA
<213> ORGANISM: Homo sapiens

<400> SEQUENCE: 1236
gacaccttaa ccagtttcta ttg                                          23

<210> SEQ ID NO 1237
<211> LENGTH: 23
<212> TYPE: DNA
<213> ORGANISM: Homo sapiens

<400> SEQUENCE: 1237
accttaacca gtttctattg ttc                                          23

<210> SEQ ID NO 1238
<211> LENGTH: 23
<212> TYPE: DNA
<213> ORGANISM: Homo sapiens
```

-continued

```
<400> SEQUENCE: 1238
gacttgtgtt gatattgatg aat                                              23

<210> SEQ ID NO 1239
<211> LENGTH: 23
<212> TYPE: DNA
<213> ORGANISM: Homo sapiens

<400> SEQUENCE: 1239
atgtaatagg ctcctacatc tgt                                              23

<210> SEQ ID NO 1240
<211> LENGTH: 23
<212> TYPE: DNA
<213> ORGANISM: Homo sapiens

<400> SEQUENCE: 1240
ccggcaaaac agtaacatcg aac                                              23

<210> SEQ ID NO 1241
<211> LENGTH: 23
<212> TYPE: DNA
<213> ORGANISM: Homo sapiens

<400> SEQUENCE: 1241
accctatctc attttttagca acc                                             23

<210> SEQ ID NO 1242
<211> LENGTH: 23
<212> TYPE: DNA
<213> ORGANISM: Homo sapiens

<400> SEQUENCE: 1242
aaccgttact atttgagaaa ttt                                              23

<210> SEQ ID NO 1243
<211> LENGTH: 23
<212> TYPE: DNA
<213> ORGANISM: Homo sapiens

<400> SEQUENCE: 1243
accgttacta tttgagaaat tta                                              23

<210> SEQ ID NO 1244
<211> LENGTH: 23
<212> TYPE: DNA
<213> ORGANISM: Homo sapiens

<400> SEQUENCE: 1244
ccgttactat ttgagaaatt taa                                              23

<210> SEQ ID NO 1245
<211> LENGTH: 23
<212> TYPE: DNA
<213> ORGANISM: Homo sapiens

<400> SEQUENCE: 1245
tactatttga gaaatttaac tat                                              23

<210> SEQ ID NO 1246
<211> LENGTH: 23
<212> TYPE: DNA
```

<213> ORGANISM: Homo sapiens

<400> SEQUENCE: 1246
ttgagaaatt taactataga tgg    23

<210> SEQ ID NO 1247
<211> LENGTH: 23
<212> TYPE: DNA
<213> ORGANISM: Homo sapiens

<400> SEQUENCE: 1247
aactatagat ggctattttt act    23

<210> SEQ ID NO 1248
<211> LENGTH: 23
<212> TYPE: DNA
<213> ORGANISM: Homo sapiens

<400> SEQUENCE: 1248
gacaatgttg tggcattaga ttt    23

<210> SEQ ID NO 1249
<211> LENGTH: 23
<212> TYPE: DNA
<213> ORGANISM: Homo sapiens

<400> SEQUENCE: 1249
gagaagagat tgtattggat tga    23

<210> SEQ ID NO 1250
<211> LENGTH: 23
<212> TYPE: DNA
<213> ORGANISM: Homo sapiens

<400> SEQUENCE: 1250
ggcaagtcat tgagagaatg ttt    23

<210> SEQ ID NO 1251
<211> LENGTH: 23
<212> TYPE: DNA
<213> ORGANISM: Homo sapiens

<400> SEQUENCE: 1251
gacaaacaag gagacaatca taa    23

<210> SEQ ID NO 1252
<211> LENGTH: 23
<212> TYPE: DNA
<213> ORGANISM: Homo sapiens

<400> SEQUENCE: 1252
aaccaacaag tctgtgataa tct    23

<210> SEQ ID NO 1253
<211> LENGTH: 23
<212> TYPE: DNA
<213> ORGANISM: Homo sapiens

<400> SEQUENCE: 1253
ttcgctatta ccatttttga aga    23

<210> SEQ ID NO 1254
<211> LENGTH: 23

<212> TYPE: DNA
<213> ORGANISM: Homo sapiens

<400> SEQUENCE: 1254
cgctattacc atttttgaag aca                                           23

<210> SEQ ID NO 1255
<211> LENGTH: 23
<212> TYPE: DNA
<213> ORGANISM: Homo sapiens

<400> SEQUENCE: 1255
cagtggaaaa gggaaacaaa tat                                           23

<210> SEQ ID NO 1256
<211> LENGTH: 23
<212> TYPE: DNA
<213> ORGANISM: Homo sapiens

<400> SEQUENCE: 1256
aacaaatatg atggatcaaa tag                                           23

<210> SEQ ID NO 1257
<211> LENGTH: 23
<212> TYPE: DNA
<213> ORGANISM: Homo sapiens

<400> SEQUENCE: 1257
tccatgtgta ccatccatat agg                                           23

<210> SEQ ID NO 1258
<211> LENGTH: 23
<212> TYPE: DNA
<213> ORGANISM: Homo sapiens

<400> SEQUENCE: 1258
ctgatgaaga ccgtcttctt tgt                                           23

<210> SEQ ID NO 1259
<211> LENGTH: 23
<212> TYPE: DNA
<213> ORGANISM: Homo sapiens

<400> SEQUENCE: 1259
gtgacaactt cacagaattc agc                                           23

<210> SEQ ID NO 1260
<211> LENGTH: 23
<212> TYPE: DNA
<213> ORGANISM: Homo sapiens

<400> SEQUENCE: 1260
cagtgtacaa gtggacattg tgt                                           23

<210> SEQ ID NO 1261
<211> LENGTH: 23
<212> TYPE: DNA
<213> ORGANISM: Homo sapiens

<400> SEQUENCE: 1261
gtgtacaagt ggacattgtg tac                                           23

<210> SEQ ID NO 1262

```
<211> LENGTH: 23
<212> TYPE: DNA
<213> ORGANISM: Homo sapiens

<400> SEQUENCE: 1262
tactatgttc gaatgcaaaa acc                                              23

<210> SEQ ID NO 1263
<211> LENGTH: 23
<212> TYPE: DNA
<213> ORGANISM: Homo sapiens

<400> SEQUENCE: 1263
atgttcgaat gcaaaaacca tgt                                              23

<210> SEQ ID NO 1264
<211> LENGTH: 23
<212> TYPE: DNA
<213> ORGANISM: Homo sapiens

<400> SEQUENCE: 1264
atgcaaaaac catgtttgta tcc                                              23

<210> SEQ ID NO 1265
<211> LENGTH: 23
<212> TYPE: DNA
<213> ORGANISM: Homo sapiens

<400> SEQUENCE: 1265
ccgccatatt ggaaatgtga tgg                                              23

<210> SEQ ID NO 1266
<211> LENGTH: 23
<212> TYPE: DNA
<213> ORGANISM: Homo sapiens

<400> SEQUENCE: 1266
tggttcagat gaagaacttc acc                                              23

<210> SEQ ID NO 1267
<211> LENGTH: 23
<212> TYPE: DNA
<213> ORGANISM: Homo sapiens

<400> SEQUENCE: 1267
gacaacaatc gctgcattta tag                                              23

<210> SEQ ID NO 1268
<211> LENGTH: 23
<212> TYPE: DNA
<213> ORGANISM: Homo sapiens

<400> SEQUENCE: 1268
cccctaaacc ttgtacagaa tat                                              23

<210> SEQ ID NO 1269
<211> LENGTH: 23
<212> TYPE: DNA
<213> ORGANISM: Homo sapiens

<400> SEQUENCE: 1269
ccctaaacct tgtacagaat atg                                              23
```

-continued

```
<210> SEQ ID NO 1270
<211> LENGTH: 23
<212> TYPE: DNA
<213> ORGANISM: Homo sapiens

<400> SEQUENCE: 1270
aaccttgtac agaatatgaa tat                                              23

<210> SEQ ID NO 1271
<211> LENGTH: 23
<212> TYPE: DNA
<213> ORGANISM: Homo sapiens

<400> SEQUENCE: 1271
accttgtaca gaatatgaat ata                                              23

<210> SEQ ID NO 1272
<211> LENGTH: 23
<212> TYPE: DNA
<213> ORGANISM: Homo sapiens

<400> SEQUENCE: 1272
ttgtacagaa tatgaatata agt                                              23

<210> SEQ ID NO 1273
<211> LENGTH: 23
<212> TYPE: DNA
<213> ORGANISM: Homo sapiens

<400> SEQUENCE: 1273
ccgatgaact gggttgcaat aaa                                              23

<210> SEQ ID NO 1274
<211> LENGTH: 23
<212> TYPE: DNA
<213> ORGANISM: Homo sapiens

<400> SEQUENCE: 1274
aagaacatgt gctgaaaata tat                                              23

<210> SEQ ID NO 1275
<211> LENGTH: 23
<212> TYPE: DNA
<213> ORGANISM: Homo sapiens

<400> SEQUENCE: 1275
agcaaaattg tacccaatta aat                                              23

<210> SEQ ID NO 1276
<211> LENGTH: 23
<212> TYPE: DNA
<213> ORGANISM: Homo sapiens

<400> SEQUENCE: 1276
gggttcgaaa ccaatgtttt tga                                              23

<210> SEQ ID NO 1277
<211> LENGTH: 23
<212> TYPE: DNA
<213> ORGANISM: Homo sapiens

<400> SEQUENCE: 1277
tcgaaaccaa tgtttttgac aga                                              23
```

```
<210> SEQ ID NO 1278
<211> LENGTH: 23
<212> TYPE: DNA
<213> ORGANISM: Homo sapiens

<400> SEQUENCE: 1278
ctgacaatgt ccgaattcga aaa                                            23

<210> SEQ ID NO 1279
<211> LENGTH: 23
<212> TYPE: DNA
<213> ORGANISM: Homo sapiens

<400> SEQUENCE: 1279
gtccgaattc gaaaatataa tct                                            23

<210> SEQ ID NO 1280
<211> LENGTH: 23
<212> TYPE: DNA
<213> ORGANISM: Homo sapiens

<400> SEQUENCE: 1280
ccgaattcga aaatataatc tct                                            23

<210> SEQ ID NO 1281
<211> LENGTH: 23
<212> TYPE: DNA
<213> ORGANISM: Homo sapiens

<400> SEQUENCE: 1281
ctcagagtat cttcaagatg agg                                            23

<210> SEQ ID NO 1282
<211> LENGTH: 23
<212> TYPE: DNA
<213> ORGANISM: Homo sapiens

<400> SEQUENCE: 1282
atcttcaaga tgaggaatat atc                                            23

<210> SEQ ID NO 1283
<211> LENGTH: 25
<212> TYPE: DNA
<213> ORGANISM: Homo sapiens

<400> SEQUENCE: 1283
gggctctagg tttggtgcta tcaaa                                          25

<210> SEQ ID NO 1284
<211> LENGTH: 23
<212> TYPE: DNA
<213> ORGANISM: Homo sapiens

<400> SEQUENCE: 1284
tgcctacatc cccaactttg aat                                            23

<210> SEQ ID NO 1285
<211> LENGTH: 23
<212> TYPE: DNA
<213> ORGANISM: Homo sapiens

<400> SEQUENCE: 1285
aggaagttga cctgaaactg aaa                                            23
```

<210> SEQ ID NO 1286
<211> LENGTH: 23
<212> TYPE: DNA
<213> ORGANISM: Homo sapiens

<400> SEQUENCE: 1286
gacctgaaac tgaaatacgt aat                                              23

<210> SEQ ID NO 1287
<211> LENGTH: 23
<212> TYPE: DNA
<213> ORGANISM: Homo sapiens

<400> SEQUENCE: 1287
acctgaaact gaaatacgta atg                                              23

<210> SEQ ID NO 1288
<211> LENGTH: 23
<212> TYPE: DNA
<213> ORGANISM: Homo sapiens

<400> SEQUENCE: 1288
acgcattgag gtggctaaac ttg                                              23

<210> SEQ ID NO 1289
<211> LENGTH: 23
<212> TYPE: DNA
<213> ORGANISM: Homo sapiens

<400> SEQUENCE: 1289
tcccaaacta gggcttatgt tct                                              23

<210> SEQ ID NO 1290
<211> LENGTH: 23
<212> TYPE: DNA
<213> ORGANISM: Homo sapiens

<400> SEQUENCE: 1290
gggaaaggaa cctaaaatcg agt                                              23

<210> SEQ ID NO 1291
<211> LENGTH: 23
<212> TYPE: DNA
<213> ORGANISM: Homo sapiens

<400> SEQUENCE: 1291
ccgcaacatc ctggttttcg agg                                              23

<210> SEQ ID NO 1292
<211> LENGTH: 23
<212> TYPE: DNA
<213> ORGANISM: Homo sapiens

<400> SEQUENCE: 1292
gcctttctat cgattatttg aac                                              23

<210> SEQ ID NO 1293
<211> LENGTH: 23
<212> TYPE: DNA
<213> ORGANISM: Homo sapiens

<400> SEQUENCE: 1293
ttctatcgat tatttgaaca atg                                           23

<210> SEQ ID NO 1294
<211> LENGTH: 23
<212> TYPE: DNA
<213> ORGANISM: Homo sapiens

<400> SEQUENCE: 1294
aggacgttat tgaaaccata aaa                                           23

<210> SEQ ID NO 1295
<211> LENGTH: 23
<212> TYPE: DNA
<213> ORGANISM: Homo sapiens

<400> SEQUENCE: 1295
gacgttattg aaaccataaa ata                                           23

<210> SEQ ID NO 1296
<211> LENGTH: 23
<212> TYPE: DNA
<213> ORGANISM: Homo sapiens

<400> SEQUENCE: 1296
acgttattga aaccataaaa tat                                           23

<210> SEQ ID NO 1297
<211> LENGTH: 25
<212> TYPE: DNA
<213> ORGANISM: Homo sapiens

<400> SEQUENCE: 1297
ggactgatag gagagtcatt gcaaa                                         25

<210> SEQ ID NO 1298
<211> LENGTH: 23
<212> TYPE: DNA
<213> ORGANISM: Homo sapiens

<400> SEQUENCE: 1298
accagttata ctggatatct aag                                           23

<210> SEQ ID NO 1299
<211> LENGTH: 23
<212> TYPE: DNA
<213> ORGANISM: Homo sapiens

<400> SEQUENCE: 1299
gggagaagta tggaaacaaa ata                                           23

<210> SEQ ID NO 1300
<211> LENGTH: 23
<212> TYPE: DNA
<213> ORGANISM: Homo sapiens

<400> SEQUENCE: 1300
aagtatggaa acaaaataaa ttt                                           23

<210> SEQ ID NO 1301
<211> LENGTH: 23
<212> TYPE: DNA
<213> ORGANISM: Homo sapiens

<400> SEQUENCE: 1301
ttcatcaact cagatacaat aag          23

<210> SEQ ID NO 1302
<211> LENGTH: 23
<212> TYPE: DNA
<213> ORGANISM: Homo sapiens

<400> SEQUENCE: 1302
cggaggaaat tgctattttg atg          23

<210> SEQ ID NO 1303
<211> LENGTH: 23
<212> TYPE: DNA
<213> ORGANISM: Homo sapiens

<400> SEQUENCE: 1303
aggaaattgc tattttgatg aga          23

<210> SEQ ID NO 1304
<211> LENGTH: 23
<212> TYPE: DNA
<213> ORGANISM: Homo sapiens

<400> SEQUENCE: 1304
caccggaaaa tattgtgaaa tgg          23

<210> SEQ ID NO 1305
<211> LENGTH: 23
<212> TYPE: DNA
<213> ORGANISM: Homo sapiens

<400> SEQUENCE: 1305
ttgtgaaatg gcgttttcaa aag          23

<210> SEQ ID NO 1306
<211> LENGTH: 23
<212> TYPE: DNA
<213> ORGANISM: Homo sapiens

<400> SEQUENCE: 1306
caggattctt ccactataga agg          23

<210> SEQ ID NO 1307
<211> LENGTH: 23
<212> TYPE: DNA
<213> ORGANISM: Homo sapiens

<400> SEQUENCE: 1307
ggcagatctt aacatggata ttg          23

<210> SEQ ID NO 1308
<211> LENGTH: 23
<212> TYPE: DNA
<213> ORGANISM: Homo sapiens

<400> SEQUENCE: 1308
ggcaatgagt gaagactttg tca          23

<210> SEQ ID NO 1309
<211> LENGTH: 23
<212> TYPE: DNA
<213> ORGANISM: Homo sapiens

```
<400> SEQUENCE: 1309
atctgaaaat gtggataata aga                                    23

<210> SEQ ID NO 1310
<211> LENGTH: 23
<212> TYPE: DNA
<213> ORGANISM: Homo sapiens

<400> SEQUENCE: 1310
ctgaaaatgt ggataataag aat                                    23

<210> SEQ ID NO 1311
<211> LENGTH: 23
<212> TYPE: DNA
<213> ORGANISM: Homo sapiens

<400> SEQUENCE: 1311
gtggataata agaattatgg aag                                    23

<210> SEQ ID NO 1312
<211> LENGTH: 23
<212> TYPE: DNA
<213> ORGANISM: Homo sapiens

<400> SEQUENCE: 1312
tggataataa gaattatgga agt                                    23

<210> SEQ ID NO 1313
<211> LENGTH: 23
<212> TYPE: DNA
<213> ORGANISM: Homo sapiens

<400> SEQUENCE: 1313
tggaatctct tcaaacgaaa atc                                    23

<210> SEQ ID NO 1314
<211> LENGTH: 23
<212> TYPE: DNA
<213> ORGANISM: Homo sapiens

<400> SEQUENCE: 1314
atctcttcaa acgaaaatct aaa                                    23

<210> SEQ ID NO 1315
<211> LENGTH: 23
<212> TYPE: DNA
<213> ORGANISM: Homo sapiens

<400> SEQUENCE: 1315
ctcttcaaac gaaaatctaa aca                                    23

<210> SEQ ID NO 1316
<211> LENGTH: 23
<212> TYPE: DNA
<213> ORGANISM: Homo sapiens

<400> SEQUENCE: 1316
ttcaaacgaa aatctaaaca aac                                    23

<210> SEQ ID NO 1317
<211> LENGTH: 23
<212> TYPE: DNA
<213> ORGANISM: Homo sapiens
```

```
<400> SEQUENCE: 1317
aacgaaaatc taaacaaact acc                                      23

<210> SEQ ID NO 1318
<211> LENGTH: 23
<212> TYPE: DNA
<213> ORGANISM: Homo sapiens

<400> SEQUENCE: 1318
aacaaactac caactttgaa aat                                      23

<210> SEQ ID NO 1319
<211> LENGTH: 23
<212> TYPE: DNA
<213> ORGANISM: Homo sapiens

<400> SEQUENCE: 1319
taccaacttt gaaaatccaa tct                                      23

<210> SEQ ID NO 1320
<211> LENGTH: 23
<212> TYPE: DNA
<213> ORGANISM: Homo sapiens

<400> SEQUENCE: 1320
aactttgaaa atccaatcta tgc                                      23

<210> SEQ ID NO 1321
<211> LENGTH: 23
<212> TYPE: DNA
<213> ORGANISM: Homo sapiens

<400> SEQUENCE: 1321
tgcaacagaa gacactttta aag                                      23

<210> SEQ ID NO 1322
<211> LENGTH: 23
<212> TYPE: DNA
<213> ORGANISM: Homo sapiens

<400> SEQUENCE: 1322
caccgcaaat cttgttaaag aag                                      23

<210> SEQ ID NO 1323
<211> LENGTH: 23
<212> TYPE: DNA
<213> ORGANISM: Homo sapiens

<400> SEQUENCE: 1323
cgcaaatctt gttaaagaag act                                      23

<210> SEQ ID NO 1324
<211> LENGTH: 23
<212> TYPE: DNA
<213> ORGANISM: Homo sapiens

<400> SEQUENCE: 1324
ctctgaagta tagctatacc agc                                      23

<210> SEQ ID NO 1325
<211> LENGTH: 23
<212> TYPE: DNA
```

```
<213> ORGANISM: Homo sapiens

<400> SEQUENCE: 1325
accagctatt tagggaataa tta                                              23

<210> SEQ ID NO 1326
<211> LENGTH: 23
<212> TYPE: DNA
<213> ORGANISM: Homo sapiens

<400> SEQUENCE: 1326
cagctatttt a gggaataatt aga                                            23

<210> SEQ ID NO 1327
<211> LENGTH: 23
<212> TYPE: DNA
<213> ORGANISM: Homo sapiens

<400> SEQUENCE: 1327
aacacacttt tgcacatata ttt                                              23

<210> SEQ ID NO 1328
<211> LENGTH: 23
<212> TYPE: DNA
<213> ORGANISM: Homo sapiens

<400> SEQUENCE: 1328
cacacttttg cacatatatt ttt                                              23

<210> SEQ ID NO 1329
<211> LENGTH: 23
<212> TYPE: DNA
<213> ORGANISM: Homo sapiens

<400> SEQUENCE: 1329
tacaaacaga tgaaaaaagt taa                                              23

<210> SEQ ID NO 1330
<211> LENGTH: 23
<212> TYPE: DNA
<213> ORGANISM: Homo sapiens

<400> SEQUENCE: 1330
aagttaacat tcagtacttt atg                                              23

<210> SEQ ID NO 1331
<211> LENGTH: 23
<212> TYPE: DNA
<213> ORGANISM: Homo sapiens

<400> SEQUENCE: 1331
ttcagtactt tatgaaaaaa ata                                              23

<210> SEQ ID NO 1332
<211> LENGTH: 23
<212> TYPE: DNA
<213> ORGANISM: Homo sapiens

<400> SEQUENCE: 1332
cagtacttta tgaaaaaaat ata                                              23

<210> SEQ ID NO 1333
<211> LENGTH: 23
```

```
<212> TYPE: DNA
<213> ORGANISM: Homo sapiens

<400> SEQUENCE: 1333
ccgtctcata tttttacaaa taa                                              23

<210> SEQ ID NO 1334
<211> LENGTH: 23
<212> TYPE: DNA
<213> ORGANISM: Homo sapiens

<400> SEQUENCE: 1334
tacaaataat tatcacaatg tac                                              23

<210> SEQ ID NO 1335
<211> LENGTH: 23
<212> TYPE: DNA
<213> ORGANISM: Homo sapiens

<400> SEQUENCE: 1335
atcacaatgt actatatgta tat                                              23

<210> SEQ ID NO 1336
<211> LENGTH: 23
<212> TYPE: DNA
<213> ORGANISM: Homo sapiens

<400> SEQUENCE: 1336
cacaatgtac tatatgtata tct                                              23

<210> SEQ ID NO 1337
<211> LENGTH: 23
<212> TYPE: DNA
<213> ORGANISM: Homo sapiens

<400> SEQUENCE: 1337
atgtactata tgtatatctt tgc                                              23

<210> SEQ ID NO 1338
<211> LENGTH: 23
<212> TYPE: DNA
<213> ORGANISM: Homo sapiens

<400> SEQUENCE: 1338
ctgaagttgt ctgaaggtaa tac                                              23

<210> SEQ ID NO 1339
<211> LENGTH: 23
<212> TYPE: DNA
<213> ORGANISM: Homo sapiens

<400> SEQUENCE: 1339
ctgaaggtaa tactataaat ata                                              23

<210> SEQ ID NO 1340
<211> LENGTH: 23
<212> TYPE: DNA
<213> ORGANISM: Homo sapiens

<400> SEQUENCE: 1340
ttgtaaattt tggaaagatt atc                                              23

<210> SEQ ID NO 1341
```

```
<211> LENGTH: 23
<212> TYPE: DNA
<213> ORGANISM: Homo sapiens

<400> SEQUENCE: 1341
tggaaagatt atcctgttac tga                                              23

<210> SEQ ID NO 1342
<211> LENGTH: 23
<212> TYPE: DNA
<213> ORGANISM: Homo sapiens

<400> SEQUENCE: 1342
aagattatcc tgttactgaa ttt                                              23

<210> SEQ ID NO 1343
<211> LENGTH: 23
<212> TYPE: DNA
<213> ORGANISM: Homo sapiens

<400> SEQUENCE: 1343
atcctgttac tgaatttgct aat                                              23

<210> SEQ ID NO 1344
<211> LENGTH: 23
<212> TYPE: DNA
<213> ORGANISM: Homo sapiens

<400> SEQUENCE: 1344
tcctgttact gaatttgcta ata                                              23

<210> SEQ ID NO 1345
<211> LENGTH: 23
<212> TYPE: DNA
<213> ORGANISM: Homo sapiens

<400> SEQUENCE: 1345
tactgaattt gctaataaag atg                                              23

<210> SEQ ID NO 1346
<211> LENGTH: 23
<212> TYPE: DNA
<213> ORGANISM: Homo sapiens

<400> SEQUENCE: 1346
gtgatcatta tagtaaatga tcc                                              23

<210> SEQ ID NO 1347
<211> LENGTH: 23
<212> TYPE: DNA
<213> ORGANISM: Homo sapiens

<400> SEQUENCE: 1347
tagtaaatga tccaacaaga aaa                                              23

<210> SEQ ID NO 1348
<211> LENGTH: 23
<212> TYPE: DNA
<213> ORGANISM: Homo sapiens

<400> SEQUENCE: 1348
tccaacaaga aaggaattg act                                               23
```

```
<210> SEQ ID NO 1349
<211> LENGTH: 23
<212> TYPE: DNA
<213> ORGANISM: Homo sapiens

<400> SEQUENCE: 1349
cactcatatt tcctataaaa tta                                              23

<210> SEQ ID NO 1350
<211> LENGTH: 23
<212> TYPE: DNA
<213> ORGANISM: Homo sapiens

<400> SEQUENCE: 1350
ctcatatttc ctataaaatt atc                                              23

<210> SEQ ID NO 1351
<211> LENGTH: 23
<212> TYPE: DNA
<213> ORGANISM: Homo sapiens

<400> SEQUENCE: 1351
gtccattttt acacattagc act                                              23

<210> SEQ ID NO 1352
<211> LENGTH: 23
<212> TYPE: DNA
<213> ORGANISM: Homo sapiens

<400> SEQUENCE: 1352
tagcacttaa ttaatgttca ata                                              23

<210> SEQ ID NO 1353
<211> LENGTH: 23
<212> TYPE: DNA
<213> ORGANISM: Homo sapiens

<400> SEQUENCE: 1353
agcacttaat taatgttcaa tat                                              23

<210> SEQ ID NO 1354
<211> LENGTH: 23
<212> TYPE: DNA
<213> ORGANISM: Homo sapiens

<400> SEQUENCE: 1354
cacttaatta atgttcaata tta                                              23

<210> SEQ ID NO 1355
<211> LENGTH: 23
<212> TYPE: DNA
<213> ORGANISM: Homo sapiens

<400> SEQUENCE: 1355
ttcaatatta catgtcaatt tga                                              23

<210> SEQ ID NO 1356
<211> LENGTH: 23
<212> TYPE: DNA
<213> ORGANISM: Homo sapiens

<400> SEQUENCE: 1356
ttgattaatg gctatgttga tag                                              23
```

```
<210> SEQ ID NO 1357
<211> LENGTH: 23
<212> TYPE: DNA
<213> ORGANISM: Homo sapiens

<400> SEQUENCE: 1357
ggccactatg tgttgtatag aca                                              23

<210> SEQ ID NO 1358
<211> LENGTH: 23
<212> TYPE: DNA
<213> ORGANISM: Homo sapiens

<400> SEQUENCE: 1358
cactatgtgt tgtatagaca tct                                              23

<210> SEQ ID NO 1359
<211> LENGTH: 23
<212> TYPE: DNA
<213> ORGANISM: Homo sapiens

<400> SEQUENCE: 1359
aggtaggaaa agcaattcag ttt                                              23

<210> SEQ ID NO 1360
<211> LENGTH: 23
<212> TYPE: DNA
<213> ORGANISM: Homo sapiens

<400> SEQUENCE: 1360
gccaagacaa cattttattt tgt                                              23

<210> SEQ ID NO 1361
<211> LENGTH: 23
<212> TYPE: DNA
<213> ORGANISM: Homo sapiens

<400> SEQUENCE: 1361
gacaacattt ttatttgtga tgt                                              23

<210> SEQ ID NO 1362
<211> LENGTH: 23
<212> TYPE: DNA
<213> ORGANISM: Homo sapiens

<400> SEQUENCE: 1362
atgaggaaat cccatatcat taa                                              23

<210> SEQ ID NO 1363
<211> LENGTH: 23
<212> TYPE: DNA
<213> ORGANISM: Homo sapiens

<400> SEQUENCE: 1363
tgcattgagt ttgtggttaa tta                                              23

<210> SEQ ID NO 1364
<211> LENGTH: 23
<212> TYPE: DNA
<213> ORGANISM: Homo sapiens

<400> SEQUENCE: 1364
ttgagtttgt ggttaattaa atg                                              23
```

<210> SEQ ID NO 1365
<211> LENGTH: 23
<212> TYPE: DNA
<213> ORGANISM: Homo sapiens

<400> SEQUENCE: 1365
agctgaattt ctgaaaccaa atc                                              23

<210> SEQ ID NO 1366
<211> LENGTH: 23
<212> TYPE: DNA
<213> ORGANISM: Homo sapiens

<400> SEQUENCE: 1366
accaaatctg tgtcttcata aaa                                              23

<210> SEQ ID NO 1367
<211> LENGTH: 23
<212> TYPE: DNA
<213> ORGANISM: Homo sapiens

<400> SEQUENCE: 1367
tgggtttttg tttctatgaa aat                                              23

<210> SEQ ID NO 1368
<211> LENGTH: 23
<212> TYPE: DNA
<213> ORGANISM: Homo sapiens

<400> SEQUENCE: 1368
ttgtttctat gaaatatca tta                                               23

<210> SEQ ID NO 1369
<211> LENGTH: 23
<212> TYPE: DNA
<213> ORGANISM: Homo sapiens

<400> SEQUENCE: 1369
ttctatgaaa atatcattat aat                                              23

<210> SEQ ID NO 1370
<211> LENGTH: 23
<212> TYPE: DNA
<213> ORGANISM: Homo sapiens

<400> SEQUENCE: 1370
atgaaaatat cattataatc act                                              23

<210> SEQ ID NO 1371
<211> LENGTH: 23
<212> TYPE: DNA
<213> ORGANISM: Homo sapiens

<400> SEQUENCE: 1371
atcattataa tcactattta ttt                                              23

<210> SEQ ID NO 1372
<211> LENGTH: 23
<212> TYPE: DNA
<213> ORGANISM: Homo sapiens

<400> SEQUENCE: 1372
aaccattctt attaagctttt tta                                      23

<210> SEQ ID NO 1373
<211> LENGTH: 23
<212> TYPE: DNA
<213> ORGANISM: Homo sapiens

<400> SEQUENCE: 1373
accattctta ttaagctttt tat                                       23

<210> SEQ ID NO 1374
<211> LENGTH: 23
<212> TYPE: DNA
<213> ORGANISM: Homo sapiens

<400> SEQUENCE: 1374
gtggctaaat gtgtacattt ata                                       23

<210> SEQ ID NO 1375
<211> LENGTH: 23
<212> TYPE: DNA
<213> ORGANISM: Homo sapiens

<400> SEQUENCE: 1375
tggctaaatg tgtacattta tat                                       23

<210> SEQ ID NO 1376
<211> LENGTH: 23
<212> TYPE: DNA
<213> ORGANISM: Homo sapiens

<400> SEQUENCE: 1376
ggctaaatgt gtacatttat att                                       23

<210> SEQ ID NO 1377
<211> LENGTH: 23
<212> TYPE: DNA
<213> ORGANISM: Homo sapiens

<400> SEQUENCE: 1377
atgtgtacat ttatattaga atg                                       23

<210> SEQ ID NO 1378
<211> LENGTH: 23
<212> TYPE: DNA
<213> ORGANISM: Homo sapiens

<400> SEQUENCE: 1378
cagatctttt ctttaattct tat                                       23

<210> SEQ ID NO 1379
<211> LENGTH: 23
<212> TYPE: DNA
<213> ORGANISM: Homo sapiens

<400> SEQUENCE: 1379
atcttttctt taattcttat tgg                                       23

<210> SEQ ID NO 1380
<211> LENGTH: 23
<212> TYPE: DNA
<213> ORGANISM: Homo sapiens

<400> SEQUENCE: 1380
ttctttaatt cttattggtt ttt                                              23

<210> SEQ ID NO 1381
<211> LENGTH: 23
<212> TYPE: DNA
<213> ORGANISM: Homo sapiens

<400> SEQUENCE: 1381
ctcttaaata gtgggtatag tct                                              23

<210> SEQ ID NO 1382
<211> LENGTH: 23
<212> TYPE: DNA
<213> ORGANISM: Homo sapiens

<400> SEQUENCE: 1382
gtgctaatat tgcacatttg tta                                              23

<210> SEQ ID NO 1383
<211> LENGTH: 23
<212> TYPE: DNA
<213> ORGANISM: Homo sapiens

<400> SEQUENCE: 1383
tgctaatatt gcacatttgt taa                                              23

<210> SEQ ID NO 1384
<211> LENGTH: 23
<212> TYPE: DNA
<213> ORGANISM: Homo sapiens

<400> SEQUENCE: 1384
atggatgaat gaatgaaaca tat                                              23

<210> SEQ ID NO 1385
<211> LENGTH: 23
<212> TYPE: DNA
<213> ORGANISM: Homo sapiens

<400> SEQUENCE: 1385
atgaatgaaa catatactac tga                                              23

<210> SEQ ID NO 1386
<211> LENGTH: 23
<212> TYPE: DNA
<213> ORGANISM: Homo sapiens

<400> SEQUENCE: 1386
atgaaacata tactactgat tat                                              23

<210> SEQ ID NO 1387
<211> LENGTH: 23
<212> TYPE: DNA
<213> ORGANISM: Homo sapiens

<400> SEQUENCE: 1387
aacatatact actgattatt tta                                              23

<210> SEQ ID NO 1388
<211> LENGTH: 23
<212> TYPE: DNA
<213> ORGANISM: Homo sapiens

```
<400> SEQUENCE: 1388
ctgactgtaa ttactttgat tag                                              23

<210> SEQ ID NO 1389
<211> LENGTH: 23
<212> TYPE: DNA
<213> ORGANISM: Homo sapiens

<400> SEQUENCE: 1389
ctgtaattac tttgattaga taa                                              23

<210> SEQ ID NO 1390
<211> LENGTH: 23
<212> TYPE: DNA
<213> ORGANISM: Homo sapiens

<400> SEQUENCE: 1390
tagataaaca actggaaata atg                                              23

<210> SEQ ID NO 1391
<211> LENGTH: 23
<212> TYPE: DNA
<213> ORGANISM: Homo sapiens

<400> SEQUENCE: 1391
ctgctgaaaa agttctaata aat                                              23

<210> SEQ ID NO 1392
<211> LENGTH: 23
<212> TYPE: DNA
<213> ORGANISM: Homo sapiens

<400> SEQUENCE: 1392
tgctgaaaaa gttctaataa atg                                              23

<210> SEQ ID NO 1393
<211> LENGTH: 21
<212> TYPE: DNA
<213> ORGANISM: Homo sapiens

<400> SEQUENCE: 1393
ccctcagaga cctgagctct t                                                21

<210> SEQ ID NO 1394
<211> LENGTH: 21
<212> TYPE: DNA
<213> ORGANISM: Homo sapiens

<400> SEQUENCE: 1394
cctgtaataa acactactct t                                                21
```